US009981961B2

(12) United States Patent
Radu et al.

(10) Patent No.: US 9,981,961 B2
(45) Date of Patent: *May 29, 2018

(54) DEOXYCYTIDINE KINASE INHIBITORS

(71) Applicants: The Regents of the University of California, Oakland, CA (US); The Board of Trustees of the University of Illinois, Urbana, IL (US)

(72) Inventors: Caius G. Radu, Los Angeles, CA (US); Zheng Li, Oakland, CA (US); Raymond M. Gipson, Los Angeles, CA (US); Jue Wang, Los Angeles, CA (US); Nagichettiar Satyamurthy, Los Angeles, CA (US); Arnon Lavie, Chicago, IL (US); Jennifer M. Murphy, Los Angeles, CA (US); David A. Nathanson, Los Angeles, CA (US); Michael E. Jung, Los Angeles, CA (US)

(73) Assignees: The Regents of the University of California, Oakland, CA (US); The Board of Trustees of the University of Illinois, Urbana, IL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/421,258

(22) Filed: Jan. 31, 2017

(65) Prior Publication Data
US 2017/0204090 A1 Jul. 20, 2017

Related U.S. Application Data

(63) Continuation of application No. 14/992,396, filed on Jan. 11, 2016, now Pat. No. 9,598,404, which is a continuation of application No. PCT/US2014/050931, filed on Aug. 13, 2014.

(60) Provisional application No. 61/865,468, filed on Aug. 13, 2013.

(51) Int. Cl.
| | |
|---|---|
| *C07D 417/14* | (2006.01) |
| *A61K 31/506* | (2006.01) |
| *C07D 417/12* | (2006.01) |
| *C07B 59/00* | (2006.01) |
| *A61K 31/426* | (2006.01) |
| *A61K 31/513* | (2006.01) |
| *A61K 31/44* | (2006.01) |

(52) U.S. Cl.
CPC .......... *C07D 417/14* (2013.01); *A61K 31/426* (2013.01); *A61K 31/44* (2013.01); *A61K 31/506* (2013.01); *A61K 31/513* (2013.01); *C07B 59/002* (2013.01); *C07D 417/12* (2013.01); *C07B 2200/05* (2013.01)

(58) Field of Classification Search
CPC .... C07D 417/12; C07D 417/14; A61K 31/44; A61K 31/426; A61K 31/513; A61K 31/506
USPC .......................... 544/317, 324; 514/274, 275
See application file for complete search history.

(56) References Cited

U.S. PATENT DOCUMENTS 9,598,404 B2 * 3/2017 Radu .................... C07D 405/12
2008/0146571 A1 6/2008 Augeri et al.

FOREIGN PATENT DOCUMENTS

WO WO-2012/122368 A1 9/2002

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1995.*
Austin, W.R. et al. (Nov. 19, 2012, e-published Nov. 12, 2012). "Nucleoside salvage pathway kinases regulate hematopoiesis by linking nucleotide metabolism with replication stress," *J Exp Med* 209(12):2215-2228.
Bartek, J. et al. (Jan. 2012, e-published Jan. 5, 2012). "Thresholds of replication stress signaling in cancer development and treatment," *Nature structural & molecular biology* 19(1):5-7.
Beyaert, M. et al. (Nov. 24, 2015). "A crucial role for ATR in the regulation of deoxycytidine kinase activity," *Biochem Pharmacol* http://dx.doi.org/10.1016/j.bcp.2015.11.022, 7 pages.
Boulos, N. et al. (Mar. 31, 2011, e-published Jan. 24, 2011). "Chemotherapeutic agents circumvent emergence of dasatinib-resistant BCR-ABL kinase mutations in a precise mouse model of Philadelphia chromosome-positive acute lymphoblastic leukemia," *Blood* 117(13):3585-3595.
Csapo, Z. et al. (Jun. 15, 2003). "Activation of deoxycytidine kinase by gamma-irradiation and inactivation by hyperosmotic shock in human lymphocytes," *Biochem Pharmacol* 65(12):2031-2039.
Datta, N.S. et al. (Jun. 5, 1989). "Kinetic properties and inhibition of human T lymphoblast deoxycytidine kinase," *J Biol Chem* 264(16):9359-9364.
Fong, P.C. et al. (Jul. 9, 2009, e-published Jun. 24, 2009). "Inhibition of poly(ADP-ribose) polymerase in tumors from BRCA mutation carriers," *N Engl J Med* 361(2):123-134.

(Continued)

*Primary Examiner* — Deepak R Rao
(74) *Attorney, Agent, or Firm* — Mintz Levin Cohn Ferris Glovsky and Popeo, P.C.

(57) ABSTRACT

Provided herein are compounds that bind to dCK and methods for treating cancer.

23 Claims, 31 Drawing Sheets

(56) References Cited

OTHER PUBLICATIONS

Gura, T. (Nov. 7, 1997). "Systems for identifying new drugs are often faulty," *Science* 278(5340):1041-1042.
Jessop, T.C. et al. (Dec. 1, 2009, e-published Sep. 25, 2009). "Lead optimization and structure-based design of potent and bioavailable deoxycytidine kinase inhibitors," *Bioorg Med Chem Lett* 19(23):6784-6787.
Johnson, J.I. et al. (May 18, 2001). "Relationships between drug activity in NCI preclinical in vitro and in vivo models and early clinical trials," *Br J Cancer* 84(10)1 424-1431.
Jordheim, L.P. et al. (Aug. 15, 2004). "Characterization of a gemcitabine-resistant murine leukemic cell line: reversion of in vitro resistance by a mononucleotide prodrug," Clin Cancer res 10(16):5614-5621.
Laing, R.E. et al. (Feb. 24, 2009, e-published Feb. 5, 2009). "Noninvasive prediction of tumor responses to gemcitabine using positron emission tomography," *Proc Natl Acad Sci USA* 106(8):2847-2852.
Le. T.M. et al. (Aug. 14, 2017). "ATR inhibition facilitates targeting of leukemia dependence on convergent nucleotide biosynthetic pathways," *Nat Commun* 8(1):241.
Matsuoka, S. et al. (May 25, 2007). "ATM and ATR substrate analysis reveals extensive protein networks responsive to DNA damage," *Science* 316(5828):1160-1166.
Murphy, J.M. et al. (Sep. 12, 2013, e-published Aug. 15, 2013). Development of new deoxycytidine kinase inhibitors and noninvasive in vivo evaluation using positron emission tomography, *J Med Chem* 56(17):6696-6708.
Nathanson, D.A. et al. (Mar. 10, 2014, e-published Feb. 24, 2014). "Co-targeting of convergent nucleotide biosynthetic pathways for leukemia eradication," *J Exp Med* 211(3):473-486.
Nomme, J. et al. (Jan. 2014, e-published Dec. 24, 2013). "Structural characterization of new deoxycytidine kinase inhibitors rationalizes the affinity-determining moieties of the molecules," *Acta Crystallogr D Biol Crystallogr* 70(Part 1):68-78.
Nomme, J. et al. (Nov. 26, 2014, e-published Nov. 7, 2014). "Structure-guided development of deoxycytidine kinase inhibitors with nanomolar affinity and improved metabolic stability," *J Med Chem* 57(22):9480-9494.
Ooi, K. et al. (Oct. 1996). "Increased deoxycytidine kinase activity by etoposide in L1210 murine leukemic cells," *Biol Pharm Bull* 19(10):1382-1383.

Pearce, H.L. et al. (2008). "Failure modes in anticancer drug discovery and development," Chapter 18 in *Cancer Drug Design and Discovery*, edited by Stephen Neidle, pp. 424-435.
Radu, C.G. et al. (Jul. 2008, e-published Jun. 8, 2008). "Molecular imaging of lymphoid organs and immune activation by positron emission tomography with a new [18F]-labeled 2'-deoxycytidine analog," *Nat Med* 14(7):783-788.
Sabini, E. et al. (Jun. 28, 2007, e-published May 27, 2007). "Nonenantioselectivity property of human deoxycytidine kinase explained by structures of the enzyme in complex with L- and D-nucleosides," *J Med Chem* 50(13):3004-3014.
Schoppy, D.W. et al. (Jan. 2012, e-published Dec. 1, 2011). "Oncogenic stress sensitizes murine cancers to hypomorphic suppression of ATR," *J Clin Invest* 122(1):241-252.
Shu, C.J. et al. (Jul. 2010, e-published Jun. 16, 2010). "Novel PET Probes Specific for Deoxycytidine Kinase," *J Nucl Med* 51(7):1092-1098.
Simone, J.V. et al. (1995). Oncology: Introduction in *Cecil Textbook of Medicine*, 20$^{th}$ Edition, vol. 1, pp. 1004-1010.
Tarver, J.E. et al. (Dec. 1, 2009, e-published Sep. 25, 2009). "5-Fluorocytosine derivatives as inhibitors of deoxycytidine kinase," *Bioorg Med Chem Lett* 19(23):6780-6783.
Toy, G. et al. (Mar. 23, 2010, e-published Dec. 31, 2009). "Requirement for deoxycytidine kinase in T and B lymphocyte development," *Proc Natl Acad Sci USA* 107(12):5551-5556.
Ward, A.D. et al. (Jan. 1977). "Irreversible enzyme inhibitors. 200. Active-site-directed inhibitors of deoxycytidine kinase," *J Med Chem* 20(1):88-92.
Williams, R.T. et al. (Apr. 25, 2006, e-published Apr. 17, 2006). "Arf gene loss enhances oncogenicity and limits imatinib response in mouse models of Bcr-Abl-induced acute lymphoblastic leukemia," *Proc Natl Acad Sci USA* 103(17):6688-6693.
Xu, Y.Z. et al. (Jan. 13, 1995). "Functional compartmentation of dCTP pools. Preferential utilization of salvaged deoxycytidine for DNA repair in human lymphoblasts," *J Biol Chem* 270(2):631-637.
Yang, C et al. (Oct. 2012, e-published Jul. 31, 2012). "Deoxycytidine kinase regulates the G2/M checkpoint through interaction with cyclin-dependent kinase 1 in response to DNA damage," *Nucleic Acids Res* 40(19):9621-9632.
Yu, X-C. et al. (Jan. 2010, e-published Dec. 3, 2009). ". Novel Potent Inhibitors of Deoxycytidine Kinase Identified and Compared by Multiple Assays," *J Biomol Screening* 15(1):72-79.
International Search Report dated Nov. 14, 2014, for PCT Application No. PCT/US2014/050931, filed on Aug. 13, 2014, 4 pages.
Written Opinion dated Nov. 14, 2014, for PCT Application No. PCT/US2014/050931, filed on Aug. 13, 2014, 4 pages.

* cited by examiner

| Compound | Steady state kinetics | | CEM cells |
| --- | --- | --- | --- |
| | $IC_{50}^{app}$ (nM) | $K_i^{app}$ (nM) | $IC_{50}$ (nM) |
| Ia | 14.5 ± 2.8 | 0.8 ± 0.7 | 1.4 |
| Ib | 14.1 ± 3.0 | 0.5 ± 0.5 | 4.9 |

FIG. 2A
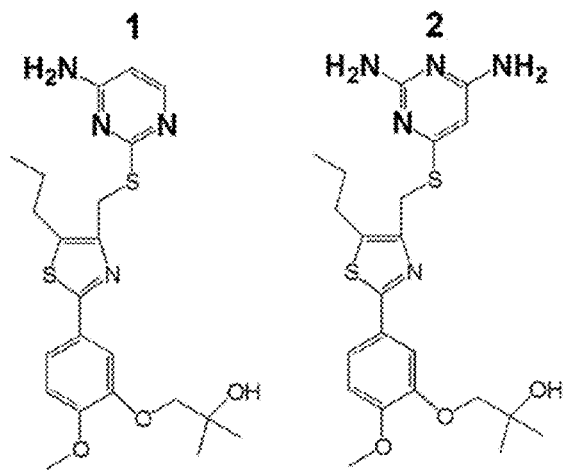
FIG. 2B
| Compound | Steady state kinetics | | CEM cells |
|---|---|---|---|
| | $IC_{50}^{app}$ (nM) | $K_i^{app}$ (nM) | $IC_{50}$ (nM) |
| 1 | 11.2 ± 1.1 | 1.8 ± 1.7 | 21.8 |
| 2 | 754 ± 58 | 735 ± 55 | N.D. |
FIG. 2C
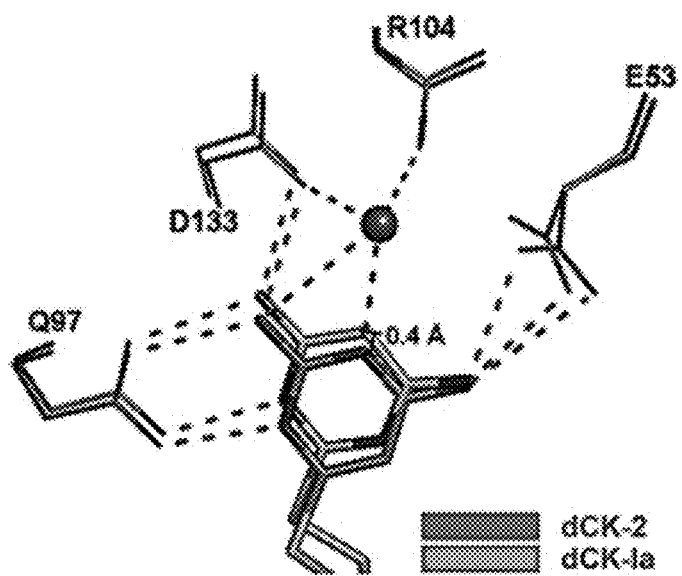

FIG. 3A
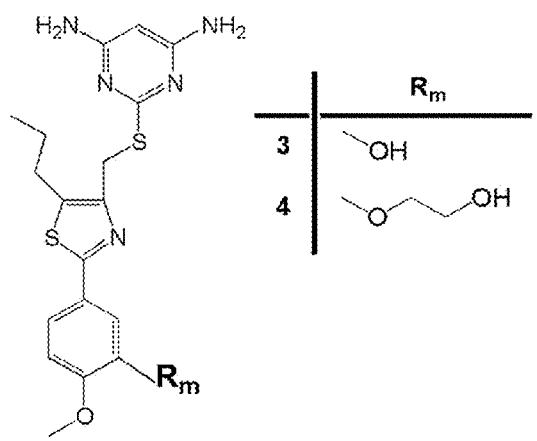
FIG. 3B
| Compound | Steady state kinetics | | CEM cells |
|---|---|---|---|
| | $IC_{50}^{app}$ (nM) | $K_i^{app}$ (nM) | $IC_{50}$ (nM) |
| 3 | 26.1 ± 4.0 | 8.9 ± 0.9 | 18.6 |
| 4 | 14.6 ± 3.6 | 0.5 ± 0.4 | 1.15 |
FIG. 3C
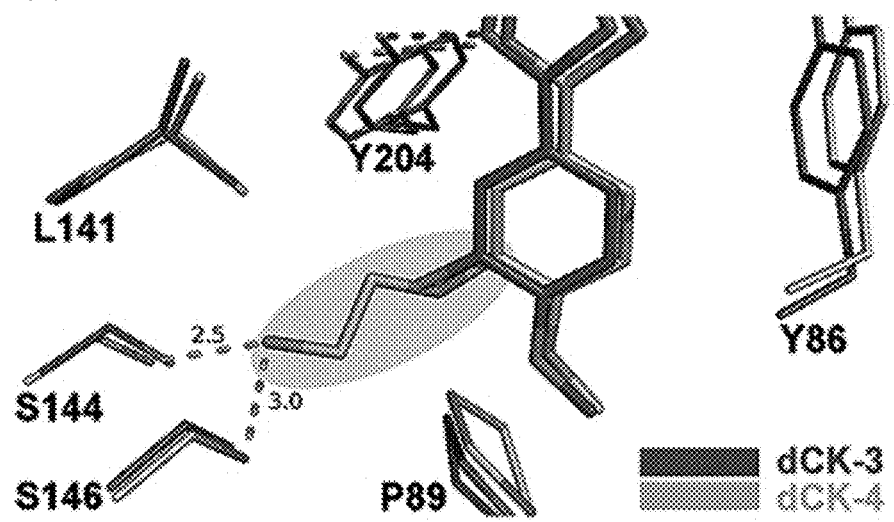

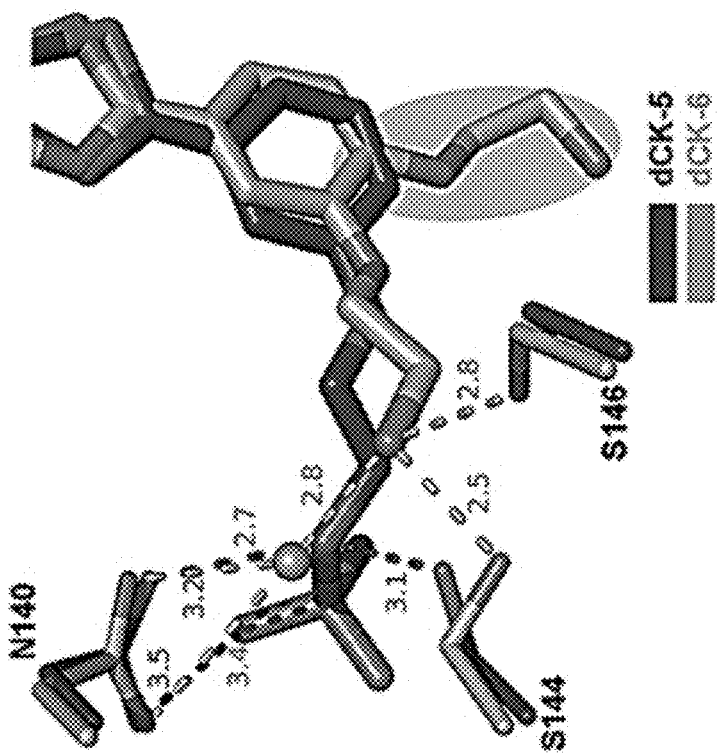
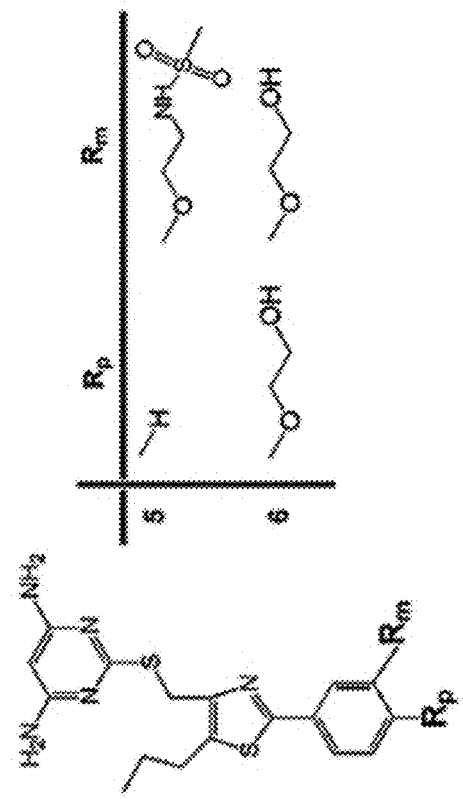
FIG. 4A
FIG. 4B
FIG. 4C

FIG. 5A
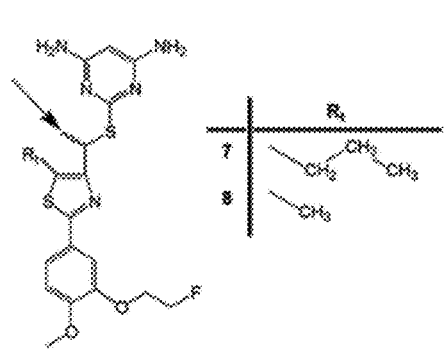
FIG. 5C
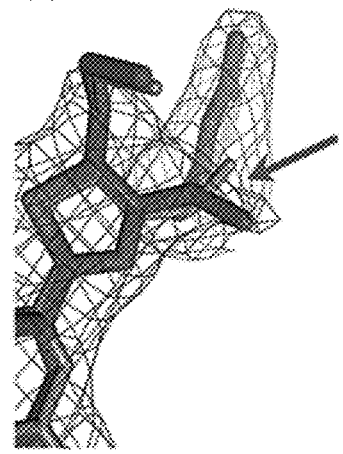
FIG. 5B
| Compound | Steady state kinetics | | CEM cells |
|---|---|---|---|
| | IC$_{50}$$^{app}$ (nM) | K$_i$$^{app}$ (nM) | IC$_{50}$ (nM) |
| 7 | 37.2 ± 7.4 | 18.6 ± 3.3 | 10.0 |
| 8 | 24.7 ± 4.3 | 6.8 ± 1.6 | 7.0 |
FIG. 5D
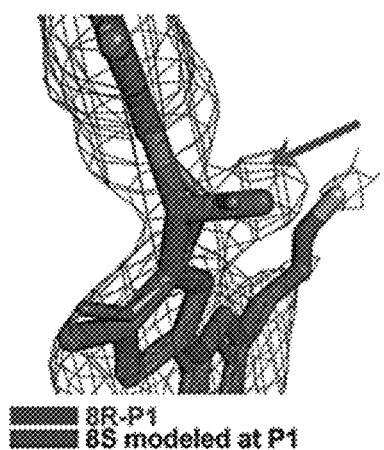
FIG. 5E
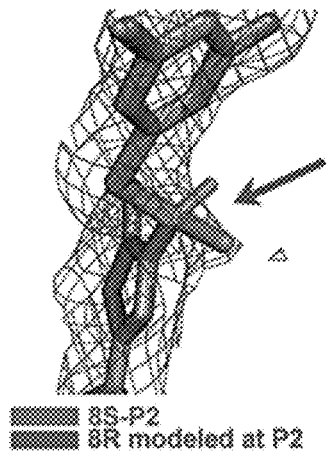

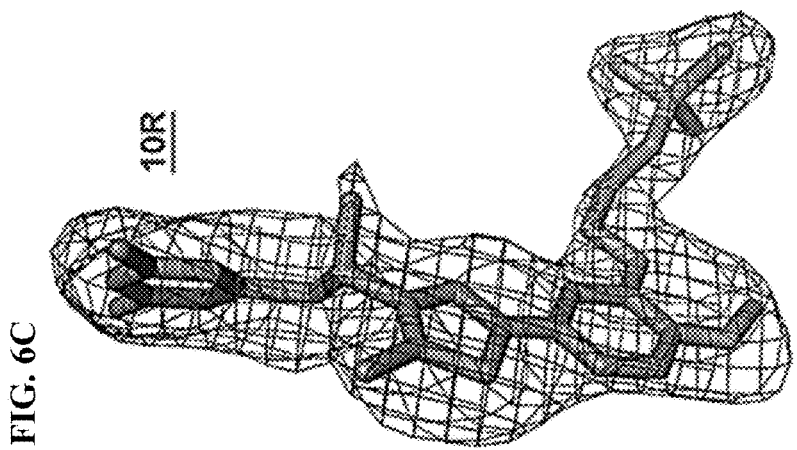
FIG. 6A
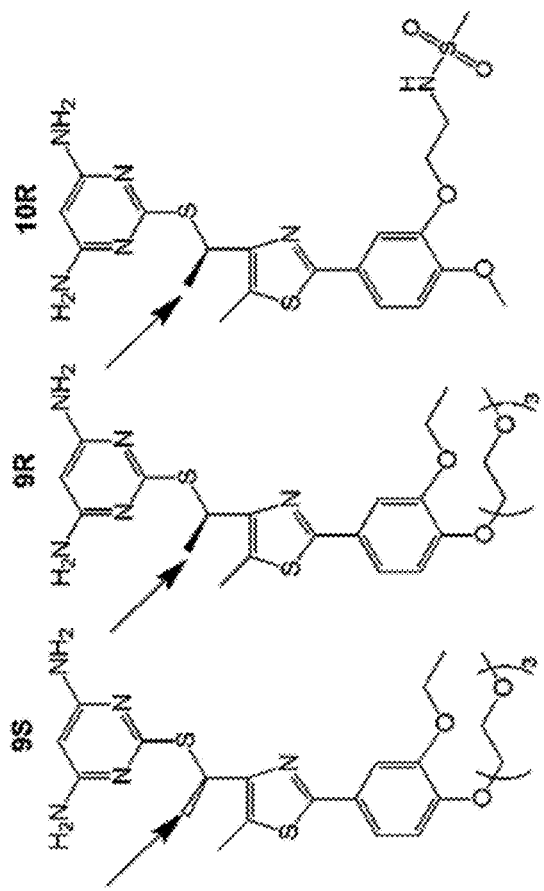
FIG. 6C
FIG. 6B

FIG. 7A    FIG. 7B    FIG. 7C    FIG. 7D
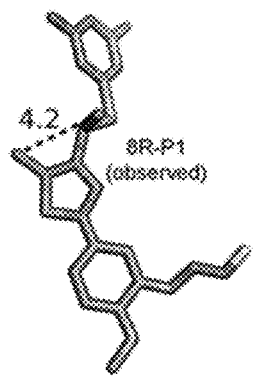 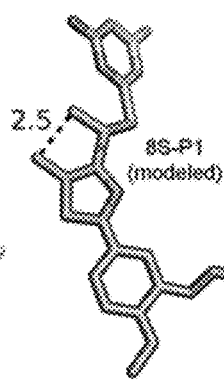 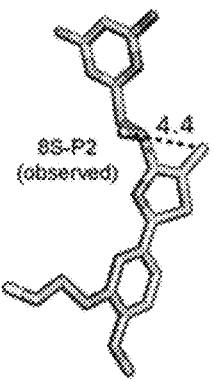 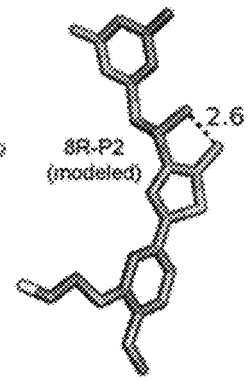
FIG. 7E    FIG. 7F
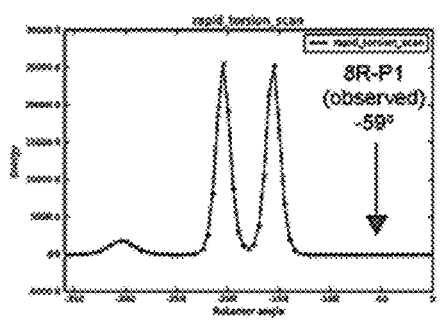 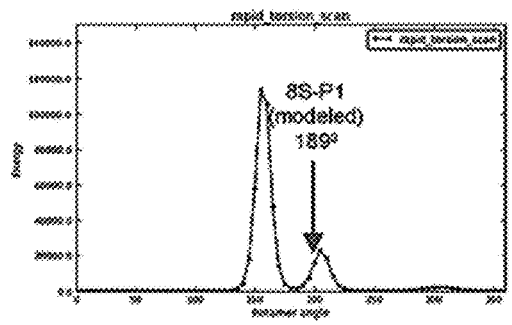
FIG. 7G    FIG. 7H
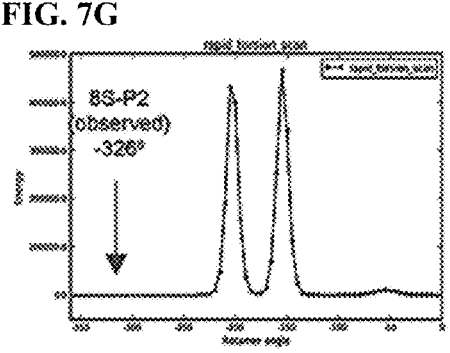 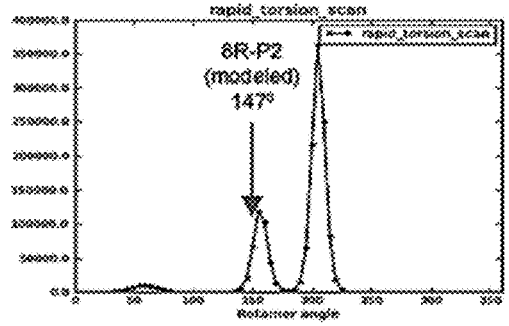

FIG. 11A
FIG. 11B
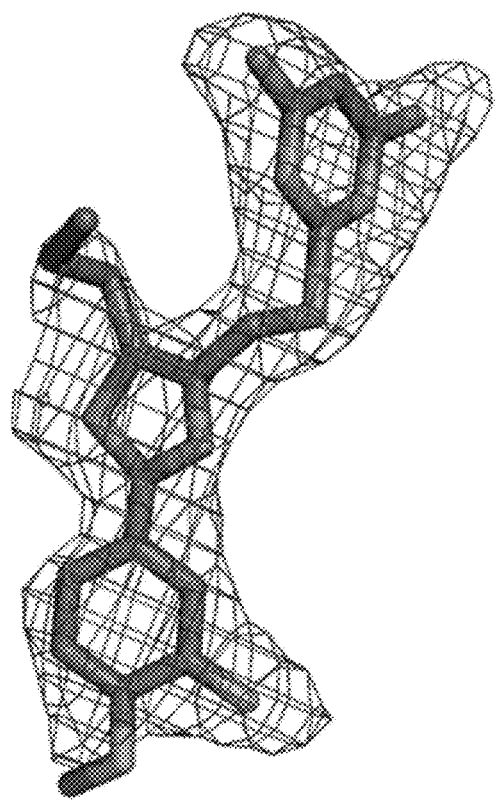
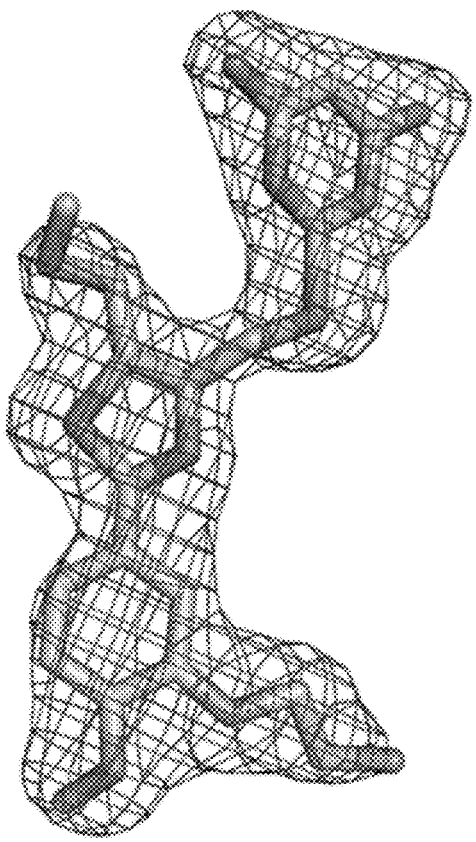
Compound 3
Compound 4

Compound 5

Compound 6

Compound 7

Compound 8R/S

FIG. 17A
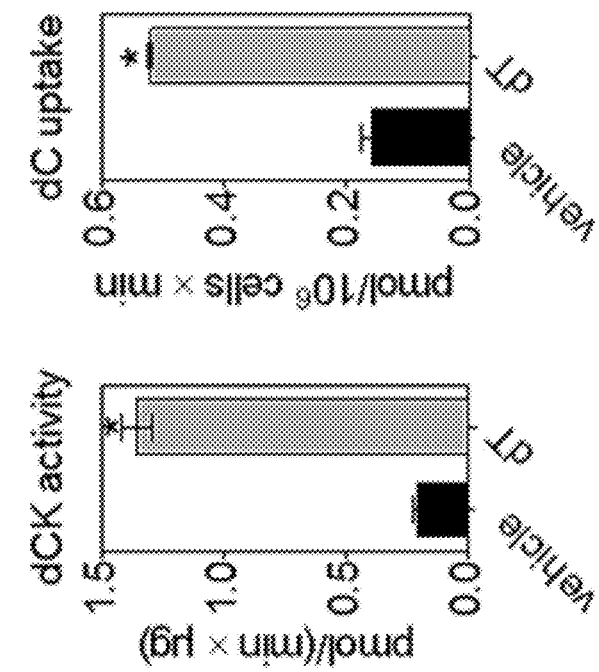
FIG. 17B
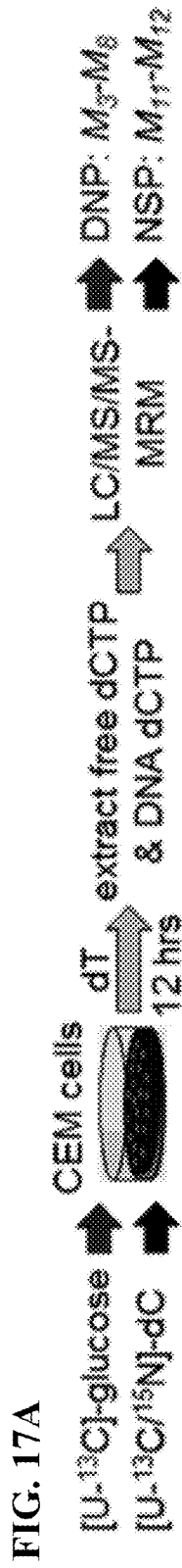
FIG. 17C
FIG. 17D
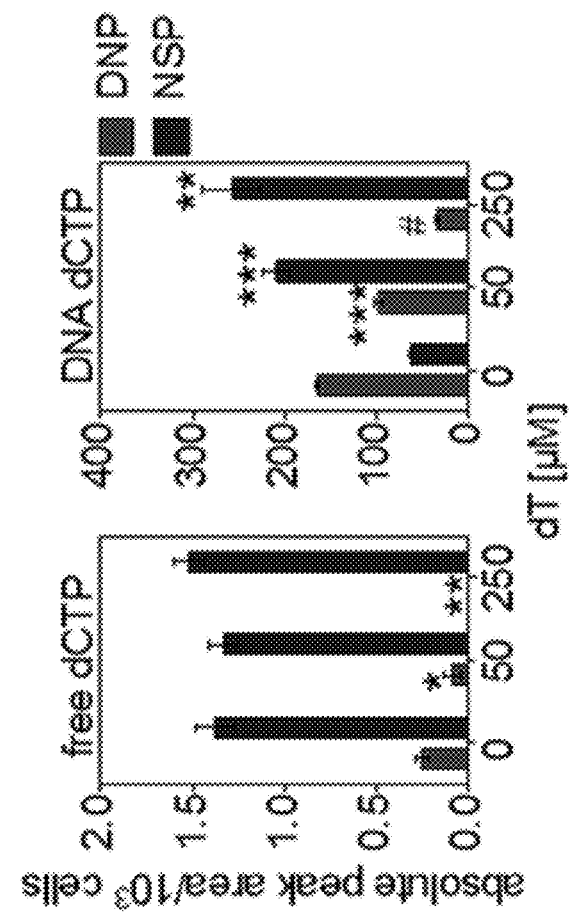

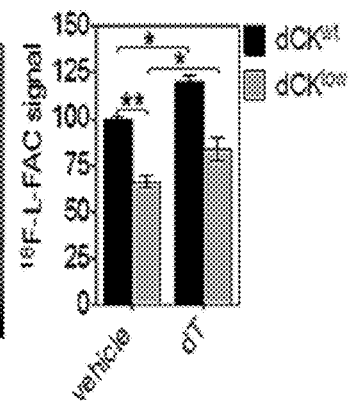

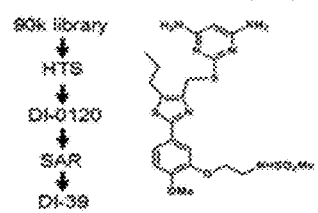
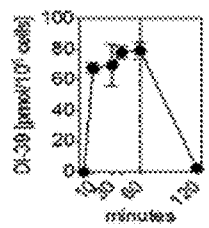
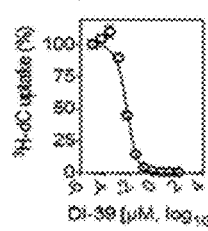
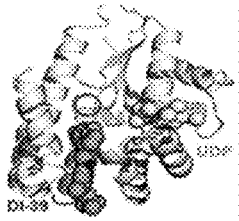
FIG. 20A  FIG. 20B  FIG. 20C  FIG. 20D  FIG. 20E
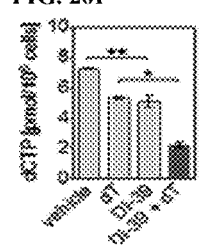
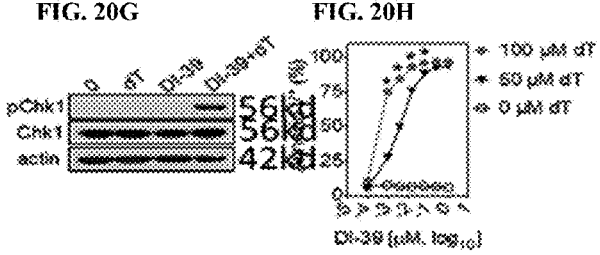
FIG. 20F  FIG. 20G  FIG. 20H  FIG. 20I
FIG. 20J
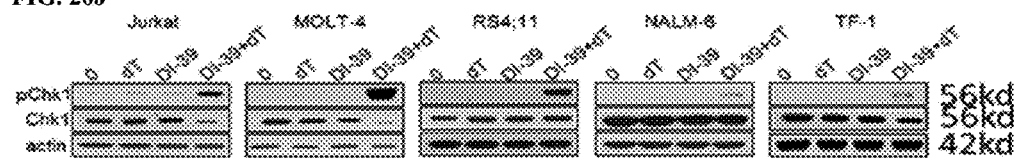
FIG. 20K
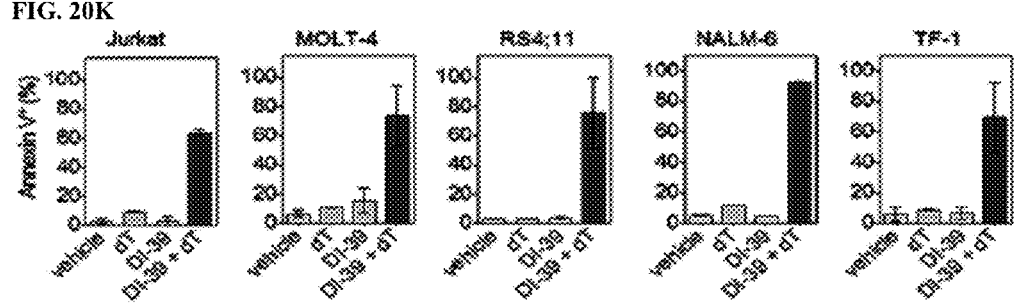

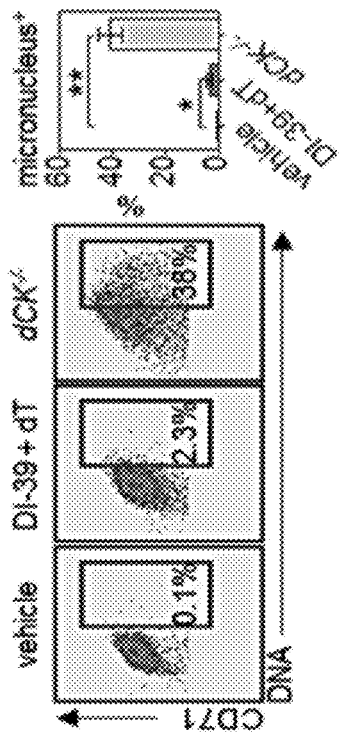
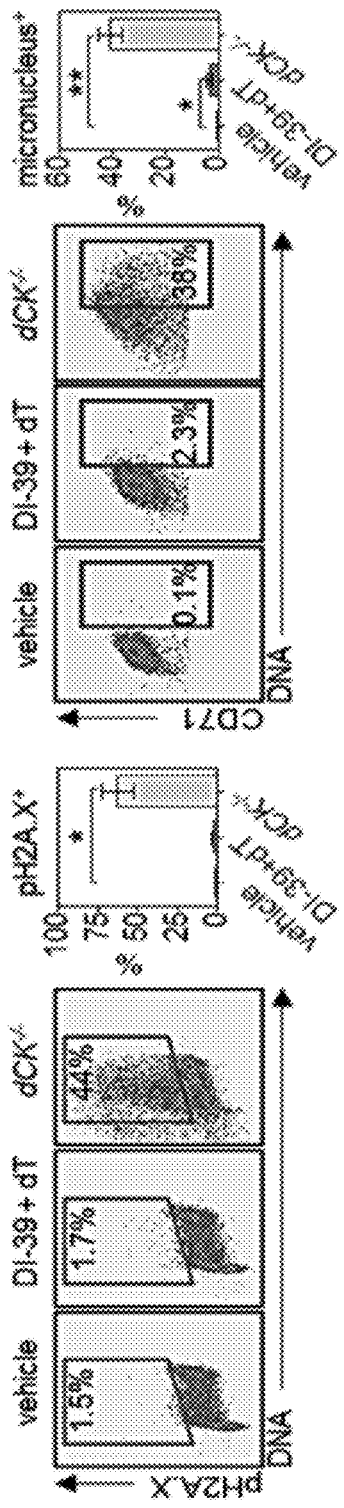
FIG. 24A
FIG. 24B
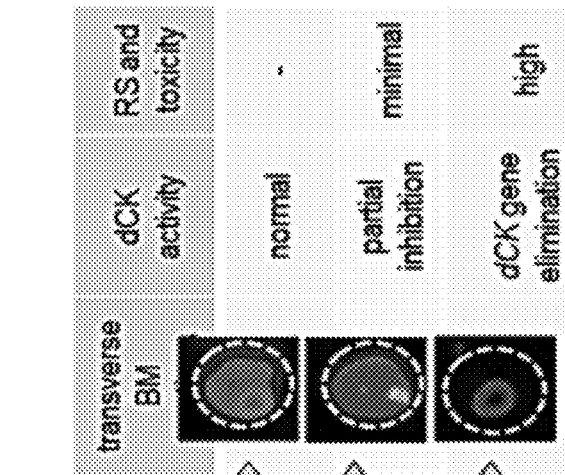
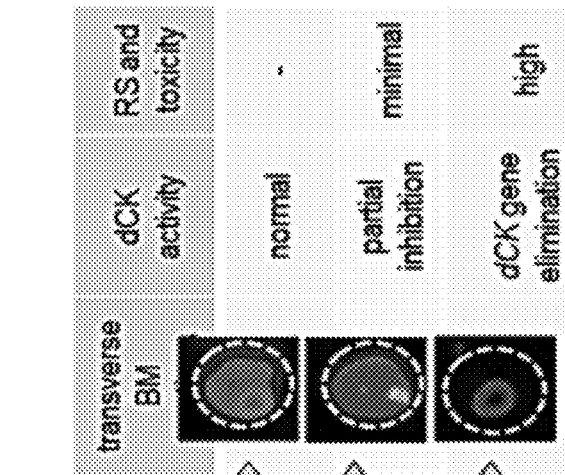
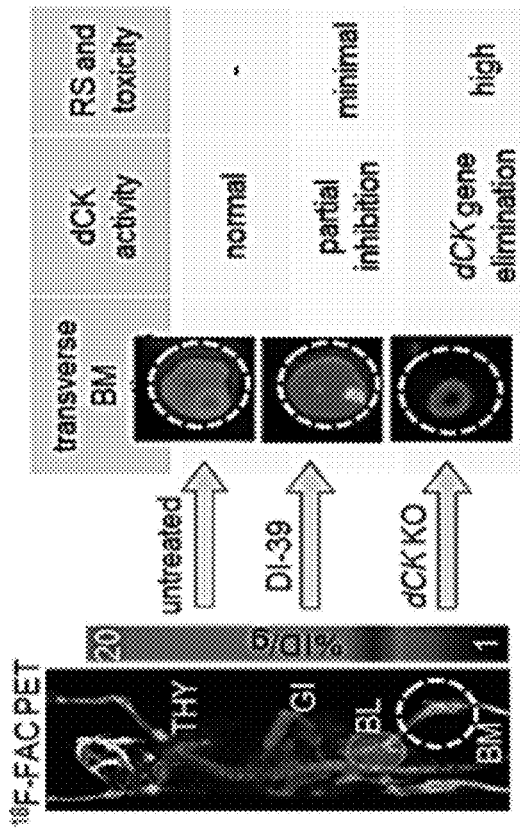
FIG. 24D
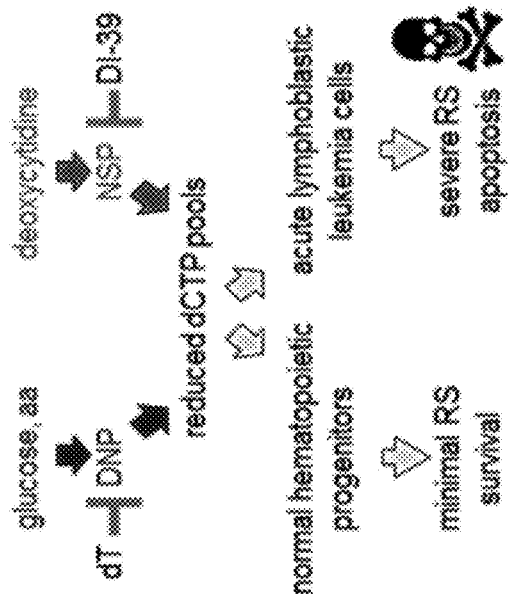
FIG. 24C

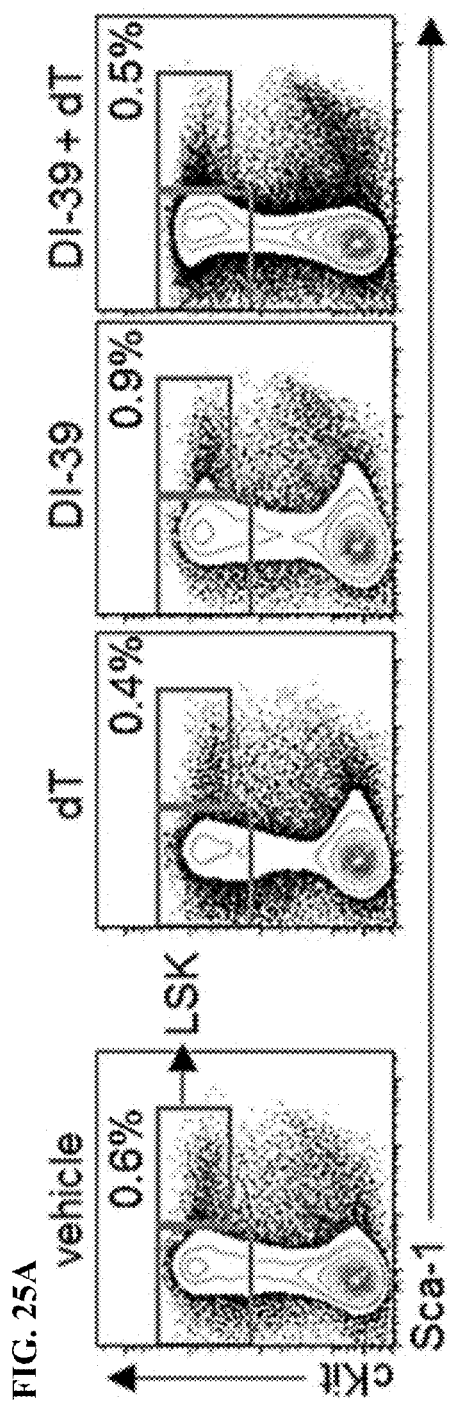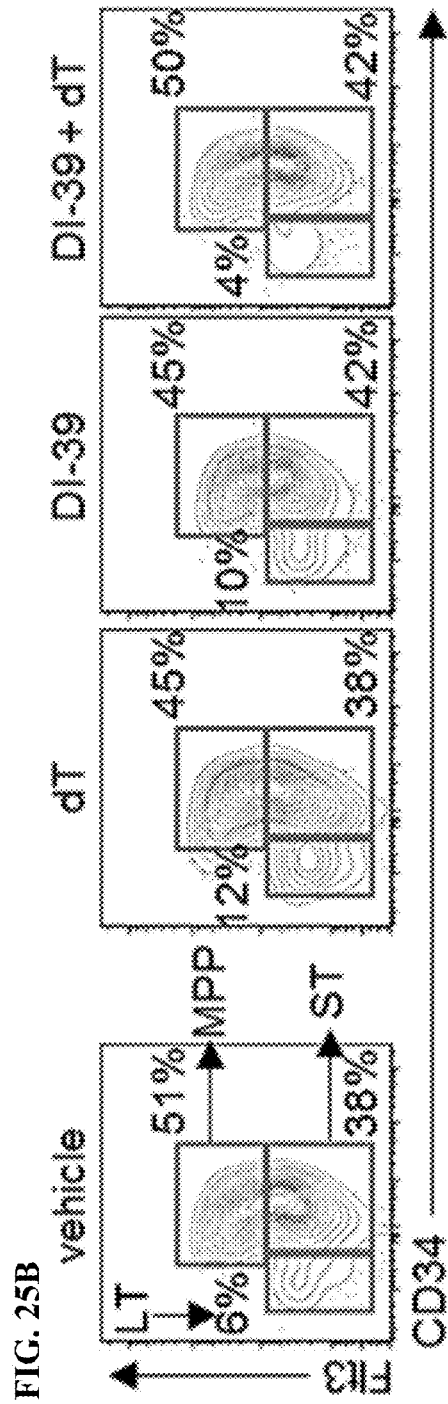
FIG. 25A
FIG. 25B

FIG. 28A
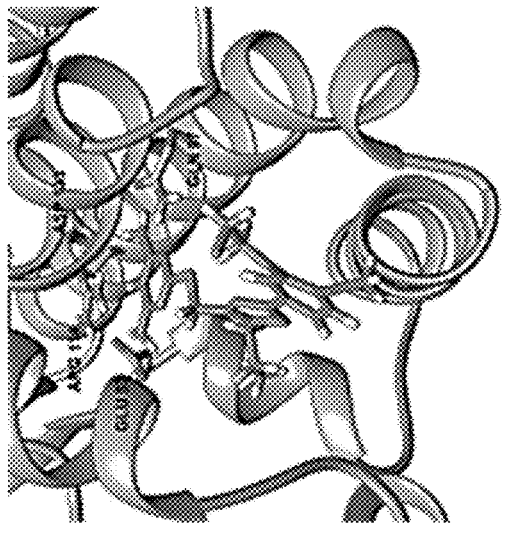
FIG. 28B
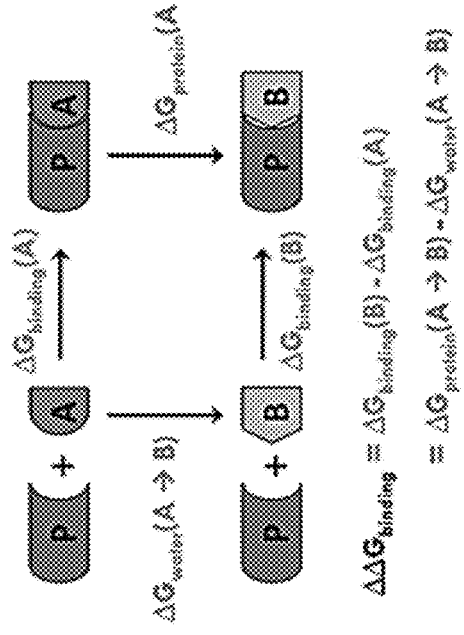
FIG. 28C
| | $\Delta G_{protein}$ | $\Delta G_{water}$ | $\Delta\Delta G_{binding}$ |
|---|---|---|---|
| 15b to 15c | 1.964 ± 0.050 | 2.802 ± 0.046 | -0.838 ± 0.068 |
| 15c to 15b | -1.251 ± 0.029 | -2.832 ± 0.046 | 1.581 ± 0.054 |
| Average | | | 1.210 in favor of 15c |

FIG. 29A  FIG. 29B
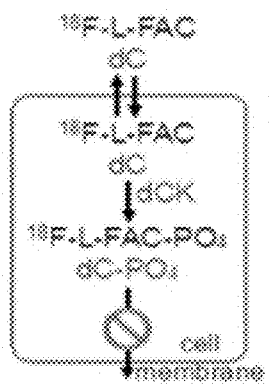
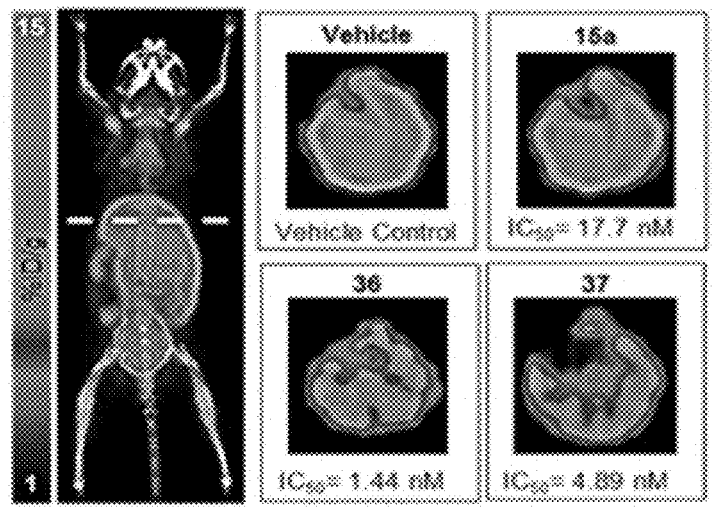
FIG. 29C
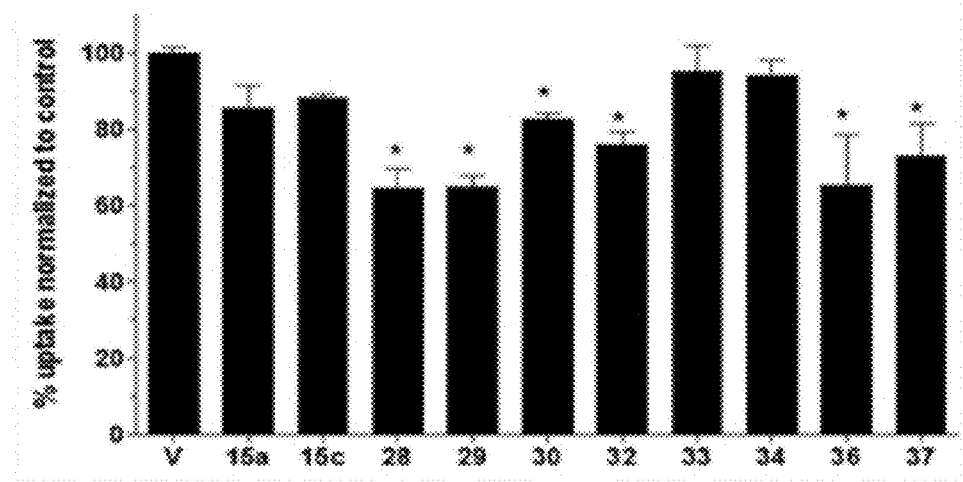
FIG. 29D
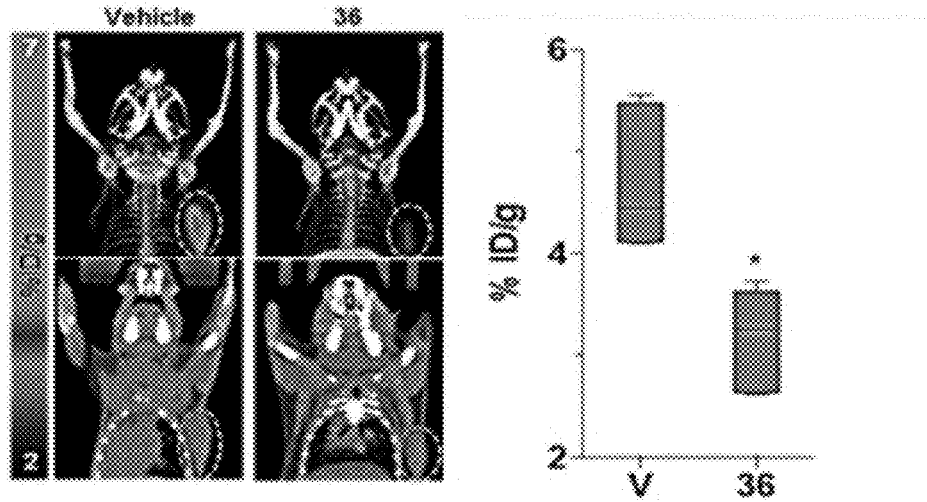

DEOXYCYTIDINE KINASE INHIBITORS

CROSS-REFERENCES TO RELATED APPLICATIONS

This application is a continuation of U.S. application Ser. No. 14/992,396, filed Jan. 11, 2016, which is a continuation of International Appl. No. PCT/US2014/050931, filed Aug. 13, 2014, which claims priority to U.S. Provisional Application No. 61/865,468, filed Aug. 13, 2013, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant numbers CA086306, CA151819 and EB013685 awarded by the National Institutes of Health. The Government has certain rights in the invention.

BACKGROUND OF THE INVENTION

Deoxycytidine kinase (dCK) is a deoxyribonucleoside kinase capable of phosphorylating deoxycytidine, deoxyadenosine, and deoxyguanosine to their monophosphate forms using either ATP or UTP as phosphoryl donors.[1] Phosphorylation by dCK is the rate-limiting step in the biochemical pathway responsible for converting salvaged deoxycytidine into dCTP and, in certain cell types into dTTP, making them substrates for DNA polymerases. Apart from the physiological role of generating dNTPs, dCK plays a crucial role in activating multiple nucleoside analog prodrugs ('nucs') that are widely used in anticancer.[2] Accordingly, identifying therapeutics targeting dCK has significant value. Provided herein are solutions to these and other problems in the art.

BRIEF SUMMARY OF THE INVENTION

Provided herein are compounds having the formula:

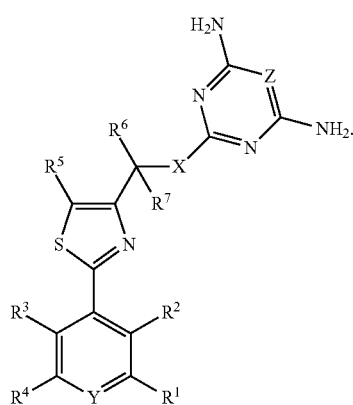

(I)

In the compound of formula (I), Y is $C(R^8)$ or N. Z is $C(R^9)$ or N. X is $CH_2$, O, $N(R^{10})$, S, S(O) or $S(O)_2$. $R^1$ is hydrogen, halogen, $-N_3$, $-CF_3$, $-CCl_3$, $-CBr_3$, $-CI_3$, $-CN$, $-COR^{1A}$, $-OR^{1A}$, $-NR^{1A}R^{1B}$, $-C(O)OR^{1A}$, $-C(O)NR^{1A}R^{1B}$, $-NO_2$, $-SR^{1A}$, $-S(O)_{n1}R^{1A}$, $-S(O)_{n1}OR^{1A}$, $-S(O)_{n1}NR^{1A}R^{1B}$, $-NHNR^{1A}R^{1B}$, $-ONR^{1A}R^{1B}$, $-NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-CI_3$, $-CN$, $-COR^{2A}$, $-OR^{2A}$, $-NR^{2A}R^{2B}$, $-C(O)OR^{2A}$, $-C(O)NR^{2A}R^{2B}$, $-NO_2$, $-SR^{2A}$, $-S(O)_{n2}R^{2A}$, $-S(O)_{n2}OR^{2A}$, $-S(O)_{n2}NR^{2A}R^{2B}$, $-NHNR^{2A}R^{2B}$, $-ONR^{2A}R^{2B}$, $-NHC(O)NHNR_{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-N_3$, $-CF_3$, $-CCl_3$, $-CBr_3$, $-CI_3$, $-CN$, $-COR^{3A}$, $-OR^{3A}$, $-NR^{3A}R^{3B}$, $-C(O)OR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$, $-NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, $-N_3$, $-CF_3$, $-CCl_3$, $-CBr_3$, $-CI_3$, $-CN$, $-COR^{4A}$, $-OR^{4A}$, $-NR^{4A}R^{4B}$, $-C(O)OR^{4A}$, $-C(O)NR^{4A}R^{4B}$, $-NO_2$, $-SR^{4A}$, $-S(O)_{n4}R^{4A}$, $-S(O)_{n4}OR^{4A}$, $-S(O)_{n4}NR^{4A}$, $-NHNR^{4A}R^{4B}$, $-ONR^{4A}R^{4B}$, $-NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently hydrogen, halogen, $-N_3$, $-CF_3$, $-CCl_3$, $-CBr_3$, $-CI_3$, $-CN$, $-COR^{5A}$, $-OR^{5A}$, $-NR^{5A}R^{5B}$, $-C(O)OR^{5A}$, $-C(O)NR^{5A}R^{5B}$, $-NO_2$, $-SR^{5A}$, $-S(O)_{n5}R^{5A}$, $-S(O)_{n5}OR^{5A}$, $-S(O)_{n5}NR^{5A}R^{5B}$, $-NHNR^{5A}R^{5B}$, $-ONR^{5A}R^{5B}$, $-NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^5$ and $R^6$ are optionally combined to form a substituted or unsubstituted cycloalkyl; $R^6$ is unsubstituted $C_1$-$C_6$ alkyl or halogen (e.g. F). $R^7$ is H, D, F or $-CH_3$. $R^8$ is hydrogen, halogen, $-N_3$, $-CF_3$, $-CCl_3$, $-CBr_3$, $-CI_3$, $-CN$, $-COR^{8A}$, $-OR^{8A}$, $-NR^{8A}R^{8B}$, $-C(O)OR^{8A}$, $-C(O)NR^{8A}R^{8B}$, $-NO_2$, $-SR^{8A}$, $-S(O)_{n8}R^{8A}$, $-S(O)_{n8}OR^{8A}$, $-S(O)_{n8}NR^{8A}R_{8B}$, $-NHNR^{8A}R^{8B}$, $-ONR^{8A}R^{8B}$, $-NHC(O)NHNR^{8A}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-N_3$, $-CF_3$, $-CCl_3$, $-CBr_3$, $-CI_3$, $-CN$, $-COR^{9A}$, $-OR^{9A}$, $-NR^{9A}R^{9B}$, $-C(O)OR^{9A}$, $-C(O)NR^{9A}R^{9B}$, $-NO_2$, $-SR^{9A}$, $-S(O)_{n9}R^{9A}$, $-S(O)_{n9}OR^{9A}$, $-S(O)_{n9}NR^{9A}R^{9B}$, $-NHNR^{9A}R^{8B}$, $-ONR^{9A}R^{9B}$, $-NHC(O)NHNR^{9A}R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is H, $-CH_3$, $-C_2H_5$, $-C_3H_7$, $-CH_2C_6H_5$. $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{8A}$, $R^{8B}$, $R^{9A}$, and $R^{9B}$ are independently hydrogen, oxo, halogen, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n5, n8, and n9 are independently 1, 2, or 3.

Also provided herein are pharmaceutical compositions. In one aspect is a pharmaceutical composition that includes a compound described herein and a pharmaceutically acceptable excipient.

Further provided herein are methods of inhibiting a deoxycytidine kinase by contacting a deoxycytidine kinase with an effective amount of the compound described herein, thereby inhibiting the deoxycytidine kinase.

Further provided herein are methods of treating a disease in a subject in need thereof by administering an effective amount of a compound as described herein. In one aspect is a method of treating cancer in a subject in need thereof, by administering to the subject an effective amount of a compound described herein.

BRIEF DESCRIPTION OF THE DRAWINGS

(FIG. 1A) Schematic representation of lead compounds Ia and Ib. These compounds are composed of four parts: Part A indicates the pyrimidine ring; part B is the linker connecting to a 5-substituted-thiazole ring (part C), which is followed by a phenyl ring (part D). Compounds Ia and Ib differ at the substituent present at the phenyl meta position ($R_m$). (FIG. 1B) In vitro ($IC_{50}^{app}$ and $K_i^{app}$) and cell ($IC_{50}$) properties for Ia and Ib.

FIGS. 2A-2C. Modifications to the pyrimidine ring. (FIG. 2A) Schematic representation of compound 1 that has a single exocyclic amino group, and of compound 2 that has a ring nitrogen atom between the two exocyclic amino groups. (FIG. 2B) In vitro ($IC_{50}^{app}$ and $K_i^{app}$) and cell ($IC_{50}$) properties for 1 and 2. (FIG. 2C) Overlay of the dCK-2 and dCK-Ia structures with a focus on the pyrimidine ring. Note the ~0.4 Å shifted position of 2 relative to Ia that is due to the presence of a water molecule (sphere). Binding of this water molecule is made possible by the ring N-atom in compound 2.

FIG. 3A-3C. Modifications to the phenyl ring meta position. (FIG. 3A) Schematic representation of compounds 3 and 4 that differ by the nature of the meta position substituent. (FIG. 3B) In vitro ($IC_{50}^{app}$ and $K_i^{app}$) and cell ($IC_{50}$) properties for 3 and 4. (FIG. 3C) Overlay of the dCK-3 and dCK-4 structures with a focus on the phenyl ring meta position. The tighter binding of 4 relative to 3 can be rationalized by the interaction of the longer meta substituent with S144/S146 of dCK.

FIGS. 4A-4C. Modifications to the phenyl ring para position. (FIG. 4A) Schematic representation of compounds 5 and 6 that differ by the nature of the para position substituent. (FIG. 4B) In vitro ($IC_{50}^{app}$ and $K_i^{app}$) and cell ($IC_{50}$) properties for 5 and 6. (FIG. 4C) Overlay of the dCK-5 (teal) and dCK-6 (beige) structures with a focus on the phenyl ring para position. The inhibitors bind very similarly; the meta position substituents make a direct interaction with the enzyme, but the para substituent does not. The very similar $IC_{50}^{app}$ and $K_i^{app}$ values of 5 and 6 are explained by the lack of direct interactions to the enzyme via the para position. In contrast, the presence of a para position substituent lowers the cell-based determined $IC_{50}$ value.

FIGS. 5A-5E. Modifications to the linker. (FIG. 5A) Schematic representation of compounds 7 and 8. Both compounds were synthesized as the racemic mixture (R/S)—the addition of a methyl group (arrow) to the methylene linker group makes these compounds chiral. Whereas 7 has a propyl group at the thiazole ring 5-position ($R_t$), 8 has a methyl group. (FIG. 5B) In vitro ($IC_{50}^{app}$ and $K_i^{app}$) and cell ($IC_{50}$) properties for 7 and 8. (FIG. 5C) The propyl group at the thiazole ring makes 7 bind as a single molecule to binding site Position-1 of dCK (see text for details). Notably, despite forming the enzyme-inhibitor with racemic 7, in the crystal structure we observe only the R-isomer (compound 7, Fo-Fc omit map contoured at 2 sigma). A theoretical model of the S-isomer demonstrates that only the R-isomer fits the electron density. (FIG. 5D) The methyl group at the thiazole ring permits two molecules of 8 to bind to dCK; one to Position-1 and one to Position-2. In Position-1 we observe only the R-isomer (8R-P1; Fo-Fc omit map contoured at 2 sigma). A theoretical model of the S-isomer at Position-1 clearly demonstrates that only the R-isomer fits the electron density (arrow). (FIG. 5E) In Position-2 we observe only the S-isomer (8S-P2; Fo-Fc omit map contoured at 1.5 sigma). A theoretical model of the R-isomer at Position-2 clearly demonstrates that only the S-isomer fits the electron density (arrow).

FIGS. 6A-6C. The R-isomer is the relevant isomer regarding dCK inhibition. (FIG. 6A) Schematic representation of compounds 9S, 9R and 10R (R or S designate the chirality of the linker methylene carbon; arrow point at the added methyl group). (FIG. 6B) In vitro ($IC_{50}^{app}$ and $K_i^{app}$) and cell ($IC_{50}$) properties for 9S, 9R, and 10R. The R-isomer of both 9 and 10 is responsible for the observed inhibition of the enzyme. (FIG. 6C) dCK was crystallized in the presence of enantiomerically pure 10R and the enzyme-inhibitor complex structure was solved. Fo-Fc omit map (1.6 sigma) for the Position-1 binding site clearly shows the presence of 10R. Despite the thiazole methyl group in 10R (which is compatible with molecules also binding to Position-2), we do not observe a second 10R molecule at Position-2. This is consistent with the results with compound 8 (FIGS. 5A-5E) that showed that only the S-isomer binds to Position-2.

FIGS. 7A-7H. Chiral selectivity is due to conformational selection by the enzyme's binding site. (FIG. 7A) The observed inhibitor 8R binding at Position-1 (8R-P1) adopts a conformation that is dictated by the Position-1 binding site. In this conformation the distance between the chiral linker methyl group and the thiazole ring methyl group is 4.2 Å. (FIG. 7B) The theoretical model of 8S binding with the same conformation as 8R in Position-1 (8S-P1) shows that the homologous distance is reduced to 2.5 Å. (FIG. 7C) The observed inhibitor 8S binding at Position-2 (8S-P2) adopts a conformation dictated by the Position-2 binding site. In this conformation the distance between the chiral linker methyl group and the thiazole ring methyl group is 4.4 Å. (FIG. 7D) The theoretical model of 8R binding with the same conformation as 8S in Position-2 (8R-P2) shows that the homologous distance is reduced to 2.6 Å. (FIG. 7E) For 8R-P1, the observed torsion angle between the thiazole ring and the linker is −59°. Scanning possible torsion angles shows that this value represents a low energy conformation of 8R. (FIG. 7F) For 8S-P1, the observed torsion angle is 189°. This value corresponds to a high-energy conformation. (FIG. 7G) For 8S-P2, the observed torsion angle is −326°. Scanning possible torsion angles shows that this value is at a low energy conformation of 8S. (FIG. 7H) For 8R-P2, the observed torsion angle is 147°. This value corresponds to a high-energy conformation.

(FIG. 8A) Quantification of PET probe, $^{18}$F-L-FAC, uptake in the liver of C57Bl/6 female mice treated with compounds 10 (25 mg/kg) via intraperitoneal injection. Dose formulation: 50% PEG/Tris, pH 7.4. Data are mean values±SEM for at least n=5 mice/time point. (FIG. 8B) Plasma pharmacokinetic profile of compound 10. C57Bl/6 female mice were dosed via intraperitoneal injection with 50 mg/Kg compound 10 formulated in 50% PEG/Tris, pH 7.4. Data are mean values±SEM for n=4 mice/time point.

(FIG. 9A) Ribbon diagram of a dCK monomer with the observed molecule of Ia bound (spheres) at the active site. The nucleotide UDP was also present in the complex. (FIG. 9B) The interactions between Ia and dCK. dCK residues contributing to the interaction with Ia (sticks) are represented as sticks. Polar interactions are indicated as broken black lines.

FIGS. 11A-11B. Fo-Fc map contoured at 2.5 sigma around compounds 3 and 4 from protomer A. (FIG. 11A) Compound 3 was removed from the model that then underwent several rounds of refinement to eliminate model bias. (FIG. 11B) Same for compound 4.

(FIG. 12A) Compound 5 was removed from the model that then underwent several rounds of refinement to eliminate model bias. (FIG. 12B) Same for compound 6.

(FIG. 13A) Compound 7 was removed from the model that then underwent several rounds of refinement to eliminate model bias. (FIG. 13B) Same for compound 8. This inhibitor binds two molecules at the active site of dCK. Due to the presence of a chiral carbon within the linker and the use of a racemic mixture, we observe the R enantiomer binding at Position-1 (8R-P1) and the S enantiomer binding at Position-2 (8S-P2).

(FIG. 14A) 8R/8S, as seen in structure. (FIG. 14B) 8S overlaid on 8R based on pyrimidine ring. Note the different relative orientations of the thiazole and phenyl rings between 8R and 8S.

(FIG. 16A) Allosteric control of DNP dCTP production by dT via dTTP. RNR: ribonucleotide reductase. (FIG. 16B) Effects of dT treatment (24 hr) on dCTP and dTTP pools. Values represent mean±SEM. (FIG. 16C) CEM cell cycle analysis following treatment with vehicle or dT (50 µM)-/+2.5 µM dC for 24 hr. (FIG. 16D) CEM cell cycle analysis following treatment with hydroxyurea (50 µM), 5-fluorouracil (15 µM) or cisplatin (1.6 µM) for 24 hr-/+2.5 µM dC. (FIG. 16E) Representative immunoblots of dCK and actin expression and (FIG. 16F) dCK kinase assay in CEM dCK$^{wt}$ (scrambled shRNA) cells and dCK$^{low}$ (shRNA against dCK) cells. Values are mean±SEM, * P<0.001 (FIG. 16G) dCTP levels in CEM dCK$^{wt}$ and dCK$^{low}$ cells treated for 24 hr with vehicle or dT (50 µM)-/+ dC (2.5 µM). Values are mean±SEM, * P<0.001 (FIG. 16H) Cell cycle analysis of CEM dCK$^{low}$ cells treated with vehicle or dT (50 µM)-/+2.5 µM dC for 24 hr. (FIG. 16I) Representative immunoblots detecting Chk1, pChk1 (Ser345), Chk2, pChk2 (Thr68), dCK and actin in CEM dCK$^{wt}$ and dCK$^{low}$ cells treated with vehicle or dT (50 µM) in the presence of 2.5 µM dC for 24, 48 and 72 hr. (FIG. 16J) pH2A.X (Ser139) and DNA content (DAPI) in CEM dCK$^{wt}$ and dCK$^{low}$ cells treated with vehicle or dT (50 µM) in the presence of 2.5 µM dC for 24 hr. (FIG. 16K) Representative images and quantification of the COMET assay conducted on CEM dCK$^{wt}$ and dCK$^{low}$ cells 48 hr after treatment with vehicle or dT (50 µM) in the presence of 2.5 µM dC. Values represent the mean Olive Tail Moment±SEM from 100 cells per image×4 images/group; n=2 independent experiments. * P<0.001. Magnification: 4×. (FIG. 16L) Annexin V staining of CEM dCK$^{wt}$ and dCK$^{low}$ cells following treatment with vehicle, dC (2.5 µM), dT (50 µM) or dC+dT for 72 hr. All values are mean±SEM from at least three replicates/data point. * P<0.001. All data in FIGS. 16A-16L are representative of n=3 independent experiments, unless indicated.

FIGS. 17A-17D. Treatment with dT triggers a metabolic switch to NSP-mediated dCTP biosynthesis in T-ALL cells and upregulates the NSP (FIG. 17A) Schematic of the [U-$^{13}$C]-glucose and [U-$^{13}$C/$^{15}$N]-deoxycytidine (dC) stable isotope labeling approach used to determine the source (DNP or NSP) of the free dCTP pool and of the dCTP incorporated into the DNA of CEM cells treated with various dT concentrations. (FIG. 17B) dCTP derived from [U-$^{13}$C]-glucose (DNP) and [U-$^{13}$C/$^{15}$N]-dC (NSP) in the free dCTP pool and incorporated into the DNA of CEM cells after 12 hr of incubation with stable isotope-labeled DNP and NSP precursors, in the presence or absence of dT. Values are the average of absolute peak area/$10^3$ cell±SEM, * P<0.05,  P<0.01, * P<0.001, compared with 0 µM dT control. Data are representative of n=2 independent experiments. (FIG. 17C) Quantification of dCK kinase activity in CEM cells at baseline and after 8 hr of treatment with 50 µM dT. Data are representative of n=2 independent experiments. Values are mean±SEM, * P<0.001. (FIG. 17D). Quantification of the uptake of $^3$H-labeled deoxycytidine (dC) by CEM cells at baseline and after 4 hr of treatment with 50 µM dT. Data are representative of n=2 independent experiments. Values represent mean±SEM, * P<0.001.

(FIG. 18A) Left axis: Plasma dT levels in NSG mice treated with dT (2 g/kg; single-dose). Values are mean±SEM from n=3 mice/time point; n=2 independent experiments. Right axis: dTTP concentrations from CEM dCK$^{wt}$ and dCK$^{low}$ tumors at various time points following single-dose dT (2 g/kg) treatment; values are mean±SEM, n=4 mice/time point; n=2 independent experiments. (FIG. 18B) Representative immunoblot (n=3 independent experiments) showing pChk1 (Ser345) levels at various time points in bilateral s.c. CEM dCK$^{wt}$ and dCK$^{low}$ tumors implanted in NSG mice treated with dT (2 g/kg; single-dose). (FIG. 18C) dCTP concentrations from CEM dCK$^{wt}$ and dCK$^{low}$ tumors at various time points following single-dose dT (2 g/kg) treatment; values are mean±SEM, n=5 mice/time point; n=2 independent experiments. * P<0.001. (FIG. 18D) Schematic of experimental design for quantifying the incorporation of [U-$^{13}$C/$^{15}$N]-dC into the DNA of dCK$^{wt}$ and dCK$^{low}$ CEM tumors 4 hr after single-dose treatment with 2 g/kg dT or vehicle. (FIG. 18E) Quantification of the LC/MS/MS-MRM data for labeled dCTP incorporation into the DNA. Data are mean±SEM of n=6 mice/group; n=2 independent experiments.  P<0.01. (FIG. 18F) Schematic of the in vivo PET assay of dCK activity. (FIG. 18G) $^{18}$F-L-FAC uptake in s.c. CEM dCK$^{wt}$ and dCK$^{low}$ tumor xenografts 4 hr following vehicle or dT injection. Values represent the mean % decrease in $^{18}$F-FAC signal relative to dCK$^{wt}$ vehicle±SEM, n=4 mice/group; n=2 independent experiments.  P<0.01, * P<0.001.

(FIG. 19C) Tumor weights (mg) from (A). Values represent the mean±SEM; n=2 independent experiments. *** P<0.001.

FIGS. 20A-20K. Development of DI-39, a small molecule dCK inhibitor that synergizes with inhibition of de novo dCTP biosynthesis in leukemic cells (FIG. 20A) Schematic illustrating the development of DI-39, beginning with high-throughput screen (HTS) of a 90,000 compound library, which provided the initial hit DI-0120. Further structural activity relationship (SAR) yielded 80 novel compounds including DI-39. (FIG. 20B) Chemical structure of DI-39. (FIG. 20C) LC/MS/MS-MRM measurements of DI-39 in CEM cells exposed to 1 µM drug for indicated periods of time. Cells were washed three times after 60 min (indicated by vertical line) and cellular drug retention was measured again 60 min later. Values represent mean±SEM (FIG. 20D) IC$_{50}$ value of DI-39 determined by % inhibition of $^3$H-dC uptake by CEM cells. Values represent mean±SEM (FIG. 20E) 2.1 Å crystal structure of dCK with bound DI-39 and uridine diphosphate (UDP). (FIG. 20F) Intracellular dCTP concentrations in cultured CEM dCK$^{wt}$ cells treated with vehicle, dT (50 µM), DI-39 (1 µM) or DI-39+ dT for 24 hr. Values represent the mean±SEM; n=2 independent experiments. * P<0.001. (FIG. 20G) Representative immunoblots detecting Chk1, pCh1 (Ser345), and actin in CEM cells treated with vehicle, dT (1 mM), DI-39 (100 nM) or DI-39+ dT in the presence of 2.5 µM dC for 24 hr. (FIG. 20H) Annexin V staining of CEM cells treated for 72 hr with indicated concentrations of DI-39 and dT in the presence of 2.5 µM dC. Values are mean±SEM; n=2 independent experiments, * P<0.001 compared with 50 µM dT. (FIG. 20I) Annexin V staining of L1210-10 dCK null cells treated for 72 hr with indicated concentrations of DI-39. Values represent the mean % cells staining positive for Annexin V±SEM; n=2 independent experiments. (FIG. 20J). Representative immunoblots of Jurkat, MOLT-4, RSR4;11, NALM-6 and TF-1 leukemia cells treated with vehicle, dT (1 mM), DI-39 (100 nM) or DI-39+dT in the presence of 2.5 µM dC for 24 hr (NALM-6) or 72 hr (Jurkat, MOLT-4, RSR4;11, TF-1). (FIG. 20K) Annexin V staining of the same panel of leukemia cell lines as in (FIG. 20J) treated for 72 hr with vehicle, dT (1 mM), DI-39 (100 nM), or DI-39+dT. Cultures were supplemented with 2.5 µM dC. Values represent mean % cells staining positive for Annexin V±SEM; n=3 independent experiments. * P<0.05,  P<0.01, * P<0.001.

(FIG. 21B) LC/MS/MS-MRM quantification of DI-39 concentrations in plasma and CEM tumors at various time points after treatment. See Methods for details. Values represent the mean±SD, n=4/group. (FIG. 21C) Schematic illustration of the $^{18}$F-FAC PET/CT study to determine in vivo dCK inhibition by DI-39 in CEM s.c. xenografts. (FIG. 21D) Time course of in vivo $^{18}$F-FAC PET/CT scans to determine dCK inhibition by DI-39 (single intraperitoneal injection, 50 mg/kg). Values represent the mean % decrease in $^{18}$F-FAC signal±SD, n=4 mice/group; n=2 independent experiments. (FIG. 21E) % incorporation of [U-$^{13}$C/$^{15}$N]-dC into the DNA of CEM xenografts 5.5 hr after single-dose treatment with vehicle, DI-39 (50 mg/kg), dT (2 g/kg) or DI-39+dT; mice were pulsed with the stable isotope-labeled dC for 30 min before sacrifice. Values represent mean±SEM, n=4/group; n=2 independent experiments.  P<0.01, * P<0.001. (FIG. 21F) Representative immunoblots of pChk1 (Ser345), Chk1, and actin in tumor tissues collected from mice 6 hr following treatment with DI-39 (50 mg/kg), dT (2 g/kg) or both agents; n=3 independent experiments.

(FIG. 22B) Tumor weights from (FIG. 22A). Values represent mean±SEM; n=2 independent experiments, n=6 mice/group. * P<0.05,  P<0.01, * P<0.001. (FIG. 22C) Representative images and quantification of TUNEL staining of tumor samples from (FIG. 22A). Magnification: 20×. Values represent mean±SEM. n=6 mice/group. * P<0.001. (FIG. 22D) Representative FACS plots and quantification of eGFP+ CEM leukemia cells in the bone marrow of NSG mice treated with vehicle, dT (2 g/kg), DI-39 (50 mg/kg) or DI-39+dT. Mice (n=6/group) were treated every 12 hr beginning at day 3 post inoculation with 1.0×10$^6$ CEM cells. Values represent mean±SEM; n=2 independent experiments.  P<0.01, *** P<0.001.

(FIG. 23B) Representative bioluminescent images (BLI) of mice (n=6/group) treated with vehicle, dT (2 g/kg), DI-39 (50 mg/kg) or DI-39+dT at day 14 post intravenous injection of 2.0×10$^4$ pre-B leukemia cells/mouse. (FIG. 23C) Quantification of BLI from in BM and spleen. * P<0.05,  P<0.01. (FIG. 23D) Representative FACS analyses and quantification of CD19+ leukemic cells in the BM of treated mice.  P<0.01, * P<0.001. (FIG. 23E) Quantification of Lineage$^-$ Sca-1$^+$ c-Kit$^+$ (LSK) populations from treated mice.  P<0.01.

(FIG. 23F) LSK cells from BM of treated mice were analyzed for expression of CD34 and Flt3 to identify and quantify long-term (LT, CD34⁻, Flt3⁻), short-term (ST, CD34⁺, Flt3⁻), and multipotent progenitor (MPP, CD34⁺, Flt3⁺) stem cells. (FIG. 23G) Body weights as well as RBC, hemoglobin, platelet, and neutrophil measurements (FIG. 23H) of NSG mice (n=6/group) treated with vehicle, dT (2 g/kg), DI-39 (50 mg/kg), or DI-39+ dT every 12 hr for 7 days. Data represent mean±SEM. All data are representative of at least two independent experiments.

FIGS. 24A-24D. Assessment of potential toxicity of the DI-39/dT combination therapy and model (FIG. 24A) Representative FACS staining of pH2A.X and data quantification in EryA (CD71⁺/high forward scatter) erythroblasts to estimate endogenous (for dCK$^{-/-}$ mice, n=4 mice/group) or potential pharmacologically-induced (DI-39+dT) genotoxic stress. NSG mice (n=5 mice/group) were treated with vehicle or combination of DI-39 (50 mg/kg) and dT (2 g/kg) every 12 hr for 8 days. Values are mean±SEM. ** $P<0.01$. (FIG. 24B) Representative FACS plots and quantification of micronucleated erythrocytes indicative of endogenous (for dCK$^{-/-}$ mice) or potential pharmacologically-induced (DI-39+dT) genotoxic stress. Values represent mean±SEM from n=2 independent experiments. * $P<0.05$, *** $P<0.001$. (FIG. 24C, FIG. 24D) Proposed rationale for explaining the selectivity of the combination therapy for leukemia cells relative to normal hematopoietic progenitors (see text for details).

FIGS. 25A-25B. FACS gating strategy to identify hematopoietic progenitor populations quantified in FIGS. 23E-23F, depicted in FIGS. 25A-25B, respectively.

(FIG. 27A) Ribbon diagram of a dCK monomer with the two observed molecules of 15a bound (spheres) at the active site. The nucleotide UDP was also present in the complex. (FIG. 27B) The interactions between 15a and dCK. Polar interactions are indicated as broken lines. The two phosphate groups of UDP (top right) demonstrate the relative orientation of 15a-I and 15a-II to the nucleotide. (FIG. 27C) The methyl group of the 15a-I and 15a-II thiazole ring (arrows) stack against each other, occupying a hydrophobic pocket.

FIGS. 28A-28C. (FIG. 28A) The complete thermodynamic cycle relating the binding energies to the perturbation of molecule A into molecule B. $\Delta G_{protein}(A \rightarrow B)$ denotes the change in free energy upon perturbation of A into B in the solvated inhibitor-protein complex, while $\Delta G_{water}(A \rightarrow B)$ denotes the free energy change when the perturbation takes place in water alone. The difference in free energies of binding, $\Delta \Delta G_{binding}$, is equal to the change in free energy when molecule A binds with the protein [$\Delta G_{binding}(A)$] subtracted from the change in free energy when molecule B binds [$\Delta G_{binding}(B)$]. Because the sum of all components in a complete thermodynamic cycle must equal zero, $\Delta \Delta G_{binding}$ is therefore also equivalent to $\Delta G_{protein}(A \rightarrow B) - \Delta G_{water}(A \rightarrow B)$. (FIG. 28B) Computational model of compound 15c in complex with dCK. Binding pocket residues Glu 53, Gln 97, Arg 114, and Asp 133 are shown explicitly, while the remainder of the protein is illustrated as a ribbon structure. (FIG. 28C) Free energy changes (kcal/mol) associated with the perturbation of the alkyl chain at the 5-position of the thiazole. $\Delta G_{protein}$ is the change in free energy for the solvated inhibitor-protein complex. $\Delta G_{water}$ is the free energy change for the inhibitor in water alone. The change in free energy upon binding is denoted as $\Delta \Delta G_{binding}$.

FIGS. 29A-29D. In vivo evaluation of dCK inhibitors via PET analysis. (FIG. 29A) Schematic of the mechanism by which $^{18}$F-L-FAC accumulates in dCK expressing cells. (FIG. 29B) Representative transverse images of $^{18}$F-L-FAC PET/CT liver scans of C57Bl/6 mice treated with compounds 15a, 36, and 37. (FIG. 29C) Quantification of $^{18}$F-L-FAC uptake in the liver for a sample of inhibitors with low nanomolar in vitro potency. Data are mean values±SEM for at least n=3 mice/group. *, $P<0.03$. (FIG. 29D) Representative images and quantification of $^{18}$F-L-FAC PET/CT scans of CCRF-CEM tumor bearing NSG mice that were treated with vehicle, or compound 36. Data are displayed as box and whisker plots for at least n=4 mice/group. *, $P<0.0012$.

(FIG. 31A) Ribbon diagram of a dCK monomer with the single observed molecule of 36 bound (spheres) at the active site. The nucleotide UDP (spheres) was also present in the complex. (FIG. 31B) Detail of the interactions between 36 and dCK. dCK residues involved in polar and hydrophobic interactions with 36. Polar interactions are indicated as broken black lines.

DETAILED DESCRIPTION OF THE INVENTION

Figures 1A, 1B:
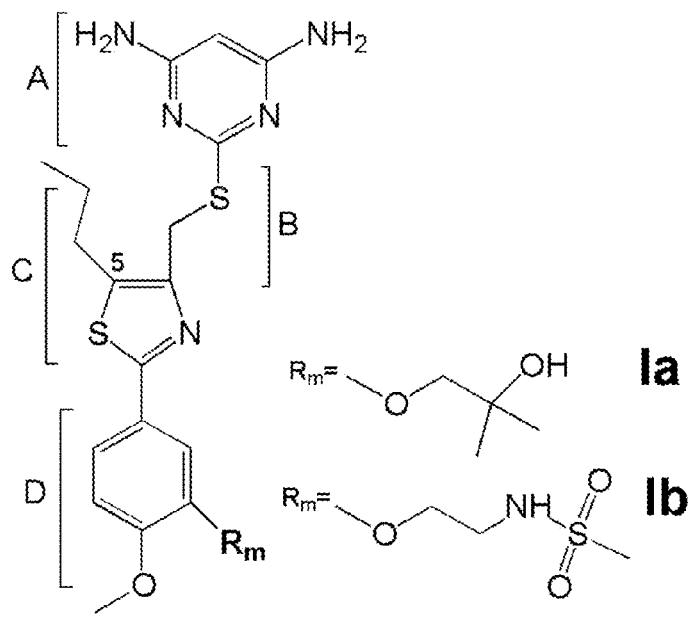
FIGS. 1A-1B. dCK inhibitors lead compounds.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene)

group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, and heteroaryl, substituted with at least one substituent selected from:
(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds described herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}F$, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), fluoride ($^{18}F$), iodine-125 ($^{125}I$), or carbon-14 ($^{14}C$). All isotopic variations of the compounds of the present invention, whether radioactive or not, are encompassed within the scope of the present invention.

The symbol " —⁀— " denotes the point of attachment of a chemical moiety to the remainder of a molecule or chemical formula.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Analog," or "analogue" are used in accordance with plain ordinary meaning within Chemistry and Biology and refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

The terms "Deoxycytidine kinase," "DCK," and "dCK" are here used interchangeably and according to their common, ordinary meaning and refer to proteins of the same or similar names and functional fragments and homologs thereof. The term includes any recombinant or naturally occurring form of dCK (NP000779.1 GI:4503269), or variants thereof that maintain dCK activity (e.g. within at least 30%, 40%, 50%, 60%, 70%, 80%, 90%, 95%, or 100% activity compared to dCK).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical or enzymatic changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. The protein may be deoxycytidine kinase. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13: 293-306, 1996; Chonn, *Curr. Opin. Biotechnol.* 6: 698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds described herein can be used in combination with one another, with other active drugs known to be useful in treating a disease (e.g. anti-cancer drugs) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anticancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cancer such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. A "cancer-patient" is a patient suffering from, or prone to developing cancer.

"Disease" or "condition" refer to a state of being or health status of a patient or subject capable of being treated with the compounds or methods provided herein. Disease as used herein may refer to cancer.

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. An anti-cancer agent may be an agent approved by the FDA or similar regulatory agency of a country other than the USA, for treating cancer. Examples of anti-cancer agents include, but are not limited to, MEK (e.g. MEK1, MEK2, or MEK1 and MEK2)

inhibitors (e.g. XL518, CI-1040, PD035901, selumetinib/ AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; tnacetyluridine; tnciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Iso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™) cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

I. Compositions

Provided herein are compounds having the formula:

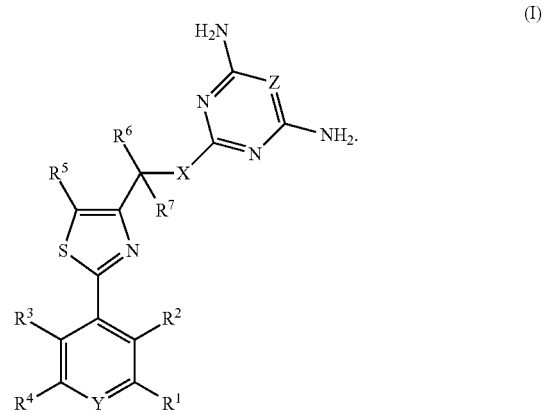

(I)

Y is C(R$^8$) or N. Z is C(R$^9$) or N. X is —CH$_2$—, —O—, —N(R$^{10}$)—, —S—, —S(O)—, or —S(O)$_2$—. R$^1$ is hydrogen, halogen, —N$_3$, —CF$_3$, —CCl$_3$, —CBr$_3$, —CI$_3$, —CN, —COR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —N$_3$, —CF$_3$, —CCl$_3$, —CBr$_3$, —CI$_3$, —CN, —COR$^{4A}$, —OR$^{4A}$R$^{4B}$, —C(O)OR$^{4A}$, —C(O)NR$^{4A}$R$^{4B}$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is independently hydrogen, halogen, —N$_3$, —CF$_3$, —CCl$_3$, —CBr$_3$, —CI$_3$, —CN, —COR$^{5A}$, —OR$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^5$ and $R^6$ are optionally combined to form a substituted or unsubstituted cycloalkyl. $R^6$ is unsubstituted $C_1$-$C_6$ alkyl. $R^7$ is H, D, F or —$CH_3$. $R^8$ is hydrogen, halogen, —$N_3$, —$CF_3$, —$CCl_3$, —$CBr_3$, —$CI_3$, —CN, —$COR^{8A}$, —$OR^{8A}$, —$NR^{8A}R^{8B}$, —$C(O)NR^{8A}R^{8B}$, —$NO_2$, —$SR^{8A}$, —$S(O)_{n8}R^{8A}$, —$S(O)_{n8}OR^{8A}$, —$S(O)_{n8}NR^{8A}R^{8B}$, —$NHNR^{8A}R^{8B}$, —$ONR^{8A}R^{8B}$, —$NHC(O)NHNR^{8A}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, —$N_3$, —$CF_3$, —$CCl_3$, —$CBr_3$, —$CI_3$, —CN, —$COR^{9A}$, —$OR^{9A}$, —$NR^{9A}R^{9B}$, —$C(O)OR^{9A}$, —$C(O)NR^{9A}R^{9B}$, —$NO_2$, —$SR^{9A}$, —$S(O)_{n9}R^{9A}$, —$S(O)_{n9}OR^{9A}$, —$S(O)_{n9}NR^{9A}R^{9B}$, —$NHNR^{9A}R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is H, —$CH_3$, —$C_2H_5$, —$C_3H_7$, —$CH_2C_6H_5$. $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{8A}$, $R^{8B}$, $R^{9A}$, and $R^{9B}$ are independently hydrogen, oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n3, n4, n5, n8, and n9 are independently 1, 2, or 3.

$R^1$ may be hydrogen, halogen, —$N_3$, —$CF_3$, —$CCl_3$, —$CBr_3$, —$CI_3$, —CN, —$COR^{1A}$, —$OR^{1A}$, $NR^{1A}R^{1B}$, —$C(O)OR^{1A}$, —$C(O)NR^{1A}R^{1B}$, —$NO_2$, —$SR^{1A}$, —$S(O)_{n1}R^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, or —$NHC(O)NHNR^{1A}R^{1B}$. $R^1$ may be hydrogen, halogen, —$OR^{1A}$. $R^1$ may be hydrogen. $R^1$ may be halogen. $R^1$ may be —$OR^{1A}$. $R^{1A}$ is as described herein.

$R^1$ may be hydrogen, halogen, —$OR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be —$OR^{1A}$, where $R^{1A}$ is as described herein. $R^1$ may be —$OR^{1A}$, where $R^{1A}$ is hydrogen, substituted or unsubstituted alkyl, or substituted or unsubstituted heteroalkyl. $R^1$ may be —$OR^{1A}$, where $R^{1A}$ is substituted or unsubstituted alkyl, or substituted or unsubstituted heteroalkyl.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or $R^{1A}$-substituted or unsubstituted heteroaryl.

$R^1$ may be substituted or unsubstituted alkyl. $R^1$ may be substituted alkyl. $R^1$ may be unsubstituted alkyl. $R^1$ may be substituted or unsubstituted $C_1$-$C_{20}$ alkyl. $R^1$ may be substituted $C_1$-$C_{20}$ alkyl. $R^1$ may be unsubstituted $C_1$-$C_{20}$ alkyl. $R^1$ may be substituted or unsubstituted $C_1$-$C_{10}$ alkyl. $R^1$ may be substituted $C_1$-$C_{10}$ alkyl. $R^1$ may be unsubstituted $C_1$-$C_{10}$ alkyl. $R^1$ may be substituted or unsubstituted $C_1$-$C_5$ alkyl. $R^1$ may be substituted $C_1$-$C_5$ alkyl. $R^1$ may be unsubstituted $C_1$-$C_5$ alkyl. $R^1$ may be methyl. $R^1$ may be ethyl. $R^1$ may be propyl.

$R^1$ may be $R^{1A}$-substituted or unsubstituted alkyl. $R^1$ may be $R^{1A}$-substituted alkyl. $R^1$ may be unsubstituted alkyl. $R^1$ may be $R^{1A}$-substituted or unsubstituted $C_1$-$C_{20}$ alkyl. $R^1$ may be $R^{1A}$-substituted $C_1$-$C_{20}$ alkyl. $R^1$ may be unsubstituted $C_1$-$C_{20}$ alkyl. $R^1$ may be $R^{1A}$-substituted or unsubstituted $C_1$-$C_{10}$ alkyl. $R^1$ may be $R^{1A}$-substituted $C_1$-$C_{10}$ alkyl. $R^1$ may be unsubstituted $C_1$-$C_{10}$ alkyl. $R^1$ may be $R^{1A}$-substituted or unsubstituted $C_1$-$C_5$ alkyl. $R^1$ may be $R^{1A}$-substituted $C_1$-$C_5$ alkyl. $R^1$ may be unsubstituted $C_1$-$C_5$ alkyl.

$R^1$ may be substituted or unsubstituted heteroalkyl. $R^1$ may be substituted heteroalkyl. $R^1$ may be unsubstituted heteroalkyl. $R^1$ may be substituted or unsubstituted 2 to 20 membered heteroalkyl. $R^1$ may be substituted 2 to 20 membered heteroalkyl. $R^1$ may be unsubstituted 2 to 20 membered heteroalkyl. $R^1$ may be substituted or unsubstituted 2 to 10 membered heteroalkyl. $R^1$ may be substituted 2 to 10 membered heteroalkyl. $R^1$ may be unsubstituted 2 to 10 membered heteroalkyl. $R^1$ may be substituted or unsubstituted 2 to 6 membered heteroalkyl. $R^1$ may be substituted 2 to 6 membered heteroalkyl. $R^1$ may be unsubstituted 2 to 6 membered heteroalkyl.

$R^1$ may be $R^{1A}$-substituted or unsubstituted heteroalkyl. $R^1$ may be $R^{1A}$-substituted heteroalkyl. $R^1$ may be unsubstituted heteroalkyl. $R^1$ may be $R^{1A}$-substituted or unsubstituted 2 to 20 membered heteroalkyl. $R^1$ may be $R^{1A}$-substituted 2 to 20 membered heteroalkyl. $R^1$ may be unsubstituted 2 to 20 membered heteroalkyl. $R^1$ may be $R^{1A}$-substituted or unsubstituted 2 to 10 membered heteroalkyl. $R^1$ may be $R^{1A}$-substituted 2 to 10 membered heteroalkyl. $R^1$ may be unsubstituted 2 to 10 membered heteroalkyl. $R^1$ may be $R^{1A}$-substituted or unsubstituted 2 to 6 membered heteroalkyl. $R^1$ may be $R^{1A}$-substituted 2 to 6 membered heteroalkyl. $R^1$ may be unsubstituted 2 to 6 membered heteroalkyl.

$R^1$ may be substituted or unsubstituted cycloalkyl. $R^1$ may be substituted cycloalkyl. $R^1$ may be unsubstituted cycloalkyl. $R^1$ may be substituted or unsubstituted 3 to 10 membered cycloalkyl. $R^1$ may be substituted 3 to 10 membered cycloalkyl. $R^1$ may be unsubstituted 3 to 10 membered cycloalkyl. $R^1$ may be substituted or unsubstituted 3 to 8 membered cycloalkyl. $R^1$ may be substituted 3 to 8 membered cycloalkyl. $R^1$ may be unsubstituted 3 to 8 membered cycloalkyl. $R^1$ may be substituted or unsubstituted 3 to 6 membered cycloalkyl. $R^1$ may be substituted 3 to 6 membered cycloalkyl. $R^1$ may be unsubstituted 3 to 6 membered cycloalkyl. $R^1$ may be substituted or unsubstituted 3 membered cycloalkyl. $R^1$ may be substituted or unsubstituted 4 membered cycloalkyl. $R^1$ may be substituted or unsubstituted 5 membered cycloalkyl. $R^1$ may be substituted or unsubstituted 6 membered cycloalkyl.

$R^1$ may be $R^{1A}$-substituted or unsubstituted cycloalkyl. $R^1$ may be $R^{1A}$-substituted cycloalkyl. $R^1$ may be unsubstituted cycloalkyl. $R^1$ may be $R^{1A}$-substituted or unsubstituted 3 to 10 membered cycloalkyl. $R^1$ may be $R^{1A}$-substituted 3 to 10 membered cycloalkyl. $R^1$ may be unsubstituted 3 to 10 membered cycloalkyl. $R^1$ may be $R^{1A}$-substituted or unsubstituted 3 to 8 membered cycloalkyl. $R^1$ may be $R^{1A}$-substituted 3 to 8 membered cycloalkyl. $R^1$ may be unsubstituted 3 to 8 membered cycloalkyl. $R^1$ may be $R^{1A}$- substituted or unsubstituted 3 to 6 membered cycloalkyl. $R^1$ may be $R^{1A}$-substituted 3 to 6 membered cycloalkyl. $R^1$ may be unsubstituted 3 to 6 membered cycloalkyl. $R^1$ may be $R^{1A}$-substituted or unsubstituted 3 membered cycloalkyl. $R^1$ may be $R^{1A}$-substituted or unsubstituted 4 membered cycloalkyl. $R^1$ may be $R^{1A}$-substituted or unsubstituted 5 membered cycloalkyl. $R^1$ may be $R^{1A}$-substituted or unsubstituted 6 membered cycloalkyl.

$R^1$ may be substituted or unsubstituted heterocycloalkyl. $R^1$ may be substituted heterocycloalkyl. $R^1$ may be unsubstituted heterocycloalkyl. $R^1$ may be substituted or unsubstituted 3 to 10 membered heterocycloalkyl. $R^1$ may be substituted 3 to 10 membered heterocycloalkyl. $R^1$ may be unsubstituted 3 to 10 membered heterocycloalkyl. $R^1$ may be substituted or unsubstituted 3 to 8 membered heterocycloalkyl. $R^1$ may be substituted 3 to 8 membered heterocycloalkyl. $R^1$ may be unsubstituted 3 to 8 membered heterocycloalkyl. $R^1$ may be substituted or unsubstituted 3 to 6 membered heterocycloalkyl. $R^1$ may be substituted 3 to 6 membered heterocycloalkyl. $R^1$ may be unsubstituted 3 to 6 membered heterocycloalkyl. $R^1$ may be substituted or unsubstituted 3 membered heterocycloalkyl. $R^1$ may be substituted or unsubstituted 4 membered heterocycloalkyl. $R^1$ may be substituted or unsubstituted 5 membered heterocycloalkyl. $R^1$ may be substituted or unsubstituted 6 membered heterocycloalkyl.

$R^1$ may be $R^{1A}$-substituted or unsubstituted heterocycloalkyl. $R^1$ may be $R^{1A}$-substituted heterocycloalkyl. $R^1$ may be unsubstituted heterocycloalkyl. $R^1$ may be $R^{1A}$-substituted or unsubstituted 3 to 10 membered heterocycloalkyl. $R^1$ may be $R^{1A}$-substituted 3 to 10 membered heterocycloalkyl. $R^1$ may be unsubstituted 3 to 10 membered heterocycloalkyl. $R^1$ may be $R^{1A}$-substituted or unsubstituted 3 to 8 membered heterocycloalkyl. $R^1$ may be $R^{1A}$-substituted 3 to 8 membered heterocycloalkyl. $R^1$ may be unsubstituted 3 to 8 membered heterocycloalkyl. $R^1$ may be $R^{1A}$-substituted or unsubstituted 3 to 6 membered heterocycloalkyl. $R^1$ may be $R^{1A}$-substituted 3 to 6 membered heterocycloalkyl. $R^1$ may be unsubstituted 3 to 6 membered heterocycloalkyl. $R^1$ may be $R^{1A}$-substituted or unsubstituted 3 membered heterocycloalkyl. $R^1$ may be $R^{1A}$-substituted or unsubstituted 4 membered heterocycloalkyl. $R^1$ may be $R^{1A}$-substituted or unsubstituted 5 membered heterocycloalkyl. $R^1$ may be $R^{1A}$-substituted or unsubstituted 6 membered heterocycloalkyl.

$R^1$ may be substituted or unsubstituted aryl. $R^1$ may be substituted aryl. $R^1$ may be unsubstituted aryl. $R^1$ may be substituted or unsubstituted 5 to 10 membered aryl. $R^1$ may be substituted 5 to 10 membered aryl. $R^1$ may be unsubstituted 5 to 10 membered aryl. $R^1$ may be substituted or unsubstituted 5 to 8 membered aryl. $R^1$ may be substituted 5 to 8 membered aryl. $R^1$ may be unsubstituted 5 to 8 membered aryl. $R^1$ may be substituted or unsubstituted 5 or 6 membered aryl. $R^1$ may be substituted 5 or 6 membered aryl. $R^1$ may be unsubstituted 5 or 6 membered aryl. $R^1$ may be substituted or unsubstituted 5 membered aryl. $R^1$ may be substituted or unsubstituted 6 membered aryl (e.g. phenyl).

$R^1$ may be $R^{1A}$-substituted or unsubstituted aryl. $R^1$ may be $R^{1A}$-substituted aryl. $R^1$ may be unsubstituted aryl. $R^1$ may be $R^{1A}$-substituted or unsubstituted 5 to 10 membered aryl. $R^1$ may be $R^{1A}$-substituted 5 to 10 membered aryl. $R^1$ may be unsubstituted 5 to 10 membered aryl. $R^1$ may be $R^{1A}$-substituted or unsubstituted 5 to 8 membered aryl. $R^1$ may be $R^{1A}$-substituted 5 to 8 membered aryl. $R^1$ may be unsubstituted 5 to 8 membered aryl. $R^1$ may be $R^{1A}$-substituted or unsubstituted 5 or 6 membered aryl. $R^1$ may be $R^{1A}$-substituted or unsubstituted 5 or 6 membered aryl. $R^1$ may be $R^{1A}$-substituted 5 or 6 membered aryl. $R^1$ may be unsubstituted 5 or 6 membered aryl. $R^1$ may be $R^{1A}$-substituted or unsubstituted 5 membered aryl. $R^1$ may be $R^{1A}$-substituted or unsubstituted 6 membered aryl (e.g. phenyl).

$R^1$ may be substituted or unsubstituted heteroaryl. $R^1$ may be substituted heteroaryl. $R^1$ may be unsubstituted heteroaryl. $R^1$ may be substituted or unsubstituted 5 to 10 membered heteroaryl. $R^1$ may be substituted 5 to 10 membered heteroaryl. $R^1$ may be unsubstituted 5 to 10 membered heteroaryl. $R^1$ may be substituted or unsubstituted 5 to 8 membered heteroaryl. $R^1$ may be substituted 5 to 8 membered heteroaryl. $R^1$ may be unsubstituted 5 to 8 membered heteroaryl. $R^1$ may be substituted or unsubstituted 5 or 6 membered heteroaryl. $R^1$ may be substituted 5 or 6 membered heteroaryl. $R^1$ may be unsubstituted 5 or 6 membered heteroaryl. $R^1$ may be substituted or unsubstituted 5 membered heteroaryl. $R^1$ may be substituted or unsubstituted 6 membered heteroaryl.

$R^1$ may be $R^{1A}$-substituted or unsubstituted heteroaryl. $R^1$ may be $R^{1A}$-substituted heteroaryl. $R^1$ may be unsubstituted heteroaryl. $R^1$ may be $R^{1A}$-substituted or unsubstituted 5 to 10 membered heteroaryl. $R^1$ may be $R^{1A}$-substituted 5 to 10 membered heteroaryl. $R^1$ may be unsubstituted 5 to 10 membered heteroaryl. $R^1$ may be $R^{1A}$-substituted or unsubstituted 5 to 8 membered heteroaryl. $R^1$ may be $R^{1A}$-substituted 5 to 8 membered heteroaryl. $R^1$ may be unsubstituted 5 to 8 membered heteroaryl. $R^1$ may be $R^{1A}$-substituted or unsubstituted 5 or 6 membered heteroaryl. $R^1$ may be $R^{1A}$-substituted 5 or 6 membered heteroaryl. $R^1$ may be unsubstituted 5 or 6 membered heteroaryl. $R^1$ may be $R^{1A}$-substituted or unsubstituted 5 membered heteroaryl. $R^1$ may be $R^{1A}$-substituted or unsubstituted 6 membered heteroaryl.

$R^1$ may be —O-$L^{1A}$-$R^{1A}$. $L^{1A}$ is substituted or unsubstituted alkylene or substituted or unsubstituted heteroalkylene. $L^{1A}$ may be substituted or unsubstituted alkylene. $L^{1A}$ may be substituted or unsubstituted $C_1$-$C_{20}$ alkyl alkylene. $L^{1A}$ may be substituted or unsubstituted $C_1$-$C_{10}$ alkylene. $L^{1A}$ may be substituted or unsubstituted $C_1$-$C_5$ alkylene. $L^{1A}$ may be substituted $C_1$-$C_{20}$ alkylene. $L^{1A}$ may be unsubstituted $C_1$-$C_{20}$ alkylene. $L^{1A}$ may be substituted $C_1$-$C_{10}$ alkylene. $L^{1A}$ may be unsubstituted $C_1$-$C_{10}$ alkylene. $L^{1A}$ may be substituted $C_1$-$C_5$ alkylene. $L^{1A}$ may be unsubstituted $C_1$-$C_5$ alkylene. $L^{1A}$ may be —$(CH_2)_m$—$R^{1A}$, where m is an integer selected from 1, 2, 3, 4 or 5. The symbol m may be 1. The symbol m may be 2. The symbol m may be 3. The symbol m may be 4. The symbol m may be 5.

$L^{1A}$ may be substituted or unsubstituted heteroalkylene. $L^{1A}$ may be substituted heteroalkylene. $L^{1A}$ may be unsubstituted heteroalkylene. $L^{1A}$ may be substituted or unsubstituted 2 to 20 membered heteroalkylene. $L^{1A}$ may be substituted 2 to 20 membered heteroalkylene. $L^{1A}$ may be substituted or unsubstituted 2 to 10 membered heteroalkylene. Lia may be substituted 2 to 10 membered heteroalkylene. $L^{1A}$ may be unsubstituted 2 to 10 membered heteroalkylene. $L^{1A}$ may be substituted or unsubstituted 2 to 6 membered heteroalkylene. $L^{1A}$ may be substituted 2 to 6 membered heteroalkylene. $L^{1A}$ may be unsubstituted 2 to 6 membered heteroalkylene. $L^{1A}$ may be —$(CH_2CH_2O)_{m1}$—$R^{1A}$, where m1 is an integer of 1, 2, 3, or 4. The symbol m1 may be 1. The symbol m1 may be 2. The symbol m1 may be 3. The symbol m1 may be 4.

$R^1$ may be —O-$L^{1A}$-N($R^{1C}$)—S(O)$_{n1}$—$R^{1A}$. $R^{1A}$ is as described herein. $R^{1A}$ may be hydrogen or substituted or unsubstituted alkyl (e.g. $C_1$-$C_5$ alkyl).

$R^{1A}$ is hydrogen, halogen, oxo, —$CF_3$, —CN, —$OR^{12}$, —N($R^{12.1}$)($R^{12.2}$), —$COOR^{12}$, —CON($R^{12.1}$)($R^{12.2}$), —$NO_2$, —S($R^{12}$), —S(O)$_2R^{12}$, —S(O)$_3R^{12}$, —S(O)$_4R^{12}$, $S(O)_2N(R^{12.1})(R^{12.2})$, —$NHN(R^{12.2})(R^{12.2})$, —$ON(R^{12.2})$, —$NHC(O)NHN(R^{12.1})(R^{12.2})$, —$NHC(O)N(R^{12.1})(R^{12.2})$, —$NHS(O)_2R^{12}$, —$NHC(O)R^{12}$, —$NHC(O)$—$OR^{12}$, —$NHOR^{12}$, —$OCF_3$, —$OCHF_2$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl.

$R^{11}$ is hydrogen, halogen, oxo, —$CF_3$, —$CN$, —$OH$, —$NH_2$, —$COOH$, —$CONH_2$, —$NO_2$, —$SH$, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—$OH$, —$NHOH$, —$OCF_3$, —$OCHF_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

$R^{12}$, $R^{12.1}$ and $R^{12.2}$ are independently hydrogen, halogen, oxo, —$CF_3$, —$CN$, —$OH$, —$NH_2$, —$COOH$, —$CONH_2$, —$NO_2$, —$SH$, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—$OH$, —$NHOH$, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{1A}$ may be —$CH_3$, —$C_2H_5$, —$C_3H_7$, —$CD_3$, —$CD_2CD_3$, —$(CH_2)_2OH$, —$(CH_2)_3OH$, —$CH_2CH(OH)CH_3$, —$(CH_2)_2CH(OH)CH_3$, —$CH_2C(CH_3)_2OH$, —$(CH_2)_2C(CH_3)_2OH$, —$(CH_2)_2F$, —$(CH_2)_3F$, —$CH_2CH(F)CH_3$, —$(CH_2)_2CH(F)CH_3$, —$(CH_2)_2C(CH_3)_2F$, —$(CH_2)_2Cl$, —$(CH_2)_3Cl$, —$CH_2CH(Cl)CH_3$, —$(CH_2)_2CH(Cl)CH_3$, —$CH_2C(CH_3)_2Cl$, —$(CH_2)_2C(CH_3)_2Cl$, —$(CH_2)_2NHSO_2CH_3$, —$(CH_2)_3NHSO_2CH_3$, —$(CH_2)_2N(CH_2CH_2OH)SO_2CH_3$, —$(CH_2)_3N(CH_2CH_2OH)SO_2CH_3$, —$(CH_2)_2N(CH_2CH_2F)SO_2CH_3$, —$(CH_2)_2N(CH_2CH_2Cl)SO_2CH_3$, —$(CH_2CH_2O)_nCH_2CH_2$-$G^{1A}$ or —$COCH_2CH_2COO(CH_2CH_2O)_nCH_2CH_2$-$G^{1B}$. The symbol n is 2-20. $G^{1A}$ is H, —$OH$, —$NH_2$, —$OCH_3$, —$OCF_3$, F, Cl, —$N_3$, —$NHCH_2C_6H_4NO_2$, —$NHCH_2C_6H_4F$, —$NHCH_2C_6H_4NO_2$, —$NHCH_2C_6H_4F$,

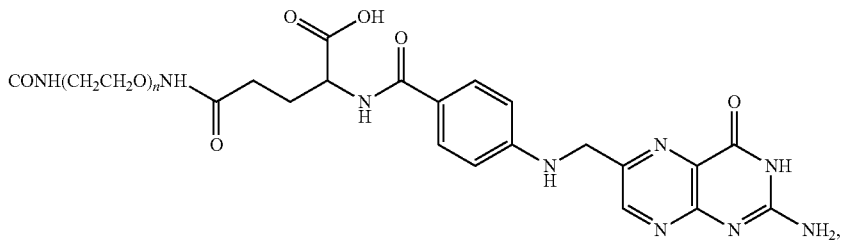

$G^{1B}$ is H, —$OH$, —$NH_2$, —$OCH_3$, F, Cl,

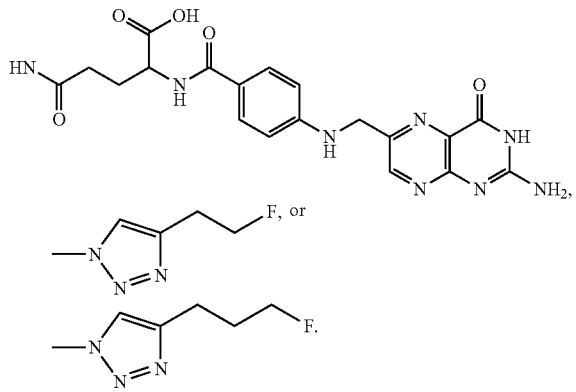

The symbol n may be 2-10. The symbol n may be 2-8. The symbol n may be 2-5. The symbol n may be 2, 3, or 4. The symbol n may be 3.

$R^{1A}$ may be —$OCH_3$, —$OCH_2CH_3$, —$O(CH_2)_2F$, —$(CH_2)_2NHSO_2CH_3$, —$(CH_2CH_2O)_nF$, —$(CH_2CH_2O)CH_3$, where n is 2 to 5.

$R^{1B}$ and $R^{1C}$ are independently hydrogen, halogen, oxo, —$OH$, —$NH_2$, —$COOH$, —$CONH_2$, —$S(O)_2Cl$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—$OH$, —$NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1B}$ may be hydrogen or substituted or unsubstituted alkyl.

$R^{1C}$ are independently hydrogen, halogen, oxo, —$OH$, —$NH_2$, —$COOH$, —$CONH_2$, —$S(O)_2Cl$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—$OH$, —$NHOH$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

The compound of formula (I) may have formula:

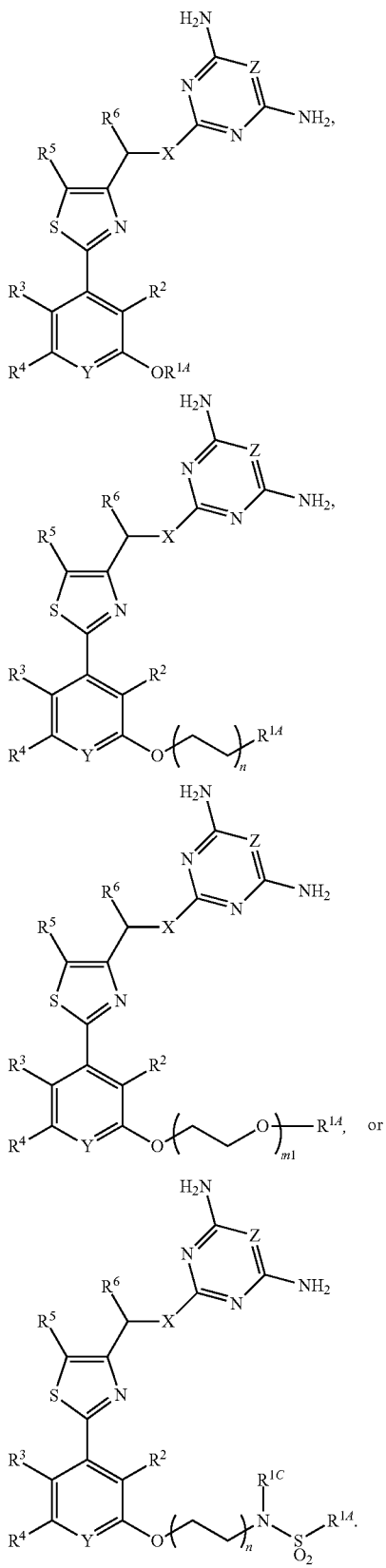

The symbol n is as described herein. The symbol n may be 1, 2, 3, or 4. The symbol n may be 1. The symbol n may be 2. The symbol n may be 3. The symbol n may be 4.

$R^2$ may be hydrogen, halogen, —$N_3$, —$CF_3$, —$CCl_3$, —$CBr_3$, —$CI_3$, —CN, —$COR^{2A}$, —$OR^{2A}$, —$NR^{2A}R^{2B}$, —$C(O)OR^{2A}$, —$C(O)NR^{2A}R^{2B}$, —$NO_2$, —$SR^{2A}$, —$S(O)_{n2}R^{2A}$, —$S(O)_{n2}OR^{2A}$, —$S(O)_{n2}NR^{2A}R^{2B}$, —$NHNR^{2A}R^{2B}$, —$ONR^{2A}R^{2B}$, or —$NHC(O)NHNR^{2A}R^{2B}$. $R^2$ may be hydrogen, halogen, —$CF_3$, —$OR^{2A}$, or —$NR^{2A}R^{2B}$. $R^2$ may hydrogen. $R^2$ may be halogen. $R^2$ may be —$CF_3$. $R^2$ may be —$OR^{2A}$. $R^2$ may be —$NR^{2A}R^{2B}$. $R^2$ and $R^3$ may be hydrogen.

$R^2$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ may be substituted or unsubstituted alkyl. $R^2$ may be unsubstituted alkyl $R^2$ may be substituted alkyl. $R^2$ may be substituted or unsubstituted $C_1$-$C_{20}$ alkyl. $R^2$ may be substituted or unsubstituted $C_1$-$C_{10}$ alkyl. $R^2$ may be substituted $C_1$-$C_{10}$ alkyl. $R^2$ may be unsubstituted $C_1$-$C_{10}$ alkyl. $R^2$ may be $C_1$-$C_5$ substituted or unsubstituted alkyl. $R^2$ may be substituted $C_1$-$C_5$ alkyl. $R^2$ may be unsubstituted $C_1$-$C_5$ alkyl. $R^2$ may be substituted or unsubstituted $C_1$-$C_3$ alkyl. $R^2$ may be unsubstituted $C_1$-$C_3$ alkyl. $R^2$ may be saturated $C_1$-$C_3$ alkyl. $R^2$ may be methyl. $R^2$ may be ethyl. $R^2$ may be propyl.

$R^2$ may be substituted or unsubstituted heteroalkyl. $R^2$ may be substituted heteroalkyl. $R^2$ may be unsubstituted alkyl. $R^2$ may be substituted or unsubstituted 2 to 10 membered heteroalkyl. $R^2$ may be substituted 2 to 10 membered heteroalkyl. $R^2$ may be unsubstituted 2 to 10 membered heteroalkyl. $R^2$ may be 2 to 6 membered heteroalkyl. $R^2$ may be substituted 2 to 6 membered heteroalkyl. $R^2$ may be unsubstituted 2 to 6 membered heteroalkyl.

$R^2$ may be substituted or unsubstituted 3 to 8 membered cycloalkyl. $R^2$ may be substituted 3 to 8 membered cycloalkyl. $R^2$ may be unsubstituted 3 to 8 membered cycloalkyl. $R^2$ may be substituted or unsubstituted 3 to 6 membered cycloalkyl. $R^2$ may be substituted 3 to 6 membered cycloalkyl. $R^2$ may be unsubstituted 3 to 6 membered cycloalkyl. $R^2$ may be substituted or unsubstituted 3 membered cycloalkyl. $R^2$ may be substituted or unsubstituted 4 membered cycloalkyl. $R^2$ may be 5 membered cycloalkyl. $R^2$ may be 6 membered cycloalkyl.

$R^2$ may be substituted or unsubstituted 3 to 8 membered heterocycloalkyl. $R^2$ may be substituted 3 to 8 membered heterocycloalkyl. $R^2$ may be unsubstituted 3 to 8 membered heterocycloalkyl. $R^2$ may be substituted or unsubstituted 3 to 6 membered heterocycloalkyl. $R^2$ may be substituted 3 to 6 membered heterocycloalkyl. $R^2$ may be unsubstituted 3 to 6 membered heterocycloalkyl. $R^2$ may be substituted or unsubstituted 3 membered heterocycloalkyl. $R^2$ may be substituted or unsubstituted 4 membered heterocycloalkyl. $R^2$ may be 5 membered heterocycloalkyl. $R^2$ may be 6 membered heterocycloalkyl.

$R^2$ may be substituted or unsubstituted 5 to 8 membered aryl. $R^2$ may be substituted 5 to 8 membered aryl. $R^2$ may be unsubstituted 5 to 8 membered aryl. $R^2$ may be substituted or unsubstituted 5 membered aryl. $R^2$ may be substituted 5 membered aryl. $R^2$ may be unsubstituted 5 membered aryl. $R^2$ may be substituted 6 membered aryl. $R^2$ may be unsubstituted 6 membered aryl (e.g. phenyl).

$R^2$ may be substituted or unsubstituted 5 to 8 membered heteroaryl. $R^2$ may be substituted 5 to 8 membered heteroaryl. $R^2$ may be unsubstituted 5 to 8 membered heteroaryl. $R^2$ may be substituted or unsubstituted 5 membered heteroaryl. $R^2$ may be substituted 5 membered aryl. $R^2$ may be unsubstituted 5 membered heteroaryl. $R^2$ may be substituted 6 membered aryl. $R^2$ may be unsubstituted 6 membered heteroaryl.

$R^3$ may be hydrogen, halogen, $-N_3$, $-CF_3$, $-CCl_3$, $-CBr_3$, $-CI_3$, $-CN$, $-COR^{3A}$, $-OR^{3A}$, $-NR^{3A}R^{3B}$, $-C(O)OR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$, or $-NHC(O)NHNR^{3A}R^{3B}$. $R^3$ may be hydrogen, halogen, $-CF_3$, $-OR^{3A}$, or $-NR^{3A}R^{3B}$. $R^3$ may hydrogen. $R^3$ may be halogen. $R^3$ may be $-CF_3$. $R^3$ may be $-OR^{3A}$. $R^3$ may be $-NR^{3A}R^{3B}$. $R^2$ and $R^3$ may be hydrogen.

$R^3$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ may be substituted or unsubstituted alkyl. $R^3$ may be unsubstituted alkyl. $R^3$ may be substituted alkyl. $R^3$ may be substituted or unsubstituted $C_1$-$C_{20}$ alkyl. $R^3$ may be substituted or unsubstituted $C_1$-$C_{10}$ alkyl. $R^3$ may be substituted $C_1$-$C_{10}$ alkyl. $R^3$ may be unsubstituted $C_1$-$C_{10}$ alkyl. $R^3$ may be $C_1$-$C_5$ substituted or unsubstituted alkyl. $R^3$ may be substituted $C_1$-$C_5$ alkyl. $R^3$ may be unsubstituted $C_1$-$C_5$ alkyl. $R^3$ may be substituted or unsubstituted $C_1$-$C_3$ alkyl. $R^3$ may be unsubstituted $C_1$-$C_3$ alkyl. $R^3$ may be saturated $C_1$-$C_3$ alkyl. $R^3$ may be methyl. $R^3$ may be ethyl. $R^3$ may be propyl.

$R^3$ may be substituted or unsubstituted heteroalkyl. $R^3$ may be substituted heteroalkyl. $R^3$ may be unsubstituted alkyl. $R^3$ may be substituted or unsubstituted 2 to 10 membered heteroalkyl. $R^3$ may be substituted 2 to 10 membered heteroalkyl. $R^3$ may be unsubstituted 2 to 10 membered heteroalkyl. $R^3$ may be 2 to 6 membered heteroalkyl. $R^3$ may be substituted 2 to 6 membered heteroalkyl. $R^3$ may be unsubstituted 2 to 6 membered heteroalkyl.

$R^3$ may be substituted or unsubstituted 3 to 8 membered cycloalkyl. $R^3$ may be substituted 3 to 8 membered cycloalkyl. $R^3$ may be unsubstituted 3 to 8 membered cycloalkyl. $R^3$ may be substituted or unsubstituted 3 to 6 membered cycloalkyl. $R^3$ may be substituted 3 to 6 membered cycloalkyl. $R^3$ may be unsubstituted 3 to 6 membered cycloalkyl. $R^3$ may be substituted or unsubstituted 3 membered cycloalkyl. $R^3$ may be substituted or unsubstituted 4 membered cycloalkyl. $R^3$ may be 5 membered cycloalkyl. $R^3$ may be 6 membered cycloalkyl.

$R^3$ may be substituted or unsubstituted 3 to 8 membered heterocycloalkyl. $R^3$ may be substituted 3 to 8 membered heterocycloalkyl. $R^3$ may be unsubstituted 3 to 8 membered heterocycloalkyl. $R^3$ may be substituted or unsubstituted 3 to 6 membered heterocycloalkyl. $R^3$ may be substituted 3 to 6 membered heterocycloalkyl. $R^3$ may be unsubstituted 3 to 6 membered heterocycloalkyl. $R^3$ may be substituted or unsubstituted 3 membered heterocycloalkyl. $R^3$ may be substituted or unsubstituted 4 membered heterocycloalkyl. $R^3$ may be 5 membered heterocycloalkyl. $R^3$ may be 6 membered heterocycloalkyl.

$R^3$ may be substituted or unsubstituted 5 to 8 membered aryl. $R^3$ may be substituted 5 to 8 membered aryl. $R^3$ may be unsubstituted 5 to 8 membered aryl. $R^3$ may be substituted or unsubstituted 5 membered aryl. $R^3$ may be substituted 5 membered aryl. $R^3$ may be unsubstituted 5 membered aryl. $R^3$ may be substituted 6 membered aryl. $R^3$ may be unsubstituted 6 membered aryl (e.g. phenyl).

$R^3$ may be substituted or unsubstituted 5 to 8 membered heteroaryl. $R^3$ may be substituted 5 to 8 membered heteroaryl. $R^3$ may be unsubstituted 5 to 8 membered heteroaryl. $R^3$ may be substituted or unsubstituted 5 membered heteroaryl. $R^3$ may be substituted 5 membered aryl. $R^3$ may be unsubstituted 5 membered heteroaryl. $R^3$ may be substituted 6 membered aryl. $R^3$ may be unsubstituted 6 membered heteroaryl.

$R^4$ may be hydrogen, halogen, $-N_3$, $-CF_3$, $-CCl_3$, $-CBr_3$, $-CI_3$, $-CN$, $-COR^{4A}$, $-OR^{4A}$, $-NR^{4A}R^{4B}$, $-C(O)OR^{4A}$, $-C(O)NR^{4A}R^{4B}$, $-NO_2$, $-SR^{4A}$, $-S(O)_{n4}R^{4A}$, $-S(O)_{n4}OR^{4A}$, $-S(O)_{n4}NR^{4A}R^{4B}$, $-NHNR^{4A}R^{4B}$, $-ONR^{4A}R^{4B}$, or $-NHC(O)NHNR^{4A}R^{4B}$. $R^4$ may be hydrogen or halogen. $R^4$ may be hydrogen. $R^4$ may be halogen.

$R^4$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ may be substituted or unsubstituted alkyl. $R^4$ may be unsubstituted alkyl. $R^4$ may be substituted alkyl. $R^4$ may be substituted or unsubstituted $C_1$-$C_{20}$ alkyl. $R^4$ may be substituted or unsubstituted $C_1$-$C_{10}$ alkyl. $R^4$ may be substituted $C_1$-$C_{10}$ alkyl. $R^4$ may be unsubstituted $C_1$-$C_{10}$ alkyl. $R^4$ may be $C_1$-$C_5$ substituted or unsubstituted alkyl. $R^4$ may be substituted $C_1$-$C_5$ alkyl. $R^4$ may be unsubstituted $C_1$-$C_5$ alkyl. $R^4$ may be substituted or unsubstituted $C_1$-$C_3$ alkyl. $R^4$ may be unsubstituted $C_1$-$C_3$ alkyl. $R^4$ may be saturated $C_1$-$C_3$ alkyl. $R^4$ may be methyl. $R^4$ may be ethyl. $R^4$ may be propyl.

$R^4$ may be substituted or unsubstituted heteroalkyl. $R^4$ may be substituted heteroalkyl. $R^4$ may be unsubstituted alkyl. $R^4$ may be substituted or unsubstituted 2 to 10 membered heteroalkyl. $R^4$ may be substituted 2 to 10 membered heteroalkyl. $R^4$ may be unsubstituted 2 to 10 membered heteroalkyl. $R^4$ may be 2 to 6 membered heteroalkyl. $R^4$ may be substituted 2 to 6 membered heteroalkyl. $R^4$ may be unsubstituted 2 to 6 membered heteroalkyl.

$R^4$ may be substituted or unsubstituted 3 to 8 membered cycloalkyl. $R^4$ may be substituted 3 to 8 membered cycloalkyl. $R^4$ may be unsubstituted 3 to 8 membered cycloalkyl. $R^4$ may be substituted or unsubstituted 3 to 6 membered cycloalkyl. $R^4$ may be substituted 3 to 6 membered cycloalkyl. $R^4$ may be unsubstituted 3 to 6 membered cycloalkyl. $R^4$ may be substituted or unsubstituted 3 membered cycloalkyl. $R^4$ may be substituted or unsubstituted 4 membered cycloalkyl. $R^4$ may be 5 membered cycloalkyl. $R^4$ may be 6 membered cycloalkyl.

$R^4$ may be substituted or unsubstituted 3 to 8 membered heterocycloalkyl. $R^4$ may be substituted 3 to 8 membered heterocycloalkyl. $R^4$ may be unsubstituted 3 to 8 membered heterocycloalkyl. $R^4$ may be substituted or unsubstituted 3 to 6 membered heterocycloalkyl. $R^4$ may be substituted 3 to 6 membered heterocycloalkyl. $R^4$ may be unsubstituted 3 to 6 membered heterocycloalkyl. $R^4$ may be substituted or unsubstituted 3 membered heterocycloalkyl. $R^4$ may be substituted or unsubstituted 4 membered heterocycloalkyl. $R^4$ may be 5 membered heterocycloalkyl. $R^4$ may be 6 membered heterocycloalkyl.

$R^4$ may be substituted or unsubstituted 5 to 8 membered aryl. $R^4$ may be substituted 5 to 8 membered aryl. $R^4$ may be unsubstituted 5 to 8 membered aryl. $R^4$ may be substituted or unsubstituted 5 membered aryl. $R^4$ may be substituted 5 membered aryl. $R^4$ may be unsubstituted 5 membered aryl. $R^4$ may be substituted 6 membered aryl. $R^4$ may be unsubstituted 6 membered aryl (e.g. phenyl).

$R^4$ may be substituted or unsubstituted 5 to 8 membered heteroaryl. $R^4$ may be substituted 5 to 8 membered heteroaryl. $R^4$ may be unsubstituted 5 to 8 membered heteroaryl. $R^4$ may be substituted or unsubstituted 5 membered heteroaryl. $R^4$ may be substituted 5 membered aryl. $R^4$ may be unsubstituted 5 membered heteroaryl. $R^4$ may be substituted 6 membered aryl. $R^4$ may be unsubstituted 6 membered heteroaryl.

$R^5$ may be hydrogen, halogen, $-N_3$, $-CF_3$, $-CCl_3$, $-CBr_3$, $-CI_3$, $-CN$, $-COR^{5A}$, $-OR^{5A}$, $-NR^{5A}R^{5B}$, $-C(O)OR^{5A}$, $-C(O)NR^{5A}R^{5B}$, $-NO_2$, $-SR^{5A}$, $-S(O)_{n5}R^{5A}$, $-S(O)_{n5}OR^{5A}$, $-S(O)_{n5}NR^{5A}R^{5B}$, $-NHNR^{5A}R^{5B}$, $-ONR^{5A}R^{5B}$, or $-NHC(O)NHNR^{5A}R^{5B}$.

$R^5$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ may be substituted or unsubstituted alkyl or substituted or unsubstituted heteroalkyl. $R^5$ may be substituted or unsubstituted alkyl. $R^5$ may be unsubstituted alkyl. $R^5$ may be substituted alkyl. $R^5$ may be substituted or unsubstituted $C_1$-$C_{20}$ alkyl. $R^5$ may be substituted $C_1$-$C_{20}$ alkyl. $R^5$ may be unsubstituted $C_1$-$C_{20}$ alkyl. $R^5$ may be substituted or unsubstituted $C_1$-$C_{10}$ alkyl. $R^5$ may be substituted $C_1$-$C_{10}$ alkyl. $R^5$ may be unsubstituted $C_1$-$C_{10}$ alkyl. $R^5$ may be $C_1$-$C_6$ substituted or unsubstituted alkyl. $R^4$ may be substituted $C_1$-$C_6$ alkyl. $R^5$ may be unsubstituted $C_1$-$C_6$ alkyl. $R^5$ may be substituted or unsubstituted $C_1$-$C_3$ alkyl. $R^5$ may be unsubstituted $C_1$-$C_3$ alkyl. $R^5$ may be saturated $C_1$-$C_3$ alkyl. $R^5$ may be methyl. $R^5$ may be ethyl. $R^5$ may be propyl.

$R^5$ may be substituted or unsubstituted heteroalkyl. $R^5$ may be substituted heteroalkyl. $R^5$ may be unsubstituted alkyl. $R^5$ may be substituted or unsubstituted 2 to 10 membered heteroalkyl. $R^5$ may be substituted 2 to 10 membered heteroalkyl. $R^5$ may be unsubstituted 2 to 10 membered heteroalkyl. $R^5$ may be 2 to 6 membered heteroalkyl. $R^5$ may be substituted 2 to 6 membered heteroalkyl. $R^5$ may be unsubstituted 2 to 6 membered heteroalkyl.

$R^5$ may be substituted or unsubstituted 3 to 8 membered cycloalkyl. $R^5$ may be substituted 3 to 8 membered cycloalkyl. $R^5$ may be unsubstituted 3 to 8 membered cycloalkyl. $R^5$ may be substituted or unsubstituted 3 to 6 membered cycloalkyl. $R^5$ may be substituted 3 to 6 membered cycloalkyl. $R^5$ may be unsubstituted 3 to 6 membered cycloalkyl. $R^5$ may be substituted or unsubstituted 3 membered cycloalkyl. $R^5$ may be substituted or unsubstituted 4 membered cycloalkyl. $R^5$ may be 5 membered cycloalkyl. $R^5$ may be 6 membered cycloalkyl.

$R^5$ may be substituted or unsubstituted 3 to 8 membered heterocycloalkyl. $R^5$ may be substituted 3 to 8 membered heterocycloalkyl. $R^5$ may be unsubstituted 3 to 8 membered heterocycloalkyl. $R^5$ may be substituted or unsubstituted 3 to 6 membered heterocycloalkyl. $R^5$ may be substituted 3 to 6 membered heterocycloalkyl. $R^5$ may be unsubstituted 3 to 6 membered heterocycloalkyl. $R^5$ may be substituted or unsubstituted 3 membered heterocycloalkyl. $R^5$ may be substituted or unsubstituted 4 membered heterocycloalkyl. $R^5$ may be 5 membered heterocycloalkyl. $R^5$ may be 6 membered heterocycloalkyl.

$R^5$ may be substituted or unsubstituted 5 to 8 membered aryl. $R^5$ may be substituted 5 to 8 membered aryl. $R^5$ may be unsubstituted 5 to 8 membered aryl. $R^5$ may be substituted or unsubstituted 5 membered aryl. $R^5$ may be substituted 5 membered aryl. $R^5$ may be unsubstituted 5 membered aryl. $R^5$ may be substituted 6 membered aryl. $R^5$ may be unsubstituted 6 membered aryl (e.g. phenyl).

$R^5$ may be substituted or unsubstituted 5 to 8 membered heteroaryl. $R^5$ may be substituted 5 to 8 membered heteroaryl. $R^5$ may be unsubstituted 5 to 8 membered heteroaryl. $R^5$ may be substituted or unsubstituted 5 membered heteroaryl. $R^5$ may be substituted 5 membered aryl. $R^5$ may be unsubstituted 5 membered heteroaryl. $R^5$ may be substituted 6 membered aryl. $R^5$ may be unsubstituted 6 membered heteroaryl.

$R^5$ and $R^6$ may optionally be combined to form a substituted or unsubstituted cycloalkyl. $R^5$ and $R^6$ may optionally be combined to form a substituted cycloalkyl. $R^5$ and $R^6$ may optionally be combined to form an unsubstituted cycloalkyl. $R^5$ and $R^6$ may optionally be combined to form a substituted or unsubstituted 3 to 10 membered cycloalkyl. $R^5$ and $R^6$ may optionally be combined to form a substituted 3 to 10 membered cycloalkyl. $R^5$ and $R^6$ may optionally be combined to form an unsubstituted 3 to 10 membered cycloalkyl. $R^5$ and $R^6$ may optionally be combined to form a substituted or unsubstituted 3 to 8 membered cycloalkyl. $R^5$ and $R^6$ may optionally be combined to form a substituted 3 to 8 membered cycloalkyl. $R^5$ and $R^6$ may optionally be combined to form an unsubstituted 3 to 8 membered cycloalkyl. $R^5$ and $R^6$ may optionally be combined to form a substituted or unsubstituted 3 to 6 membered cycloalkyl. $R^5$ and $R^6$ may optionally be combined to form a substituted 3 to 6 membered cycloalkyl. $R^5$ and $R^6$ may optionally be combined to form an unsubstituted 3 to 6 membered cycloalkyl. $R^5$ and $R^6$ may optionally be combined to form a substituted or unsubstituted 3 membered cycloalkyl. $R^5$ and $R^6$ may optionally be combined to form a substituted or unsubstituted 4 membered cycloalkyl. $R^5$ and $R^6$ may optionally be combined to form a substituted or unsubstituted 5 membered cycloalkyl. $R^5$ and $R^6$ may optionally be combined to form a substituted or unsubstituted 6 membered cycloalkyl.

$R^5$ and $R^6$ may optionally be combined to form a $R^{5A}$-substituted or unsubstituted cycloalkyl. $R^5$ and $R^6$ may optionally be combined to form a $R^{5A}$-substituted $R^5$ and $R^6$ may optionally be combined to form a $R^{5A}$-substituted or unsubstituted 3 to 10 membered cycloalkyl. $R^5$ and $R^6$ may optionally be combined to form a $R^{5A}$-substituted 3 to 10 membered cycloalkyl. $R^5$ and $R^6$ may optionally be combined to form a $R^{5A}$-substituted or unsubstituted 3 to 8 membered cycloalkyl. $R^5$ and $R^6$ may optionally be combined to form a $R^{5A}$-substituted 3 to 8 membered cycloalkyl. $R^5$ and $R^6$ may optionally be combined to form a $R^{5A}$-substituted or unsubstituted 3 to 6 membered cycloalkyl. $R^5$ and $R^6$ may optionally be combined to form a $R^{5A}$-substituted 3 to 6 membered cycloalkyl. $R^5$ and $R^6$ may optionally be combined to form a $R^{5A}$-substituted or unsubstituted 3 membered cycloalkyl. $R^5$ and $R^6$ may optionally be combined to form a $R^{5A}$-substituted 3 membered cycloalkyl. $R^5$ and $R^6$ may optionally be combined to form an unsubstituted 3 membered cycloalkyl. $R^5$ and $R^6$ may optionally be combined to form a $R^{5A}$-substituted or unsubstituted 4 membered cycloalkyl. $R^5$ and $R^6$ may optionally be combined to form a $R^{5A}$-substituted 4 membered cycloalkyl. $R^5$ and $R^6$ may optionally be combined to form an unsubstituted 4 membered cycloalkyl. $R^5$ and $R^6$ may optionally be combined to form a $R^{5A}$-substituted or unsubstituted 5 membered cycloalkyl. $R^5$ and $R^6$ may optionally be combined to form a $R^{5A}$-substituted 5 membered cycloalkyl. $R^5$ and $R^6$ may optionally be combined to form an unsubstituted 5 membered cycloalkyl. $R^5$ and $R^6$ may optionally be combined to form a $R^{5A}$-substituted or unsubstituted 6 membered cycloalkyl. $R^5$ and $R^6$ may optionally be combined to form a $R^{5A}$-substituted 6 membered cycloalkyl. $R^5$ and $R^6$ may optionally be combined to form an unsubstituted 6 membered cycloalkyl.

$R^5$ and $R^6$ may independently be unsubstituted $C_1$-$C_6$ alkyl. $R^5$ and $R^6$ may independently be unsubstituted $C_1$-$C_4$ alkyl. $R^5$ and $R^6$ may independently be methyl, ethyl, or propyl. $R^5$ and $R^6$ may independently be methyl. When $R^5$ is methyl or propyl, $R^6$ may be methyl.

$R^6$ may be unsubstituted $C_1$-$C_6$ alkyl. $R^6$ may be unsubstituted $C_1$-$C_5$ alkyl. $R^6$ may be unsubstituted $C_1$-$C_4$ alkyl. $R^6$ may be unsubstituted $C_1$-$C_3$ alkyl. $R^6$ may be methyl, ethyl, or propyl. $R^6$ may be methyl. $R^6$ may be ethyl. $R^6$ may be propyl. $R^6$ may be methyl and $R^5$ may be methyl, ethyl, or propyl. $R^6$ may be methyl and $R^5$ may be methyl. $R^6$ may be methyl and $R^5$ may be ethyl. $R^6$ may be methyl and $R^5$ may be propyl. $R^6$ may be halogen.

$R^6$ may be described as herein and attached to a carbon having (R) stereochemistry. $R^6$ may be (R)-$C_1$-$C_6$ alkyl. $R^6$ may be (R)-$C_1$-$C_5$ alkyl. $R^6$ may be a (R)-$C_1$-$C_4$ alkyl. $R^6$ may be a (R)-$C_1$-$C_3$ alkyl. $R^6$ may be (R)-methyl. $R^6$ may be (R)-ethyl. $R^6$ may be a (R)-propyl.

$R^6$ may be as described herein and attached to a carbon having (S) stereochemistry. $R^6$ may be (S)-$C_1$-$C_6$ alkyl. $R^6$ may be (S)-$C_1$-$C_5$ alkyl. $R^6$ may be a (S)-$C_1$-$C_4$ alkyl. $R^6$ may be a (S)-$C_1$-$C_3$ alkyl. $R^6$ may be (S)-methyl. $R^6$ may be (S)-ethyl. $R^6$ may be a (S)-propyl. When $R^5$ is methyl or propyl, $R^6$ may be (R)-methyl.

$R^7$ may be hydrogen, halogen, —$N_3$, —$CF_3$, —$CCl_3$, —$CBr_3$, —$CI_3$, —CN, —$COR^{7A}$, —$OR^{7A}$, —$NR^{7A}R^{7B}$, —C(O)$OR^{7A}$, —C(O)$NR^{7A}R^{7B}$, —$NO_2$, —$SR^{7A}$, —S(O)$_{n7}R^{7A}$, —S(O)$_{n7}OR^{7A}$, —S(O)$_{n7}NR^{7A}R^{7B}$, —$NHNR^{7A}R^{7B}$, —$ONR^{7A}R^{7B}$, or —NHC(O)$NHNR^{7A}R^{7B}$. $R^7$ may be hydrogen, halogen, —$CF_3$, —$OR^{7A}$, or —$NR^{7A}R^{7B}$. $R^7$ may hydrogen. $R^7$ may be halogen. $R^7$ may be —$CF_3$. $R^7$ may be —$OR^{7A}$. $R^7$ may be —$NR^{7A}R^{7B}$.

$R^7$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ may be substituted or unsubstituted alkyl. $R^7$ may be unsubstituted alkyl $R^7$ may be substituted alkyl. $R^7$ may be substituted or unsubstituted $C_1$-$C_{20}$ alkyl. $R^7$ may be substituted or unsubstituted $C_1$-$C_{10}$ alkyl. $R^7$ may be substituted $C_1$-$C_{10}$ alkyl. $R^7$ may be unsubstituted $C_1$-$C_{10}$ alkyl. $R^7$ may be $C_1$-$C_5$ substituted or unsubstituted alkyl. $R^7$ may be substituted $C_1$-$C_5$ alkyl. $R^7$ may be unsubstituted $C_1$-$C_5$ alkyl. $R^7$ may be substituted or unsubstituted $C_1$-$C_3$ alkyl. $R^7$ may be unsubstituted $C_1$-$C_3$ alkyl. $R^7$ may be saturated $C_1$-$C_3$ alkyl. $R^7$ may be methyl. $R^7$ may be ethyl. $R^7$ may be propyl.

$R^7$ may be substituted or unsubstituted heteroalkyl. R2 may be substituted heteroalkyl. $R^7$ may be unsubstituted alkyl. $R^7$ may be substituted or unsubstituted 2 to 10 membered heteroalkyl. $R^7$ may be substituted 2 to 10 membered heteroalkyl. $R^7$ may be unsubstituted 2 to 10 membered heteroalkyl. $R^7$ may be 2 to 6 membered heteroalkyl. $R^7$ may be substituted 2 to 6 membered heteroalkyl. $R^7$ may be unsubstituted 2 to 6 membered heteroalkyl.

$R^7$ may be substituted or unsubstituted 3 to 8 membered cycloalkyl. $R^7$ may be substituted 3 to 8 membered cycloalkyl. $R^7$ may be unsubstituted 3 to 8 membered cycloalkyl. $R^7$ may be substituted or unsubstituted 3 to 6 membered cycloalkyl. $R^7$ may be substituted 3 to 6 membered cycloalkyl. $R^7$ may be unsubstituted 3 to 6 membered cycloalkyl. $R^7$ may be substituted or unsubstituted 3 membered cycloalkyl. $R^7$ may be substituted or unsubstituted 4 membered cycloalkyl. R2 may be 5 membered cycloalkyl. $R^7$ may be 6 membered cycloalkyl.

$R^7$ may be substituted or unsubstituted 3 to 8 membered heterocycloalkyl. $R^7$ may be substituted 3 to 8 membered heterocycloalkyl. $R^7$ may be unsubstituted 3 to 8 membered heterocycloalkyl. $R^7$ may be substituted or unsubstituted 3 to 6 membered heterocycloalkyl. $R^7$ may be substituted 3 to 6 membered heterocycloalkyl. $R^7$ may be unsubstituted 3 to 6 membered heterocycloalkyl. $R^7$ may be substituted or unsubstituted 3 membered heterocycloalkyl. $R^7$ may be substituted or unsubstituted 4 membered heterocycloalkyl. $R^7$ may be 5 membered heterocycloalkyl. $R^7$ may be 6 membered heterocycloalkyl.

$R^7$ may be substituted or unsubstituted 5 to 8 membered aryl. $R^7$ may be substituted 5 to 8 membered aryl. $R^7$ may be unsubstituted 5 to 8 membered aryl. $R^7$ may be substituted or unsubstituted 5 membered aryl. $R^7$ may be substituted 5 membered aryl. $R^7$ may be unsubstituted 5 membered aryl. $R^7$ may be substituted 6 membered aryl. $R^7$ may be unsubstituted 6 membered aryl (e.g. phenyl).

$R^7$ may be substituted or unsubstituted 5 to 8 membered heteroaryl. $R^7$ may be substituted 5 to 8 membered heteroaryl. $R^7$ may be unsubstituted 5 to 8 membered heteroaryl. $R^7$ may be substituted or unsubstituted 5 membered heteroaryl. $R^7$ may be substituted 5 membered aryl. $R^7$ may be unsubstituted 5 membered heteroaryl. $R^7$ may be substituted 6 membered aryl. $R^7$ may be unsubstituted 6 membered heteroaryl.

Y may be N. Y may be C($R^8$). Z may be N. Z may be C($R^9$). Y and Z may be N. Y may be C($R^8$), where $R^8$ is as described herein and Z may be C($R^9$), where $R^9$ is as described herein. Y may be C($R^8$), where $R^8$ is as described herein and Z may be C($R^9$), where $R^9$ is independently hydrogen. Y may be N and Z may be C($R^9$), where $R^9$ is as described herein. Y may be N and Z may be C($R^9$), where $R^9$ is independently hydrogen.

X may be —$CH_2$. X may be O, N($R^{10}$), or S, where $R^{10}$ is as described herein. X may be S(O) or S(O)$_2$. X may be S. X may be O. X may be N($R^{10}$), where $R^{10}$ is as described herein.

$R^{10}$ may be hydrogen. $R^{10}$ may be —$CH_3$, —$C_2H_5$, —$C_3H_7$, —$CH_2C_6H_5$. $R^{10}$ may be hydrogen or methyl. $R^{10}$ may be hydrogen or —$C_2H_5$. $R^{10}$ may be hydrogen or —$C_3H_7$. $R^{10}$ may be hydrogen or —$CH_2C_6H_5$. $R^{10}$ may be —$CH_3$. $R^{10}$ may be —$C_2H_5$. $R^{10}$ may be —$C_3H_7$. $R^{10}$ may be —$CH_2C_6H_5$.

$R^8$ may be hydrogen, halogen, —$N_3$, —$CF_3$, —$CCl_3$, —$CBr_3$, —$CI_3$, —CN, —$COR^{8A}$, —$OR^{8A}$, —O-L$^{8A}$-$R^{8C}$, —$NR^{8A}R^{8B}$, —C(O)$OR^{8A}$, —C(O)$NR^{8A}R^{8B}$, —$NO_2$, —$SR^{8A}$, —S(O)$_n R^{8A}$, —S(O)$_{n8}OR^{8A}$, —S(O)$_n^8 NR^{8A}R^{8B}$, —$NHNR^{8A}R^{8B}$, —$ONR^{8A}R^{8B}$, or —NHC(O)$NHNR^{8A}R^{8B}$. $R^8$ may be hydrogen, halogen, —$OR^{8A}$. $R^8$ may be hydrogen. $R^8$ may be halogen. $R^8$ may be —$OR^{8A}$. $R^{8A}$ is as described herein.

$R^8$ may be hydrogen, halogen, —$OR^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ may be —$OR^{8A}$, where $R^{8A}$ is as described herein. $R^8$ may be —$OR^{8A}$, where $R^{8A}$ is hydrogen, substituted or unsubstituted alkyl, or substituted or unsubstituted heteroalkyl. $R^8$ may be —$OR^{8A}$, where $R^{8A}$ is substituted or unsubstituted alkyl, or substituted or unsubstituted heteroalkyl.

$R^8$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ may be $R^{8A}$-substituted or unsubstituted alkyl, $R^{8A}$-substituted or unsubstituted heteroalkyl, $R^{8A}$-substituted or unsubstituted cycloalkyl, $R^{8A}$-substituted or unsubstituted heterocycloalkyl, $R^{8A}$-substituted or unsubstituted aryl, or $R^{8A}$-substituted or unsubstituted heteroaryl.

$R^8$ may be substituted or unsubstituted alkyl. $R^8$ may be substituted alkyl. $R^8$ may be unsubstituted alkyl. $R^8$ may be substituted or unsubstituted $C_1$-$C_{20}$ alkyl. $R^8$ may be substituted $C_1$-$C_{20}$ alkyl. $R^8$ may be unsubstituted $C_1$-$C_{20}$ alkyl. $R^8$ may be substituted or unsubstituted $C_1$-$C_{10}$ alkyl. $R^8$ may be substituted $C_1$-$C_{10}$ alkyl. $R^8$ may be unsubstituted $C_1$-$C_{10}$ alkyl. $R^8$ may be substituted or unsubstituted $C_1$-$C_5$ alkyl. $R^8$ may be substituted $C_1$-$C_5$ alkyl. $R^8$ may be unsubstituted $C_1$-$C_5$ alkyl. $R^8$ may be methyl. $R^8$ may be ethyl. $R^8$ may be propyl.

$R^8$ may be $R^{8A}$-substituted or unsubstituted alkyl. $R^8$ may be $R^{8A}$-substituted alkyl. $R^8$ may be unsubstituted alkyl. $R^8$ may be $R^{8A}$-substituted or unsubstituted $C_1$-$C_{20}$ alkyl. $R^8$ may be $R^{8A}$-substituted $C_1$-$C_{20}$ alkyl. $R^8$ may be unsubstituted $C_1$-$C_{20}$ alkyl. $R^8$ may be $R^{8A}$-substituted or unsubstituted $C_1$-$C_{10}$ alkyl. $R^8$ may be $R^{8A}$-substituted $C_1$-$C_{10}$ alkyl. $R^8$ may be unsubstituted $C_1$-$C_{10}$ alkyl. $R^8$ may be $R^{8A}$-substituted or unsubstituted $C_1$-$C_5$ alkyl. $R^8$ may be $R^{8A}$-substituted $C_1$-$C_5$ alkyl. $R^8$ may be unsubstituted $C_1$-$C_5$ alkyl.

$R^8$ may be substituted or unsubstituted heteroalkyl. $R^8$ may be substituted heteroalkyl. $R^8$ may be unsubstituted heteroalkyl. $R^8$ may be substituted or unsubstituted 2 to 20 membered heteroalkyl. $R^8$ may be substituted 2 to 20 membered heteroalkyl. $R^8$ may be unsubstituted 2 to 20 membered heteroalkyl. $R^8$ may be substituted or unsubstituted 2 to 10 membered heteroalkyl. $R^8$ may be substituted 2 to 10 membered heteroalkyl. $R^8$ may be unsubstituted 2 to 10 membered heteroalkyl. $R^8$ may be substituted or unsubstituted 2 to 6 membered heteroalkyl. $R^8$ may be substituted 2 to 6 membered heteroalkyl. $R^8$ may be unsubstituted 2 to 6 membered heteroalkyl.

$R^8$ may be $R^{8A}$-substituted or unsubstituted heteroalkyl. $R^8$ may be $R^{8A}$-substituted heteroalkyl. $R^8$ may be unsubstituted heteroalkyl. $R^8$ may be $R^{8A}$-substituted or unsubstituted 2 to 20 membered heteroalkyl. $R^8$ may be $R^{8A}$-substituted 2 to 20 membered heteroalkyl. $R^8$ may be unsubstituted 2 to 20 membered heteroalkyl. $R^8$ may be $R^{8A}$-substituted or unsubstituted 2 to 10 membered heteroalkyl. $R^8$ may be $R^{8A}$-substituted 2 to 10 membered heteroalkyl. $R^8$ may be unsubstituted 2 to 10 membered heteroalkyl. $R^8$ may be $R^{8A}$-substituted or unsubstituted 2 to 6 membered heteroalkyl. $R^8$ may be $R^{8A}$-substituted 2 to 6 membered heteroalkyl. $R^8$ may be unsubstituted 2 to 6 membered heteroalkyl.

$R^8$ may be substituted or unsubstituted cycloalkyl. $R^8$ may be substituted cycloalkyl. $R^8$ may be unsubstituted cycloalkyl. $R^8$ may be substituted or unsubstituted 3 to 10 membered cycloalkyl. $R^8$ may be substituted 3 to 10 membered cycloalkyl. $R^8$ may be unsubstituted 3 to 10 membered cycloalkyl. $R^8$ may be substituted or unsubstituted 3 to 8 membered cycloalkyl. $R^8$ may be substituted 3 to 8 membered cycloalkyl. $R^8$ may be unsubstituted 3 to 8 membered cycloalkyl. $R^8$ may be substituted or unsubstituted 3 to 6 membered cycloalkyl. $R^8$ may be substituted 3 to 6 membered cycloalkyl. $R^8$ may be unsubstituted 3 to 6 membered cycloalkyl. $R^8$ may be substituted or unsubstituted 3 membered cycloalkyl. $R^8$ may be substituted or unsubstituted 4 membered cycloalkyl. $R^8$ may be substituted or unsubstituted 5 membered cycloalkyl. $R^8$ may be substituted or unsubstituted 6 membered cycloalkyl.

$R^8$ may be $R^{8A}$-substituted or unsubstituted cycloalkyl. $R^8$ may be $R^{8A}$-substituted cycloalkyl. $R^8$ may be unsubstituted cycloalkyl. $R^8$ may be $R^{8A}$-substituted or unsubstituted 3 to 10 membered cycloalkyl. $R^8$ may be $R^{8A}$-substituted 3 to 10 membered cycloalkyl. $R^8$ may be unsubstituted 3 to 10 membered cycloalkyl. $R^8$ may be $R^{8A}$-substituted or unsubstituted 3 to 8 membered cycloalkyl. $R^8$ may be $R^{8A}$-substituted 3 to 8 membered cycloalkyl. $R^8$ may be unsubstituted 3 to 8 membered cycloalkyl. $R^8$ may be $R^{8A}$-substituted or unsubstituted 3 to 6 membered cycloalkyl. $R^8$ may be $R^{8A}$-substituted 3 to 6 membered cycloalkyl. $R^8$ may be unsubstituted 3 to 6 membered cycloalkyl. $R^8$ may be $R^{8A}$-substituted or unsubstituted 3 membered cycloalkyl. $R^8$ may be $R^{8A}$-substituted or unsubstituted 4 membered cycloalkyl. $R^8$ may be $R^{8A}$-substituted or unsubstituted 5 membered cycloalkyl. $R^8$ may be $R^{8A}$-substituted or unsubstituted 6 membered cycloalkyl.

$R^8$ may be substituted or unsubstituted heterocycloalkyl. $R^8$ may be substituted heterocycloalkyl. $R^8$ may be unsubstituted heterocycloalkyl. $R^8$ may be substituted or unsubstituted 3 to 10 membered heterocycloalkyl. $R^8$ may be substituted 3 to 10 membered heterocycloalkyl. $R^8$ may be unsubstituted 3 to 10 membered heterocycloalkyl. $R^8$ may be substituted or unsubstituted 3 to 8 membered heterocycloalkyl. $R^8$ may be substituted 3 to 8 membered heterocycloalkyl. $R^8$ may be unsubstituted 3 to 8 membered heterocycloalkyl. $R^8$ may be substituted or unsubstituted 3 to 6 membered heterocycloalkyl. $R^8$ may be substituted 3 to 6 membered heterocycloalkyl. $R^8$ may be unsubstituted 3 to 6 membered heterocycloalkyl. $R^8$ may be substituted or unsubstituted 3 membered heterocycloalkyl. $R^8$ may be substituted or unsubstituted 4 membered heterocycloalkyl. $R^8$ may be substituted or unsubstituted 5 membered heterocycloalkyl. $R^8$ may be substituted or unsubstituted 6 membered heterocycloalkyl.

$R^8$ may be $R^{8A}$-substituted or unsubstituted heterocycloalkyl. $R^8$ may be $R^{8A}$-substituted heterocycloalkyl. $R^8$ may be unsubstituted heterocycloalkyl. $R^8$ may be $R^{8A}$-substituted or unsubstituted 3 to 10 membered heterocycloalkyl. $R^8$ may be $R^{8A}$-substituted 3 to 10 membered heterocycloalkyl. $R^8$ may be unsubstituted 3 to 10 membered heterocycloalkyl. $R^8$ may be $R^{8A}$-substituted or unsubstituted 3 to 8 membered heterocycloalkyl. $R^8$ may be $R^{8A}$-substituted 3 to 8 membered heterocycloalkyl. $R^8$ may be unsubstituted 3 to 8 membered heterocycloalkyl. $R^8$ may be $R^{8A}$-substituted or unsubstituted 3 to 6 membered heterocycloalkyl. $R^8$ may be $R^{8A}$-substituted 3 to 6 membered heterocycloalkyl. $R^8$ may be unsubstituted 3 to 6 membered heterocycloalkyl. $R^8$ may be $R^{8A}$-substituted or unsubstituted 3 membered heterocycloalkyl. $R^8$ may be $R^{8A}$-substituted or unsubstituted 4 membered heterocycloalkyl. $R^8$ may be $R^{8A}$-substituted or unsubstituted 5 membered heterocycloalkyl. $R^8$ may be $R^{8A}$-substituted or unsubstituted 6 membered heterocycloalkyl.

$R^8$ may be substituted or unsubstituted aryl. $R^8$ may be substituted aryl. $R^8$ may be unsubstituted aryl. $R^8$ may be substituted or unsubstituted 5 to 10 membered aryl. $R^8$ may be substituted 5 to 10 membered aryl. $R^8$ may be unsubstituted 5 to 10 membered aryl. $R^8$ may be substituted or unsubstituted 5 to 8 membered aryl. $R^8$ may be substituted 5 to 8 membered aryl. $R^8$ may be unsubstituted 5 to 8 membered aryl. $R^8$ may be substituted or unsubstituted 5 or 6 membered aryl. $R^8$ may be substituted 5 or 6 membered aryl. $R^8$ may be unsubstituted 5 or 6 membered aryl. $R^8$ may be substituted or unsubstituted 5 membered aryl. $R^8$ may be substituted or unsubstituted 6 membered aryl (e.g. phenyl).

$R^8$ may be $R^{8A}$-substituted or unsubstituted aryl. $R^8$ may be $R^{8A}$-substituted aryl. $R^8$ may be unsubstituted aryl. $R^8$ may be $R^{8A}$-substituted or unsubstituted 5 to 10 membered aryl. $R^8$ may be $R^{8A}$-substituted 5 to 10 membered aryl. $R^8$ may be unsubstituted 5 to 10 membered aryl. $R^8$ may be $R^{8A}$-substituted or unsubstituted 5 to 8 membered aryl. $R^8$ may be $R^{8A}$-substituted 5 to 8 membered aryl. $R^8$ may be unsubstituted 5 to 8 membered aryl. $R^8$ may be $R^{8A}$-substituted or unsubstituted 5 or 6 membered aryl. $R^8$ may be $R^{8A}$-substituted 5 or 6 membered aryl. $R^8$ may be unsubstituted 5 or 6 membered aryl. $R^8$ may be $R^{8A}$-substituted or unsubstituted 5 membered aryl. $R^8$ may be $R^{8A}$-substituted or unsubstituted 6 membered aryl (e.g. phenyl).

$R^8$ may be substituted or unsubstituted heteroaryl. $R^8$ may be substituted heteroaryl. $R^8$ may be unsubstituted heteroaryl. $R^8$ may be substituted or unsubstituted 5 to 10 membered heteroaryl. $R^8$ may be substituted 5 to 10 membered heteroaryl. $R^8$ may be unsubstituted 5 to 10 membered heteroaryl. $R^8$ may be substituted or unsubstituted 5 to 8 membered heteroaryl. $R^8$ may be substituted 5 to 8 membered heteroaryl. $R^8$ may be unsubstituted 5 to 8 membered heteroaryl. $R^8$ may be substituted or unsubstituted 5 or 6 membered heteroaryl. $R^8$ may be substituted 5 or 6 membered heteroaryl. $R^8$ may be unsubstituted 5 or 6 membered heteroaryl. $R^8$ may be substituted or unsubstituted 5 membered heteroaryl. $R^8$ may be substituted or unsubstituted 6 membered heteroaryl.

$R^8$ may be $R^{8A}$-substituted or unsubstituted heteroaryl. $R^8$ may be $R^{8A}$-substituted heteroaryl. $R^8$ may be unsubstituted heteroaryl. $R^8$ may be $R^{8A}$-substituted or unsubstituted 5 to 10 membered heteroaryl. $R^8$ may be $R^{8A}$-substituted 5 to 10 membered heteroaryl. $R^8$ may be unsubstituted 5 to 10 membered heteroaryl. $R^8$ may be $R^{8A}$-substituted or unsubstituted 5 to 8 membered heteroaryl. $R^8$ may be $R^{8A}$-substituted 5 to 8 membered heteroaryl. $R^8$ may be unsubstituted 5 to 8 membered heteroaryl. $R^8$ may be $R^{8A}$-substituted or unsubstituted 5 or 6 membered heteroaryl. $R^8$ may be $R^{8A}$-substituted 5 or 6 membered heteroaryl. $R^8$ may be unsubstituted 5 or 6 membered heteroaryl. $R^8$ may be $R^{8A}$-substituted or unsubstituted 5 membered heteroaryl. $R^8$ may be $R^{8A}$-substituted or unsubstituted 6 membered heteroaryl.

$R^8$ may be $-O-L^{8A}-R^{8A}$. $L^{8A}$ is substituted or unsubstituted alkylene or substituted or unsubstituted heteroalkylene. $L^{8A}$ may be substituted or unsubstituted alkylene. $L^{8A}$ may be substituted or unsubstituted $C_1$-$C_{20}$ alkylene. $L^{8A}$ may be substituted or unsubstituted $C_1$-$C_{10}$ alkylene. $L^{8A}$ may be substituted or unsubstituted $C_1$-$C_5$ alkylene. $L^{8A}$ may be substituted $C_1$-$C_{20}$ alkylene. $L^{8A}$ may be unsubstituted $C_1$-$C_{20}$ alkylene. $L^{8A}$ may be substituted $C_1$-$C_{10}$ alkylene. $L^{8A}$ may be unsubstituted $C_1$-$C_{10}$ alkylene. $L^{8A}$ may be substituted $C_1$-$C_5$ alkylene. $L^{8A}$ may be unsubstituted $C_1$-$C_5$ alkylene. $L^{8A}$ may be $-(CH_2)_m-R^{8A}$, where m is an integer of 1, 2, 3, 4 or 5.

$L^{8A}$ may be substituted or unsubstituted heteroalkylene. $L^{8A}$ may be substituted heteroalkylene. $L^{8A}$ may be unsubstituted heteroalkylene. $L^{8A}$ may be substituted or unsubstituted 2 to 20 membered heteroalkylene. $L^{8A}$ may be substituted 2 to 20 membered heteroalkylene. $L^{8A}$ may be unsubstituted 2 to 20 membered heteroalkylene. $L^{8A}$ may be substituted or unsubstituted 2 to 10 membered heteroalkylene. $L^{8A}$ may be substituted 2 to 10 membered heteroalkylene. $L^{8A}$ may be unsubstituted 2 to 10 membered heteroalkylene. $L^{8A}$ may be substituted or unsubstituted 2 to 6 membered heteroalkylene. $L^{8A}$ may be substituted 2 to 6 membered heteroalkylene. $L^{8A}$ may be unsubstituted 2 to 6 membered heteroalkylene. $L^{8A}$ may be $-(CH_2CH_2O)_{m1}-R^{8A}$, where m1 is an integer selected from 1, 2, 3, or 4.

$R^8$ may be $-O-L^{8A}-N(R^{8C})-S(O)_{n8}-R^{8A}$, where $R^{8A}$ is as described herein. $R^8$ may be $-O-L^{8A}-N(R^{8C})-S(O)_{n8}-R^{8A}$, where $R^{8A}$ is hydrogen or substituted or unsubstituted alkyl (e.g. $C_1$-$C_5$ alkyl).

$R^{8A}$ is hydrogen, halogen, oxo, $-CF_3$, $-CN$, $-OR^{15}$, $-N(R^{15.1})(R^{15.2})$, $-COOR^{15}$, $-CON(R^{15.1})(R^{15.2})$, $-NO_2$, $-SR^{15}$, $-S(O)_2R^{15}$, $-S(O)_4R^{15}$, $-S(O)_2N(R^{15.1})(R^{15.2})$, $-NHN(R^{15.1})$, $-ON(R^{15.1})(R^{15.2})$, $-NHC(O)NHN(R^{15.1})(R^{15.2})$, $-NHC(O)N(R^{15.1})(R^{15.2})$, $-NHS(O)_2R^{15}$, $-NHC(O)R^{15}$, $-NHC(O)-OR^{15}$, $-NHOR^{15}$, $-OCF_3$, $-OCHF_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^{15}$, $R^{15.1}$, and $R^{15.2}$ are independently hydrogen, halogen, oxo, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

$R^{16}$ is hydrogen, halogen, oxo, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl.

$R^{8C}$ may be hydrogen, halogen, oxo, $-OH$, $-NH_2$, $-COOH$, $-CONH_2$, $-S(O)_2Cl$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl.

$R^8$ may be hydrogen, halogen, $-OR^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ may be $-OR^{8A}$, where $R^{8A}$ is hydrogen, substituted or unsubstituted alkyl, or substituted or unsubstituted heteroalkyl. $R^{8A}$ may be substituted or unsubstituted alkyl, or substituted or unsubstituted heteroalkyl.

$R^{8A}$ may be $-CH_3$, $-C_2H_5$, $-CD_3$, $-CD_2CD_3$, $-(CH_2)_2OH$, $-(CH_2CH_2)_3OH$, $-CH_2C(CH_3)_2OH$, $-(CH_2)_2C(CH_3)_2OH$, $-(CH_2)_2F$, $-(CH_2)_3F$, $-CH_2C(CH_3)_2F$, $-(CH_2)_2C(CH_3)_2F$,

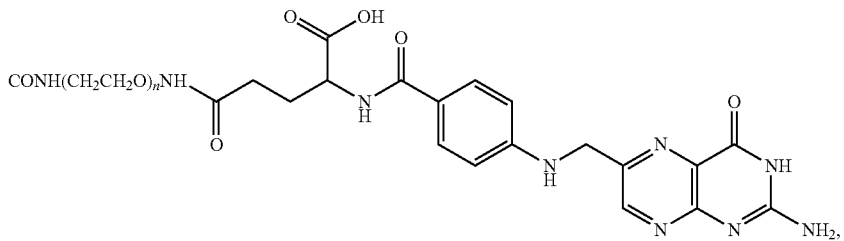

—(CH$_2$CH$_2$O)$_n$CH$_2$CH$_2$-G$^{8A}$, or —CO(CH$_2$)$_2$COO(CH$_2$CH$_2$O)$_n$CH$_2$CH$_2$-G$^{8B}$, where n is 2-20. G$^{8A}$ is H, —OH, —NH$_2$, —OCH$_3$, —OCF$_3$, F, Cl, N$_3$, —NHCH$_2$C$_6$H$_4$NO$_2$, —NHCH$_2$C$_6$H$_4$F, NHCH$_2$C$_6$H$_4$NO$_2$, —NHCH$_2$C$_6$H$_4$F,

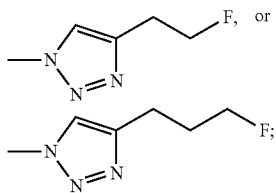

G$^{8B}$ is H, —OH, —NH$_2$, —OCH$_3$, F, Cl,

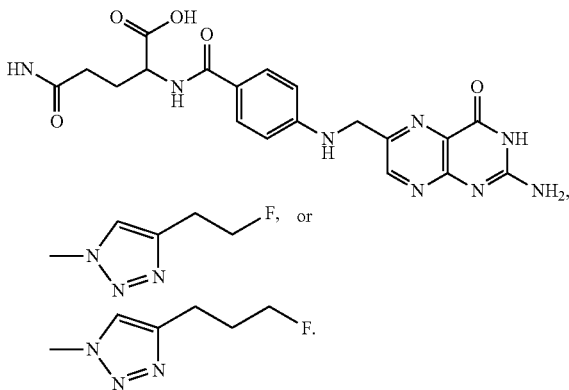

R$^{8A}$ may be —(CH$_2$)$_2$NHSO$_2$CH$_3$, —(CH$_2$)$_2$F, —(CH$_2$)$_3$F, —(CH$_2$CH$_2$O)$_n$F, or —(CH$_2$CH$_2$O)CH$_3$, wherein n is 2 to 5.

R$^{1A}$ and R$^{8A}$ may independently be substituted or unsubstituted alkyl or substituted or unsubstituted heteroalkyl as described herein. R$^{1A}$ may be —O-L$^{1A}$-R$^{1A}$, where L$^{1A}$ is as described herein and R$^{8A}$ may be —O-L$^{8A}$-R$^{8A}$, where L$^{8A}$ is as described herein. L$^{1A}$ may independently be —(CH$_2$)$_m$—R$^{1A}$, and L$^{8A}$ may be —(CH$_2$)$_m$—R$^{8A}$ where R$^{1A}$, R$^{8A}$ and m are as described herein. L$^{1A}$ may be —(CH$_2$CH$_2$O)$_{m1}$—R$^{1A}$, and L$^{8A}$ may be —(CH$_2$CH$_2$O)$_{m1}$—R$^{8A}$, where R$^{1A}$, R$^{8A}$, and m are as described herein. The symbol m may independently be 1, 2, or 3. The symbol m1 may independently be 1, 2, 3, or 4.

R$^{1}$ may be —O-L$^{1A}$-N(R$^{1C}$)—S(O)$_{n1}$—R$^{1A}$ as described herein and R$^{8A}$ may be OR$^{8A}$, where R$^{8A}$ is substituted or unsubstituted alkyl. R$^{1}$ may be —O-L$^{1A}$-N(R$^{1C}$)—S(O)$_{n1}$—R$^{1A}$ as described herein and R$^{8A}$ may be —OR$^{8A}$, where R$^{8A}$ is unsubstituted C$_1$-C$_3$ alkyl.

R$^{9}$ may be hydrogen, halogen, —N$_3$, —CF$_3$, —CCl$_3$, —CBr$_3$, —CI$_3$, —CN, —COR$^{9A}$, —OR$^{9A}$, —NR$^{9A}$R$^{9B}$, —C(O)OR$^{9A}$, —C(O)NR$^{9A}$R$^{9B}$, —NO$_2$, —SR$^{9A}$, —S(O)$_{n9}$R$^{9A}$, —S(O)$_{n9}$OR$^{9A}$, —S(O)$_{n9}$NR$^{9A}$R$^{9B}$, —NHNR$^{9A}$R$^{9B}$, —ONR$^{9A}$R$^{9B}$, or —NHC(O)NHNR$^{9A}$R$^{9B}$. R$^{9}$ may be hydrogen, halogen, —CF$_3$, —OR$^{9A}$, or —NR$^{9A}$R$^{9B}$. R$^{9}$ may hydrogen. R$^{9}$ may be halogen. R$^{9}$ may be —CF$_3$. R$^{9}$ may be —OR$^{9A}$. R$^{9}$ may be —NR$^{9A}$R$^{9B}$.

R$^{9}$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{9}$ may be substituted or unsubstituted alkyl. R$^{9}$ may be unsubstituted alkyl R$^{9}$ may be substituted alkyl. R$^{9}$ may be substituted or unsubstituted C$_1$-C$_{20}$ alkyl. R$^{9}$ may be substituted or unsubstituted C$_1$-C$_{10}$ alkyl. R$^{9}$ may be substituted C$_1$-C$_{10}$ alkyl. R$^{9}$ may be unsubstituted C$_1$-C$_{10}$ alkyl. R$^{9}$ may be C$_1$-C$_5$ substituted or unsubstituted alkyl. R$^{9}$ may be substituted C$_1$-C$_5$ alkyl. R$^{9}$ may be unsubstituted C$_1$-C$_5$ alkyl. R$^{9}$ may be substituted or unsubstituted C$_1$-C$_3$ alkyl. R$^{9}$ may be unsubstituted C$_1$-C$_3$ alkyl. R$^{9}$ may be saturated C$_1$-C$_3$ alkyl. R$^{9}$ may be methyl. R$^{9}$ may be ethyl. R$^{9}$ may be propyl.

R$^{9}$ may be substituted or unsubstituted heteroalkyl. R2 may be substituted heteroalkyl. R$^{9}$ may be unsubstituted alkyl. R$^{9}$ may be substituted or unsubstituted 2 to 10 membered heteroalkyl. R$^{9}$ may be substituted 2 to 10 membered heteroalkyl. R$^{9}$ may be unsubstituted 2 to 10 membered heteroalkyl. R$^{9}$ may be 2 to 6 membered heteroalkyl. R$^{9}$ may be substituted 2 to 6 membered heteroalkyl. R$^{9}$ may be unsubstituted 2 to 6 membered heteroalkyl.

R$^{9}$ may be substituted or unsubstituted 3 to 8 membered cycloalkyl. R$^{9}$ may be substituted 3 to 8 membered cycloalkyl. R$^{9}$ may be unsubstituted 3 to 8 membered cycloalkyl. R$^{9}$ may be substituted or unsubstituted 3 to 6 membered cycloalkyl. R$^{9}$ may be substituted 3 to 6 membered cycloalkyl. R$^{9}$ may be unsubstituted 3 to 6 membered cycloalkyl. R$^{9}$ may be substituted or unsubstituted 3 membered cycloalkyl. R$^{9}$ may be substituted or unsubstituted 4 membered cycloalkyl. R2 may be 5 membered cycloalkyl. R$^{9}$ may be 6 membered cycloalkyl.

R$^{9}$ may be substituted or unsubstituted 3 to 8 membered heterocycloalkyl. R$^{9}$ may be substituted 3 to 8 membered heterocycloalkyl. R$^{9}$ may be unsubstituted 3 to 8 membered heterocycloalkyl. R$^{9}$ may be substituted or unsubstituted 3 to 6 membered heterocycloalkyl. R$^{9}$ may be substituted 3 to 6 membered heterocycloalkyl. R$^{9}$ may be unsubstituted 3 to 6 membered heterocycloalkyl. R$^{9}$ may be substituted or unsubstituted 3 membered heterocycloalkyl. R$^{9}$ may be substituted or unsubstituted 4 membered heterocycloalkyl. R$^{9}$ may be 5 membered heterocycloalkyl. R$^{9}$ may be 6 membered heterocycloalkyl.

$R^9$ may be substituted or unsubstituted 5 to 8 membered aryl. $R^9$ may be substituted 5 to 8 membered aryl. $R^9$ may be unsubstituted 5 to 8 membered aryl. $R^9$ may be substituted or unsubstituted 5 membered aryl. $R^9$ may be substituted 5 membered aryl. $R^9$ may be unsubstituted 5 membered aryl. $R^9$ may be substituted 6 membered aryl. $R^9$ may be unsubstituted 6 membered aryl (e.g. phenyl).

$R^9$ may be substituted or unsubstituted 5 to 8 membered heteroaryl. $R^9$ may be substituted 5 to 8 membered heteroaryl. $R^9$ may be unsubstituted 5 to 8 membered heteroaryl. $R^9$ may be substituted or unsubstituted 5 membered heteroaryl. $R^9$ may be substituted 5 membered aryl. $R^9$ may be unsubstituted 5 membered heteroaryl. $R^9$ may be substituted 6 membered aryl. $R^9$ may be unsubstituted 6 membered heteroaryl.

$R^{1B}$, $R^{2A}$, $R^{2B}$, $R^{3A}$, $R^{3B}$, $R^{4A}$, $R^{4B}$, $R^{5A}$, $R^{5B}$, $R^{7A}$, $R^{7B}$, $R^{8A}$, $R^{8B}$, $R^{9A}$, and $R^{9B}$, may independently be hydrogen, halogen, or substituted or unsubstituted alkyl.

The compound of formula (I) may have the formula:

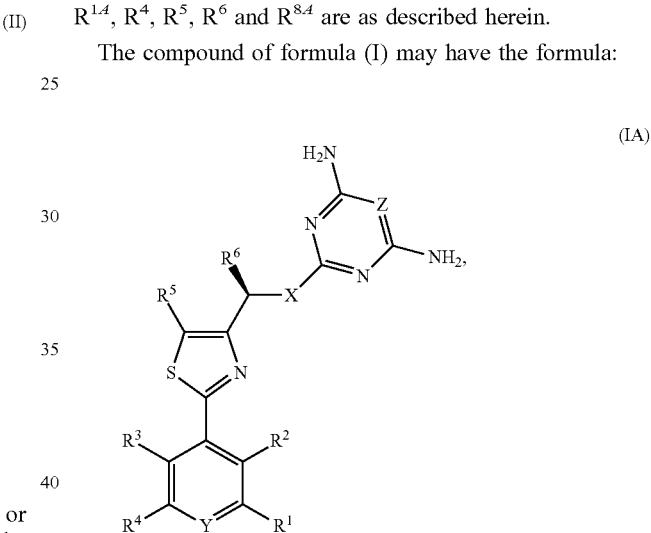

(II)

where $R^1$, $R^4$, $R^5$, $R^6$, Y and X are as described herein.

In the compound of formula (II), $R^4$ may be hydrogen or halogen. In the compound of formula (II), $R^5$ may be substituted or unsubstituted alkyl. $R^5$ may be $C_1$-$C_5$ unsubstituted alkyl. $R^5$ may be methyl. $R^5$ may be ethyl. $R^5$ may be propyl. $R^6$ may be $C_1$-$C_4$ unsubstituted alkyl. $R^6$ may be methyl. $R^6$ may be ethyl. $R^6$ may be propyl.

The compound of formula (I) may have the formula:

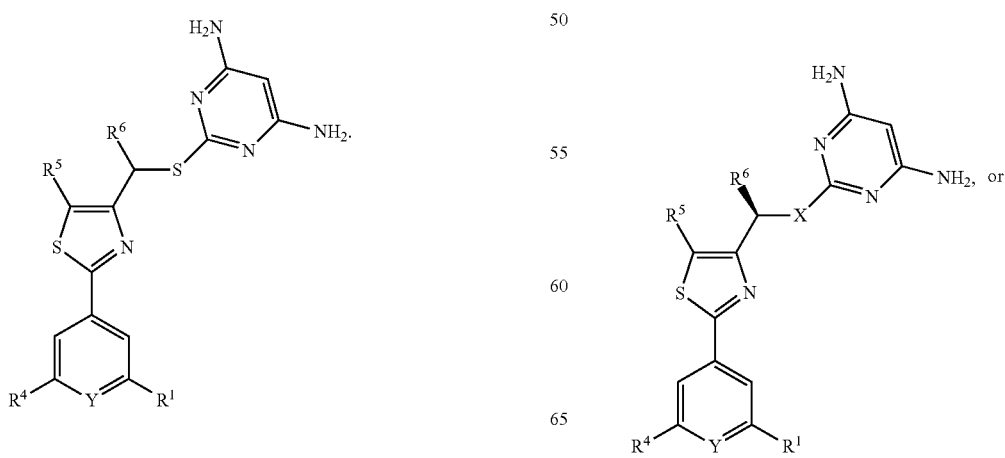

Y, $R^1$, $R^4$, $R^5$, and $R^6$ are as described herein.

The compound of formula (I) may have the formula:

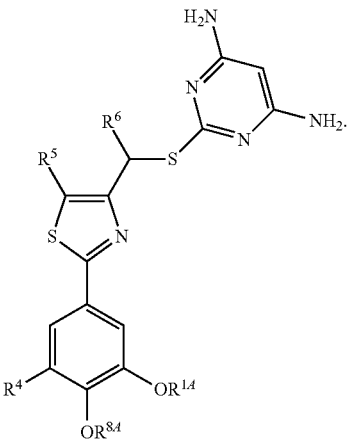

$R^{14}$, $R^4$, $R^5$, $R^6$ and $R^{8A}$ are as described herein.

The compound of formula (I) may have the formula:

(IA)

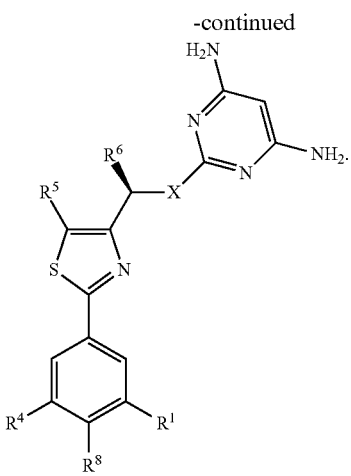

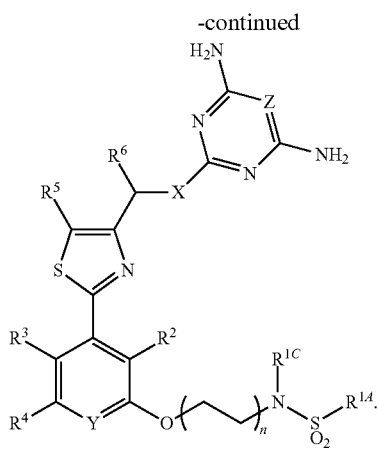

Y, $R^1$, $R^4$, $R^5$, and $R^6$ are as described herein. $R^1$ may be —$OR^{1A}$, wherein $R^{1A}$ is —$OCH_3$, —$OCH_2CH_3$, —$O(CH_2)_2$F, —$(CH_2)_2NHSO_2CH_3$, —$(CH_2CH_2O)_nF$, —$(CH_2CH_2O)_n$$CH_3$, and the symbol n is 2 to 5. $R^4$ may be hydrogen or halogen. $R^5$ may be methyl or propyl. $R^6$ may be methyl. $R^8$ may be —$OR^{8A}$, where $R^{8A}$ may be —$OCH_3$, —$(CH_2)_2$$NHSO_2CH_3$, —$(CH_2)_2F$, $(CH_2)_3F$, —$(CH_2CH_2O)_nF$, or —$(CH_2CH_2O)_nCH_3$, wherein n is 2 to 5.

The compound of formula (I) may have the formula

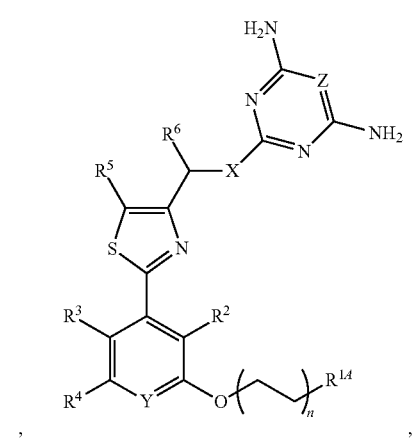

,

X, Y, Z, $R^1$, $R^{1A}$, $R^{1C}$, $R^2$, $R^3$, $R^4$, $R^5$, $R^6$ and $R^{8A}$ are as described herein. The symbol n and m1 may independently be 1, 2, 3, or 4. $R^{1A}$ may be unsubstituted alkyl. $R^{1A}$ may be methyl. $R^{1A}$ may be hydrogen. $R^5$ may be methyl, ethyl, or propyl and $R^6$ may be methyl.

The compound of formula (I) may have the formula

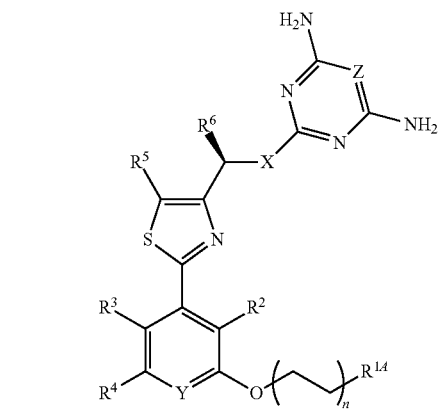

,

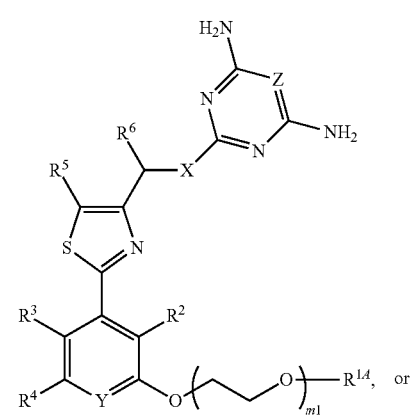

, or

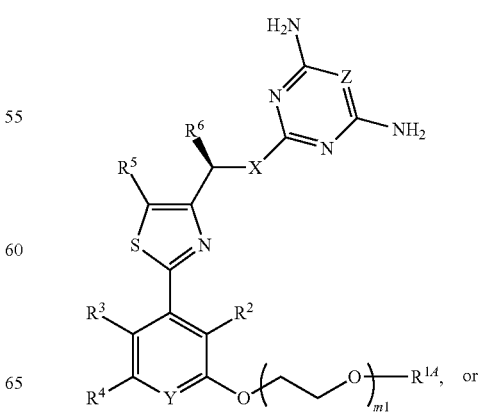

, or

-continued

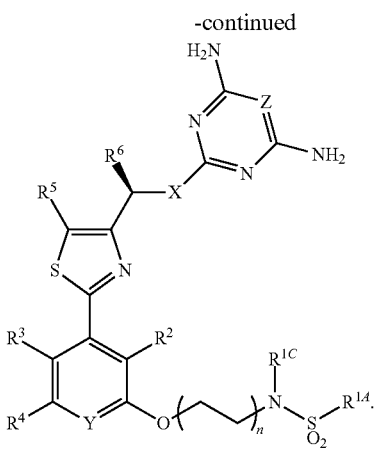

X, Y, Z, $R^1$, $R^{1A}$, $R^{1C}$, $R^2$, $R^3$, $R^4$, $R^5$, $R^6$ and $R^{8A}$ are as described herein. The symbol n and m1 may independently be 1, 2, 3, or 4. $R^{1A}$ may be unsubstituted alkyl. $R^{1A}$ may be methyl. $R^{1A}$ may be hydrogen. $R^5$ may be methyl, ethyl, or propyl and $R^6$ may be methyl.

The compound of formula (I) may have the formula:

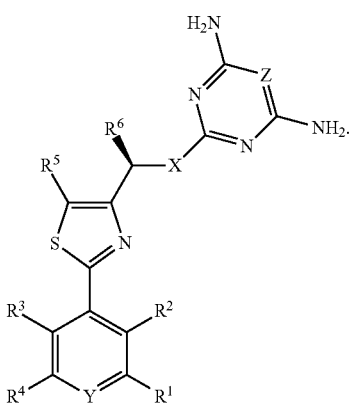

(IA)

The compound of formula (I) may have the formula:

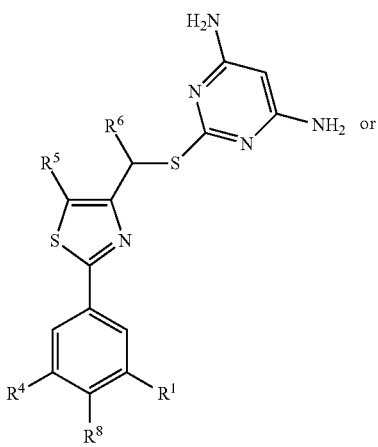

-continued

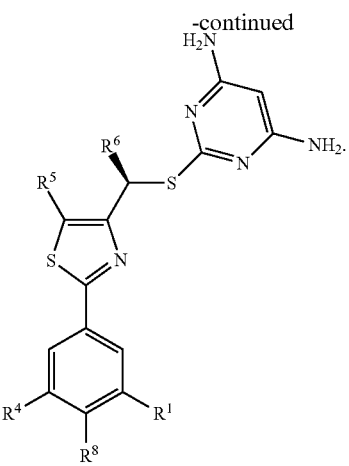

II. Pharmaceutical Compositions

Also provided herein are pharmaceutical formulations. In one aspect is a pharmaceutical composition that includes a compound described herein and a pharmaceutically acceptable excipient.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For the compounds described herein, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity.

The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. Methods of Inhibiting

Further provided herein are methods of inhibiting a deoxycytidine kinase. In one aspect, the method includes contacting a deoxycytidine kinase with an effective amount of the compound described herein thereby inhibiting the deoxycytidine kinase. The contacting may be performed in vitro. The contacting may be performed in vivo.

IV. Methods of Treating

Further provided herein are methods of treating a disease in a subject in need thereof. In one aspect is a method of treating cancer in a subject in need thereof, by administering to the subject an effective amount of a compound described herein.

The cancer may be leukemia or lymphoma. The cancer may be leukemia. The cancer may be acute lymphoblastic leukemia (ALL). The cancer may be lymphoma. The cancer may be a solid tumor cancer. The solid tumor cancer may be characterized by high levels of replication stress as determined by measuring gamma H2A.X expression. The cancer may be ovarian cancer, pancreatic cancer, lung cancer, glioblastoma, hepatocellular carcinoma, breast cancer, triple negative breast cancer, prostate cancer, or head and neck cancer. The cancer may be ovarian cancer. The cancer may be pancreatic cancer. The cancer may be lung cancer. The cancer may be glioblastoma. The cancer may be hepatocellular carcinoma. The cancer may be breast cancer. The cancer may be triple negative breast cancer. The cancer may be prostate cancer. The cancer may be head and neck cancer.

V. Other Aspects

Provided herein, in another aspect, are compositions and methods of treating a disease. The following definitions and embodiments apply to only to the compounds of formula (pI), this section (i.e. section V) and embodiments P1 to P25 listed below.

For purposes of this section, the term "alkyl" refers to and includes linear or branched univalent hydrocarbon structures and combination thereof, which may be fully saturated, mono- or polyunsaturated, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of saturated $C_1$-$C_4$ alkyl include methyl ($CH_3$), ethyl ($C_2H_5$), propyl ($C_3H_7$) and butyl ($C_4H_9$). Examples of saturated $C_1$-$C_6$ alkyl include methyl ($CH_3$), ethyl ($C_2H_5$), propyl ($C_3H_7$), butyl ($C_4H_9$), pentyl ($C_5H_{11}$) and hexyl ($C_6H_{13}$).

An alkyl group may be substituted (i.e., one or more hydrogen atoms are replaced with univalent or divalent radicals) with one more substituents, such as radicals described herein, for example, fluoro, chloro, bromo, iodo, hydroxyl, alkoxy, thio, amino, acylamino, alkoxycarbonylamido, carboxyl, acyl, alkoxycarbonyl, sulfonyl, cycloalkyl, aryl, heterocyclyl and heteroaryl, and other functional groups known in the art. A "perfluoroalkyl" refers to an alkyl group where every hydrogen atom is replaced with a fluorine atom. Examples of saturated $C_1$-$C_6$ perfluroalkyl include trifluoromethyl ($CF_3$), pentafluoroethyl ($C_2F_5$), heptafluoropropyl ($C_3F_7$), nonafluorobutyl ($C_4F_9$), undecafluoropentyl ($C_5F_{11}$) and tridecafluorohexyl ($C_6F_{13}$).

For purposes of this section, the term "cycloalkyl" refers to and includes cyclic univalent hydrocarbon structures, which may be fully saturated, mono- or polyunsaturated, having the number of carbon atoms designated (i.e., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

For purposes of this section, the term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of hetercyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

For purposes of this section, the term "aryl" refers to and includes polyunsaturated aromatic hydrocarbon substituents. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

For purposes of this section, the term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

Cycloalkyl, aryl, heterocyclyl and heteroaryl groups as referred to within this section may also be substituted with one or more substituents, such as radicals detailed herein, for example, fluoro, chloro, bromo, iodo, hydroxyl, alkoxy, thio, amino, acylamino, alkoxycarbonylamido, carboxyl, acyl, alkoxycarbonyl, sulfonyl, alkyl, cycloalkyl, aryl, hetercyclyl and herteroaryl, and other functional groups known in the art.

For purposes of this section, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, such as those known in the art, for example, described in *Remington's Pharmaceutical Sciences* 16th edition, Osol, A. Ed. (1980).

As used in this section, "treatment" or "treating" is an approach for obtaining beneficial or desired results including and preferably clinical results. For example, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used in this section, the phrase "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used in this section, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this section, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used in this section, "in conjunction with" refers to administration of one treatment modality in addition to another treatment modality. As such, "in conjunction with" refers to administration of one treatment modality before, during or after administration of the other treatment modality to the individual.

Unless clearly indicated otherwise, for purposes of this section, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. The aspects described in this section may find use in both human medicine and in the veterinary context.

As used in this section and in the appended embodiments P1-P25, the singular forms "a," "an," and "the" include plural reference unless the context clearly indicates otherwise.

It is understood that aspect and variations of the aspects described in this section include "consisting" and/or "consisting essentially of" aspects and variations.

Methods of Treatment

In another aspect of this section, compounds provided herein bind to a deoxycytidine kinase polypeptide and inhibit its activity. Thus provided in this section are methods for inhibiting dCK activity and treating diseases and disorders where dCK activity is implicated.

Potency of dCK inhibitory activities of the compounds can be tested by measuring cellular substrate uptake and phosphorylation, for examples, uptake of [$^3$H]-deoxycytidine (dCyd or dC) into CEM (human) or L1210 (mouse) cells. The compounds may be further screened for low off-target toxicity (e.g., inhibition of growth and proliferation of dCK negative cells) and selectivity over other nucleoside kinases (e.g., thymidine kinase).

In some embodiments of this section, provided is a method for inhibiting a deoxycytidine kinase (dCK) activity comprising contacting a compound detailed in section V, (e.g., a compound of formula (pI)) with the deoxycytidine kinase, either in vitro (e.g., in an enzymatic or an cell based assay setting) or in vivo (e.g., in animal models or an individual subject in need of treatment).

In some embodiments of this section, provided is a method for treating cancer in an individual comprising administering to the individual an effective amount of a compound detailed in Section V (e.g., a compound of formula (pI)), or a pharmaceutically acceptable salt thereof, and thymidine. The compound is administered in conjunction with thymidine. In some embodiments, the compound is administered before, during or after administration of thymidine. Examples of cancer treated include, but is not limited to leukemia, lymphoma, breast cancer, ovarian cancer, lung cancer, pancreatic cancer, hepatocellular carcinoma, melanoma, sarcoma, head and neck cancer, glioma, glioblastoma, and a cancer independent of tissue of origin that are characterized by genomic instability and/or activation of the DNA damage response. Inhibition of dCK by a compound detailed herein (e.g., a compound of formula (pI)), or a pharmaceutically acceptable salt thereof, synergizes with thymidine to induce cell cycle arrest in tumors.

Without wishing to be bound by theory, in embodiments of this section, pharmacological approaches induce nucleotide insufficiency in highly proliferative tumors in order to block their proliferation by arresting them in the S-phase of cell cycle. For example, deoxycytidine triphosphate (dCTP) pools are depleted by thymidine combined with deoxycytidine kinase (dCK) inhibitors. The function of thymidine is to block the ability of ribonucleotide reductase (RR), the rate limiting enzyme in deoxyribonucleotide synthesis, to produce deoxycytidine triphosphate (dCTP), one of the 4 building blocks of DNA. The only other way of generating dCTP in cancer cells is by recycling preformed deoxycytidine from the extracellular environment; deoxycytidine kinase is essential for the recycling process; small molecule inhibitors that block dCK activity and, in combination with thymidine, starve cancer cells of dCTP, thus preventing their proliferation.

In some embodiments of this section, provided is a method for treating an immune disorder in an individual in need thereof comprising administering to the individual an effective amount of a compound detailed herein (e.g., a compound of formula (pI)), or a pharmaceutically acceptable salt thereof. The immune disorder may be an autoimmune disorder or transplant rejection. In some embodiments of this section, the autoimmune disorder is a T cell mediated autoimmune disorder. In some embodiments of this section, the autoimmune disorder is selected from the group consisting of multiple sclerosis, lupus (including systemic lupus erythematosus), inflammatory bowel disease, rheumatoid arthritis and type 1 diabetes.

Also provided are compositions, such as pharmaceutical compositions, comprising a compound described in this section (e.g. formula (pI)), or a salt thereof, and a pharmaceutically acceptable carrier. Pharmaceutical compositions according to this section may take a form suitable for oral, buccal, parenteral, nasal, topical or rectal administration, or a form suitable for administration by injection, i.v., infusion or inhalation.

The compounds described in this section (e.g., a compound of formula (I)), as well as methods of using the same, unless otherwise stated, include all salt forms of the compounds. Also included all non-salt forms of any salt of a compound described in this section, as well as other salts of any salt of a compound described in this section. In some embodiments of this section, the salts of the compounds are pharmaceutically acceptable salts. The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts. Examples of inorganic salts of base compounds include, but are not limited to, hydrofluoride, hydrochloride, hydrobromide, hydroiodide, sulfate, hydrogen sulfate, phosphate, hydrogen phosphate, dihydrogen phosphate, carbonate, bicarbonate, and nitrate salts. Examples of organic salts of base compounds include, but are not limited to, tartrate, citrate, maleate, fumarate, and succinate.

PET Probe and Imaging

Also provided in this section is a method of imaging, comprising: contacting a PET probe described herein with a biological material; using PET imaging to determine a local concentration of the compound in the biological material; and correlating the local concentration of the compound with a local immune response or the presence of neoplastic tissue. In some embodiments in this section, contacting the compound with a biological material comprises administering a quantity of the compound to an animal or human; and correlating the local concentration of the compound in the animal or human with a local immune response or neoplastic tissue in the animal or human. In some embodiments of this section, the method further comprising using the local concentration of the compound to diagnose cancer and/or monitor cancer treatment. In some embodiments of this section, the animal or human has a condition selected from the group consisting of cancer, an autoimmune disorder, a development disorder, viral infection, bacterial infection, parasitical infection, infection, a metabolic disease, and inflammation. In some embodiments of this section, the animal or human has a condition selected from the group consisting of lymphadenopathy, melanoma, leukemia, and glioma. In some embodiments of this section, the animal or human has a condition selected from the group consisting of rheumatoid arthritis, inflammatory bowel disease, Experimental Autoimmune Encephalomyelitis (EAE), multiple sclerosis, type 1 diabetes, and atherosclerosis. In some embodiments of this section, the animal or human is undergoing a therapy selected from the group consisting of cancer immunotherapy, immunotherapy, interferon therapy, vaccination, radiation therapy, chemotherapy, and antibiotic therapy. In some embodiments of this section, contacting the compound with a biological material comprises administering a quantity of the compound to an animal or human; and correlating the local concentration of the compound in the animal or human with abnormal activity in an organ or portion of the lymphatic system, for example, a lymph node or the spleen. In one variation of the methods of this section, the method further comprises correlating the local concentration of the compound with a lymphoma lesion or a malignant lymphoid disease. In some embodiments of this section, the local immune response is the accumulation of activated T lymphocytes. In one variation of the methods of this section, the activated T lymphocytes take up more compound per cell than non-activated T lymphocytes.

Also provided in this section is a method of predicting resistance to an oncolytic agent, comprising: contacting a PET probe detailed herein with a neoplasm; using PET imaging to determine a local concentration of the compound in the neoplasm; comparing the local concentration of the compound with a baseline level; correlating a local concentration of the compound substantially lower than the baseline level with low dCK expression of the neoplasm; correlating low dCK expression of the neoplasm with oncolytic nucleoside analog resistance, wherein the baseline level corresponds to a measured concentration of the compound in representative neoplastic cells that express dCK, concentration of the compound in representative neoplastic cells that do not express dCK, or a weighted average. In some embodiments in this section, the neoplasm is of the T lymphocyte lineage. In some embodiments in this section, the neoplasm is selected from the group consisting of leukemia, acute non-lymphocytic leukemia, acute lymphocytic leukemia, blast phase of chronic myelocytic leukemia, meningeal leukemia, pancreatic cancer, ovarian cancer, breast cancer, non-small cell lung cancer, B-cell chronic lymphocytic leukemia, hairy cell leukemia, relapsed acute lymphoblastic leukemia, and refractory acute lymphoblastic leukemia cells.

Further provided in this section is a method for examining the use of a compound in a PET process, the method comprising the steps:

a) incorporating a "cold" fluorine 19 atom at a defined position in the compound of a PET probe detailed herein;

b) substituting the "cold" fluorine 19 atom with a "hot" fluorine 18 atom;

c) administering the compound of step (b) to a mammal; and d) detecting and/or quantifying the compound of step (b) throughout the body of the mammal with PET imaging.

In some embodiments of this section, the method further comprises the steps of:

e) building a kinetic model of drug biodistribution in vivo with the PET data; and f) repeating steps (a) through (e) to further modify and improve the PK of compounds identified by PET imaging to have unfavorable biodistribution in mice and/or humans.

Also provided in this section is a method for evaluating efficacy of a dCK inhibitor compound, comprising: administering a dCK inhibitor compound to an individual; providing an $^{18}$F-PET probe to the individual; imaging to determine a local concentration of the $^{18}$F-PET probe; and correlating the local concentration of the $^{18}$F-PET probe with efficacy of the dCK inhibitor compound. In some embodiments of this section, the individual is a mammal, such as an experimental mouse used in an animal model for testing dCK inhibition. The method provides an efficient way of screening for in vivo efficacy of compounds in animal models. The method may be applied to any dCK inhibitors such as the dCK inhibitor compounds detailed herein, or a pharmaceutically acceptable salt thereof.

Certain embodiments of the aspects of this section are further described below. In describing embodiments, specific terminology is employed for the sake of clarity. However, the aspects in this section are not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

As noted above, dCK is a clinically important polypeptide target because of, for example, its role in cellular divisional (e.g. as a rate-limiting enzyme in the deoxyribonucleoside salvage metabolism), as well as its association with drug resistance and/or drug sensitivity. Studies using a dCK knock out mouse model developed by our group indicate that dCK activity is required for the formation of deoxycytidine triphosphate (dCTP), an essential nucleotide used for DNA repair in lymphocytes and in certain types of cancer. Studies also show that dCK may function as a back-up mechanism to produce deoxyribonucleotides (dNTPs) for DNA replication when the output of the main metabolic pathway used by cells to make dNTPs becomes insufficient to support the rapid growth of cancer cells. The instant disclosure illustrates the development of compounds that bind this polypeptide (including small molecule inhibitors).

The compounds that bind dCK including the small molecule inhibitors that are described in this section are useful in variety of contexts, for example as probes in positron emission tomography techniques. In addition, these compounds are useful in the development of new therapeutic agents for certain pathological conditions such as cancer and cell-mediated autoimmune disorders. The small molecule inhibitors of dCK disclosed herein are also useful in processes designed to study nucleic acid metabolism in normal and malignant tissues. Such processes can be used for example to assist the development of new therapies for cancer and autoimmune disorders that work by selectively interfering with the ability of rapidly proliferating pathogenic cells to repair and replicate their DNA.

One illustrative strategy used to develop the dCK inhibitors described in this section takes advantage of the Positron Emission Tomography (PET) technologies. In this context, illustrative therapeutic candidate compounds have been designed to readily incorporate a fluorine 19 atom. The fluorine 19 atom included in the scaffold of the compounds disclosed herein can then easily be replaced by a fluorine 18 radioisotope in order to generate a radiolabeled version of the compound, one that can be detected and quantified non-invasively throughout the body of living organisms using PET imaging techniques. By using compounds designed in this way (e.g. to take advantage of PET imaging techniques), artisans can then use of a variety of non-invasive pharmacokinetic (PK) techniques to study the therapeutic potential of these compounds (e.g. in animal models). This strategy is generally applicable in drug research and development and can accelerate this process while reducing its costs (e.g. by enabling rapid identification of therapeutic candidates with optimal PK properties).

As noted above, the small molecule dCK inhibitors disclosed in this section have been designed to be readily amenable to one-step fluorine 18 radiolabeling for PET imaging studies of drug PK in animal models and in humans. This design provides these compounds with a significant advantage over chemically distinct small molecule dCK inhibitors that require multiple steps for radiolabeling. An important additional element is provided by the FAC series of PET imaging probes which are described in U.S. patent application Ser. No. 12/234,478, the contents of which are incorporated by reference. These FAC probes enable artisans to non-invasively characterize the pharmacodynamic (PD) properties of the candidate therapeutic compounds in a variety of animal species (e.g. mice and humans).

As noted above, the compounds described in this section provide small molecule inhibitors of deoxycytidine kinase (dCK), a rate-limiting enzyme in the deoxyribonucleoside salvage metabolism. We developed and validated PET probes to measure dCK activity in vivo (see, e.g. Nat. Med. 2008 July; 14(7):783-8; JNM. 2010 July; 51(7):1092-8). Consequently, these validated PET probes can be used as pharmacodynamic biomarkers to validate the efficacy of the new dCK binding compounds disclosed herein.

As noted, in certain embodiments of the compounds of this section are used as probes in imaging techniques designed to monitor one or more aspects cellular physiology. In this context, embodiments of this section can be used, for example, to monitor immune function throughout the body, a monitoring technique that may significantly impact the diagnosis and treatment evaluation of immunological disorders. In certain embodiments of this section, a compound is used as a PET probe in a process for imaging one or more features of a biological material as part of a diagnostic or therapeutic technique. For example, the PET probe can be used in the diagnosis and treatment of a condition selected from the group consisting of rheumatoid arthritis, inflammatory bowel disease, type 1 diabetes, EAE (Experimental Autoimmune Encephalomyelitis), multiple sclerosis, atherosclerosis, an autoimmune disorder, and cancer. In addition, the PET probe can be used to evaluate the efficacy in the treatment of cancer of anticancer agents that are taken up into cells via nucleoside transporters and deoxycytidine kinase (dCK)-mediated phosphorylation. As evident to one of ordinary skill in the art, in addition to the compound, the compositions of this section can include one or more pharmaceutically acceptable carriers and/or excipients. One of ordinary skill in the art will be able to selection appropriate pharmaceutically acceptable carriers and/or excipients based on the envisioned application.

Illustrative methods of imaging according to the aspects described in this section typically include one or more of the following steps. A PET probe can be contacted with biological material. PET imaging can then be used to determine a local concentration of the PET probe in the biological material. And the local concentration of the PET probe can then be correlated with localized nucleotide metabolism, for example, the accumulation of activated T lymphocytes (e.g. as activated T lymphocytes take up more PET probe per cell than non-activated T lymphocytes). In this manner, PET imaging can be used to determine a local concentration of the PET probe administered to an animal or a human, and the local concentration of the PET probe can then be correlated with aspects of nucleotide metabolism, for example, with a local immune response or abnormal cell growth. For example, the local concentration of the PET probe can be correlated with abnormal cellular activity in an organ or portion of the lymphatic system, for example, in a lymph node or in the spleen. Similarly, the local concentration of the PET probe can be correlated with a lymphoma lesion or with a malignant lymphoid disease.

The animal or human in which a compound disclosed herein is used can, for example, have a condition such as cancer, lymphadenopathy, melanoma, leukemia, glioma, an autoimmune disorder, a development disorder, viral infection, bacterial infection, parasitical infection, infection, a metabolic disease, inflammation, rheumatoid arthritis, inflammatory bowel disease, type 1 diabetes, Experimental Autoimmune Encephalomyelitis (EAE), multiple sclerosis, and/or atherosclerosis. In such contexts, the PET probe can be used in procedure for the diagnosis and/or treatment of such a condition. For example, the animal or human can be undergoing a therapy such as cancer immunotherapy, immunotherapy, interferon therapy, vaccination, radiation therapy, chemotherapy, and/or antibiotic therapy. In an illustrative embodiment of this section, the local concentration of the PET probe can be used to diagnose cancer and/or monitor cancer treatment.

In a specific illustrative embodiment of this section, lymphocyte activation can be non-invasively monitored by injecting a subject animal or human with a trace amount of an PET probe disclosed herein, allowing the probe to accumulate at sites of local immune activation and then monitoring the subject at a whole body level using a PET scanner. Such a PET probe can be administered to an animal or a human for diagnostic purposes such as to determine the presence or extent of a disease or disorder (e.g., cancer, autoimmune disease, developmental disorder, viral infection, bacterial infection, parasitical infection, other infections, metabolic disease, or inflammation). In embodiments of this section, the PET probe can be administered to monitor the progress of cancer or other disease-based types of immunotherapy, interferon therapy, vaccination, radiation therapy, and antibiotic therapy.

Embodiments of this section further provide methods of evaluating the usage efficacy of particular classes of anti-cancer agents in the treatment of cancer such as those that are taken up into cells via nucleoside transporters and deoxycytidine kinase (dCK)-mediated phosphorylation. For example, the PET probe can be used to evaluate the efficacy in the treatment of cancer of an anticancer agent, e.g., cytarabine or 2'-difluorodeoxycytidine, that is taken up into cells via nucleoside transporters and deoxycytidine kinase (dCK)-mediated phosphorylation. An additional aspect of this section relates to methods of diagnosis and treatment of conditions that implicate cells with high deoxyribonucleoside salvage pathway activity, e.g., lymphocytes, bone marrow cells, and intestinal enterocytes. In another aspect of this section are compositions incorporating the compounds disclosed herein. In still another aspect of this section are kits comprising any embodiment of this section.

Other embodiments of this section include articles of manufacture and/or kits, for example those containing materials useful in diagnostic imaging techniques. Alternatively, the articles of manufacture and/or kits of this section can contain materials useful in treating a pathological condition such as an immune disorder or a cancer. In typical embodiments of this section, the kit comprises at least one container, typically with a label. Suitable containers include, for example, blister packs, bottles, vials, and test tubes. The containers may be formed from a variety of materials such as metal (e.g., a metal foil), glass or plastic. In some embodiments of this section, the one or more containers holds one or more compositions having an active agent which is effective in diagnostic imaging techniques. In other embodiments of this section, the one or more containers holds one or more compositions having an active agent which is effective in treating a pathological condition such as an immune disorder or a cancer. In certain embodiments of this section, an active agent in the composition is a dCK binding compound as disclosed herein. In some embodiments of this section, the kit comprises a composition including a dCK binding compound as described in this section and thymidine (e.g. in a combined formulation or "cocktail"). In some embodiments of this section the kit comprises a first composition including a dCK binding compound in a first container, and a second composition including thymidine in a second container. Typically, the label on the one or more containers indicates that the one or more compositions is used for diagnostic imaging techniques or in treating a pathological condition such as an immune disorder and/or a cancer. Such labels may also indicate directions for either in vivo or in vitro use, such as those described herein. The kits of this section can also comprise the one or more containers described above and a further container comprising a buffer. Kits of this section may further include other materials desirable from a commercial and user standpoint, including other buffers, diluents, filters, needles, syringes, and package inserts with instructions for use.

The present section also provides a research tool comprising a compound of this section for studying nucleic acid metabolism in normal and malignant tissues. In certain embodiments of this section, a FAC series of PET imaging probes, as described in U.S. patent application Ser. No. 12/234,478, which is incorporated herein by reference, are used to non-invasively determine the pharmacodynamic (PD) properties of the therapeutic candidates in mice, other animal species and in humans.

In certain embodiments of this section, a composition of matter comprising a compound disclosed herein may be used as a therapeutic agent for cancer. In other embodiments of this section, the composition of matter is used as a therapeutic agent for autoimmune disorders. In some instances, the composition of matter may be used as a therapeutic agent for cancer and/or autoimmune disorders by binding dCK in a manner that selectively interferes with the ability of rapidly proliferating pathogenic cells to repair and replicate their DNA. Typically the therapeutic agents used in the methods of this section combined with at pharmaceutically acceptable carrier. The term "pharmaceutically acceptable carrier" is used in this section is used according to its art accepted meaning and is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of this section. Supplementary active compounds can also be incorporated into the compositions. A pharmaceutical composition of this section is formulated to be compatible with its intended route of administration.

Examples herein provide further disclosure on aspects and embodiments of this section.

Although the foregoing section has been described in some detail by way of illustration and example for purposes of clarity of understanding, it is apparent to those skilled in the art that certain minor changes and modifications will be practiced in light of the above teaching. Therefore, the description and examples should not be construed as limiting the scope of any invention described herein.

All references cited herein, including patent applications and publications, are hereby incorporated by reference in their entirety.

VI. Examples

1. Example 1

Deoxycytidine kinase (dCK) is a deoxyribonucleoside kinase capable of phosphorylating deoxycytidine, deoxyadenosine, and deoxyguanosine to their monophosphate forms using either ATP or UTP as phosphoryl donors.[1] Phosphorylation by dCK is the rate-limiting step in the biochemical pathway responsible for converting salvaged deoxycytidine into dCTP and, in certain cell types into dTTP, making them substrates for DNA polymerases. Apart from the physiological role of generating dNTPs, dCK plays a crucial role in activating multiple nucleoside analog prodrugs ('nucs') that are widely used in anticancer.[2] Recently, dCK was identified in hematopoiesis in lymphoid and erythroid progenitors. The kinase has also been implicated in regulating the G2/M transition in response to DNA damage in cancer cells.[6] More recently we have shown that partial inhibition of dCK activity combined with perturbations of nucleotide de novo synthesis pathways was synthetically lethal to acute lymphoblastic leukemia cells, but not to normal hematopoietic cells.[7] These aspects of dCK's biology and its potential role as a new therapeutic target in cancer prompted us to develop small molecule inhibitors of its enzymatic activity.

Hit compounds from a high throughput screen were developed, and subsequent optimization of the molecules to lead to compounds Ia and Ib.[8] That work detailed the structure-activity relationship (SAR) of the compounds, that is, the relationship between the structure of the small molecules and their inhibition potency. Lacking a crystal structure of the complex between the enzyme target and the small molecule, traditional SAR studies confront incomplete understanding as to the observed differences in inhibition potency between related molecules. This makes it challenging to confidently identify sites on the previously identified hits that can be modified in order to gain binding affinity and/or increase metabolic stability. Lead compounds Ia and Ib can be divided into 4 distinct structural parts (FIG. 1A). Part A is the pyrimidine ring, which is connected by a linker (part B) to a 5-substituted-thiazole ring (part C), which in turn is connected to a phenyl ring (part D). Conceptually, each of these parts can be modified to attain desired 'drug-like' properties. In previous work we focused on the thiazole ring, and the crystal structure of dCK with one of the early compounds suggested that the ring 5-position could accommodate hydrophobic substituents, which lead to the discovery that a propyl group at the 5-position is strongly favored over a methyl group.[8, 9]

To guide and rationalize the medicinal chemistry efforts in other parts of the molecule, we solved the crystal structures of human dCK with several of the inhibitors we developed. The crystal structures illuminate the relationship between the enzyme structure, the small molecule structure, and its inhibition potency. This effort ultimately resulted in lead compounds Ia and Ib. Unfortunately, despite nanomolar affinity for dCK of our lead compounds, when tested in a liver microsomal assay these compounds exhibited low metabolic stability. This shortcoming was recapitulated by pharmacokinetic studies in mice.[8, 7]

To identify inhibitors with improved in vivo properties, we set out to explore additional chemical modifications, specifically those that maintain the low nanomolar binding affinity of the lead compounds. Crystal structures of chiral compounds described herein bound to dCK played a key role in elucidating the chirality of the active form of the inhibitor. By combining organic chemistry intuition with detailed structural information of the target-inhibitor complex we have identified a lead compound that retains the nanomolar affinity for dCK but has gained significant in vivo metabolic stability. This compound could play a vital role in any therapeutic strategy based on induction of DNA replication stress overload by perturbing a cancer cell's dNTP pools.

Figure 9B:
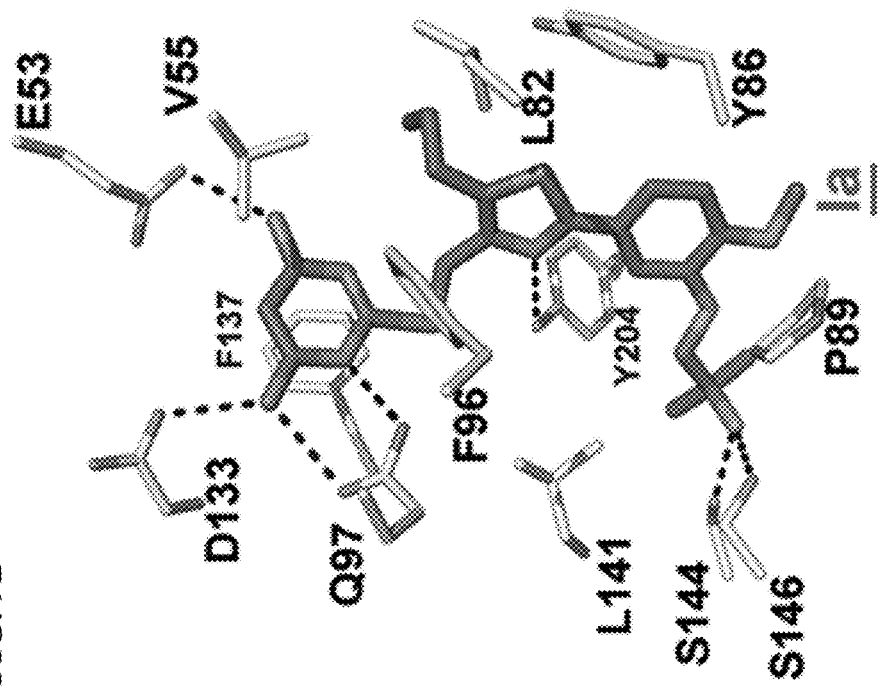
FIGS. 9A-9B. Binding of Ia to human dCK.
Figure 9A:
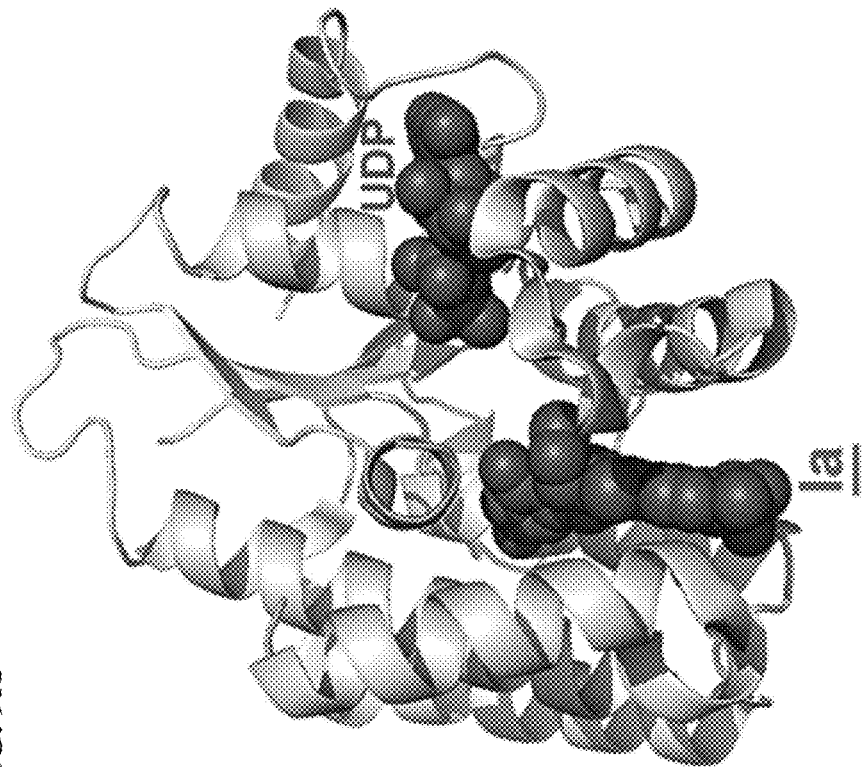

The pyrimidine ring (part A of the molecules, FIG. 1A) was predicted to be the difficult part of the molecule to improve. This is because, as observed in the crystal structures of dCK in complex with lead compounds Ia and Ib (PDB codes 4L5B and 4KCG, respectively) the inhibitor's pyrimidine ring binds to dCK at a position nearly identical to that adopted by the pyrimidine ring of the physiological substrate dC, making several hydrogen bond, hydrophobic, and π-π stacking interactions (FIGS. 9A-9B). This binding mode suggested an already optimized enzyme-pyrimidine ring interaction. For compounds Ia and Ib, both pyrimidine ring exocyclic amino groups formed hydrogen-bonding interactions with side chains of Glu53, Gln97 and Asp133. Hence, not surprising, simultaneous removal of both amino groups resulted in complete loss of dCK inhibition.[8] In contrast, removal of a single amino group to generate compound 1 (FIG. 9A), which is identical to Ia except for a having a single exocyclic amino group in the pyrimidine ring (FIG. 1A), resulted in similarly tight binding affinity as measured for Ib (FIGS. 1B & 2B). To explain how the affinity of 1 for dCK is maintained with only a single exocyclic amino group we sought the crystal structure of the complex but unfortunately we were unable to obtain diffraction quality crystals. Without being bound by any particular theory, we speculate that the sole exocyclic amino group present in compound 1 is oriented in the dCK active site such that it maintains its interaction with Asp133, since only in that orientation can the neighboring pyrimidine ring N-atom maintain its interaction with the side chain of Gln97 (FIGS. 9A-9B). The interaction with Glu53 made by an exocyclic amino group, when present, likely provides only moderate additional binding energy. While a single exocyclic pyrimidine ring amino group is sufficient for a tight interaction with dCK, in our CEM cell-based assay compound 1 exhibited a much-increased $IC_{50}$ value (21.8 nM, FIG. 2B) relative to compound Ib (4.9 nM, FIG. 1B). This result showcases the importance of evaluating the interaction between an inhibitor and its target both in using an enzymatic in vitro assay and a cell-based assay. Due to the reduced inhibition of dCK activity of 1 in the cell-based assay, all future compounds contained the two exocyclic amino groups.

We examined if the position of the pyrimidine ring N-atoms is important by synthesizing compound 2 (FIG. 2A). This compound was measured to bind with ~50-fold higher $IC_{50}^{app}$ relative to the very similar lead compound Ia (FIG. 1A), which only differ in the position of one pyrimidine ring nitrogen atom. We solved the 2.0 Å resolution crystal structure of the dCK-compound 2 complex to understand how this subtle change so drastically impacted the interaction with the enzyme (see Table 1 for the data collection and refinement statistics).

All of the examined compounds bind to the open state of the enzyme, which is also the catalytically incompetent state (for a discussion about the open and closed states of dCK see[10, 11]). Inhibitors bind within a deep cavity, with the pyrimidine ring of the inhibitors positioned deepest and occupying the same position occupied by the pyrimidine ring of the nucleoside substrate.[8, 9] While preventing the binding of the nucleoside substrate, our inhibitors do not interfere with binding of nucleotide to the phosphoryl donor-binding site. In fact, all crystal structures of dCK in complex with inhibitors also contained UDP at the donor site.

Figure 10:
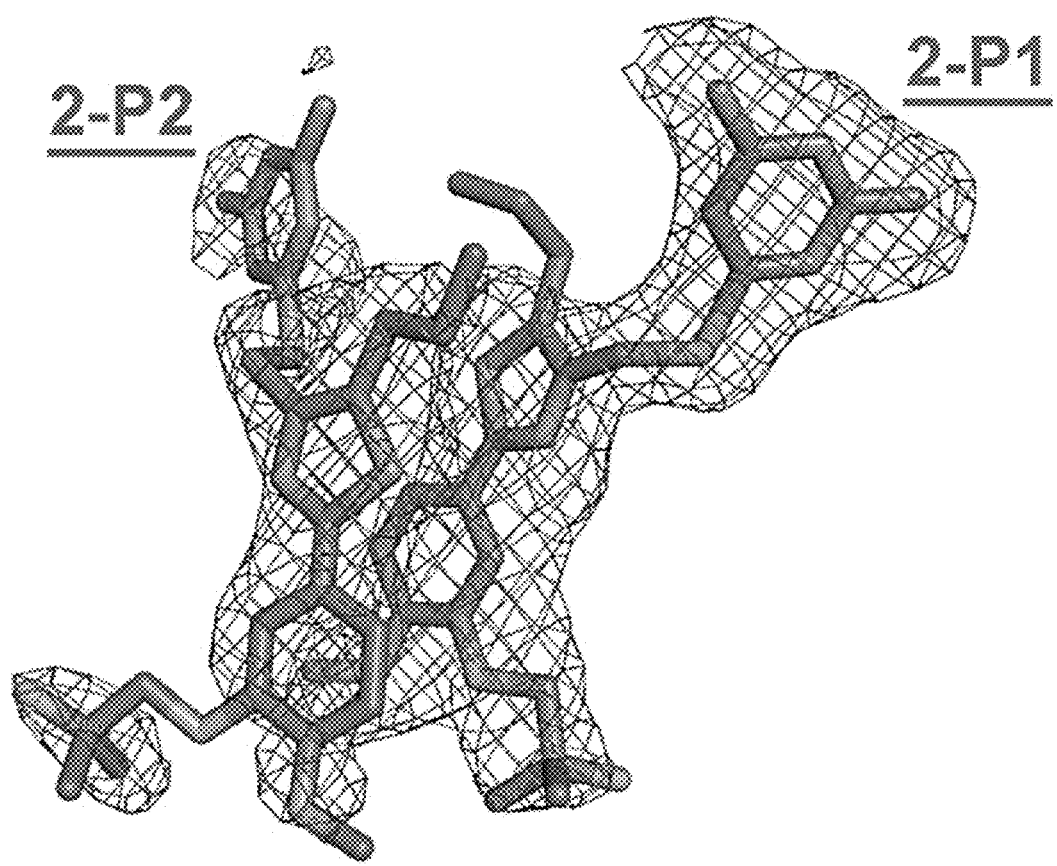
FIG. 10. Fo-Fc map contoured at 3 sigma around compound 2 from protomer A. Compound 2 was removed from the model that then underwent several rounds of refinement to eliminate model bias. This inhibitor binds as two molecules at the active site of dCK at Position-1 and -2 and labeled 2-P1 and 2-P2 respectively.

Despite significantly different $IC_{50}^{app}$ values between compound Ia (14.5 nM) and compound 2 (754 nM), the pyrimidine ring of these related molecules interacts with the enzyme via similar hydrophobic and polar interactions. The latter include Glu53, Gln97 and Asp133. However, the entire molecule 2 is displaced about 0.4 Å away from the floor of the binding cavity relative to compound Ia. (FIG. 2C and FIG. 10). The crystal structure suggests that the factor responsible for this shift is the recruitment of a water molecule (orange sphere, FIG. 2C) by the pyrimidine ring N-present in compound 2. In contrast, for compound Ia the CH-group in this position eliminates the potential for a hydrogen bond. This water molecule is also held in place through interactions with Arg104 and Asp133. Hence, despite forming this additional water-mediated interaction with the enzyme, the displacement away from the enzyme caused by allowing the water molecule to bind at that position ultimately reduces the binding affinity of 2.

Based on these results, we decided to maintain the original structure of the pyrimidine ring and to focus on the other parts of the molecule as potential modification sites. We examined the effect of various substituents at different phenyl group positions (part D of the molecule, FIG. 1A).

TABLE 1

Data collection and refinement statistics

| | Complex | | | |
|---|---|---|---|---|
| PDB codes | 2<br>4Q18 | 3<br>4Q19 | 4<br>4Q1A | 5<br>4Q1B |
| Data collection statistics | | | | |
| X-ray source and detector | LS-CAT ID-G<br>MARCCD 300 | LS-CAT ID-G<br>MARCCD 300 | LS-CAT ID-G<br>MARCCD 300 | LS-CAT ID-G<br>MARCCD 300 |
| Wavelength (Å) | 0.9785 | 0.9785 | 0.9785 | 0.9785 |
| Temperature (K) | 100 | 100 | 100 | 100 |
| Resolution$^a$ (Å) | 2.0<br>(2.1-2.0) | 2.09<br>(2.21-2.09) | 1.90<br>(2.01-1.90) | 2.15<br>(2.28-2.15) |
| Number of Reflections | | | | |
| Observed | 194185 | 201554 | 273877 | 191219 |
| Unique | 38119 | 32496 | 43643 | 30472 |
| Completeness (%) | 99.4 (99.9) | 98.8 (93.9) | 99.3 (98.4) | 98.3 (97.4) |
| $R_{sym}$ (%) | 5.9 (54.7) | 7.3 (67.9) | 4.4 (62.9) | 5.2 (55.2) |
| Average I/σ(I) | 13.6 (2.7) | 14.2 (2.5) | 20.64 (2.54) | 17.42 (2.87) |
| Space group | $P4_1$ | $P4_1$ | $P4_1$ | $P4_1$ |
| Unit cell (Å): a = b, c | 68.75, 122.45 | 68.53, 119.79 | 68.66, 120.36 | 68.97, 121.94 |

TABLE 1-continued

Data collection and refinement statistics

Refinement statistics

| | | | | |
|---|---|---|---|---|
| Refinement program | Refmac5 | Refmac5 | Refmac5 | Refmac5 |
| Twinning fraction | 0.5 | 0.5 | 0.5 | 0.5 |
| Rcryst (%) | 18.3 | 22.9 | 20.2 | 17.3 |
| Rfree (%) | 21.6 | 26.1 | 25.0 | 25.3 |
| Resolution range (Å) | 30.0-2.0 | 30-2.09 | 30-1.9 | 30-2.15 |
| Protein molecules per a.u. | 2 | 2 | 2 | 2 |
| Number of atoms: | | | | |
| Protein (protA, protB) | 1921, 1902 | 1877, 1889 | 1890, 1904 | 1877, 1873 |
| Water molecules | 88 | 103 | 105 | 92 |
| Inhibitor | 32 × 4 | 27 × 2 | 30 × 2 | 32 × 2 |
| UDP | 25 × 2 | 25 × 2 | 25 × 2 | 25 × 2 |
| R.m.s. deviation from ideal: | | | | |
| Bond length (Å) | 0.012 | 0.013 | 0.011 | 0.012 |
| Bond angles (°) | 1.66 | 1.84 | 1.65 | 1.70 |
| Average B-factors (Å$^2$) | | | | |
| Protein (protA, protB) | 47.0, 46.9 | 30.1, 30.1 | 40.6, 40.7 | 53.8, 54.6 |
| Water molecules | 39.8 | 29.8 | 39.3 | 45.4 |
| Inhibitor | | | | |
| protA (301, 302) | 46.6, 45.8 | 29.9, — | 39.7, — | 58.7, — |
| protB (301, 302) | 53.4, 41.2 | 30.0, — | 40.1, — | 58.3, — |
| UDP (protA, protB) | 51.6, 49.0 | 30.1, 30.3 | 41.4, 39.9 | 58.4, 58.5 |
| Ramachandran plot (%): | | | | |
| most favored regions | 90.0 | 88.7 | 91.9 | 87.3 |
| additionally allowed regions | 9.5 | 10.8 | 7.6 | 12.3 |
| generously allowed/disallowed regions | 0.5 | 0.5 | 0.5 | 0.4 |

| | Complex | | | |
|---|---|---|---|---|
| | 6 | 7 | 8 | 10R |
| PDB codes | 4Q1C | 4Q1D | 4Q1E | 4Q1F |
| Data collection statistics | | | | |
| X-ray source and detector | LS-CAT ID-G MARCCD 300 | Rigaku RU-200 R-AXIS IV++ | Rigaku RU-200 R-AXIS IV++ | Rigaku RU-200 R-AXIS IV++ |
| Wavelength (Å) | 0.9785 | 1.5418 | 1.5418 | 1.5418 |
| Temperature (K) | 100 | 93 | 93 | 93 |
| Resolution$^a$ (Å) | 2.0 (2.12-2.00) | 2.0 (2.12-2.00) | 1.85 (1.96-1.85) | 2.1 (2.23-2.10) |
| Number of Reflections | | | | |
| Observed | 194108 | 144843 | 158177 | 175767 |
| Unique | 36902 | 37712 | 46762 | 32727 |
| Completeness (%) | 98.8 (96.1) | 99.5 (98.5) | 96.9 (82.8) | 99.5 (98.7) |
| $R_{sym}$ (%) | 5.1 (71.6) | 3.3 (67.1) | 2.8 (40.4) | 4.3 (75.6) |
| Average I/σ(I) | 16.57 (2.04) | 19.38 (1.79) | 21.62 (1.99) | 21.66 (2.12) |
| Space group | P4$_1$ | P4$_1$ | P4$_1$ | P4$_1$ |
| Unit cell (Å): a = b, c | 68.66, 119.27 | 68.73, 120.62 | 68.74, 122.20 | 68.78, 121.28 |
| Refinement statistics | | | | |
| Refinement program | Refmac5 | Refmac5 | Refmac5 | Phenix 1.8.4 |
| Twinning fraction | 0.5 | 0.5 | 0.5 | 0.5 |
| Rcryst (%) | 20.5 | 19.1 | 17.4 | 20.3 |
| Rfree (%) | 23.8 | 25.3 | 21.8 | 23.1 |
| Resolution range (Å) | 30-2.0 | 30-2.0 | 30-1.85 | 30-2.1 |
| Protein molecules per a.u. | 2 | 2 | 2 | 2 |
| Number of atoms: | | | | |
| Protein (protA, protB) | 1897, 1870 | 1890, 1842 | 1905, 1904 | 1897, 1897 |
| Water molecules | 109 | 92 | 185 | 170 |
| Inhibitor | 32 × 2 | 31 × 2 | 29 × 4 | 33 × 2 |
| UDP | 25 × 2 | 25 × 2 | 25 × 2 | 25 × 2 |
| R.m.s. deviation from ideal: | | | | |
| Bond length (Å) | 0.012 | 0.011 | 0.013 | 0.006 |
| Bond angles (°) | 1.72 | 1.68 | 1.67 | 1.03 |

TABLE 1-continued

| Data collection and refinement statistics | | | | |
|---|---|---|---|---|
| Average B-factors (Å$^2$) | | | | |
| Protein (protA, protB) | 29.5, 29.5 | 51.8, 51.8 | 37.6, 39.2 | 47.8, 48.7 |
| Water molecules | 29.3 | 46.8 | 38.4 | 44.2 |
| Inhibitor | | | | |
| protA (301, 302) | 29.4, — | 55.8, — | 43.1, 44.5 | 47.3, — |
| protB (301, 302) | 29.5, — | 52.8, — | 40.0, 48.5 | 54.5, — |
| UDP (protA, protB) | 29.6, 29.5 | 53.3, 53.6 | 38.5, 39.4 | 49.8, 51.2 |
| Ramachandran plot (%): | | | | |
| most favored regions | 91.6 | 89.2 | 90.3 | 88.6 |
| additionally allowed regions | 8.4 | 10.3 | 9.2 | 10.9 |
| generously allowed/disallowed regions | 0.5 | 0.5 | 0.5 | 0.5 |

[a]High resolution shells in parentheses

A compound with no phenyl ring substituents but otherwise identical to compound Ia showed modest potency in our CEM cell based assay ($IC_{50}$ 37 nM[8]). Adding a hydroxyl group at the meta position decreased the $IC_{50}$ in that assay by about half (compound 3, previously compound 31[3], FIGS. 3A-3C). Adding a longer hydroxyethoxy group at that position (compound 4, previously compound 32[3]), yielded an $IC_{50}$ of ~1 nM (FIGS. 3A-3C). Primary hydroxyls as in 4 are prone to oxidation or glucuronidation,[12] but these studies do inform us as to the importance of the type of substituent at the phenyl meta position.

To understand the difference in affinities to dCK between compounds 3 and 4, we determined the structures of dCK in complex with these molecules, solved at 2.09 Å and 1.9 Å resolution, respectively (Table 1). The structures reveal that the hydroxyethoxy group as present in compound 4 interacts with the side chains of Ser144 and Ser146, whereas the hydroxyl group at the same position in compound 3 is too far to make any inhibitor-enzyme interactions (FIG. 3C and FIGS. 11A-11B). We attribute this added interaction for the superior binding of compound 4 versus compound 3.

In terms of the importance of substituents at the phenyl meta position, it is clear that having none or a short one such as a hydroxyl (compound 3) diminishes the interaction with dCK. On the other hand, the binding affinity measured by both the in vitro kinetic assay and by the cell-based CEM assay of larger substituents—as present in compounds Ia, Ib, and 4—are comparable. Previous crystal structures of dCK in complex with compound Ia (PDB ID 4L5B) and Ib (PDB ID 4KCG) also show an interaction between the substituent at the phenyl meta position and the enzyme—this time to Ser144. Additional side chains such as 2-fluoroethoxy poly (ethylene glycol) (n=2) $(PEG)_2$ (S16, S17, S19), 2-hydroxyethyl $(PEG)_2$ (S11), 2-methoxyethyl $(PEG)_2$ (S20, S22-23, S25-28, S29), and 2-(4,6-diaminopyrimidine-2-thio)ethyl $(PEG)_2$ (S10) substituents were well tolerated at the meta position (Table 3).

TABLE 3

In vitro biological data in CEM cells for compounds S1-S31[a,b]

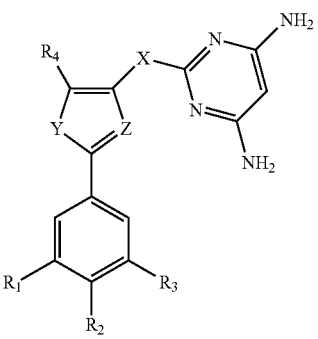

| Compound | R$^1$ | R$^2$ | R$^3$ | R$^4$ | Y | Z | X | IC$_{50}$ (nM) |
|---|---|---|---|---|---|---|---|---|
| S1 DI-47 | H | OCH$_3$ | OCH$_2$C(CH$_3$)$_2$OH | CH$_2$CH$_2$CH$_3$ | S | N | CD$_2$S | 4.0 (±2.2) |
| S2 DI-50 | H | Note[a] | OCH$_2$CH$_2$NHSO$_2$Me | CH$_2$CH$_2$CH$_3$ | S | N | CH$_2$S | 1,200 (±312) |
| S3 DI-51 | H | OCH$_3$ | OCH$_2$CH$_2$F | CH$_2$CH$_2$CH$_3$ | S | N | CH$_2$S | 2.5 (±0.35) |
| S4 DI-52 | H | OCH$_2$CH$_2$F | OCH$_3$ | CH$_2$CH$_2$CH$_3$ | S | N | CH$_2$S | 2.8 (±1.6) |
| S5 DI-53 | H | F | OCH$_2$CH$_2$F | CH$_2$CH$_2$CH$_3$ | S | N | CH$_2$S | 31.7 (±11.9) |
| S6 DI-54 | H | F | OCH$_2$CH$_2$F | CH$_2$CH$_2$CH$_3$ | S | N | CH$_2$S | 23.3 (±13) |
| S7 DI-55 | H | N/A[d] | OCH$_2$CH$_2$F | CH$_2$CH$_2$CH$_3$ | S | N | CH$_2$S | 6.8 (±1.7) |
| S8 DI-56 | H | N/A[d] | OCH$_2$CH$_2$F | CH$_2$CH$_2$CH$_3$ | S | N | CD$_2$S | 30 (±4) |
| S9 DI-57 | H | OCH$_3$ | OCH$_2$CH$_2$F | CH$_2$CH$_2$CH$_3$ | S | N | CD$_2$S | 3.1 (±1.1) |

TABLE 3-continued

In vitro biological data in CEM cells for compounds S1-S31[a,b]

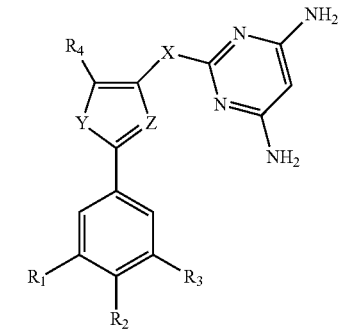

| Compound | R[1] | R[2] | R[3] | R[4] | Y | Z | X | IC$_{50}$ (nM) |
|---|---|---|---|---|---|---|---|---|
| S10 DI-58 | H | OCH$_3$ | O(CH$_2$)$_2$O(CH$_2$)$_2$O(CH$_2$)$_2$X[e] | CH$_2$CH$_2$CH$_3$ | S | N | CH$_2$S | 4.7 (±1.6) |
| S11 DI-59 | H | OCH$_3$ | O(CH$_2$)$_2$O(CH$_2$)$_2$O(CH$_2$)$_2$OH | CH$_2$CH$_2$CH$_3$ | S | N | CH$_2$S | 1.06 (±0.15) |
| S12 DI-60 | H | OCH$_3$ | OCH$_2$CH$_2$F | CH$_3$ | O | C | CH$_2$S | 13,480 (±280) |
| S13 DI-61 | H | OCH$_3$ | OCH$_2$CH$_2$NHSO$_2$Me | CH$_2$CH$_2$CH$_3$ | S | N | CD$_2$S | 3.04 (±0.704) |
| S14 DI-62 | H | OCH$_2$CH$_2$F | OCH$_3$ | CH$_3$ | O | C | CH$_2$S | 276 (±179) |
| S15 DI-64 | H | OCH$_3$ | OCH$_2$CH$_2$F | CH$_2$CH$_2$CH$_3$ | S | N | CH$_2$CH$_2$ | 664 (±36) |
| S16 DI-65 | H | OCH$_3$ | O(CH$_2$)$_2$O(CH$_2$)$_2$F | CH$_2$CH$_2$CH$_3$ | S | N | CH$_2$S | 4.22 (±1.98) |
| S17 DI-66 | H | H | O(CH$_2$)$_2$O(CH$_2$)$_2$O(CH$_2$)$_2$F | CH$_2$CH$_2$CH$_3$ | S | N | CH$_2$S | 69.08 (±46.41) |
| S18 DI-67 | H | OCH$_2$CH$_2$F | OCH$_3$ | CH$_3$ | S | C | CH$_2$S | 262 (±150) |
| S19 DI-69 | F | H | O(CH$_2$)$_2$O(CH$_2$)$_2$O(CH$_2$)$_2$F | CH$_2$CH$_2$CH$_3$ | S | N | CH$_2$S | 33.68 (±3.59) |
| S20 DI-70 | H | OCH$_3$ | O(CH$_2$)$_2$O(CH$_2$)$_2$O(CH$_2$)$_2$OCH$_3$ | CH$_2$CH$_2$CH$_3$ | S | N | CH$_2$S | 3.31 (±0.44) |
| S21 DI-71 | H | Note[f] | OCH$_2$CH$_3$ | CH$_2$CH$_2$CH$_3$ | S | N | CH$_2$S | 2.37 (±0.44) |
| S22 DI-73 | H | OCH$_3$ | O(CH$_2$)$_2$O(CH$_2$)$_2$O(CH$_2$)$_2$OCH$_3$ | CH$_2$CH$_2$CH$_3$ | S | N | CH(CH$_3$)S | 6.0 (±2.4) |
| S23 DI-74 | H | OCH$_3$ | O(CH$_2$)$_2$O(CH$_2$)$_2$O(CH$_2$)$_2$OCH$_3$ | CH$_3$ | S | N | CH(CH$_3$)S | 8.03 (±3.16) |
| S24 DI-76 | H | Note[f] | OCH$_3$ | CH$_3$ | S | N | CH(CH$_3$)S | 6.1 (±3.2) |
| S25 DI-77 | H | OCH$_3$ | O(CH$_2$)$_2$O(CH$_2$)$_2$O(CH$_2$)$_2$OCH$_3$ | Cpr[g] | S | N | CH$_2$S | 23 (±20) |
| S26 DI-79 | H | OCH$_3$ | O(CH$_2$)$_2$O(CH$_2$)$_2$O(CH$_2$)$_2$OCH$_3$ | CH$_3$ | S | N | CH$_2$S | 9.1 (n = 1) |
| S27 DI-80 | H | OCH$_3$ | O(CH$_2$)$_2$O(CH$_2$)$_2$O(CH$_2$)$_2$OCH$_3$ | Cpr[g] | S | N | CH(CH$_3$)S | 3.7 (n = 1) |
| S28 DI-81 | H | OCH$_3$ | O(CH$_2$)$_2$O(CH$_2$)$_2$O(CH$_2$)$_2$OCH$_3$ | Phenyl | S | N | CH(CH$_3$)S | 98.9 (n = 1) |
| S29 DI-83 | H | Note[h] | O(CH$_2$)$_2$O(CH$_2$)$_2$O(CH$_2$)$_2$OCH$_3$ | CH$_3$ | S | N | CH(CH$_3$)S | 61.4 (n = 1) |
| S30 DI-84 | H | Note[h] | OCH$_2$CH$_2$NHSO$_2$Me | CH$_3$ | S | N | CH(CH$_3$)S | 200.3 (n = 1) |
| S31 DI-85 | F | H | OCH$_2$CH$_2$NHSO$_2$Me | CH$_3$ | S | N | CH(CH$_3$)S | 9.07 (±2.24) |

[a]IC$_{50}$s values based on inhibition of $^3$H-deoxycytidine (dCyd) uptake in CEM cells. Values reproted are the mean ± SD of at lean n = 2 independent experiments.
[b]Value reported for n = 1.
[c]R$_2$ = N(SO$_2$Me)(CH$_2$CH$_2$NHSO$_2$Me).
[d]2,4-disubstituted pyridine ring.
[e]3,5-diaminopyrimidine thiol.
[f]R$_2$ = O(CH$_2$)$_2$O(CH$_2$)$_2$O(CH$_2$)$_2$OCH$_3$.
[g]Cpr = cyclopropyl.
[h]R$_2$ = OCH$_2$CH$_2$NHSO$_2$Me.

The precise nature of the substituent at the phenyl meta position may not be critical, as long as it contains a polar group that can extend to the proximity of Ser144/Ser146.

Figure 12A:
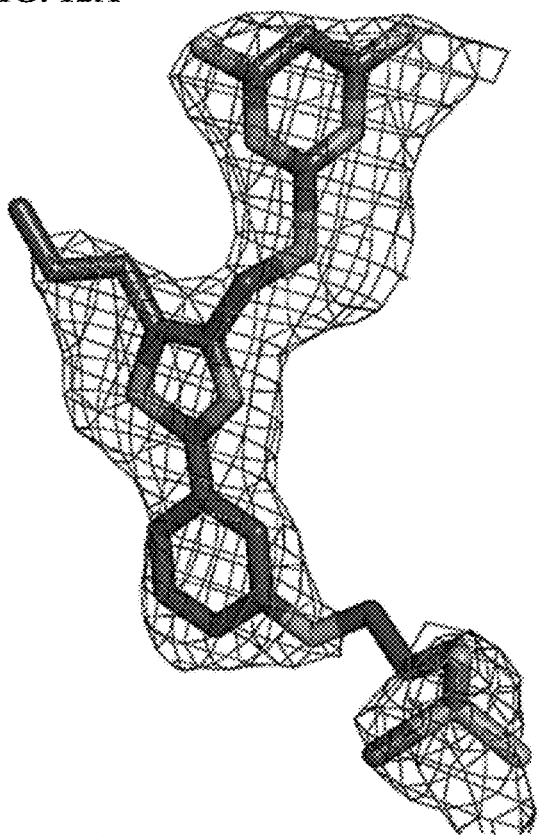
FIGS. 12A-12B. Fo-Fc map contoured at 2.0 sigma around compounds 5 and 6 from protomer A.
Figure 12B:
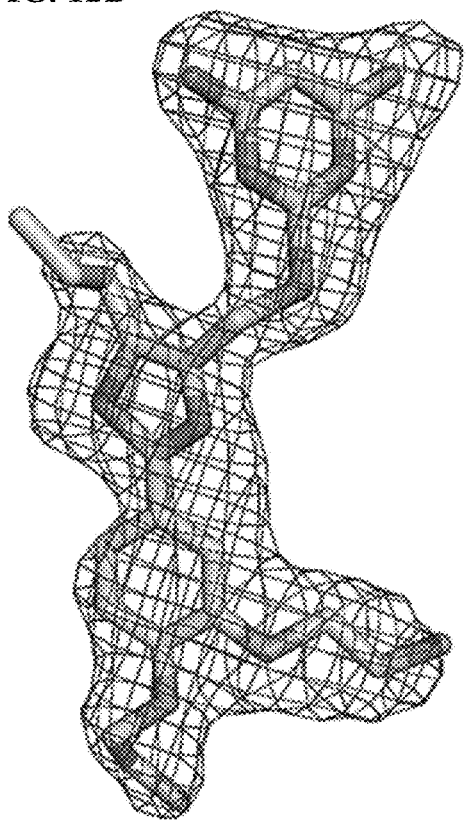

We prepared compound 5 (previously compound 28[3]), which only differs from compound Ib by lacking a para position substituent (FIG. 4A). The in vitro measured binding affinity values (IC$_{50}^{app}$; K$_i^{app}$) of compound 5 are nearly identical to that of Ib (FIG. 4B). This indicates that substituents at the para position are not required for tight binding, and is explained by the crystal structures of dCK in complex with compounds 5 and 6 (previously compound 30[3]) that show a nearly identical binding mode, one that is also very similar to that observed for compound Ib (FIG. 4C and FIGS. 12A-12B). The crystal structures also reveal that no significant inhibitor-enzyme interactions occur via the para substituent, if present. This conclusion is supported by the properties of compound 6, which in contrast to the methoxy group in compounds Ia and Ib, has the longer hydroxyethoxy group, but similar binding affinity. Hence, the in vitro binding affinities are largely unchanged between having no substituent at the phenyl group para position, having a methoxy, or the longer hydroxyethoxy. However, we did notice a ~10-fold difference between compounds 5 and 6 in the CEM cell-based assay, with compound 5 being less potent. Furthermore, substituents at the phenyl ring's para position such as 2-fluoroethoxy (S4, S14, S18), fluoro (S5, S6), methoxy-methyl terminated (PEG)$_2$ (S21, S24), and N-substituted methanesulfonamide (S29, S30) were relatively well tolerated (Table 3). Groups attached to the thiazole like 4-pyridinyl (S7), meta monosubstituted phenyl (S17), and 3,5-disubstituted phenyl ring (S31) substituents were also tolerated (Table 3). Therefore, while not directly important for the binding affinity, having even a small substituent at the phenyl group para position improves the relevant cell-based measurements. As a result, most subsequent compounds contained the methoxy group at that position.

We demonstrated that the nature of the substituent at the thiazole ring 5-position (part C of the molecule, FIG. 1A) plays a crucial role in binding affinity.[9] In short we compared having no substituent at that position to having a methyl, ethyl, or propyl. It is the latter that dramatically improved the binding affinity, and as a result, compounds with a propyl at the 5-position became lead compounds (i.e. compound Ia, Ib, FIGS. 1A-1B). Interestingly, compounds with a small/no substituent at the thiazole 5-position were observed to bind two inhibitor molecules per dCK active site. In contrast, the tighter binding propyl-containing molecules were observed to bind with a single inhibitor molecule per dCK active site.[9] In our previous report we discuss the implication of single/double binding of inhibitor molecules to dCK; in short, we conclude that binding of two molecules is not required for tight binding, and that the inhibitor molecule bound in what we refer to as Position-1 is responsible for the observed inhibition of dCK activity, whereas the molecule bound at Position-2 does not appreciably enhance dCK inhibition.

However, when tested for metabolic stability, we discovered that the propyl-group containing compounds Ia and Ib are less stable relative to those having the shorter methyl group, e.g. compound 15a. (Table 2). We also explored the activity of cyclopropyl and phenyl groups at the thiazolyl 5-position (Table 3). The cyclopropyl analog (S27) had a good $IC_{50}$ value, but it failed in the PET L-FAC assay, which was described in [8]. The phenyl analog (S28) demonstrated poor affinity. Hence we were forced to revert to the methyl thiazole ring substituent despite a weaker interaction with dCK. To compensate for the loss of affinity provided by the thiazole propyl group, we searched for a compensating modification that would restore the in vitro binding affinity and at the same time maintain acceptable metabolic stability. For that purpose we decided to explore modifications on the linker moiety (part B of the compounds, FIG. 1A).

TABLE 2

Human microsomal intrinsic clearance assay[a]

| Compound | NADPH-dependent $CL_{int}{}^a$ (μl min$^{-1}$ mg$^{-1}$) | NADPH-dependent $T_{1/2}{}^b$ (min) | Comment |
| --- | --- | --- | --- |
| Verapamil | 201 | 11.5 | High clearance control |
| warfarin | 0.0 | >240 | Low clearance control |
| Ia | 561 | 4.1 | |
| Ib | 870 | 2.7 | |
| 15a (Murphy et al) | 142 | 16.3 | |
| 7(R/S) | 419 | 5.5 | |
| 8(R/S) | 254 | 9.1 | |
| 10R | 22.7 | 102 | |

[a]Test concentration of compounds was 1 μM

The —S—CH$_2$— group acts to link the pyrimidine and thiazole rings of our compounds. We tested a variety of different linkers, such as its deuterated analog (—S—CD$_2$-) for the purpose of a kinetic isotope study. Without being bound by any particular theory, we hypothesized that if the linker was implicated in hydrolytic metabolism then, due to the kinetic isotope effect, a deuterated (—S—CD$_2$-) analog would show an improvement in metabolic stability. The deuterium analogs (S1, S8, S9, S13) had affinity similar to their isotopologues, as expected (Table 3). However the deuterated compounds failed to show an improvement in the PET L-FAC liver assay, indicating that a hydrolytic mechanism is probably not involved in the metabolism of the —S—CH$_2$— linker. We also tested the replacement of the sulfur atom of the S—CH$_2$— group with a methylene group (—CH$_2$CH$_2$—). Replacing the sulfur atom of the linker with a carbon atom resulted in a decrease in dCK affinity and metabolic stability (Table 3). We tested a linker in which the methylene was substituted to contain a methyl group (—S—CH(CH$_3$)—). These racemic methyl-linker compounds showed promising biological results and increased metabolic stability (see Scheme 1 and Scheme 2 for the synthesis of compounds 7 and 8). Therefore, we carefully examined the synthetic route in an attempt to reduce the synthetic steps and improve the total yield. We succeeded in developing a six-step synthetic route towards 9 in an overall yield of 43% (Scheme 3). Commercially available 3-hydroxy-4-methoxybenzonitrile A was subjected to an aqueous ammonium sulfide solution under basic conditions to provide thioamide B. Cyclization to form the thiazole core of C was achieved via condensation of thioamide B with 4-bromopentane-2,3-dione[13] in refluxing ethanol. Introduction of a PEG chain into the phenyl ring of compound D with 13-chloro-2,5,8,11-tetraoxatridecane[14] under basic conditions was achieved in 89% yield. Reduction of the resulting ketone-containing compound with diisobutylaluminum hydride (DIBALH) afforded racemic secondary alcohol E in high yield. Alcohol E was converted to the respective chloride F with thionyl chloride. The acyl chloride was reacted in crude form with 4,6-diamino-2-mercaptopyrimidine to generate product 9R/S.

Scheme 1. Synthesis route for racemic methyl linker compound 7.

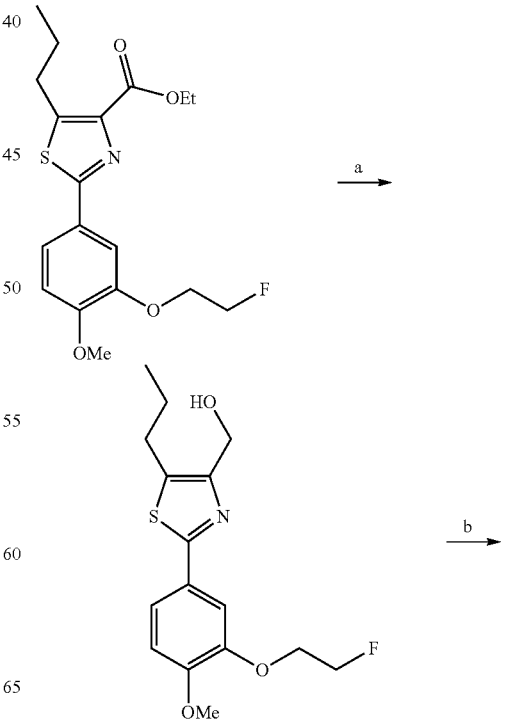

-continued
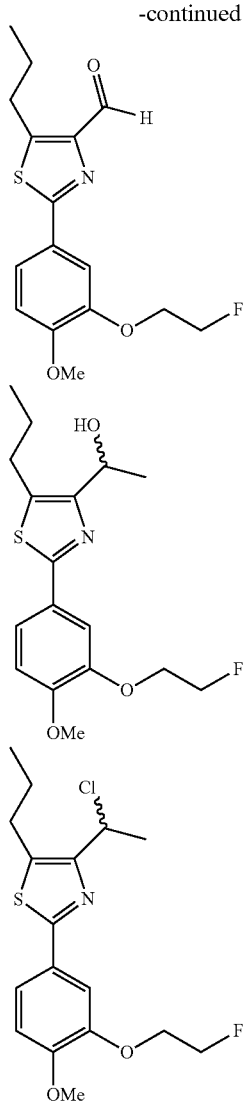
Reagents and conditions: (a) Diisobutylaluminium hydride, tetrahydrofuran, (previous work); (b) Dess-Martin periodinane, dichloromethane, 23° C., 80%; (c) Methylmagnesium iodide, tetrahydrofuran, 0° C., 86%; (d) Thionyl chloride, dichloromethane, 23° C., 96%; (e) 4,6-diamino-2-mercaptopyrimidine, potassium carbonate, DMF, 80° C., 66%.
Scheme 2. Synthesis route for racemic methyl linker compound 8
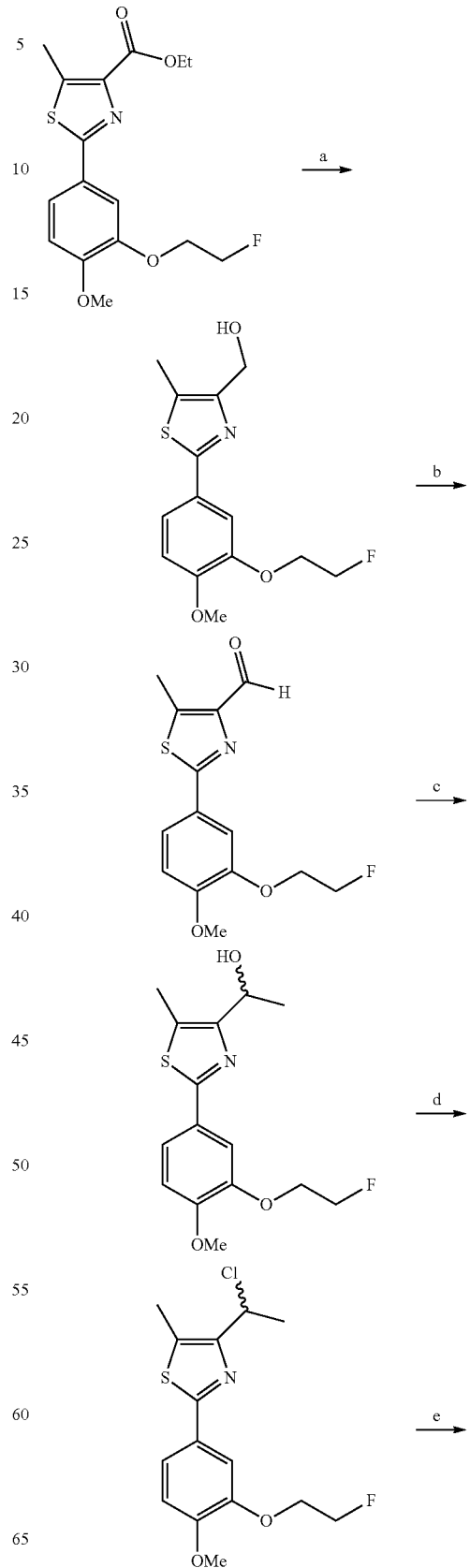

85
-continued

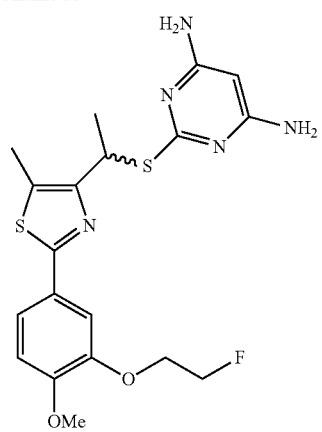

Reagents and conditions: (a) Diisobutylaluminium hydride, tetrahydrofuran, (previous work); (b) Dess-Martin periodinane, dichloromethane, 23° C., 70%; (c) Methylmagnesium iodide, tetrahydrofuran, 0° C., 68%; (d) Thionyl chloride, dichloromethane, 23° C., 94%; (e) 4,6-diamino-2-mercaptopyrimidine, potassium carbonate, DMF, 80° C., 64%.

Scheme 3. Synthesis route for methyl linker compound 9R/S

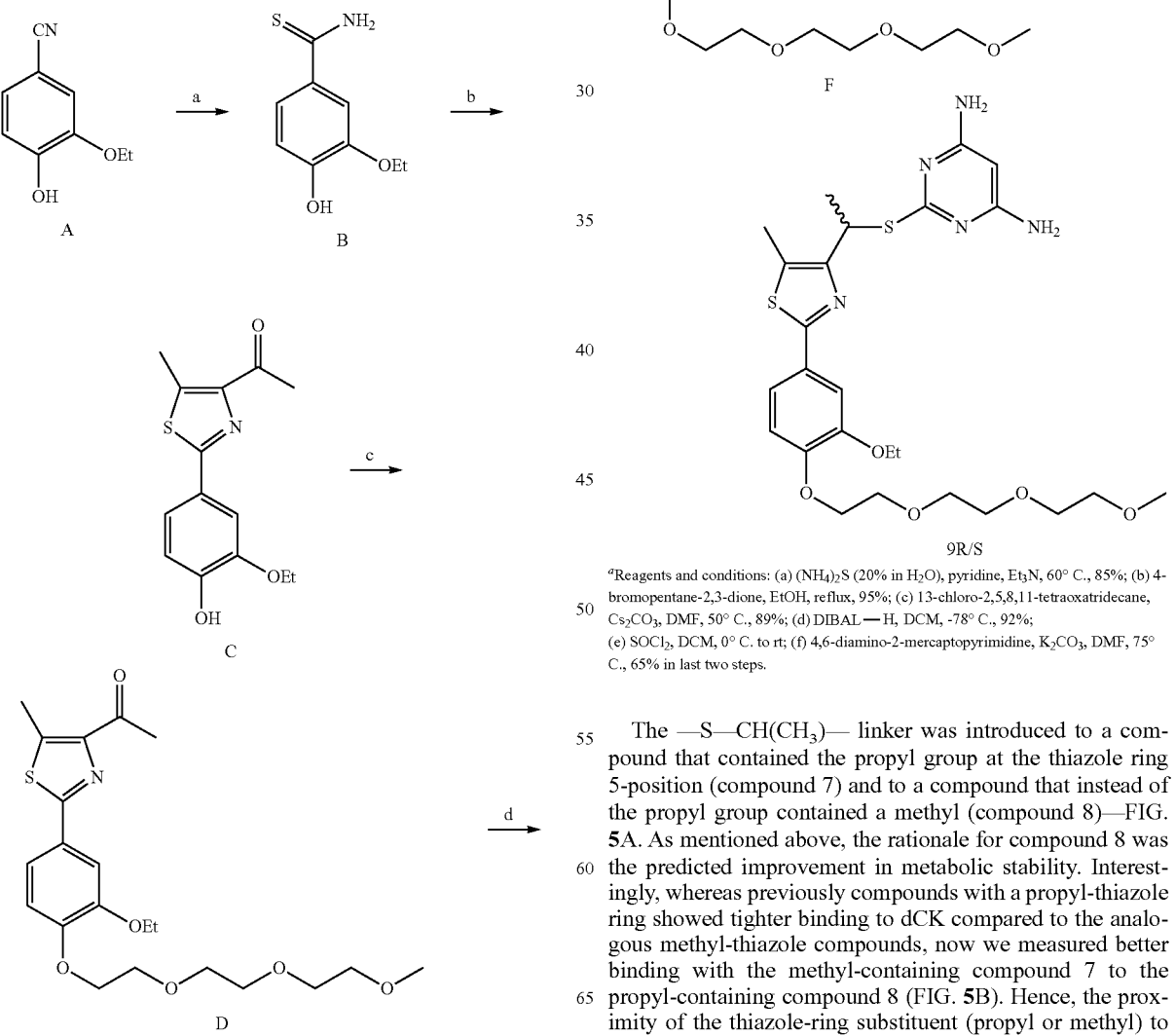

86
-continued

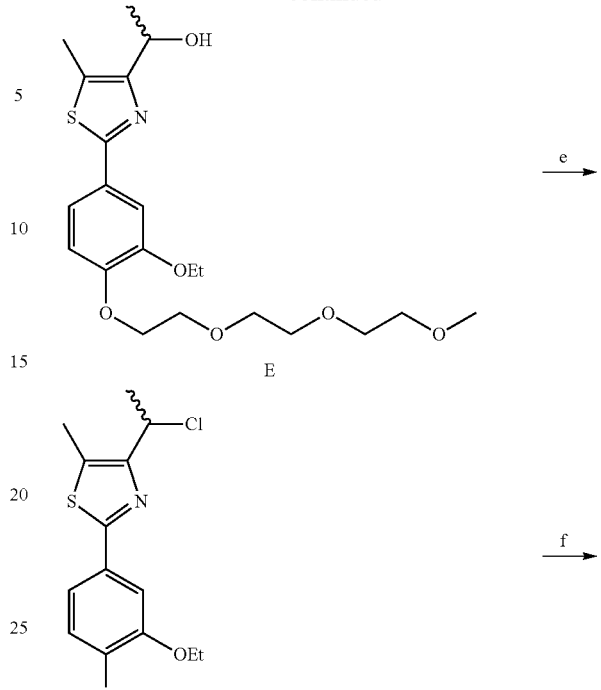

9R/S $^a$Reagents and conditions: (a) (NH$_4$)$_2$S (20% in H$_2$O), pyridine, Et$_3$N, 60° C., 85%; (b) 4-bromopentane-2,3-dione, EtOH, reflux, 95%; (c) 13-chloro-2,5,8,11-tetraoxatridecane, Cs$_2$CO$_3$, DMF, 50° C., 89%; (d) DIBAL—H, DCM, -78° C., 92%; (e) SOCl$_2$, DCM, 0° C. to rt; (f) 4,6-diamino-2-mercaptopyrimidine, K$_2$CO$_3$, DMF, 75° C., 65% in last two steps.

The —S—CH(CH$_3$)— linker was introduced to a compound that contained the propyl group at the thiazole ring 5-position (compound 7) and to a compound that instead of the propyl group contained a methyl (compound 8)—FIG. 5A. As mentioned above, the rationale for compound 8 was the predicted improvement in metabolic stability. Interestingly, whereas previously compounds with a propyl-thiazole ring showed tighter binding to dCK compared to the analogous methyl-thiazole compounds, now we measured better binding with the methyl-containing compound 7 to the propyl-containing compound 8 (FIG. 5B). Hence, the proximity of the thiazole-ring substituent (propyl or methyl) to the methyl-linker substituent resulted in the larger propyl group being not as accommodating in the dCK active site. Despite the improved in vitro binding parameters for 8 over 7, the cell-based assay yielded similar $IC_{50}$ values, yet consistent with 8 being superior (FIG. 5B).

Figure 13A:
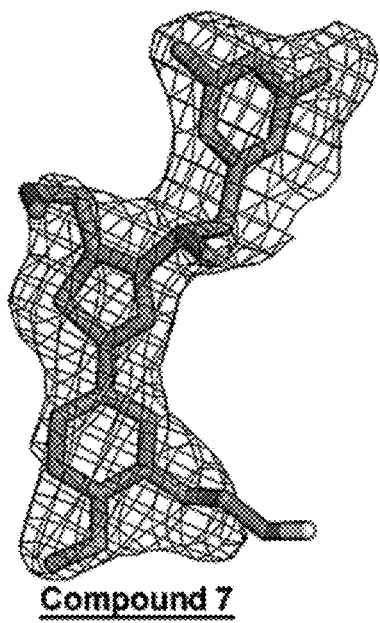
FIGS. 13A-13B. Fo-Fc map contoured at 2.0 sigma around compounds 7 and 8 from protomer A.
Figure 13B:
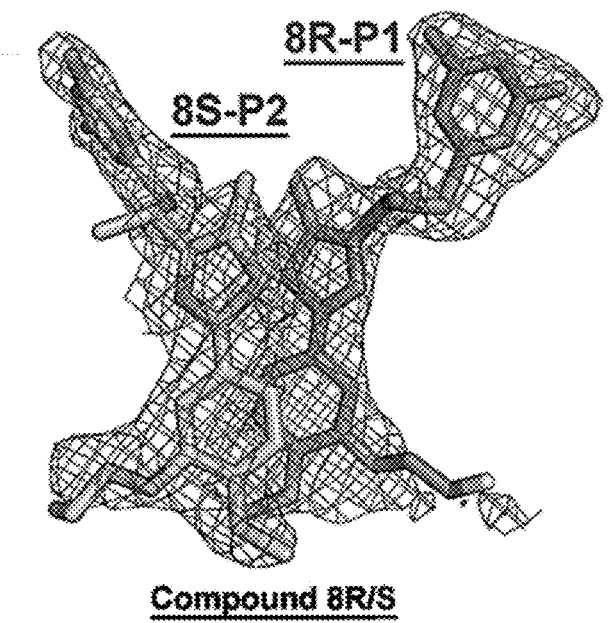

Both compounds 7 and 8 were prepared as racemic mixtures; the introduced linker-methyl group makes that position a new chiral center (arrow, FIG. 5A). To elucidate which of the two enantiomers is the active dCK inhibitor we determined the crystal structure of dCK in complex with compounds 7 & 8 (solved at 2.0 Å and 1.85 Å resolution, respectively, Table 1). Compound 7 binds as a single molecule to dCK, specifically in Position-1. Interestingly, despite the fact that a racemic mixture of 7 was used to form the complex to dCK, the crystal structure provides unambiguous evidence for the R-isomer binding to Position-1 (FIG. 5C and FIGS. 13A-13B). Likewise, inspection of the structure of the complex between racemic 8 and dCK shows that it is the R-isomer that occupies the most relevant Position-1 binding site (FIG. 5D and FIGS. 13A-13B). Since compound 8 contains the methyl substituent in the thiazole ring, which allows for a molecule to also occupy Position-2, indeed we observe compound 8 at that position as well. However, whereas it is the R-isomer of 8 that binds to Position-1, it is the S-isomer that binds to Position-2 (FIG. 5E and FIGS. 13A-13B).

Position-1 may represent the binding site for this family of inhibitors. This would suggest that the measured in vitro inhibition values of racemic 8 are reflecting the preferential binding of the R-isomer. To test this prediction, we synthesized compound 9, which is a slight modification of 8 (the nature of the phenyl group substituents), but notably, had the racemic mixture separated to yield the pure isomers 9R and 9S (FIG. 6A). We determined the in vitro binding affinities of the enantiomerically pure compounds and observed that 9S has ~400-fold weaker binding affinity relative to 9R (FIG. 6B). In addition to providing clear evidence that it is the R-form that is responsible for the tight interaction with dCK, this result also validates our structure-based interpretation that Position-1 is the one most relevant inhibitor binding site for dCK inhibition, and Position-2 being occupied due to the high concentration of the inhibitor used in the crystallization set ups.

Having discovered that it is the R-isomer of compounds 7, 8, and 9 appears responsible for the dCK inhibition, we set out to develop an asymmetric synthesis (Scheme 2). The chiral synthesis developed by our group for compound 10R, which is a close analog of 8, features a chiral Corey-Bakshi-Shibata (CBS) reaction[15] of ketone D. Chiral alcohol E was synthesized according to this method with an enantiomeric excess of 96%, as determined via chiral HPLC. Employing mesic or tosic anhydride to give the sulfonates under different basic condition such as $Et_3N$, pyridine, or DMAP resulted in elimination to the alkene, presumably due to the stability of the secondary benzylic-like carbocation. The use of trifluoroacetic anhydride (TFAA) at 0° C. converted alcohol E into the corresponding trifluoroacetate (TFA) F without a significant decrease in the % ee of the ester. Finally, compound F was reacted with 4,6-diamino-2-mercaptopyrimidine to generate 10R in 61% yield over two steps with an enantiomeric excess of 40%. Presumably a portion of the reaction occurs via a direct SN2 pathway while another part occurs via an SN1 pathway and thereby partially racemized material was obtained. Chiral resolution via recrystallization generated 10R with an enantiomeric excess of over 90%. Likewise, (S)-(−)-2-methyl-CBS-oxazaborolidine was used in the CBS reduction to synthesize 10S.

Compound 10R (FIG. 6A) was measured to have very similar in vitro binding affinities as did 9R (FIG. 6B). Significantly, just as the affinity of 9S was much reduced relative to 9R, the affinity to dCK of 10S was much reduced relative to 10R. This reiterated the preference of dCK for compounds that contain the R-isomer of the linker.

We solved the dCK-10R complex crystal structure. Based on the previous structure with compound 9 (observing 9R bound to Position-1) and our kinetic results using enantiomerically pure 9S, 9R, 10S, and 10R (observing higher affinities for the R-isomers), and since the crystals were formed with the enantiomerically pure 10R, we expected 10R to bind only in Position-1. Additionally, lacking the S-isomer, we expected a vacant Position-2 binding site. Indeed, the crystal structure of the dCK-10R complex revealed a single inhibitor molecule at Position-1 (FIG. 6C). This result suggests that the R-isomer has very low affinity to the binding site at Position-2. Notably, while the interaction between the R-isomer and dCK is limited to the Position-1 binding site, this does not diminish the binding affinity for the enzyme.

Without being bound by any particular theory we hypothesized the steric considerations relating the inhibitor and enzyme, where the chiral methyl group of the linker clashes with enzyme residues in the case of one isomer but not the other provided potency. However, inspection of the crystal structures solved with compounds 8 (R/S) and 10R does not support this interpretation; we could model the S-isomer bound to Position-1 (FIG. 5D) and the R-isomer bound at Position-2 (FIG. 5E) with no apparent clashes.

Figure 14A:
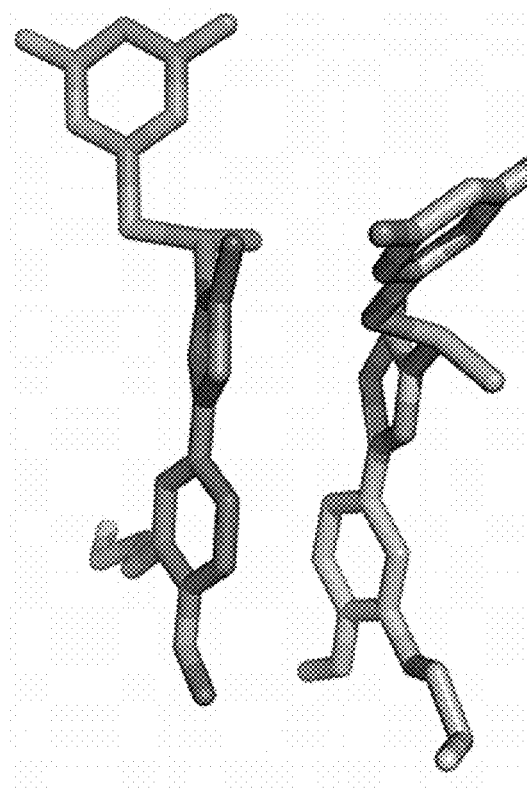
FIGS. 14A-14B. Relative orientation of 8R and 8S rings upon dCK binding.
Figure 14B:
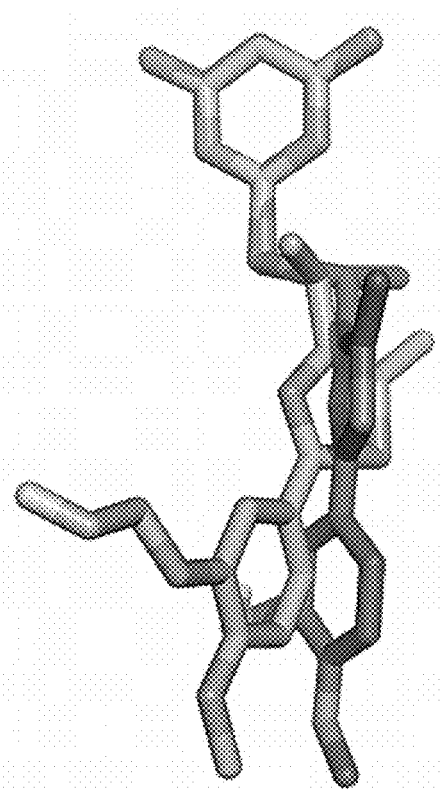

Comparison of the binding mode between 8R and 8S reveals that the relative orientations of the rings are very different (FIGS. 14A-14B). That is, each isomer has adjusted its conformation to best fit its binding site (i.e. induced fit). This suggests, without being bound by any particular theory, that the enzyme dictates the relative orientations between the pyrimidine ring, linker, thiazole ring, and phenyl ring. We examined a theoretical model of the S-isomer that is orientated in the same way as 8R. Indeed, where for 8R in Position-1, the observed distance between the chiral methyl of the linker and the thiazole ring methyl group is 4.2 Å (FIG. 7A), for the modeled 8S bound to Position-1, that distance would be an unfavorable 2.5 Å (FIG. 7B). Likewise, whereas for 8S in Position-2 the observed distance between the chiral methyl and the thiazole methyl is 4.4 Å (FIG. 7C), for the modeled R-isomer adopting the same conformation as 8S, that distance would be an unfavorable 2.6 Å (FIG. 7D). Hence, the strict chiral selection to either Position-1 or Position-2 is due to the enzyme dictating a particular inhibitor orientation that is vastly different between the binding sites. In the case of Position-1, that orientation is not compatible with the S-isomer, and for Position-2, that orientation is not compatible with the R-isomer.

Figure 15:
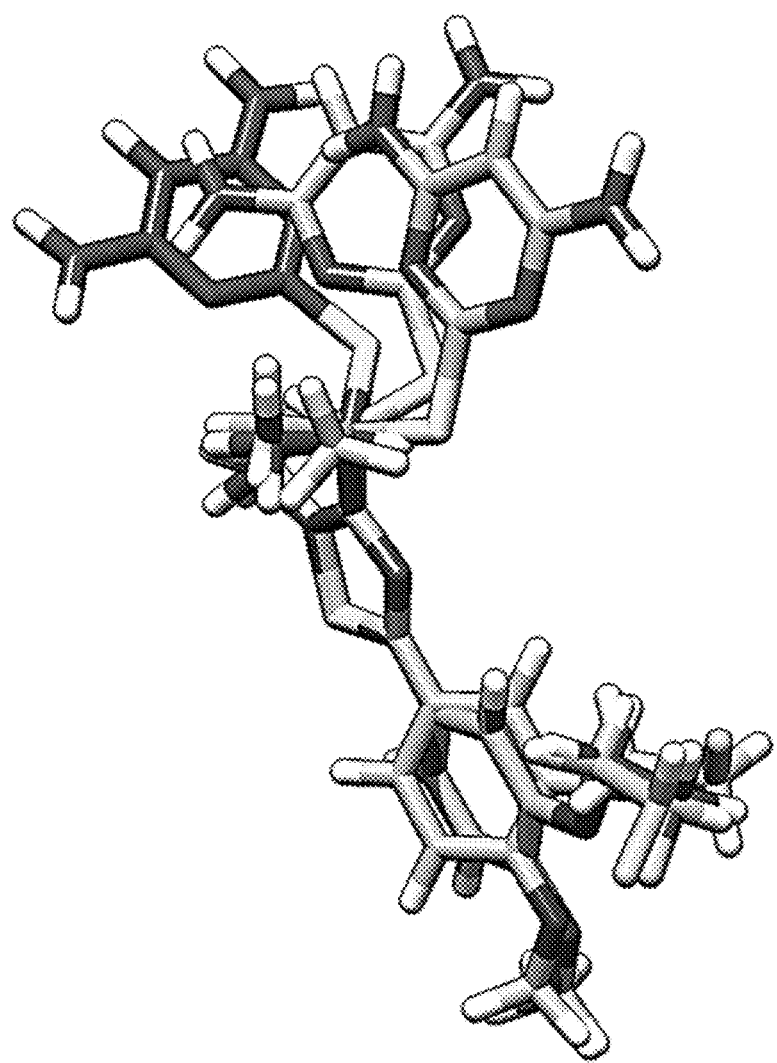
FIG. 15. Relative orientation of 8R and 8S optimized in solution, compared to the pose of 8R bound at Position 1 in crystal structure. The structures are aligned according to the thiazole rings. This illustrates the conformational change that must occur for the molecule to move out of solution and bind with the protein. Both 8R and 8S incur an energy penalty in undergoing this conformational change, but the penalty for 8R is much less than the penalty for 8S.

Using computer simulations, we obtain a qualitative estimate of the conformational penalty incurred by 8R and 8S upon binding with the protein. The conformational penalty is the energy difference between the preferred solution-phase geometry of a substrate and the geometry that it assumes upon binding: $\Delta E = E_{solution} - E_{bound}$. Each enantiomer was docked with the solvated protein at Position-1 and allowed to equilibrate (see details in Experimental section and FIG. 15). The equilibrated, docked inhibitor structures were removed from the protein and their energies were assessed with the semi empirical PDDG/PM3 method[16-21]. Unbound structures of 8R and 8S were optimized in implicit solvent to determine their low-energy solution-phase conformations. As with the bound structures, energies of the unbound structures were assessed with PDDG/PM3. The resulting energies were used to obtain qualitative conformational penalties for each enantiomer. The conformational penalty for 8S was almost twice the conformational penalty for 8R (45 kcal/mol larger penalty for 8S), further demonstrating that 8R needs to undergo a much less unfavorable structural rearrangement in order to bind with the protein.

Another way of considering this issue is to examine the energy of the inhibitor as a function of rotation around the bond that connects the thiazole ring to the chiral linker atom (bond marked with * in FIGS. 7A-7D). For 8R bound to dCK at Position-1, the observed dihedral angle that specifies this rotation is −59°, and fits a low energy conformation (FIG. 7E). In contrast, the modeled S-isomer at this binding site would have a torsion angle of 189°, which is clearly a high-energy conformation (FIG. 7F). The same pattern is observed for Position-2; the S-isomer binds to dCK with a torsion angle of −326°, which is a low energy conformation, while the modeled R-isomer at that position is a high-energy conformation (FIG. 7H). Hence, the chiral selectivity does not come directly from the enzyme sterically favoring one isomer over the other. Rather, the enzyme dictates a particular conformation, and the selectivity comes from one isomer being able to adopt that particular conformation, whereas the energy penalty for the other isomer precludes its binding.

In addition to explaining the chiral selectivity for the compounds discussed here, this understanding can be used for the design of chiral molecules that bind to either binding site. Specifically, the prediction would be that replacing the thiazole methyl group with a hydrogen atom would eliminate any steric clash to the chiral methyl group, and hence either isomer could bind to either inhibitor binding site.

Figure 8A:
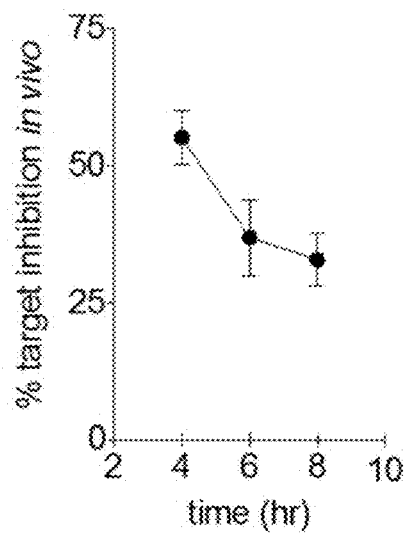
FIGS. 8A-8B. In vivo evaluation of compound 10.
Figure 8B:
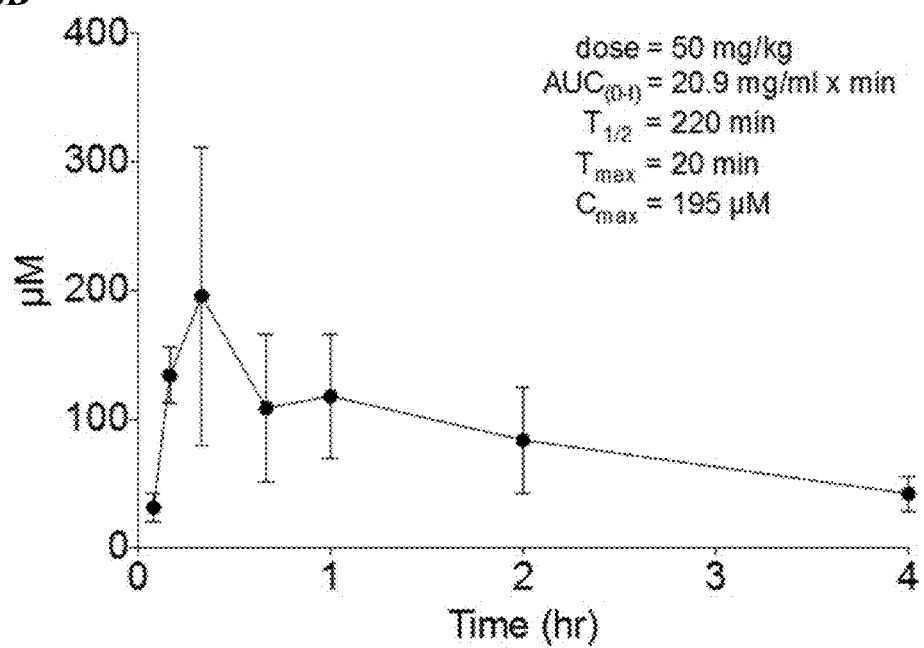

We determined the metabolic stability of 10R in a standard microsomal liver clearance assay. The NADPH-dependent $T_{1/2}$ of 10R was ~37 fold longer than that of our previous lead compound Ib (Table 2). We then tested compound 10 in mice, using a previously described Positron Emission Tomography (PET) assay.[8] Whereas the earlier lead compound Ib retained only ~25% inhibition of dCK activity 4 hours after dosing by intraperitoneal injection,[3] compound 10 (given as the racemic mixture) exhibited >50% inhibition of dCK activity at this time point (FIG. 8A). Furthermore, 8 hours after treatment with compound 10, dCK inhibition was still above 30%. We then determined the pharmacokinetic properties of compound 10 to compare with our previous lead compounds Ia and Ib.[7, 8] As shown in FIG. 8B, the pharmacokinetic properties of compound 10 were significantly improved relative to the previously published values for compounds Ia and Ib.[7, 8] Collectively, these findings demonstrate that introduction of the chiral linker plus replacement of the thiazole ring propyl substituent by a methyl group yields a dCK inhibitor with improved metabolic stability.

Structural and inhibition studies, performed using both the purified recombinant enzyme and a cell-based assay, of the compounds discussed here revealed and rationalized the essential determinants for binding to dCK, and also guided the type and placement of substituents. This informed the development of the initial leads, compounds Ia and Ib. These compounds contain a propyl group at the 5-position of the thiazole ring, since as shown earlier, the propyl substituent provides improved affinity for dCK compared to compounds with a methyl group at that position. This affinity-strengthening propyl group compromised the metabolic stability relative to compounds containing a methyl group at that position. This forced us to revert to the weaker-binding but more metabolically stable scaffold of a methyl group at the thiazole ring. With the goal of improving metabolic stability, a chiral methylene methyl sulfur linker between the thiazole and pyrimidine moieties was tested. This linker was found to confer two positive effects: one, in terms of affinity for dCK, the modified linker compensated for the lack of the thiazole propyl group, and two, the compounds exhibited improved metabolic stability. The interaction of dCK with compounds containing this linker is specific to the R-isomer. This was proven by the dCK-inhibitor crystal structure and by comparing the binding affinities of the R versus S enantiomers. The new lead compound 10R is a promising dCK inhibitor, which by perturbing the dNTP pools and inducing DNA replication stress overload could be used in combination with other drugs to specifically trigger synthetic lethality in cancer cells.

Materials.

General laboratory reagents were purchased from Fisher (Pittsburgh, Pa., USA) and SigmaAldrich (St Louis, Mo., USA). Nucleotides were obtained from Sigma. All inhibitors were synthesized at UCLA. Chiral Technologies Inc. (800 North Five Points Road, West Chester, Pa. 19380 USA) performed the separation of R and S enantiomers.

Chemistry. General Procedures.

Unless otherwise noted, reactions were carried out in oven-dried glassware under an atmosphere of nitrogen using commercially available anhydrous solvents. Solvents used for extractions and chromatography were not anhydrous. 4,6-Diamino-2-mercapto-pyrimidine was obtained from drying the hydrate over dynamic vacuum at 110° C. for 20 hours. All other reagents obtained from commercial suppliers were reagent grade and used without further purification unless specified. Reactions and chromatography fractions were analyzed by thin-layer chromatography (TLC) using Merck precoated silica gel 60 $F_{254}$ glass plates (250 µm). Visualization was carried out with ultraviolet light, vanillin stain, permanganate stain, or p-anisaldehyde stain. Flash column chromatography was performed using E. Merck silica gel 60 (230-400 mesh) with compressed air. $^1$H and $^{13}$C NMR spectra were recorded on a ARX500 (500 MHz), Avance500 (500 MHz), or Avance300 (300 MHz) spectrometers. Chemical shifts are reported in parts per million (ppm, δ) using the residual solvent peak as the reference. The coupling constants, J, are reported in Hertz (Hz) and the resonance patterns are reported with notations as the following: br (broad), s (singlet), d (doublet), t (triplet), q (quartet), and m (multiplet). Electrospray mass spectrometry data were collected with a Waters LCT Premier XE time of flight instrument controlled by MassLynx 4.1 software. Samples were dissolved in methanol and infused using direct loop injection from a Waters Acquity UPLC into the Multi-Mode Ionization source. The purity of all final compounds was determined to be >95%. Analytical HPLC analysis was performed on a Knauer Smartline HPLC system with a Phenomenex reverse-phase Luna column (5 µm, 4.6×250 mm) with inline Knauer UV (254 nm) detector. Mobile phase: A: 0.1% TFA in $H_2O$, B: 0.1% TFA in MeCN. Eluent gradient is specified for each described compound. Percent enantiomeric excess (% ee) values was determined via chiral HPLC with a CHIRALPAK®IA-3/IA polysaccharide-based Immobilized type column (3 µm, 4.6×150 mm) with inline Knauer UV (310 nm) detector. Mobile phase: A: 0.1% TFA in hexanes, B: 0.1% TFA in propanol. Eluent gradient: 50% phase A and 50% phase B. Chromatograms were collected by a GinaStar (Raytest USA, Inc.; Wilmington, N.C., USA) analog to digital converter and GinaStar software (Raytest USA, Inc.).

For Scheme 1

3-Ethoxy-4-hydroxybenzothioamide (B)

To a mixture of 3-ethoxy-4-hydroxybenzonitrile A (2.50 g, 15.3 mmol) in pyridine (35 mL) and triethylamine (2.5 mL) was added ammonium sulfide solution (20% wt. in $H_2O$, 15.65 mL, 46.0 mmol). The mixture was stirred for 18 h at 60° C. The reaction mixture was cooled and concentrated in vacuo to remove residual solvent. The resulting residue was washed with brine and extracted with ethyl acetate. The organic layer was dried over anhydrous $Na_2SO_4$, concentrated in vacuo, and purified by flash column chromatography over silica gel (3:1 ethyl acetate: hexanes) to yield B (2.56 g, 13.0 mmol, 85%) as a yellow solid. $^1H$ NMR (300 MHz, $CDCl_3$) δ 7.68 (d, J=2.1 Hz, 1H), 7.48 (br s, 1H), 7.28 (dd, J=8.5, 2.1 Hz, 1H), 7.11 (br s, 1H), 6.89 (d, J=8.5 Hz, 1H), 6.03 (s, 1H), 4.21 (q, J=6.9 Hz, 2H), 1.47 (t, J=6.9 Hz, 3H); $^{13}C$ NMR (125 MHz, Acetone-$d_6$) δ 200.5, 150.3, 145.8, 131.0, 121.0, 114.0, 112.6, 64.3, 14.1.

1-(2-(3-Ethoxy-4-hydroxyphenyl)-5-methylthiazol-4-yl)ethan-1-one (C)

A mixture of thioamide B (1.50 g, 7.6 mmol) and 4-bromopentane-2,3-dione (2.04 g, 11.4 mmol) in ethanol (40 mL) was stirred under refluxing conditions for 4 h. The resulting mixture was cooled and concentrated in vacuo to remove residual solvent. The crude residue was purified by flash column chromatography over silica gel (10:3 hexanes: ethyl acetate) to yield the desired thiazole intermediate C (2.00 g, 7.2 mmol, 95%) as a white solid. $^1H$ NMR (300 MHz, $CDCl_3$) δ 7.47 (d, J=1.8 Hz, 1H), 7.35 (dd, J=8.2, 1.8 Hz, 1H), 6.96 (d, J=8.1 Hz, 1H), 5.93 (s, 1H), 4.23 (q, J=7.2 Hz, 2H), 2.77 (s, 3H), 2.71 (s, 3H), 1.50 (t, J=6.9 Hz, 3H); $^{13}C$ NMR (75 MHz, $CDCl_3$) δ 196.0, 162.8, 148.9, 148.0, 146.3, 142.9, 125.9, 120.5, 114.8, 109.4, 64.9, 29.5, 14.9, 13.6.

1-(2-(3-Ethoxy-4-(2-(2-(2-methoxyethoxy)ethoxy)ethoxy)phenyl)-5-methylthiazol-4-yl)ethan-1-one (D)

To a solution of thiazole intermediate C (1.66 g, 6.0 mmol) in DMF (35 mL) was added $Cs_2CO_3$ (3.13 g, 9.6 mmol) and 13-chloro-2,5,8,11-tetraoxatridecane (2.19 g, 12.0 mmol). The mixture was stirred for 18 h at 50° C. After concentration to remove residual solvent, the resulting residue was washed with brine and extracted with ethyl acetate. The organic layer was washed with water three times, dried over anhydrous $Na_2SO_4$ and concentrated in vacuo, and the crude residue was purified by flash column chromatography over silica gel (1:1 ethyl acetate: hexanes) to yield desired ketone D (2.26 g, 5.3 mmol, 89%) as an white solid. $^1H$ NMR (500 MHz, $CDCl_3$) δ 7.48 (d, J=2.0 Hz, 1H), 7.38 (dd, J=8.5, 2.0 Hz, 1H), 6.94 (d, J=8.5 Hz, 1H), 4.24-4.20 (m, 2H), 4.17 (q, J=7.0 Hz, 2H), 3.93-3.89 (m, 2H), 3.79-3.75 (m, 2H), 3.70-3.63 (m, 4H), 3.57-3.53 (m, 2H), 3.37 (s, 3H), 2.77 (s, 3H), 2.71 (s, 3H), 1.47 (t, J=7.0 Hz, 3H); $^{13}C$ NMR (125 MHz, $CDCl_3$) δ 196.0, 162.5, 150.8, 149.4, 149.0, 143.1, 126.9, 119.8, 114.0, 111.4, 72.1, 71.1, 70.8, 70.7, 69.7, 69.0, 64.9, 59.2, 29.5, 15.0, 13.6.

1-(2-(3-Ethoxy-4-(2-(2-(2-methoxyethoxy)ethoxy)ethoxy)phenyl)-5-methylthiazol-4-yl)ethan-1-ol (E)

To a stirred solution of ketone D (1.06 g, 2.5 mmol) in $CH_2Cl_2$ (35 mL) cooled to −78° C. was added slowly diisobutylaluminum hydride (1.0M in THF, 10 mmol, 10 mL). The reaction was allowed to warm to 23° C. and stirred for 1 h. The mixture was cooled to 0° C. and slowly quenched with a saturated aqueous solution of Rochelle's salt. The cloudy solution was stirred for 1 h at 23° C. until the solution became clear again. The resulting solution was extracted with ethyl acetate, washed with brine, dried over anhydrous $Na_2SO_4$ and concentrated in vacuo to give the desired alcohol E (978 mg, 2.3 mmol, 92%) as a pale yellow solid. $^1H$ NMR (500 MHz, $CDCl_3$) δ 7.44 (d, J=2.0 Hz, 1H), 7.33 (dd, J=8.5, 2.0 Hz, 1H), 6.89 (d, J=8.5 Hz, 1H), 4.91 (q, J=6.5 Hz, 1H), 4.22-4.17 (m, 2H), 4.13 (q, J=7.0 Hz, 2H), 3.91-3.86 (m, 2H), 3.76-3.72 (m, 2H), 3.69-3.61 (m, 4H), 3.55-3.51 (m, 2H), 3.35 (s, 3H), 2.37 (s, 3H), 1.52 (d, J=6.0 Hz, 3H), 1.44 (t, J=7.0 Hz, 3H); $^{13}C$ NMR (125 MHz, $CDCl_3$) δ 164.3, 155.1, 150.0, 149.0, 127.2, 125.8, 119.3, 113.8, 111.0, 71.8, 70.8, 70.6, 70.4, 69.5, 68.7, 64.6, 64.4, 58.9, 24.0, 14.7, 10.7.

4-(1-Chloroethyl)-2-(3-ethoxy-4-(2-(2-(2-methoxyethoxy)ethoxy)ethoxy)phenyl)-5-methylthiazole (F)

To a stirred solution of alcohol E (425 mg, 1.0 mmol) in $CH_2Cl_2$ (8 mL) was added thionyl chloride (0.78 mL, 10.0 mmol) slowly at 0° C. The reaction was allowed to warm to 23° C. and stirred for 1 h. After concentration in vacuo to remove residual solvent, the resulting crude residue was used directly for next step without any further purification because of the instability of chloride F.

2-((1-(2-(3-Ethoxy-4-(2-(2-(2-methoxyethoxy)ethoxy)ethoxy)phenyl)-5-methylthiazol-4-yl)ethyl)thio)pyrimidine-4,6-diamine ((±)-9)

A mixture of crude chloride F from the previous step, 4,6-diamino-2-mercaptopyrimidine (625 mg, 4.0 mmol) and $K_2CO_3$ (552 mg, 4.0 mmol) in DMF (7 mL) was stirred at 70° C. for 1 h. The solution was cooled, concentrated in vacuo and purified by flash column chromatography over silica gel (25:1 dichloromethane:methanol) to give the desired product (±)-9 (357 mg, 0.65 mmol, 65% in two steps) as a white solid. $^1H$ NMR (500 MHz, $CDCl_3$) δ 7.49 (d, J=2.0 Hz, 1H), 7.35 (dd, J=8.5, 2.0 Hz, 1H), 6.90 (d, J=8.5 Hz, 1H), 5.24 (s, 1H), 5.02 (q, J=7.0 Hz, 1H), 4.58 (s, 4H), 4.22-4.18 (m, 2H), 4.15 (q, J=7.0 Hz, 2H), 3.91-3.87 (m, 2H), 3.78-3.75 (m, 2H), 3.69-3.63 (m, 4H), 3.56-3.53 (m, 2H), 3.37 (s, 3H), 2.50 (s, 3H), 1.81 (d, J=7.0 Hz, 3H), 1.46 (t, J=7.0 Hz, 3H); $^{13}C$ NMR (125 MHz, $CDCl_3$) δ 170.7, 163.8, 163.2 (2), 153.3, 149.9, 149.1, 127.9, 126.8, 119.4, 114.0, 111.3, 80.6, 71.9, 70.9, 70.7, 70.6, 69.7, 68.9, 64.7, 59.1, 37.7, 22.0, 14.8, 11.6; HRMS-ESI (m/z) $[M+H]^+$ calcd for $C_{25}H_{35}N_5O_5S_2H$, 550.2158; found 550.2169.

For Scheme 2

3-Hydroxy-4-methoxybenzothioamide (B)

To a mixture of 3-hydroxy-4-methoxybenzonitrile A (3.00 g, 20.11 mmol) in pyridine (30 mL) and triethylamine (3 mL) was added ammonium sulfide solution (20% wt. in $H_2O$, 20.7 mL, 60.3 mmol). The mixture was stirred for 18 h at 60° C. The reaction mixture was cooled and concentrated in vacuo to remove residual solvent. The resulting residue was washed with brine and extracted with ethyl acetate. The organic layer was dried over anhydrous $Na_2SO_4$, concentrated in vacuo, and purified by flash column chromatography over silica gel (3:1 ethyl acetate: hexanes) to yield B (3.13 g, 17.1 mmol, 85%) as a yellow solid. $^1$H NMR (500 MHz, Acetone-d$_6$) δ 8.77 (br s, 1H), 8.65 (br s, 1H), 7.85 (s, 1H), 7.59 (d, J=2.5 Hz, 1H), 7.56 (dd, J=8.5, 2.3 Hz, 1H), 6.94 (d, J=8.5 Hz, 1H), 3.88 (s, 3H); $^{13}$C NMR (125 MHz, Acetone-d$_6$) δ 200.7, 150.5, 145.7, 132.4, 119.5, 114.8, 110.2, 55.5.

1-(2-(3-Hydroxy-4-methoxyphenyl)-5-methylthiazol-4-yl)ethan-1-one (C)

A mixture of thioamide B (2.75 g, 15.0 mmol) and 4-bromopentane-2,3-dione (4.03 g, 22.5 mmol) in ethanol (70 mL) was stirred under refluxing conditions for 4 h. The resulting mixture was cooled and concentrated in vacuo to remove residual solvent. The crude residue was purified by flash column chromatography over silica gel (10:3 hexanes: ethyl acetate) to yield the desired thiazole intermediate C (3.79 g, 14.4 mmol, 96%) as a white solid. $^1$H NMR (500 MHz, DMSO-d$_6$) δ 9.53 (br s, 1H), 7.34 (d, J=2.0 Hz, 1H), 7.26 (dd, J=8.5, 2.0 Hz, 1H), 6.98 (d, J=8.5 Hz, 1H), 3.80 (s, 3H), 2.66 (s, 3H), 2.57 (s, 3H); $^{13}$C NMR (125 MHz, DMSO-d$_6$) δ 195.2, 162.5, 150.1, 148.5, 147.1, 142.7, 125.6, 118.2, 112.9, 112.5, 55.9, 29.4, 13.2.

N-(2-(5-(4-acetyl-5-methylthiazol-2-yl)-2-methoxyphenoxy)ethyl)methanesulfonamide (D)

To a solution of thiazole intermediate C (1.58 g, 6.0 mmol) in DMF (35 mL) was added Cs$_2$CO$_3$ (3.13 g, 9.6 mmol) and N-(2-bromoethyl)methanesulfonamide (2.18 g, 10.8 mmol). The mixture was stirred for 72 h at 50° C. After concentration to remove residual solvent, the resulting residue was washed with brine and extracted with ethyl acetate. The organic layer was washed with water three times, dried over anhydrous Na$_2$SO$_4$ and concentrated in vacuo, and the crude residue was purified by flash column chromatography over silica gel (3:2 ethyl acetate: hexanes) to yield desired ketone D (1.89 g, 4.9 mmol, 82%) as a white solid. $^1$H NMR (500 MHz, CDCl$_3$) δ 8.00 (s, 1H), 7.51 (d, J=2.0 Hz, 1H), 7.46 (dd, J=8.5, 2.0 Hz, 1H), 6.92 (d, J=8.5 Hz, 1H), 4.25-4.20 (m, 2H), 3.90 (s, 3H), 3.60-3.55 (m, 2H), 3.03 (s, 3H), 2.76 (s, 3H), 2.70 (s, 3H); $^{13}$C NMR (125 MHz, CDCl$_3$) δ 195.8, 162.5, 151.5, 148.9, 147.8, 143.1, 126.4, 121.1, 112.4, 111.7, 69.1, 55.9, 42.7, 40.6, 29.4, 13.4.

(S)-N-(2-(5-(4-(1-hydroxyethyl)-5-methylthiazol-2-yl)-2-methoxyphenoxy)ethyl)methane-sulfonamide (E)

To a stirred solution of (R)-(+)-2-Methyl-CBS-oxazaborolidine (6.7 mL of a 1.0 M solution in toluene, 6.7 mmol) in THF (26 mL) at −78° C. under Ar was added borane-tetrahydrofuran complex (4.4 mL of a 1.0 M solution in THF, 4.4 mmol) followed by a solution of D (284 mg, 0.74 mmol) in THF (14 mL). After finish adding the D solution with syringe pump for 6 h, the reaction mixture was stirred for another 20 min at −78° C. H$_2$O (10 mL) and MeOH (5 mL) was added and the mixture was allowed to warm to room temperature. After concentration to remove residual solvent, the resulting residue was washed with brine and extracted with ethyl acetate. The organic layer was washed with water three times, dried over anhydrous Na$_2$SO$_4$ and concentrated in vacuo, and the crude residue was purified by flash column chromatography twice over silica gel with 3:2 ethyl acetate: hexanes, and 40:1 dichloromethane:methanol as washing system separately to yield alcohol E (221 mg 0.57 mmol, 77%, ee 96%) as a white solid. $^1$H NMR (500 MHz, Acetone-d$_6$) δ 7.57 (d, J=2.0 Hz, 1H), 7.46 (dd, J=8.5, 2.0 Hz, 1H), 7.05 (d, J=8.5 Hz, 1H), 6.26 (br s, 1H), 5.02-4.95 (m, 1H), 4.21 (t, J=5.5 Hz, 2H), 3.88 (s, 3H), 3.57 (dt, J=5.5, 5.5 Hz, 2H), 3.04 (s, 3H), 2.48 (s, 3H), 1.50 (d, J=6.0 Hz, 3H); $^{13}$C NMR (125 MHz, Acetone-d$_6$) δ 162.9, 156.1, 151.3, 148.4, 127.1, 126.8, 119.7, 112.1, 111.4, 68.6, 64.1, 55.3, 42.6, 39.6, 23.0, 10.0.

(S)-1-(2-(4-Methoxy-3-(2-(methylsulfonamido)ethoxy)phenyl)-5-methylthiazol-4-yl)ethyl 2,2,2-trifluoroacetate (F)

To a stirred solution of alcohol E (221 mg, 0.57 mmol) in CH$_2$Cl$_2$ (13 mL) was added Trifluoroacetic anhydride (0.66 mL, 2.9 mmol) slowly at 0° C. After stirred at 0° C. for 30 min, the reaction was allowed to warm to 23° C. and stirred for another 30 min before stopped. After concentration in vacuo to remove residual solvent, the resulting crude residue was used directly for next step without any further purification because of the instability of the desired trifluoroacetate F.

(R)-N-(2-(5-(4-(1-((4,6-diaminopyrimidin-2-yl)thio)ethyl)-5-methylthiazol-2-yl)-2-methoxyphenoxy)ethyl)methanesulfonamide (10R) and (S)-N-(2-(5-(4-(1-((4,6-diaminopyrimidin-2-yl)thio)ethyl)-5-methylthiazol-2-yl)-2-methoxyphenoxy)ethyl)methane-sulfonamide (10S)

A mixture of crude chloride F from previous step and 4,6-diamino-2-mercaptopyrimidine (112 mg, 0.86 mmol) in DMF (5 mL) was stirred at 80° C. for 1 h. The solution was cooled, concentrated in vacuo and purified by flash column chromatography over silica gel (25:1 dichloromethane: methanol) to give the couple of enantiomers 10R and 10S (178 mg, 0.35 mmol, ee 40% of 10R, 61% total yield in two steps) as a white solid. Recrystallization of the enantiomers with MeOH\acetone solvent system gave the 10R with >93% ee. $^1$H NMR (500 MHz, Acetone-d$_6$) δ 7.55 (d, J=2.0 Hz, 1H), 7.48 (dd, J=8.5, 2.0 Hz, 1H), 7.06 (d, J=8.5 Hz, 1H), 6.26 (br s, 1H), 5.60-5.55 (m, 4H), 5.37 (s, 1H), 5.30 (q, J=7.0 Hz, 1H), 4.23 (t, J=5.5 Hz, 2H), 3.89 (s, 3H), 3.58 (dt, J=5.5, 5.5 Hz, 2H), 3.05 (s, 3H), 2.52 (s, 3H), 1.74 (d, J=7.0 Hz, 3H); $^{13}$C NMR (125 MHz, DMSO-d$_6$) δ 168.0, 163.5 (2), 162.9, 153.6, 150.6, 147.8, 126.6, 126.2, 119.5, 112.3, 110.4, 79.0, 67.9, 55.7, 41.9, 36.1, 30.7, 22.2, 11.2; HRMS-ESI (m/z) [M+F]$^+$ calcd for C$_{20}$H$_{26}$N$_6$O$_4$S$_3$H, 511.1256; found 511.1259; 10R [α]$^{19}$$_D$=+340.0 (c=0.12 acetone) (ee=93%).

Protein Expression and Purification.

Protein expression and purification was performed exactly as described by us.[9] Shortly, we used the S74E-C4S-dCK variant, which is the human dCK protein where 4 solvent-exposed cysteines are mutated into serines (C4S). We showed that the C4S mutant generates better quality crystals without altering the 3 dimensional conformation of the enzyme or its enzymatic activity.[22] Additionally, the enzyme contained the mutation of Ser74 to glutamic acid (S74E); this mutation serves to mimic the phosphorylated state of this residue. When we refer to dCK in this report, we mean the C4S-S74E-dCK variant. dCK was expressed in Escherichia coli BL21 C41(DE3) cells using a pET-14b vector; the cells were grown in 2×YT medium and induced with 0.1 mM IPTG for 4 h at 310 K. The cells were harvested and the pellet was lysed by sonication. The lysate was cleared by centrifugation at 30 000 rev/min for 1 h at 277 K and the supernatant was loaded onto a 5 ml HisTrap nickel-affinity column (GE Healthcare). The column was washed with 300 ml of a buffer composed of 25 mM Tris-HCl pH 7.5, 500 mM NaCl, 30 mM imidazole. The bound protein was eluted with the same buffer but containing 250 mM imidazole and was further purified by gel filtration using an S-200 column in a buffer consisting of 25 mM HEPES pH 7.5, 200 mM sodium citrate, 2 mM EDTA, 3 mM DTT. The protein fractions were pooled, concentrated, aliquoted, flash-frozen in liquid nitrogen and stored at 193 K until use.

Kinetic Assay.

The phosphorylation activity of dCK was determined using a spectroscopic NADH-dependent enzyme-coupled assay.[2, 23] All measurements were taken in triplicate at 310 K in a buffer consisting of 100 mM Tris pH 7.5, 200 mM KCl, 5 mM MgCl2, 0.5 mM EDTA, 0.8 mM phosphoenolpyruvate, 0.4 mM NADH with 50 nM dCK and 1 mM ATP. $IC_{50}^{app}$ and $Ki^{app}$ were determined as described by us[9] and all data were fitted using the KaleidaGraph software.

$Ic_{50}$ Determinations.

These were performed in CCRF-CEM acute lymphoblastic leukemia cells as previously described.[8, 9]

PET Studies.

PET studies to determine % inhibition of dCK activity in vivo were performed as previously described.[8, 9]

Human Microsomal Stability Assays.

These assays were performed by Cyprotex (Watertown, Mass.) according to standard operating protocols.

Plasma Pharmacokinetics of Compounds 8 and 10 in Mice.

These measurements were performed as previously described.[8, 9] Briefly, C57Bl/6 female mice were treated with the dCK inhibitors via intraperitoneal injection. The drugs were administered in 50% polyethylene glycol (PEG 400)/50 mM Tris-HCl, pH 7.5. Five minutes after drug injection, whole blood (~75 μL) was obtained at various time points from the retro-orbital sinus using hematocrit capillary tubes. Samples were centrifuged at 20,000× g for 5 min, and the supernatant (5 μL) was transferred into a clean tube. Calibration standards were prepared by spiking various amounts of 9 and 10 in 5 μL supernatant from the plasma of untreated mice to obtain final concentrations between 0.001 to 100 pmol/μL. Samples and the calibration standards were mixed with 500 μL ice-cold acetonitrile/water (50/50, v/v) containing an internal standard (Ia). All of the samples were evaporated to dryness in a vacuum centrifuge. The residue was reconstituted in 100 μL acetonitrile/water (50/50, v/v). Samples (5 μL) were injected onto a reverse phase column (Agilent ZORBAX Rapid Resolution High Definition Eclipse Plus C18, 2.1×50 mm, 1.8 μm) equilibrated in water acetonitrile/formic acid, 95/5/0.1 and eluted (200 μL/min) with an increasing concentration of solvent B (acetonitrile/formic acid 100/0.1, v/v: min/% acetonitrile; 0/5, 2/5, 8/80, 9/80, 10/5, 12/5). The effluent from the column was directed to an electrospray ion source (Agilent Jet Stream) connected to a triple quadrupole mass spectrometer (Agilent 6460 QQQ) operating in the positive ion MRM mode. The ion transitions for Ia, 9, and 10 are 476.2 to 334.5, 550.2 to 408.2, 511.1 to 369.1 respectively. The peak areas for 9 and 10 were normalized to the peak area of the internal standard and the plasma concentrations were computed using the standard curves generated by calibration standards spiked in plasma from untreated mice. Approximated values of the Area Under the Curve (AUC), half-life ($T_{1/2}$), maximum concentration in the plasma ($C_{max}$) and time to reach the maximum concentration ($T_{max}$) were calculated using Boomer/Multi-Forte P K Functions from Microsoft Excel.[24, 25]

Crystallization, X-Ray Data Collection, and Refinement.

Crystals of human dCK in complex with inhibitors and UDP were grown at 285 K using the hanging-drop vapor-diffusion method. All dCK-inhibitor complexes were prepared as follows: 1 μL dCK protein at 10-17 mg/mL in complex with a 2.5-fold molar excess of inhibitor, 2 mM UDP and 5 mM MgCl2 was mixed with 1 μL reservoir buffer solution. The reservoir solution consisted of 0.9-1.5 M trisodium citrate dehydrate and 25 mM HEPES pH 7.5. Prior to data collection, crystals were soaked in mineral oil for cryoprotection. Diffraction data for dCK in complex with compounds 2-6 were collected on the Life Sciences Collaborative Access Team (LS-CAT) beamline 21-ID-G. Data for all other complexes (compounds 7-10) were collected using the in-house X-ray source (Rigaku RU-200 rotating anode) with a R-Axis IV++ image plate detector. Data were processed and scaled with XDS and XSCALE.[26] Structures were determined by molecular replacement with MOL-REP[27] using the dCK structure (PDB entry 4JLN[9]) as a search model. Refinement was conducted using REFMAC[28] and model building using Coot.[29] All inhibitor coordinates and library descriptions were generated using the PRODRG server.[30] All data sets were perfectly twinned and iterative refinements were carried out using REFMAC with the Twin option active. Data collection and refinement statistics are listed in Table 1. Structural figures were prepared using the PyMOL Molecular Graphics System (v.1.6.0; Schrödinger).

Modeling.

The S-isomer in Position-1 and the R-isomer in Position-2 were generated by flipping the chirality of the linker carbon using Maestro v. 9.1, Schrödinger, LLC 2010. This program was also used to generate the torsion scans around the bond connecting the chiral linker carbon and the thiazole ring (torsion angle defined by CAC-CBC-CBB-NAO).

Equilibration simulations were performed using the MCPRO 2.0 software package[31] with the OPLS-AA[17] force field. The protein was solvated in a 30 Å cap of TIP4P water molecules.[16] The protein backbone and all bond lengths within the protein were held fixed. Angles and torsions within 11 Å of the center of the bound molecule were allowed to vary. All degrees of freedom of the bound molecule were sampled. Equilibration began with 5×10[6] configurations of solvent-only moves, followed by 10×10[6] configurations in which the protein and bound molecule were sampled, with additional solvent sampling at every tenth configuration. Equilibrations were performed using Metropolis Monte Carlo in the NPT ensemble at 1 atm and 25° C. For the unbound structures, optimizations were performed using OPLS-AA. Implicit solvent was simulated with the generalized Born/surface area (GB/SA) method.[19, 21] Energies were assessed using the PDDG/PM3 method[32] in the BOSS software package.[31]

| PDB ID CODES | | | | | | | | |
|---|---|---|---|---|---|---|---|---|
| | Complex | | | | | | | |
| | 2 | 3 | 4 | 5 | 6 | 7 | 8 | 10R |
| PDB codes | 4Q18 | 4Q19 | 4Q1A | 4Q1B | 4Q1C | 4Q1D | 4Q1E | 4Q1F |

Spectra for Compounds 1, 2, 7, 8, 9R, 9S, and 10S 1-(5-(4-(((4-aminopyrimidin-2-yl)thio)methyl)-5-propylthiazol-2-yl)-2-methoxyphenoxy)-2-methyl-propan-2-ol (1=DI-48)

$^1$H NMR (500 MHz, Acetone-d$_6$) δ 7.99 (d, J=6.0 Hz, 1H), 7.53 (d, J=2.0 Hz, 1H), 7.45 (dd, J=8.5, 2.0 Hz, 1H), 7.03 (d, J=8.5 Hz, 1H), 6.31 (br s, 2H), 6.28 (d, J=5.5 Hz, 1H), 4.48 (s, 2H), 3.88 (s, 3H), 3.88 (s, 2H), 2.93 (t, J=7.5 Hz, 2H), 1.73-1.64 (m, 2H), 1.32 (s, 6H), 0.99 (t, J=7.0 Hz, 3H); $^{13}$C NMR (125 MHz, Acetone-d$_6$) δ 170.4, 163.8, 163.5, 155.3, 151.5, 149.3, 148.4, 134.7, 126.9, 119.4, 112.2, 111.3, 101.0, 77.7, 69.2, 55.5, 28.3, 28.1, 26.0 (2), 25.2, 13.1; HRMS-ESI (m/z) [M+H]$^+$ calcd for C$_{22}$H$_{28}$N$_4$O$_3$S$_2$H, 461.1681; found 461.1667.

1-(5-(4-(((2,6-diaminopyrimidin-4-yl)thio)methyl)-5-propylthiazol-2-yl)-2-methoxyphenoxy)-2-methyl-propan-2-ol (2=DI-49)

$^1$H NMR (500 MHz, CDCl$_3$) δ 7.40-7.35 (m, 2H), 7.04 (d, J=8.5 Hz, 1H), 6.21 (s, 2H), 5.99 (s, 2H), 5.67 (s, 1H), 4.60 (s, 1H), 4.39 (s, 2H), 3.82 (s, 3H), 3.76 (s, 2H), 2.83 (t, J=7.5 Hz, 2H), 1.60-1.52 (m, 2H), 1.22 (s, 6H), 0.92 (t, J=7.0 Hz, 3H); $^{13}$C NMR (125 MHz, DMSO-d$_6$) δ 163.8, 163.4, 162.4, 150.8, 148.7, 148.1, 134.8, 126.0, 119.2, 112.4, 110.3, 90.2, 77.0, 68.8, 55.9, 54.9, 27.7, 26.7 (2), 26.1, 24.9, 13.5; HRMS-ESI (m/z) [M+H]$^+$ calcd for C$_{22}$H$_{29}$N$_5$O$_3$S$_2$H, 476.1790; found 476.1798.

2-((1-(2-(3-(2-fluoroethoxy)-4-methoxyphenyl)-5-propylthiazol-4-yl)ethyl)thio)pyrimidine-4,6-diamine (7=DI-68)

$^1$H NMR (500 MHz, CDCl$_3$) δ 7.55 (d, J=2.0 Hz, 1H), 7.44 (dd, J=8.5, 2.0 Hz, 1H), 6.88 (d, J=8.5 Hz, 1H), 5.25 (s, 1H), 5.24 (q, J=7.0 Hz, 1H), 4.87 (dd, J=5.6, 2.8 Hz, 1H), 4.77 (dd, J=5.6, 2.8 Hz, 1H), 4.55 (s, 4H), 4.47 (dd, J=5.0, 3.5 Hz, 1H), 4.34 (dd, J=5.0, 3.5 Hz, 1H), 3.90 (s, 3H), 2.98-2.79 (m, 2H), 1.81 (d, J=7.0 Hz, 3H), 1.75-1.58 (m, 2H), 1.00 (t, J=7.0 Hz, 3H); $^{13}$C NMR (125 MHz, CDCl$_3$) δ 170.8, 163.8, 163.2 (2), 153.0, 150.9, 148.0, 133.0, 127.4, 120.3, 111.7, 111.6, 81.9 (d, J$_{CF}$=170.6 Hz), 80.6, 68.4 (d, J$_{CF}$=20.6 Hz), 56.1, 37.8, 28.5, 25.3, 22.4, 13.9; HRMS-ESI (m/z) [M+H]$^+$ calcd for C$_{21}$H$_{26}$FN$_5$O$_2$S$_2$H, 464.1590; found 464.1567.

2-((1-(2-(3-(2-fluoroethoxy)-4-methoxyphenyl)-5-methylthiazol-4-yl)ethyl)thio)pyrimidine-4,6-diamine (8=DI-72)

$^1$H NMR (500 MHz, CD$_3$OD) δ 7.53 (s, 1H), 7.43 (d, J=8.4 Hz, 1H), 7.02 (d, J=8.4 Hz, 1H), 5.34-5.30 (m, 2H), 4.82-4.80 (m, 1H), 4.72-4.70 (m, 1H), 4.35-4.34 (m, 1H), 4.30-4.28 (m, 1H), 2.52 (s, 3H), 1.75 (d, J=7.0 Hz, 3H); $^{13}$C NMR (125 MHz, CD$_3$OD) δ 170.4, 165.8, 165.2, 154.8, 152.7, 149.7, 128.6, 128.1, 121.5, 113.3, 112.8, 83.8, 82.5, 80.6, 70.1, 70.0, 56.5, 38.4, 22.20, 11.5; HRMS-ESI (m/z) [M+H]$^+$ calcd for C$_{19}$H$_{22}$FN$_5$O$_2$S$_2$H, 436.1277; found 436.1270.

(R)-2-((1-(2-(3-Ethoxy-4-(2-(2-(2-methoxyethoxy)ethoxy)ethoxy)phenyl)-5-methylthiazol-4-yl)ethyl)thio)pyrimidine-4,6-diamine (9R=R-DI-75)

[α]$^{21}_D$=+265.7 (c=0.22 acetone) (ee=99%).

(S)-2-((1-(2-(3-Ethoxy-4-(2-(2-(2-methoxyethoxy)ethoxy)ethoxy)phenyl)-5-methylthiazol-4-yl)ethyl)thio)pyrimidine-4,6-diamine (9S=S-DI-75)

[α]$^{20}_D$=−228.6 (c=0.14 acetone) (ee=99%).

(S)-N-(2-(5-(4-(1-((4,6-diaminopyrimidin-2-yl)thio)ethyl)-5-methylthiazol-2-yl)-2-methoxyphenoxy)ethyl)methane-sulfonamide (10S=S-DI-82)

[α]$^{19}_D$=−536.4 (c=0.11 acetone) (ee=99%).

References for Example 1

1. Eriksson, S.; Munch-Petersen, B.; Johansson, K.; Eklund, H. Structure and function of cellular deoxyribonucleoside kinases. Cell Mol Life Sci 2002, 59, 1327-46.
2. Sabini, E.; Ort, S.; Monnerjahn, C.; Konrad, M.; Lavie, A. Structure of human dCK suggests strategies to improve anticancer and antiviral therapy. Nat Struct Biol 2003, 10, 513-9.
3. Toy, G.; Austin, W. R.; Liao, H. I.; Cheng, D.; Singh, A.; Campbell, D. O.; Ishikawa, T. O.; Lehmann, L. W.; Satyamurthy, N.; Phelps, M. E.; Herschman, H. R.; Czernin, J.; Witte, O. N.; Radu, C. G. Requirement for deoxycytidine kinase in T and B lymphocyte development. Proc Natl Acad Sci USA 2010, 107, 5551-6.
4. Austin, W. R.; Armijo, A. L.; Campbell, D. O.; Singh, A. S.; Hsieh, T.; Nathanson, D.; Herschman, H. R.; Phelps, M. E.; Witte, O. N.; Czernin, J.; Radu, C. G. Nucleoside salvage pathway kinases regulate hematopoiesis by linking nucleotide metabolism with replication stress. J Exp Med 2012, 209, 2215-28.
5. Choi, O.; Heathcote, D. A.; Ho, K. K.; Muller, P. J.; Ghani, H.; Lam, E. W.; Ashton-Rickardt, P. G.; Rutschmann, S. A deficiency in nucleoside salvage impairs murine lymphocyte development, homeostasis, and survival. J Immunol 2012, 188, 3920-7.
6. Yang, C.; Lee, M.; Hao, J.; Cui, X.; Guo, X.; Smal, C.; Bontemps, F.; Ma, S.; Liu, X.; Engler, D.; Parker, W. B.; Xu, B. Deoxycytidine kinase regulates the G2/M checkpoint through interaction with cyclin-dependent kinase 1 in response to DNA damage. Nucleic Acids Res 2012, 40, 9621-32.
7. Nathanson, D. A.; Armijo, A. L.; Tom, M.; Li, Z.; Dimitrova, E.; Austin, W. R.; Nomme, J.; Campbell, D. O.; Ta, L.; Le, T. M.; Lee, J. T.; Darvish, R.; Gordin, A.; Wei, L.; Liao, H. I.; Wilks, M.; Martin, C.; Sadeghi, S.; Murphy, J. M.; Boulos, N.; Phelps, M. E.; Faull, K. F.; Herschman, H. R.; Jung, M. E.; Czernin, J.; Lavie, A.; Radu, C. G. Co-targeting of convergent nucleotide biosynthetic pathways for leukemia eradication. J Exp Med 2014, 211, 473-86.
8. Murphy, J. M.; Armijo, A. L.; Nomme, J.; Lee, C. H.; Smith, Q. A.; Li, Z.; Campbell, D. O.; Liao, H. I.; Nathanson, D. A.; Austin, W. R.; Lee, J. T.; Darvish, R.; Wei, L.; Wang, J.; Su, Y.; Damoiseaux, R.; Sadeghi, S.; Phelps, M. E.; Herschman, H. R.; Czernin, J.; Alexandrova, A. N.; Jung, M. E.; Lavie, A.; Radu, C. G. Development of new deoxycytidine kinase inhibitors and noninvasive in vivo evaluation using positron emission tomography. J Med Chem 2013, 56, 6696-708.
9. Nomme, J.; Murphy, J. M.; Su, Y.; Sansone, N. D.; Armijo, A. L.; Olson, S. T.; Radu, C.; Lavie, A. Structural characterization of new deoxycytidine kinase inhibitors rationalizes the affinity-determining moieties of the molecules. Acta Crystallogr D Biol Crystallogr 2014, 70, 68-78.
10. Godsey, M. H.; Ort, S.; Sabini, E.; Konrad, M.; Lavie, A. Structural basis for the preference of UTP over ATP in human deoxycytidine kinase: illuminating the role of main-chain reorganization. Biochemistry 2006, 45, 452-61.

11. Sabini, E.; Hazra, S.; Ort, S.; Konrad, M.; Lavie, A. Structural basis for substrate promiscuity of dCK. J Mol Biol 2008, 378, 607-21.
12. Shu, Y. Z.; Johnson, B. M.; Yang, T. J. Role of biotransformation studies in minimizing metabolism-related liabilities in drug discovery. AAPS J 2008, 10, 178-92.
13. Mikhailovskii, D. I.; Mikhailovskaya, V. N. Rearrangement of Acetylenic Keto Alcohols under Meyer-Schuster Reaction Conditions. Izv. Vyssh. Uchebn. Zaved., Khim. Khim. T 1987, 30, 29-31.
14. Gudipati, V.; Curran, D. P.; Wilcox, C. S. Solution-phase parallel synthesis with oligoethylene glycol sorting tags. Preparation of all four stereoisomers of the hydroxybutenolide fragment of murisolin and related acetogenins. J Org Chem 2006, 71, 3599-607.
15. Corey, E. J.; Bakshi, R. K.; Shibate, S. Highly enantioselective borane reduction of ketones catalyzed by chiral oxazaborolidines. Mechanism and synthetic implications. J. Am. Chem. Soc. 1987, 109, 5551-5553.
16. Jorgensen, W. L.; Chandrasekhar, J.; Madura, J. D.; Impey, R. W.; Klein, M. L. Comparison of Simple Potential Functions for Simulating Liquid Water. Journal of Chemical Physics 1983, 79, 926-935.
17. Jorgensen, W. L.; Maxwell, D. S.; TiradoRives, J. Development and testing of the OPLS all-atom force field on conformational energetics and properties of organic liquids. Journal of the American Chemical Society 1996, 118, 11225-11236.
18. Jorgensen, W. L.; Tirado-Rives, J. Molecular modeling of organic and biomolecular systems using BOSS and MCPRO. Journal of Computational Chemistry 2005, 26, 1689-1700.
19. Jorgensen, W. L.; Ulmschneider, J. P.; Tirado-Rives, J. Free energies of hydration from a generalized Born model and an ALL-atom force field. Journal of Physical Chemistry B 2004, 108, 16264-16270.
20. Repasky, M. P.; Chandrasekhar, J.; Jorgensen, W. L. PDDG/PM3 and PDDG/MNDO: improved semiempirical methods. J Comput Chem 2002, 23, 1601-22.
21. Still, W. C.; Tempczyk, A.; Hawley, R. C.; Hendrickson, T. Semianalytical Treatment of Solvation for Molecular Mechanics and Dynamics. Journal of the American Chemical Society 1990, 112, 6127-6129.
22. Sabini, E.; Hazra, S.; Konrad, M.; Lavie, A. Nonenantioselectivity property of human deoxycytidine kinase explained by structures of the enzyme in complex with L- and D-nucleosides. J Med Chem 2007, 50, 3004-14.
23. Agarwal, K. C.; Miech, R. P.; Parks, R. E., Jr. Guanylate kinases from human erythrocytes, hog brain, and rat liver. Methods Enzymol 1978, 51, 483-90.
24. Bourne, D. W. MULTI-FORTE, a microcomputer program for modelling and simulation of pharmacokinetic data. Comput Methods Programs Biomed 1986, 23, 277-81.
25. Bourne, D. W. BOOMER, a simulation and modeling program for pharmacokinetic and pharmacodynamic data analysis. Comput Methods Programs Biomed 1989, 29, 191-5.
26. Kabsch, W. Xds. Acta Crystallogr D Biol Crystallogr 2010, 66, 125-32.
27. Vagin, A.; Teplyakov, A. Molecular replacement with MOLREP. Acta Crystallogr D Biol Crystallogr 2010, 66, 22-5.
28. Murshudov, G. N.; Skubak, P.; Lebedev, A. A.; Pannu, N. S.; Steiner, R. A.; Nicholls, R. A.; Winn, M. D.; Long, F.; Vagin, A. A. REFMACS for the refinement of macromolecular crystal structures. Acta Crystallogr D Biol Crystallogr 2011, 67, 355-67.
29. Emsley, P.; Lohkamp, B.; Scott, W. G.; Cowtan, K. Features and development of Coot. Acta Crystallogr D Biol Crystallogr 2010, 66, 486-501.
30. Schuttelkopf, A. W.; van Aalten, D. M. PRODRG: a tool for high-throughput crystallography of protein-ligand complexes. Acta Crystallogr D Biol Crystallogr 2004, 60, 1355-63.
31. Jorgensen, W. L.; Tirado-Rives, J. Molecular modeling of organic and biomolecular systems using BOSS and MCPRO. J Comput Chem 2005, 26, 1689-700.
32. Repasky, M. P.; Chandrasekhar, J.; Jorgensen, W. L. Improved semiempirical heats of formation through the use of bond and group equivalents. J Comput Chem 2002, 23, 498-510.

2. Example 2

The ability to reprogram cellular metabolism, a hallmark of cancer first noted long ago (Warburg et al., 1927) and recently re-appreciated, is essential for tumor progression (Hanahan and Weinberg, 2011). While cancer-initiated metabolic reprogramming processes are promising therapeutic targets (Vander Heiden, 2011), the existence of alternative, compensatory biosynthetic pathways presents a significant challenge for developing such therapies. For example, in lipid metabolism, cancer cells scavenge extracellular lipids as an alternative to energy-requiring de novo fatty acid biosynthesis (Kamphorst et al., 2011). In amino acid metabolism, glycine and serine required for tumor growth can be produced de novo and can also be scavenged from the extracellular environment (Jain et al., 2012; Maddocks et al., 2012).

Figure 16A:
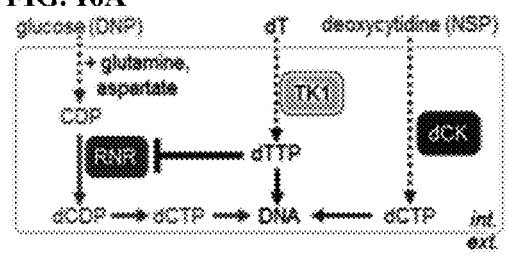
FIGS. 16A-16L. Deoxycytidine (dC) salvage via dCK prevents thymidine (dT)-induced lethal replication stress (RS) in T-ALL cells.

Nucleotide metabolism also involves redundant and convergent biosynthetic pathways. Deoxyribonucleotide triphosphate (dNTP) pools required for DNA replication and repair can be produced by the de novo pathway (DNP) or by the nucleoside salvage pathway (NSP) (FIG. 16A) (Reichard, 1988). The DNP uses glucose and amino acids to generate ribonucleotide disphosphates (NDPs), which are converted to deoxyribonucleotide diphosphates (dNDPs) by ribonucleotide reductase (RNR). The same dNDPs can also be produced via the NSP (Reichard, 1988) starting with extracellular deoxyribonucleosides (dNs) which are imported in the cell via specialized transporters. The first enzymatic steps in the cytosolic NSP are catalyzed by two kinases: thymidine kinase 1 (TK1) phosphorylates thymidine (dT), while deoxycytidine kinase (dCK) phosphorylates deoxycytidine (dC), deoxyadenosine (dA) and deoxyguanosine (dG) (Reichard, 1988). The relevance of these two NSP kinases for dNTP production in normal and malignant cells is yet to be defined. Since dN substrates for the NSP kinases are absent from most cell culture media, it has been assumed that the NSP is dispensable for DNA replication (Xu et al., 1995). However, recent in vivo findings have challenged this assumption. For example, we reported impaired hematopoiesis in dCK$^{-/-}$ mice, due to dCTP pool deficiency, resulting in replication stress (RS), S-phase arrest and DNA damage in hematopoietic progenitors (Austin et al., 2012; Toy et al., 2010). Analyses of dCK/TK1 double-knockout mice showed that NSP-derived dCTP synthesis is required to compensate for the inhibition of de novo dCTP production (Austin et al., 2012) (FIG. 16A). The mechanism of DNP inhibition involves allosteric regulation of RNR-mediated reduction of cytidine diphosphate (CDP) to deoxycytidine disphosphate (dCDP) by dTTP produced via TK1 from endogenous dT (Austin et al., 2012) (FIG. 16A).

Production of dNTPs by the NSP may be therapeutically relevant in cancer. For example, the ability of cancer cells to switch their dCTP synthesis from the DNP to the NSP may explain why dT given as a single dCTP-depleting agent showed limited efficacy in clinical trials (Chiuten et al., 1980; Kufe et al., 1980; Kufe et al., 1981). If correct, and without being bound by any particular theory, this hypothesis suggests that a combination of dT (to inhibit DNP mediated dCTP production) along with a dCK inhibitor (to co-target dCTP production by the NSP), would be more efficacious in killing tumor cells than either treatment alone. Here we investigate this possibility in the context of acute lymphoblastic leukemia (ALL). We demonstrate that co-targeting both de novo and salvage pathways for dCTP biosynthesis is well-tolerated in mice, and is efficacious in T-ALL and B-ALL models. We also describe a Positron Emission Tomography (PET)-based assay to non-invasively monitor in vivo pharmacological targeting of dCTP biosynthesis in cancer cells.

Figure 16B:
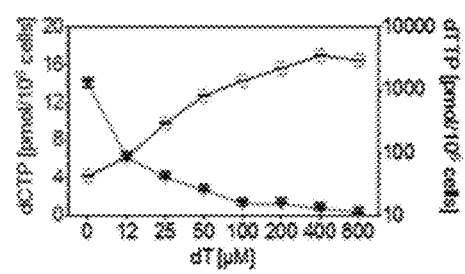
Figure 16C:
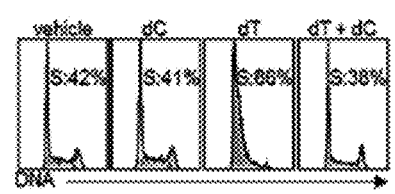
Figure 16D:
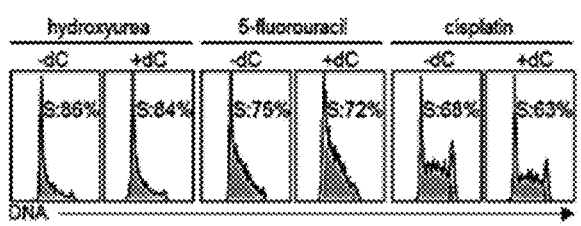

Deoxycytidine salvage via dCK prevents dT-induced lethal replication stress in T-ALL cells Treatment with dT increases cytosolic dTTP concentration, resulting in allosteric inhibition of dCTP production via the DNP (FIG. 16A) (Reichard, 1988). Accordingly, in CCRF-CEM (CEM) human T-ALL cells, dT increased dTTP and decreased dCTP in a dose-dependent manner (FIG. 16B). Early S-arrest (FIG. 16C) was induced by concentrations of dT as low as 50 µM, which increased dTTP ~20-fold and reduced dCTP ~5-fold (FIG. 16B). Supplementation of CEM cultures with 2.5 µM dC completely prevented dT-induced S-phase arrest (FIG. 16C). Addition of dC did not prevent S-phase arrest in CEM cells treated with the RNR inhibitor hydroxyurea, 5-fluorouracil (5-FU) or cisplatin (FIG. 16D), indicating that dC salvage plays a specific role in counteracting dT-induced S-phase arrest.

Figure 16E:
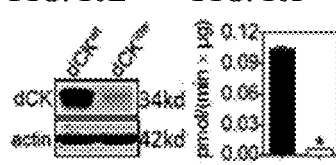
Figures 16F, 16G:
Figure 16H:
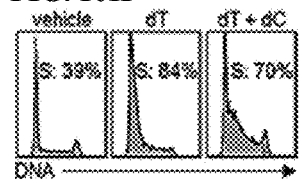
Figure 16I:
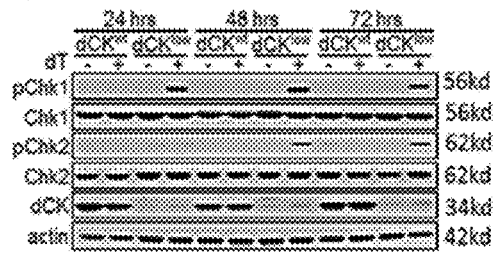
Figure 16J:
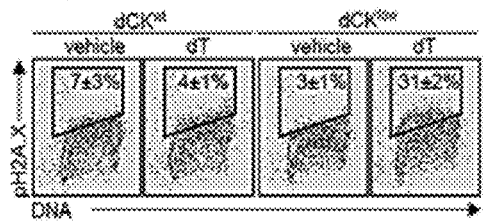
Figure 16K:
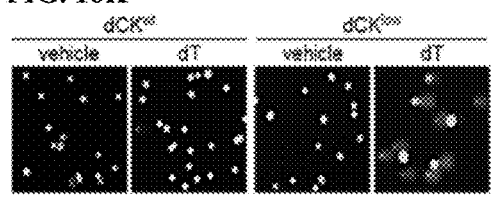
Figure 16L:
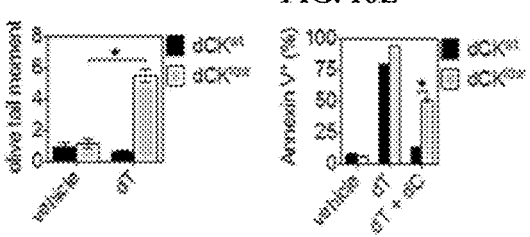

To study the role of dCK in the prevention of dT-induced S-phase arrest by dC addition, we generated CEM $dCK^{low}$ cells (FIG. 16E) using a dCK-targeted shRNA vector. Knocking down dCK reduced $^3$H-deoxycytidine uptake by ~95% (FIG. 16F) and decreased cytosolic dCTP levels by ~30% (FIG. 16G), but did not perturb normal cell cycle progression (FIG. 16H). Supplementation of cell culture media with 2.5 µM dC restored the dCTP pool in dT-treated $dCK^{wt}$ cells to ~55% of its baseline value, but had no effect on dT-induced dCTP pool depletion in $dCK^{low}$ cells (FIG. 16G). Consequently, dC addition prevented dT-induced S-phase arrest only in CEM $dCK^{wt}$ cells (FIG. 16C), but not in CEM $dCK^{low}$ cells (FIG. 16H). Accordingly, in the presence of both dT and dC, only $dCK^{low}$ but not $dCK^{wt}$ CEM cells displayed (i) activation of the RS response marker Chk1 phosphorylated on Ser345 (pChk1) (FIG. 16I), (ii) induction of DNA damage, as determined by activation of Chk2 phosphorylated on Thr68 (pChk2) (FIG. 16I), pH2A.X staining by flow cytometry (FIG. 16J), as well as by comet assay (FIG. 16K) and (iii) apoptosis (FIG. 16L). Thus, downregulation of dCK expression in CEM cells abolished ability to compensate for dT-mediated inhibition of dCTP production via the DNP, resulting in dCTP depletion, stalled DNA replication, RS, DNA damage and apoptosis.

In T-ALL cells dT triggers a metabolic switch to NSP dCTP production and upregulates dC salvage. To investigate the biochemical mechanism by which the NSP compensates for dT-mediated DNP inhibition, we quantified the contributions of each dCTP biosynthetic pathway to both the free cytosolic dCTP and the dCTP incorporated into the DNA.

CEM cells were incubated for 12 hr with [U-$^{13}$C]-glucose, the substrate for the DNP, and with [U-$^{13}$C/$^{15}$N]-dC, the substrate for the NSP (FIG. 17A). Heavy isotope labeled dCTP species were detected by combined liquid chromatography-tandem mass spectrometry in the multiple reaction-monitoring mode (LC/MS/MS-MRM). Mass additions between 3 and 8 identified dCTP produced from [U-$^{13}$C]-glucose via the DNP, while mass additions between 11 and 12 identified dCTP produced from [U-$^{13}$C/$^{15}$N]-dC via the NSP (FIG. 17A).

In untreated CEM cells, the free dCTP pool produced from dC via the NSP over a 12 hr labeling period was ~5-fold larger than the free dCTP pool originating from glucose via the DNP (FIG. 17B). However, ~2.5 fold more dCTP incorporated into DNA was produced by the DNP than by the NSP (FIG. 17B). Treatment with dT decreased dCTP production from glucose via the DNP, in both the free cytosolic and DNA dCTP pools (FIG. 17B). Moreover, dT increased the utilization of the NSP-produced dCTP for DNA synthesis more than 3-fold over baseline values (FIG. 17B). These findings support previous observations that, under basal conditions, DNA synthesis relies primarily on the DNP-produced dCTP (Xu et al., 1995). Accordingly, the large size of the NSP-derived free dCTP pool in untreated CEM cells (FIG. 17B) likely reflects its inefficient utilization for DNA replication under basal conditions. Notably, the NSP-derived free dCTP pool did not decrease in dT treated cells, even though the utilization of this pool for DNA synthesis increased significantly (FIG. 17B). This finding, suggests that dT upregulates dCTP production via the NSP, which is consistent with a marked increase in dCK activity (FIG. 17C) and in dC uptake (FIG. 17D) in dT-treated CEM cells.

Figure 18A:
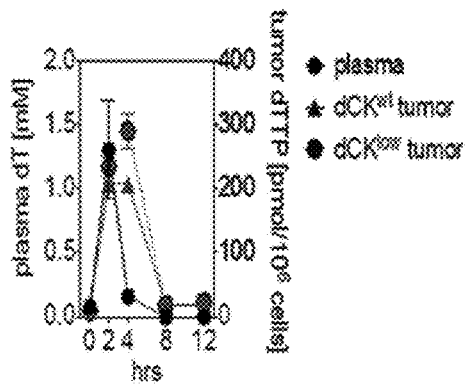
FIGS. 18A-18G. In vivo, salvage of endogenous dC rescues T-ALL cells from RS induced by dT treatment.
Figure 18B:
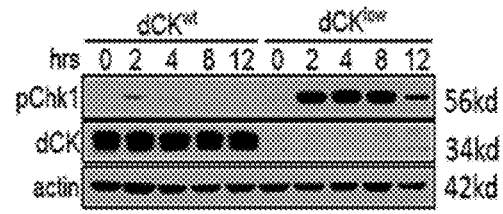

In vivo, salvage of endogenous dC rescues T-ALL cells from RS induced by dT treatment. To examine whether findings from cell culture studies (FIGS. 16A-16L; FIGS. 17A-17C) can be recapitulated in vivo, subcutaneous (s.c.) CEM $dCK^{wt}$ and $dCK^{low}$ xenografts were established in NOD SCID gamma (NSG) mice. Plasma dT peaked at 1.5 mM two hours after treatment with a single dT injection (2 g/kg, intraperitoneally) and then rapidly declined to baseline values (~10 µM) at 8 hr (FIG. 18A). Intratumoral dTTP increased in both $dCK^{wt}$ and $dCK^{low}$ tumors for at least 4 hr after dT administration (FIG. 18A). In $dCK^{wt}$ tumors, dT induced a slight and transient upregulation of pChk1 at the 2 and 4 hr time points (FIG. 18B). In marked contrast, a more pronounced and sustained pChk1 upregulation was induced by dT treatment in $dCK^{low}$ tumors (FIG. 18B). These findings suggest that dCK is required to enable CEM cells to resist RS induced by dT treatment in vivo.

Figure 18C:
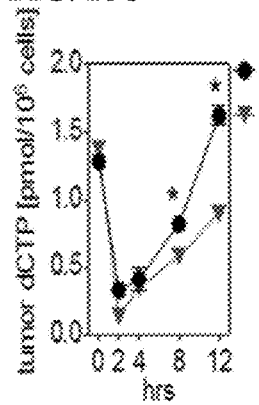
Figure 18D:
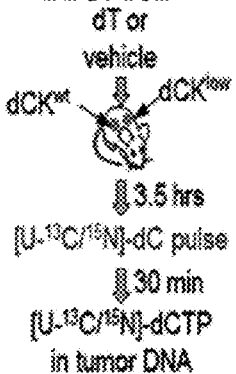
Figure 18E:
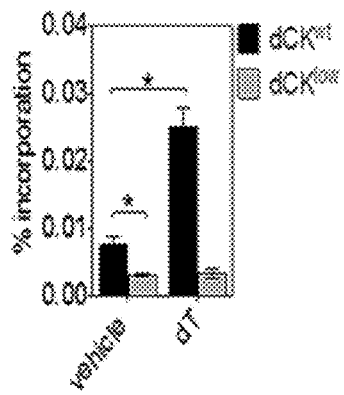

To understand the role of dCK in dCTP production and utilization in tumors from dT treated mice, we measured the free dCTP pool and incorporation of NSP-produced dCTP into the DNA. During the 0-4 hr timeframe, dCTP decreased several fold in both CEM $dCK^{wt}$ and $dCK^{low}$ xenografts and then started to recover as plasma dT dropped to baseline values (FIG. 18C). Intratumoral dCTP recovery occurred significantly slower in the $dCK^{low}$ xenografts than in their wild type counterparts (FIG. 18C). To quantify the effects of dT treatment on the utilization of the NSP-produced dCTP for DNA synthesis, tumor-bearing mice were treated with dT or vehicle for 3.5 hr and were then pulsed with [U-$^{13}$C/$^{15}$N]-labeled dC. Thirty minutes later, mice were sacrificed to measure the incorporation of dCTP produced from labeled dC into tumor DNA by LC/MS/MS-MRM (FIG. 18D). In tumors from vehicle treated mice, ~2-fold less dCTP produced from [U-$^{13}$C/$^{15}$N]-labeled dC was incorporated into the DNA of dCK$^{low}$ tumors than in the DNA of their dCK$^{wt}$ counterparts (FIG. 18E). In dT treated mice, labeled dCTP incorporation into DNA increased ~3-fold in dCK$^{wt}$ tumors, but remained unchanged in the dCK$^{low}$ xenografts (FIG. 18E). Together with the pattern of pChk1 upregulation shown in FIG. 18B, these findings suggest that upon dT treatment in vivo, dCK activity is required to maintain tumor DNA replication, thereby preventing RS induction. Moreover, similar to in vitro findings (FIG. 17B), dT treatment in vivo increases the incorporation of NSP-produced dCTP into tumor DNA.

Figure 18F:
Figure 18G:
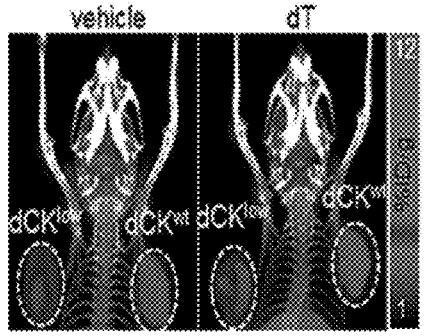

To determine if the increase in the utilization of the NSP-produced dCTP for DNA synthesis in tumors from dT treated mice is also associated with an upregulation of the NSP as shown in vitro (FIGS. 17C-17D), we took advantage of $^{18}$F-L-FAC (1-L-(2' deoxy-2',-$^{18}$Fluoroarabinofuranosyl) cytosine), a fluorinated dC analog (Radu et al., 2008; Shu et al., 2010). $^{18}$F-L-FAC crosses the cell membrane via nucleoside transporters and accumulates specifically in dCK expressing cells by a phosphorylation-dependent mechanism (FIG. 18F); dCK-dependent phosphorylated $^{18}$F-L-FAC retention in living animals can be imaged and quantified non-invasively by Positron Emission Tomography (PET). As anticipated, dCK$^{low}$ tumors accumulated ~40% less $^{18}$F-L-FAC than dCK$^{wt}$ tumors (FIG. 18F). Four hours after dT treatment, $^{18}$F-L-FAC accumulation increased by ~20% in dCK$^{wt}$ tumors (FIG. 18G). $^{18}$F-L-FAC accumulation also increased in dCK$^{low}$ tumors (FIG. 18G), likely because of their residual dCK activity. However, the NSP upregulation in the dCK$^{low}$ tumors was insufficient to maintain DNA synthesis and prevent RS induction, as indicated by both the marked and sustained pChk1 upregulation in dCK$^{low}$ tumors from dT treated mice (FIG. 18B) and by the low incorporation in dCK$^{low}$ tumors of stable isotope labeled dCTP into the DNA (FIG. 18E).

Figure 19A:
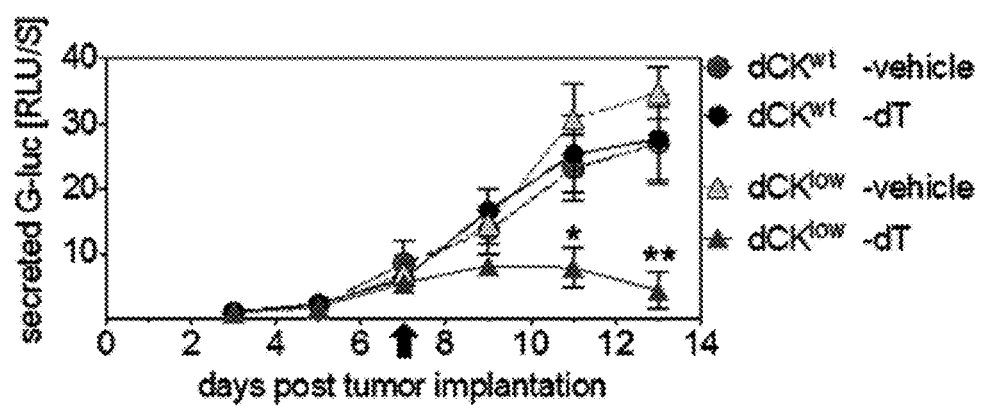
FIG. 19A-19C. dCK mediates resistance to dT in T-ALL cells in vivo (FIG. 19A) Serial secreted Gaussia luciferase measurements of peripheral blood from NSG mice bearing CEM dCK$^{wt}$ or dCK$^{low}$ s.c. tumors (n=6 mice/condition) treated every 12 hours with vehicle or dT (2 g/kg) starting at day 7 post-tumor implantation until day 13. Values represent mean±SEM; n=2 independent experiments.  P<0.01, * P<0.001 compared with dCK$^{low}$ vehicle at indicated time point (FIG. 19B) CEM dCK$^{wt}$ and dCK$^{low}$ tumors from vehicle or dT-treated mice from (A).
Figure 19B:
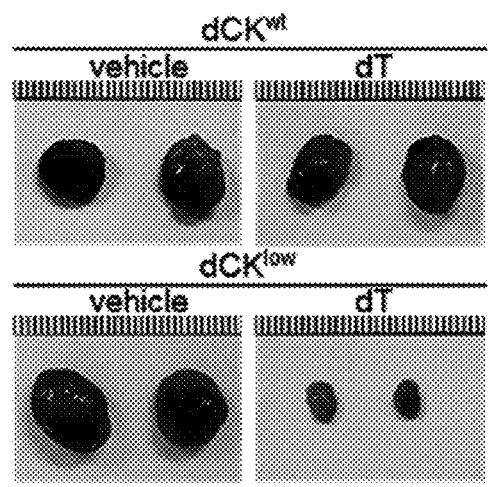
Figure 19C:
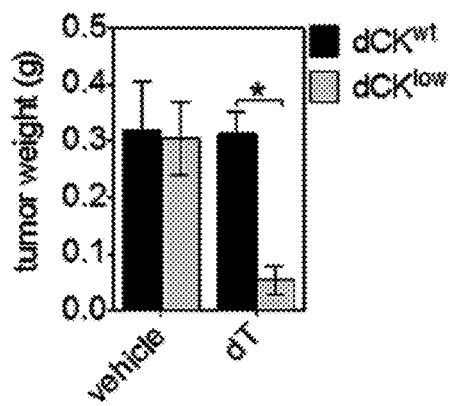

The NSP mediates T-ALL cell resistance to dT treatment in vivo. Since the NSP is required to prevent dT-induced RS in T-ALL cells in culture (FIG. 16I) and in vivo (FIG. 18C), we determined if downregulation of dCK expression synergizes with dT treatment to induce tumor regression in mice. CEM dCK$^{wt}$ and dCK$^{low}$ s.c. tumor-bearing mice were treated with dT (2 g/kg) twice daily for 6 days. Prolonged dT administration blocked the growth of CEM dCK$^{low}$ tumors without affecting the dCK$^{wt}$ xenografts, as shown by (i) serial measurements of secreted Gaussia luciferase, which served as an indicator of tumor burden in peripheral blood (Tannous, 2009) (FIG. 19A) and (ii) end point measurements of tumor sizes (FIG. 19B) and weights (FIG. 19C). The synergy between dT treatment and shRNA-mediated dCK downregulation suggests that pharmacological dCK inhibition, combined with dT administration, may provide a new therapeutic strategy in ALL.

Development of DI-39, a small molecule, high affinity dCK inhibitor which occupies the substrate binding site of the kinase. To examine whether the NSP can be exploited therapeutically through pharmacological dCK inhibition, we screened selected chemical libraries comprising ~90,000 small molecules. This high throughput screen (HTS) identified DI-0120 (FIG. 20A), a dCK inhibitor with an IC$_{50}$ of 1.4 μM in CEM cells. Subsequent structure-activity relationship (SAR) studies yielded DI-39 (FIG. 20B), a cell-permeable (FIG. 20C) lead candidate with an IC$_{50}$ of 5 nM, nearly 300-fold lower than that of DI-0120 (FIG. 20D and (Murphy et al., 2013)). To investigate how DI-39 inhibits dCK we obtained a 2.1 Å co-crystal structure, which showed DI-39 occupying the nucleoside-binding site of the kinase and not the nucleotide phosphoryl donor-binding site (FIG. 20E; Table 4). This mode of binding suggested that DI-39 is highly specific inhibitor of dCK.

To evaluate DI-39 further, we measured its effects on the dCTP pool of CEM cells. While treatment with either DI-39 (1 μM) or dT (50 μM) decreased dCTP by ~30%, the DI-39/dT combination was synergistic, reducing dCTP in CEM cells by 70% (FIG. 20F). While in the presence of dC neither dT nor DI-39 alone induced RS or apoptosis in CEM cells, the DI-39/dT combination triggered both RS, as measured by pChk1 upregulation (FIG. 20G) and apoptosis, as measured by Annexin V staining (FIG. 20H). Notably, when the dCK-null leukemia cell line L1210-10K (Jordheim et al., 2004) was treated with increasing concentrations of DI-39 far above those required to inhibit dCK activity or to kill CEM cells when combined with dT, it did not induce apoptosis, further supporting the selectivity of DI-39 for dCK (FIG. 20I). The DI-39/dT combination also induced RS (FIG. 20J) and apoptosis (FIG. 20K) in four other ALL cell lines (Jurkat, MOLT-4, RS4;11, NALM-6) as well as in an erythroleukemia cell line (TF-1). In summary, DI-39 enters cells, inhibits the NSP-dependent dCTP production, and synergizes with dT to induce lethal RS in multiple leukemia cell lines.

Figure 21A:
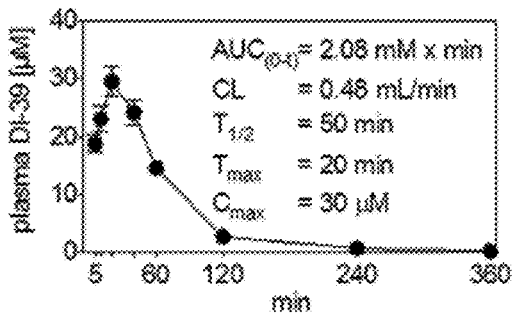
FIGS. 21A-21F. DI-39 inhibits dCK activity in vivo as determined by $^{18}$F-FAC PET and promotes RS when combined with dT (FIG. 21A) Pharmacokinetic profile of DI-39. C57Bl/6 mice were dosed with DI-39 via intraperitoneal injection. Dose formulation: 10% DMSO and 40% Captisol (SBE-β-CD, a polyanionic variably substituted sulfobutyl ether of (β-cyclodextrin, (Stella and He, 2008) in water. Approximated values of the Area Under the Curve (AUC), clearance rate (CL), half-life (T$_{1/2}$), maximum concentration in the plasma (C$_{max}$) and time to reach the maximum concentration (T$_{max}$) were calculated using Boomer/Multi-Forte P K Functions for Microsoft Excel. Values represent the mean±SD, n=4/time point; n=2 independent experiments.
Figure 21B:
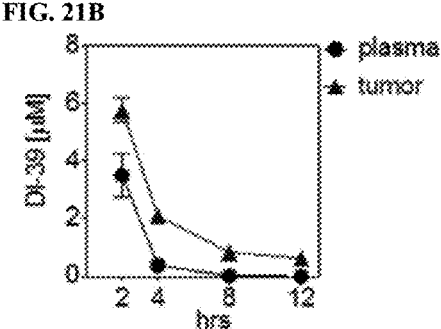
Figures 21C, 21D:
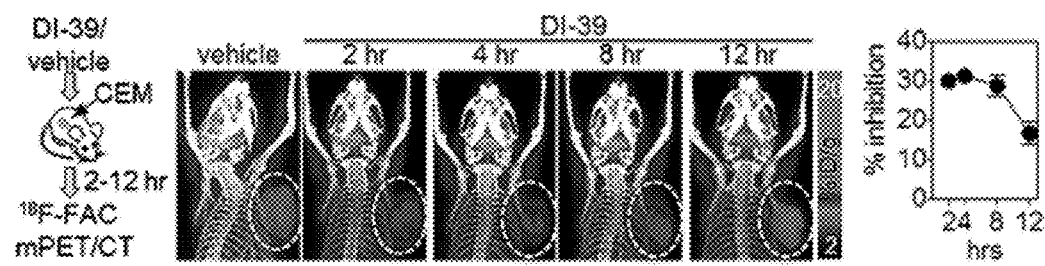

DI-39 inhibits tumor dCK activity in vivo and promotes RS when combined with dT. To evaluate DI-39 in vivo, we determined its pharmacokinetics (PK) in plasma and in tumor tissues. The plasma half-life of DI-39 was ~50 min (FIG. 21A) and detectable amounts of drug (~15 nM) were present in tumor tissues 8 hr after single dose administration (FIG. 21B). To correlate the amount of DI-39 in plasma and tumor at 2, 4, 8 and 12 hr following administration of the drug with the pharmacodynamic (PD) effect of DI-39 (i.e. inhibition of tumor dCK activity), we performed $^{18}$F-FAC PET/CT scans of CEM tumor-bearing mice at these time points (FIG. 21C). DI-39 (50 mg/kg, administered intraperitoneally) reduced $^{18}$F-FAC accumulation in tumors by ~30% for up to 8 hr (FIG. 21D). This level of reduction was comparable with that obtained in the dCK knockdown model (FIG. 18E). The timing of recovery of tumor dCK activity, determined with PET, following DI-39 administration, indicates that sustained target inhibition could be obtained by administering DI-39 every 12 hr. Notably, this information could not be obtained from conventional plasma PK measurements (FIG. 21A).

Figure 21E:
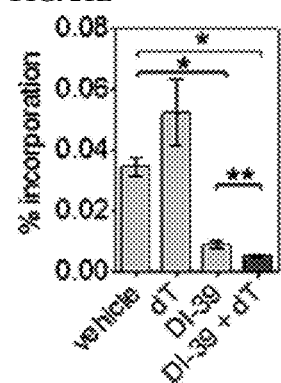
Figure 21F:
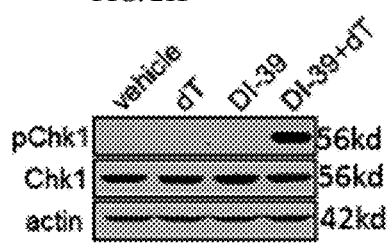

To further investigate the effects of DI-39 on tumor dCTP metabolism, 5.5 hr after treatment with dT and/or DI-39, CEM tumor-bearing mice were pulsed for 30 min with [U-$^{13}$C/$^{15}$N]-dC. LC/MS/MS-MRM was used to quantify label incorporation into DNA. Analogous to our dCK knockdown results (FIG. 18F), DI-39 significantly reduced [U-$^{13}$C/$^{15}$N]-dC incorporation into the DNA of CEM cells (FIG. 21E). Moreover, the DI-39/dT combination promoted RS in CEM tumors, as evidenced by pChk1 upregulation (FIG. 21F). Together, these findings indicate that (i) DI-39 efficiently inhibits tumor dCK activity in vivo for up to 12 hr, (ii) the DI-39/dT combination induces RS in CEM cells in vivo and (iii), PET imaging provides a useful PD companion biomarker for DI-39.

Figures 22A, 22B, 22C, 22D:
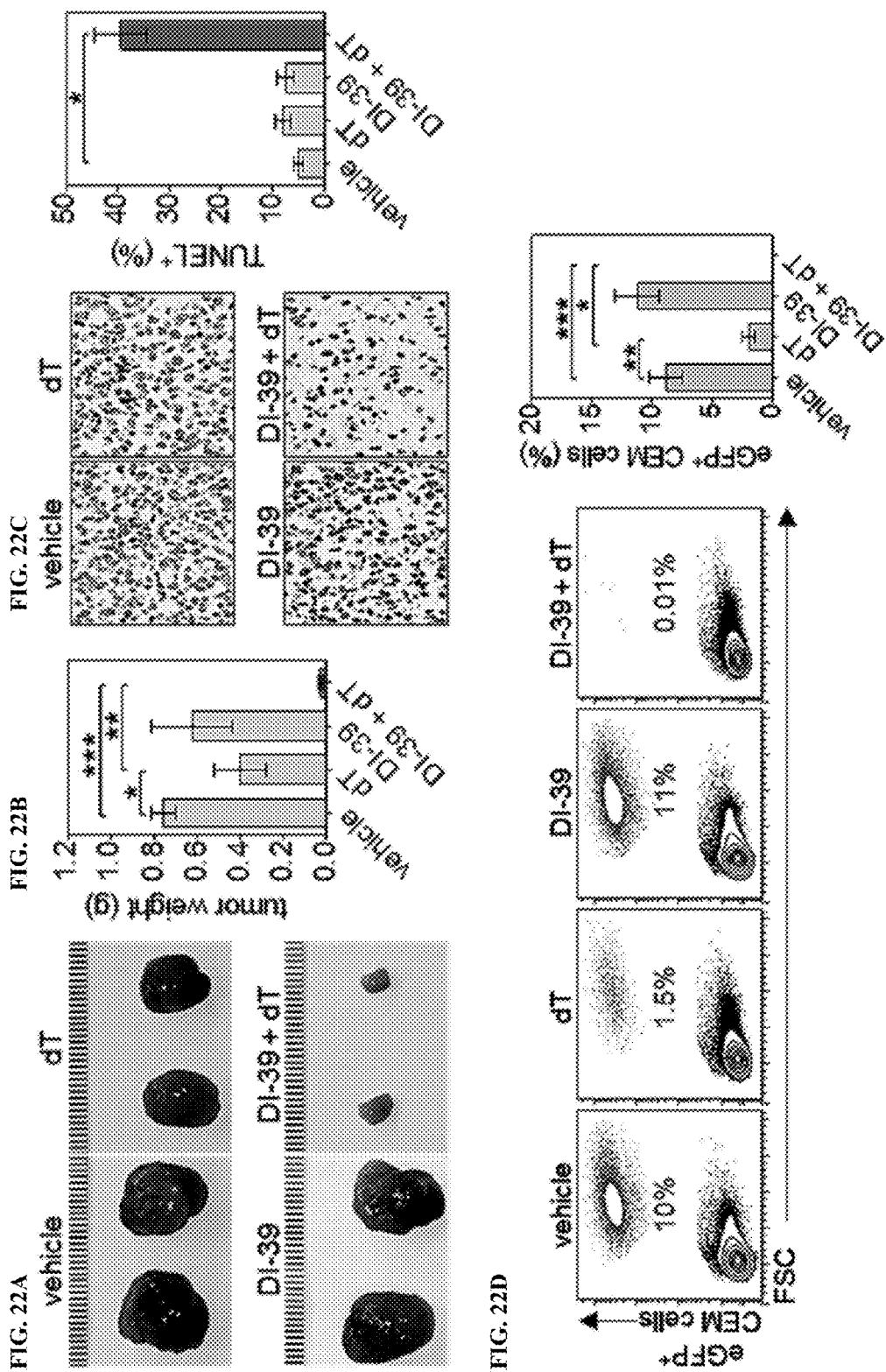
FIGS. 22A-22D. Pharmacological co-targeting of DNP and NSP dCTP production is effective against T-ALL cells in vivo (FIG. 22A) Representative images of CEM xenografts isolated from mice treated with vehicle, dT (2 g/kg), DI-39 (50 mg/kg) or DI-39+dT every 12 hr beginning at day 7 post inoculation and continuing to day 14. n=6 mice/group; n=2 independent experiments.

Pharmacological co-targeting of DNP and NSP dCTP biosynthesis with DI-39 and dT blocks the growth of T-ALL xenografts in mice. The therapeutic efficacy of the DI-39/dT combination was first tested in mice bearing established s.c. CEM xenografts. Only the combination therapy dramatically reduced tumor burden in these mice, as indicated by end point tumor sizes (FIG. 22A) and weights (FIG. 22B). In addition, TUNEL staining from harvested tumors indicated significant induction of DNA breaks only with the DI-39/dT combination (FIG. 22C). In contrast to findings shown in FIGS. 19A-19C, dT treatment alone had a small but significant effect on the size and weight of CEM tumors (FIGS. 22A-22B). This difference is likely explained by a slight increase in dT PK by the Captisol/DMSO formulation used to co-administer DI-39 with dT; DI-39 has limited solubility in aqueous saline solutions. The therapeutic efficacy of the DI-39/dT combination was further confirmed in a systemic T-ALL model, in which CEM cells were injected intravenously. In the systemic T-ALL model, treatment with dT alone induced an ~7-fold reduction in the percentage of leukemic cells in bone marrow (BM) relative to vehicle and DI-39 treated groups (FIG. 22D). This finding suggests that BM-resident leukemic cells are more susceptible to dT in vivo than they are in cell culture. However, the DI-39/dT combination reduced tumor burden by an additional 100-fold relative to dT alone, indicating strong synergy between these two therapeutic agents (FIG. 22D). Therefore, pharmacological co-targeting of both the DNP and NSP dCTP biosynthetic pathways is highly effective against CEM leukemic cells in vivo.

Figure 23A:
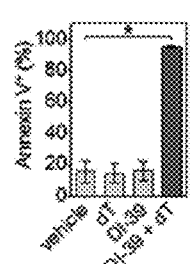
FIGS. 23A-23H. Pharmacological co-targeting of the DNP and NSP is efficacious against primary mouse p185$^{BCR-ABL}$ Arf$^{-/-}$ Pre-B ALL cells, while sparing the hematopoietic progenitor pool (FIG. 23A) Annexin V staining of p185$^{BCR-ABL}$ Arf$^{-/-}$ pre-B cells following 48 hr treatment with vehicle, dT (200 µM), DI-39 (100 nM), or DI-39+dT in the presence of 2.5 dC. Values are mean±SEM; n=2 independent experiments. ** P<0.01.
Figure 23B:
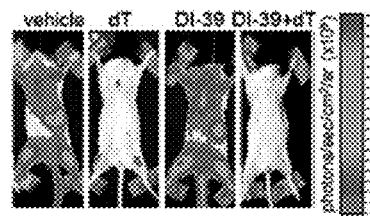
Figure 23C:
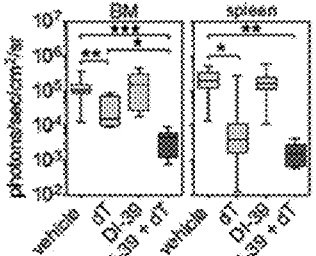
Figure 23D:
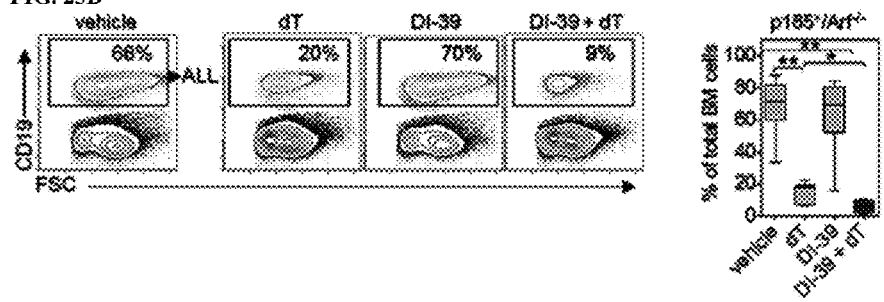

The combination therapy is effective against a primary B-ALL systemic model and has minimal effects on the normal hematopoietic progenitor pool. We next assessed the efficacy of the DI-39/dT combination therapy against We next assessed the efficacy of the DI-39/dT combination therapy against short-term cultures of murine BCR-ABL (p185), Arf$^{-/-}$ pre-B ALL cells (p185$^{BCR-ABL}$/Arf$^{-/-}$) (Boulos et al., 2011; Williams et al., 2006). While primary B-ALL cells were sensitive in culture to the DI-39/dT combination, they required 4-fold more dT than the CEM T-ALL cell line for optimal induction of apoptosis (FIG. 23A). This finding is consistent with previous clinical observations that B-ALL are less sensitive to dT treatment than T-ALL (Kufe et al., 1980). To evaluate the efficacy of dT and/or DI-39 in an in vivo B-ALL model, firefly luciferase marked p185$^{BCR-ABL}$/Arf$^{-/-}$ cells were inoculated intravenously in NSG mice. Eleven days post-inoculation, bioluminescence imaging (BLI) of firefly luciferase-marked p185$^{BCR-ABL}$/Arf$^{-/-}$ ALL-bearing NSG mice treated with vehicle or DI-39 (50 mg/kg) revealed substantial systemic disease with focal BM and spleen localization (FIG. 23B). While dT (2 g/kg) treatment significantly reduced BLI signals in BM and spleen, the addition of DI-39 had a more pronounced effect than dT alone (FIGS. 23B-23C). To confirm the BLI findings, we also analyzed the leukemia burden in BM by flow cytometry using CD19 (a B cell marker which, in NSG mice, is present only on the leukemia cells) (FIG. 23D). Treatment with dT induced a significant decrease in the percentage of p185$^{BCR-ABL}$/Arf$^{-/-}$ ALL cells relative to vehicle-treated mice (FIG. 23D). The addition of DI-39 resulted in an additional ~2-fold reduction in the percentage of leukemic cells compared to dT alone (FIG. 23D). These findings, using primary p185$^{BCR-ABL}$/Arf$^{-/-}$ cells, indicate that the DI-39/dT combination is effective against an aggressive in vivo B-ALL model.

Figure 23E:
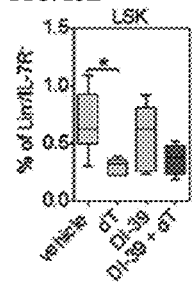
Figure 23F:
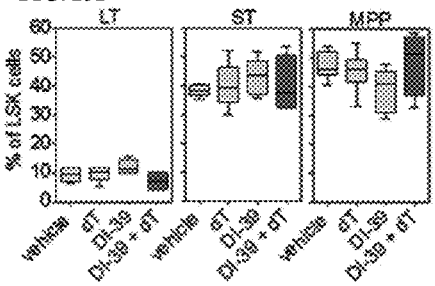
Figure 23G:
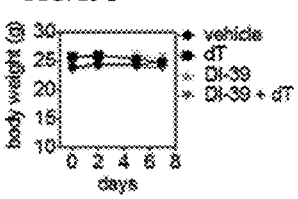
Figure 23H:

In parallel with analyses of BM resident leukemic cells, we also assessed the effects of the combination therapy on the hematopoietic progenitor pool. We analyzed the Lineage$^-$ Sca-1$^+$ c-Kit$^+$ (LSK) HSC population as well as short-term (ST), long-term (LT) and multipotent progenitor (MPP) hematopoietic progenitor cells. With the exception of a minor decrease in the percentage of LSK upon dT treatment (FIG. 23E), there were no significant changes between control and treated groups (FIGS. 23E-23F; FIGS. 25A-25B). Therefore, the combination therapy preferentially targets BM-resident leukemia cells while sparing normal hematopoietic progenitors. In addition, DI-39 alone or in combination with dT, when administered twice/day for 7 days in NSG mice, did not affect body weight (FIG. 23G), and had no detectable effects on RBCs, hemoglobin, platelets or neutrophils (FIG. 23H).

Partial inhibition of dCK in hematopoietic tissues prevents hematological toxicity from dT and DI-39. To further investigate the potential hematological toxicity of the combination therapy, we took advantage of our dCK$^{-/-}$ mice (Austin et al., 2012). This approach allowed us to directly compare the effects on the hematopoietic system induced by complete loss of dCK function in the dCK$^{-/-}$ mice with the effects induced pharmacologically in dCK wild type mice (dCK$^{+/+}$) by DI-39 and dT. In the erythroid lineage, the DI-39/dT combination induced markedly less DNA damage and genotoxicity in the dCK$^{+/+}$ mice, as measured by pH2A.X staining (FIG. 24A) and the micronucleus assay, respectively (FIG. 24B), than did dCK gene elimination alone in dCK$^{-/-}$ mice. These findings indicate that pharmacological inhibition of dCK activity by DI-39, alone or in combination with dT treatment, is better tolerated than complete elimination of dCK enzymatic activity by genetic dCK gene inactivation.

We demonstrate here a requirement for a functional nucleoside salvage pathway in T-ALL and B-ALL cells to prevent dCTP pool insufficiency, RS and apoptosis following pharmacological inhibition of de novo dCTP synthesis. We introduce DI-39, a new small molecule inhibitor of dCK; dCK is the kinase required for the compensatory metabolic switch, triggered by dT-mediated DNP inhibition, to NSP-dependent dCTP biosynthesis. We elucidate how DI-39 inhibits dCK by obtaining a high-resolution crystal structure of the inhibitor-dCK complex. We demonstrate the therapeutic efficacy of co-targeting both the DNP and NSP dCTP biosynthetic pathways, using in vivo models of T-ALL and B-ALL, without detectable toxicity against normal hematopoietic progenitors. We also describe a companion pharmacodynamic PET assay of dCK enzyme activity, which allows non-invasive in vivo imaging of pharmacological interventions targeting dCTP biosynthesis.

Selectivity of the DI-39/dT combination therapy for leukemic cells relative to normal hematopoietic progenitors. Our current working model, without being bound by any particular theory, to explain the mechanism and observed selectivity of the combination therapy for leukemia cells relative to normal hematopoietic progenitors is depicted schematically in FIGS. 24C-24D. According to this model, pharmacological co-targeting of the DNP (by dT) and of the NSP (by DI-39) is highly effective at inducing lethal RS against T- and B-ALL cells and has minimal effects on normal hematopoietic cells. As indicated by $^{18}$F-FAC PET imaging of dCK activity (FIG. 21D; FIG. 24D), DI-39 induced partial inhibition of dCK in normal BM cells compared with the complete loss of dCK activity in dCK$^{-/-}$ mice (Austin et al., 2012; Toy et al., 2010). The residual dCK activity in BM cells following DI-39 treatment may be sufficient to prevent the more substantial reductions observed for the dCTP pools of hematopoietic progenitors in the dCK$^{-/-}$ mice. This model of low or absent toxicity due to partial inhibition of the therapeutic target is reminiscent of recent work in which hypomorphic ATR suppression was lethal to tumor tissues exposed to oncogenic stress, yet had only minimal toxicity to normal tissues (Bartek et al., 2012; Schoppy et al., 2012). Furthermore, the enhanced susceptibility of ALL cells to a reduced supply of dCTP could reflect the inherent inability of these leukemic cells to mount an efficient RS response. Additional studies are required to precisely identify the defects in cell cycle checkpoints that increase the susceptibility of ALL cells to RS induced by dNTP insufficiency, when compared to normal hematopoietic progenitor cells, we note the presence of inactivating TP53 mutations in several tested ALL cell lines. In this context, it has been suggested that, in normal cells with wild type p53, the skewing in dNTP pools induced by inhibition of de novo pyrimidine synthesis by N-(phosphonacetyl)-L-aspartate (PALA) creates reversible DNA damage, sufficient to activate p53 and induce the expression of proteins that provide protective arrest at multiple cell cycle checkpoints (Hastak et al., 2008). In cancer cells with defects in p53 or in its downstream effectors, failure to arrest DNA synthesis when pyrimidine dNTP pools are depleted leads to irreversible DNA damage that eventually causes apoptosis (Hastak et al., 2008).

Potential clinical implications. High avidity for dT has been previously identified as a potential metabolic liability of certain cancers, leading to clinical studies using high dT doses as a potential therapeutic (O'Dwyer et al., 1987). Prolonged (over 5 days) dT infusions have shown responses in heavily pre-treated T-ALL and cutaneous T-cell lymphoma patients, with the side effects encountered being tolerable, manageable, and reversible (Chiuten et al., 1980; Kufe et al., 1980; Kufe et al., 1981). However, therapeutic responses to dT in these patients were, in general, limited and transient, potentially reflecting the ability of the NSP, via dCK, to compensate for the dCTP-depleting effect of dT. Since potent small molecule inhibitors of dCK have recently been described (Murphy et al., 2013; Yu et al., 2010), future clinical studies can determine if the anti-leukemic activity of dT reported in T-ALL and cutaneous T cell-lymphoma patients can be significantly improved by pharmacological blockade of the deoxycytidine salvage pathway.

Companion diagnostics for therapies targeting dCTP biosynthetic pathways in cancer. The data presented here provide some examples of both in vivo and in vitro companion diagnostics (or biomarkers) that could assist the clinical translation of the DI-39/dT combination therapy. As an example, direct assessments of temporal changes in tumor dCK activity in vivo with PET appear more useful than conventional plasma pharmacokinetic measurements for identifying the optimal schedule for the DI-39/dT combination therapy (FIGS. 21A-21F). Since our PET assays for monitoring dCK activity have already been translated to humans (Schwarzenberg et al., 2011), approaches similar to those described in our pre-clinical experiments could be used in future clinical trials to non-invasively monitor dCK inhibition in target tissues in vivo. Upregulation of pChk1 and pH2A.X levels by leukemia cells upon DI-39/dT treatment (FIG. 21F) could provide additional pharmacodynamic biomarkers of DNA damage, as shown previously for PARP inhibitors (Fong et al., 2009). Furthermore, since the efficacy of the DI-39/dT therapy depends on the capacity of tumors cells to take up large amounts of dT and convert it to dTTP, PET imaging using $^{18}$F-FLT (3'-deoxy-3'-fluorothymidine), a probe for dT metabolism (Shields et al., 1998), may enable the identification of tumors with unusually high avidity for dT. Thus, $^{18}$F-FLT PET may match the proposed definition of a predictive or enrichment biomarker (de Bono and Ashworth, 2010) for dT-based therapies.

Regulation of the NSP by the DNA damage response pathway. Our in vitro (FIG. 21C) and in vivo data (FIGS. 18E-18F) indicate that, in CEM T-ALL cells, dT treatment upregulated the activity of the NSP. While NSP upregulation by dT treatment may result from a decrease in the negative feedback by dCTP on dCK activity (Datta et al., 1989), additional mechanisms could also be involved. For example, dCK activity is increased by treatment with DNA damaging agents that do not affect dCTP production via the DNP (Csapo et al., 2003; Ooi et al., 1996). Moreover, dCK activation following DNA damage involves phosphorylation of the kinase on serine 74 (Yang et al., 2012). This serine is part of an SQ/TQ motif, which is a typical phosphorylation site for ATM and ATR kinases in the DNA damage response (DDR) pathway. Indeed, dCK has been identified as a direct target of these kinases (Matsuoka et al., 2007). Therefore, following DNA damage induced by high dose dT, and, potentially, by other genotoxic therapies, the DDR pathway may promote NSP upregulation via post-translational regulation of dCK in order to expand dNTP pools and facilitate DNA repair. If correct, this model provides a rationale for testing dCK inhibitors in combination with radiation therapy and other genotoxic therapies.

In summary, our results provide new insight into the nucleotide metabolism of leukemic cells and also demonstrate a new therapeutic strategy to overcome the redundancy and adaptability of nucleotide metabolism in ALL and, possibly, in other hematological malignancies in which uncontrolled expansion of the dTTP pool by dT treatment results in a potential metabolic liability. Similar approaches, which fit within the conceptual framework of targeting non-oncogene addiction (Luo et al., 2009), may be applicable to other redundant biosynthetic pathways that provide survival advantages to tumor cells.

Cell lines and culture conditions. Human cell lines CCRF-CEM, Jurkat, MOLT-4, RSR4;11 and TF-1, cells were obtained from ATCC. All cell lines were maintained in 5% FBS in RPMI-1640 and were grown at 37° C., 20% $O_2$, and 5% $CO_2$.

Mice were bred and housed under specific pathogen-free conditions and were treated in accordance with the UCLA Animal Research Committee protocol guidelines. The $dCK^{-/-}$ were generated and bred as previously described and backcrossed to C57BL/6 mice for n=7 generations (Austin et al., 2012; Toy et al., 2010). Age-matched (5-12 wk-old) WT and $dCK^{-/-}$ littermates were used to assess RS induction by dT in BM myeloid cells.

Thymidine, 2'-deoxycytidine, hydroxyurea, 5-FU and cisplatin were purchased from Sigma-Aldrich and were prepared in DMSO or water. Lentiviral shRNA constructs against dCK and non-targeting control were from Sigma-Aldrich. For cell culture assays, dCK inhibitors were resuspended in DMSO. Immunoblotting was performed as previously described (Austin et al., 2012). Antibodies and reagents for immunoblotting were purchased from the following vendors: Cell Signaling Technology, phospho-Chk1 Ser345, phospho-Chk2 Thr68, Chk1, Chk2, anti-mouse HRP-conjugated IgG, anti-rabbit HRP-conjugated IgG; Sigma-Aldrich, dCK, Beta-Actin; Abcam, TK1. Bound antibody was detected with using chemiluminescence immunoblotting detection reagents (Pierce). Isolation and FACS phenotyping of hematopoietic stem cells, EryA and myeloid was performed as previously described (Austin et al., 2012). The $p185^{BCR-ABL}/Arf^{-/-}$ cells were identified using an anti-CD19 (APC) antibody. For cell cycle analyses, total DNA content was determined using 1 µg/mL of DAPI or 20 µg/mL propidium iodide containing 5 µg/mL RNAase A. Annexin V staining was performed according to the manufacturer's protocol (BD Biosciences). For the micronucleus assay, isolated bone marrow cells were stained with the following antibodies from eBioscience: Ter119 PerCP-Cy5.5 (TER-119), CD71 APC (R17217), CD45 PE-Cy7 (30-F11), CD61 PE (2C9.G3), CD11b APC-eFluor780 (M1/70). Cells were stained, washed and fixed with Cytofix/Cytoperm solution (BD Biosciences). Cells were then washed and stained with 1 µg/mL DAPI in PBS/2% FBS. All flow cytometry data were acquired on a four-laser LSRII cytometer (BD Biosciences) and analyzed using FlowJo (Tree Star).

NOD SCID gamma (NSG) mice were injected with 2 g/kg dT intraperitoneally; 75 µL of whole blood was obtained at 0, 2, 4, and 8 hr through retro-orbital sinus bleed using hematocrit capillary tubes. Whole blood was immediately centrifuged at 3000× g for 5 min to isolate serum; 30 µL of serum was mixed with 1 mL methanol:acetonitrile (1:9), vortexed for 2 min, centrifuged at 14,000× g for 4 min at 4° C. Extraction was repeated and the pooled supernatant was dried under vacuum centrifugation. The residue was dissolved in 100 µL water, filtered and eluted through a Waters microBondapak C18 column under a gradient mobile phase from 2% methanol to 50% methanol over ten minutes at a flow rate of 1.5 mL/min. Thymidine was detected by absorbance intensity (254 nm), and concentrations were interpolated from standard curves.

To determine the pharmacokinetic profile of DI-39, C57Bl/6 female mice were dosed with DI-39 via intraperitoneal injection following the protocol that was described previously (Murphy et al., 2013). Dose formulation include 10% DMSO and 40% Captisol (SBE-β-CD, a polyanionic variably substituted sulfobutyl ether of β-cyclodextrin, (Stella and He, 2008)) in water. Approximately 75 µL of whole blood was obtained at various time points starting 5 to 360 minutes through retro-orbital sinus bleed using hematocrit capillary tubes. Approximated values of the Area Under the Curve (AUC), clearance rate (CL), half-life ($T_{1/2}$), maximum concentration in the plasma ($C_{max}$) and time to reach the maximum concentration ($T_{max}$) were calculated using Boomer/Multi-Forte P K Functions from Microsoft Excel.

For the DI-39 tumoral and plasma uptake study using LC/MS/MS-MRM, tumor-bearing NSG mice were injected with 50 mg/kg DI-39 intraperitoneally at 0, 2, 4, 8 and 12 hours prior to sacrifice. Whole tumors were excised, weighed and homogenized with an equal volume of 2 mm-diameter stainless steel beads (Next Advance) in 1 mL ice-cold acetonitrile/water (50/50, v/v) containing 0.5 pmol/µL of the internal standard DI-70 (2-(((2-(4-methoxy-3-(2-(2-(2-methoxyethoxy)ethoxy)ethoxy)phenyl)-5-propylthiazol-4-yl)methyl)thio)pyrimidine-4,6-diamine, $C_{25}H_{35}N_5O_5S_2$, MW=549.2 g/mol, an in-house synthesized DI-39 analog) in a Bullet Blender homogenizer (Next Advance). Tissue homogenates were left overnight at 4° C. on a shaker and the next day centrifuged at 20,000× g for 10 min. The supernatant (700 µL) was transferred to a clean tube and was evaporated to dryness in a vacuum centrifuge. The residue was reconstituted in 100 µL acetonitrile/water (50/50, v/v). For plasma measurements, ~100 µL of blood was collected through a retro-orbital sinus bleed using capillary blood collection tubes. Samples were centrifuged at 20,000× g for 5 min, and 30 µL of the supernatant was transferred into a clean tube. The sample was mixed with 500 µL ice-cold acetonitrile/water (50/50, v/v) containing the internal standard and processed in the same way as the tumor homogenates. Calibration standards were prepared by spiking working stock solution of DI-39 in tumor homogenates and plasma from untreated mice to give the following ranges: 0.02 to 20 pmol/µL. Samples (5 µL) were injected onto a reverse phase column (Agilent ZORBAX Rapid Resolution High Definition (RRHD) Eclipse Plus C18, 2.1×50 mm, 1.8 µm) equilibrated in water/acetonitrile/formic acid, 95/5/0.1 and eluted (200 µL/min) with and increasing concentration of solvent B (acetonitrile/formic acid, 100/0.1, v/v: min/% acetonitrile; 0/5, 0/5, 2/5, 8/80, 9/80, 10/5, 12/5). The effluent from the column was directed to an electrospray ion source (Agilent Jet Stream) connected to a triple quadrupole mass spectrometer (Agilent 6460 QQQ) operating in the positive ion MRM mode. The ion transitions for DI-39 and DI-70 (525.2→383.3 and 550.2→408.2 respectively) were recorded under previously optimized conditions. The DI-39 peak areas were normalized to the internal standard and tumor weight.

The experiment using CCRF-CEM cells to measure the uptake of DI-39 in cell culture followed a similar protocol as the one described above. CCRF-CEM cells were cultured in 5% FBS in RPMI-1640 media supplemented with 1 µM of DI-39 for 10, 30, 40, and 60 min before cell extraction. For some samples, the media with 1 µM DI-39 was removed and the cells were washed three times in PBS before adding fresh media without DI-39 for 60 minutes. The cells were extracted and homogenized in 1 mL ice-cold acetonitrile/water (50/50, v/v) containing 0.5 pmol/µL of the same internal standard as mentioned before. The cell extract was left overnight at 4° C. on a shaker and the next day centrifuged at 20,000× g for 10 min. The supernatant was transferred to a clean tube and was evaporated to dryness in a vacuum centrifuge. The residue was reconstituted in 100 µL acetonitrile/water (50/50, v/v). DI-39 was quantified as described above.

CEM cells were transferred into RPMI supplemented with 5% dialyzed FCS containing 10 µM uniformly labeled [U-$^{13}$C/$^{15}$N]-deoxycytidine (Cambridge Isotopes), 2 g/L uniformly-labeled [U-$^{13}$C]-glucose (Cambridge Isotopes) and 0, 50 or 250 µM dT. For the dNTP analysis, the cells were extracted overnight at −20° C. with 75% methanol. The extracts were then heated in boiling water for 3 min, pelleted, and the supernatants were transferred and dried under vacuum centrifugation. For DNA analysis, cells were collected and genomic DNA was extracted using the Quick-gDNA MiniPrep kit (Zymo Research). Genomic DNA was then digested to nucleosides using the DNA Degradase Plus kit (Zymo Research).

For the in vivo studies, tumor-bearing mice were injected with 200 µL, of 2.5 mM [U-$^{13}$C/$^{15}$N]-deoxycytidine 30 min prior to sacrifice. Tumors were harvested, mechanically digested into single cells, and cell counts were obtained. DNA extraction was carried out as described above.

DNA hydrolysis samples were diluted 1/1 with solvent A (water/formic acid, 100/0.2, v/v) and analyzed using a modified version of a previously reported method (Cohen et al., 2009) in which aliquots of the solution (10 µL) were injected onto a porous graphitic carbon column (Thermo Hypercarb, 100×2.1 mm, 3 micron particle size) equilibrated in solvent A and eluted (300 µL/min) with an increasing concentration of solvent B (acetonitrile/min/% B; 0/0, 6/60, 6.1/100, 9/100, 9.1/0, 10/0). The effluent from the column was directed to Agilent Jet Stream connected Agilent 6460 QQQ operating in the positive ion MRM mode. After verification of retention times using authentic standards, the peak areas of the MH$^+$→fragment ion transitions for the dC isotopomers ($M_0$, 228.1→112.1; $M_1$, 229.1→112.1; $M_2$, 230.1→112.1; $M_3$, 231.1→112.1; $M_4$, 232.1→112.1; $M_5$, 233.1→112.1; $M_6$, 234.1→113.1; $M_7$, 235.1→114.1; $M_8$, 236.1→115.1; 236.1→115.1; $M_{11}$, 239.1→118.1; and $M_{12}$, 240.1→119.1) were recorded with instrument manufacturer-supplied software (Agilent MassHunter), and normalized to cell number. The dC isotopomers of $M_3$ through $M_8$ for the DNP and $M_{11}$ through $M_{12}$ for NSP were detected and used for data analysis.

For free dNTP analysis a modified version of the same previously reported method (Cohen et al., 2009) was used in which dried samples were re-dissolved in solvent C (100 µL, 5 mM hexylamine, 0.5% mM diethylamine, pH 10.0) and aliquots (10 µL) were injected onto porous graphitic carbon column (Thermo Hypercarb, 150×2.1 mm, 3 micron particle size) equilibrated in solvent C and eluted (150 µL/min) with an increasing concentration of solvent D (acetonitrile/min/% D; 0/0, 5/0, 25/40, 25.1/100, 30/100, 30.1/0, 40/0). The effluent from the column was directed to the same instrument described above, operating in the negative ion mode. After verification of retention times using authentic standards, the intensities of pre-selected $(M-H)^- \rightarrow$ fragment ion transitions for various dCTP isotopmers ($M_0$, 466.0→159.0; $M_1$, 467.0→159.0; $M_2$, 468.0→159.0; $M_3$, 469.0→159.0; $M_4$, 470.0→159.0; $M_5$, 471.0→159.0; $M_6$, 472.0→159.0; $M_7$, 473.0→159.0; $M_8$, 474.0→159.0; $M_{10}$, 478.0→159.0; $M_{11}$, 479.0→159.0; and $M_{12}$, 478.0→159.0) were recorded, again with instrument manufacturer-supplied software (Agilent MassHunter), and normalized to cell number. The dCTP isotopomers of $M_5$ through $M_8$ for the DNP and $M_{12}$ for NSP were detected and used for data analysis. The $M_3$ and $M_4$, isotopomers were not detected.

Intracellular dNTP pool measurements were conducted as previously described (Austin et al., 2012).

The comet assay was performed following the Trevigen CometAssay reagent kit protocol under alkaline conditions. For quantification, four random sections of each slide containing >100 cells were imaged and Olive Tail Moment obtained using TriTek Cometscore software.

The gene encoding humanized secreted Gaussia luciferase (sGluc), pCMV-GLuc-1 (Nanolight Technology), was subcloned into the MSCV-IRES-GFP retroviral vector. Pheonix-Ampho cells were transfected with the generated vector using Lipofectamine transfection reagent (Invitrogen, Grand Island, N.Y.). Forty-eight hours after transfection, virus was harvested and used to transduce CEM dCK$^{wt}$ and CEM dCK$^{low}$ cells. GFP positive cells were sorted with a FACSAria II cell sorter (BD Biosciences).

The C4S S74E dCK variant used for crystallographic studies was expressed and purified as described elsewhere. (Nomme et al., 2014). Crystallization, X-ray data collection and refinement were also performed as described in Nomme et al. Briefly, crystals of dCK in complex with UDP, MgCl$_2$ and a 2.5-fold excess of the DI-39 inhibitor were grown using the hanging drop vapor diffusion method at 12° C. The reservoir solution contained 0.9-1.5 M trisodium citrate dehydrate and 25 mM HEPES (pH 7.5). Diffraction data were collected at the Advanced Photon Source, Argonne National Laboratory on Life Sciences-Collaborative Access Team (LS-CAT) beamlines 21 ID-G.

CEM xenograft tumors were developed in 8 to 12 week old female NSG mice by implanting 2×10$^6$ CEM dCK$^{wt}$-sGluc-GFP and/or dCK$^{low}$-sGluc-GFP cells in 100 µL of equal volume Matrigel (BD Biosciences) and RPMI subcutaneously in the flanks. Tumor growth was monitored daily by caliper measurements ([(length×width$^2$)/2]) and blood Gaussia luciferase (GLuc) assay (Tannous, 2009). Ten µL of blood was collected via tail vein nick and mixed with 2 µL 50 mM EDTA. One µL of blood was mixed with 99 µL PBS and transferred to a 96 well OptiPlate (Perkin Elmer). One hundred µL of 20 µM coelenterazine substrate was mixed and luciferase activity was measured using a plate luminescence microplate reader SpectraMax L (Molecular Devices). Systemic tumor models were established by intravenous injection of 10$^6$ CEM dCK$^{wt}$-sGluc-GFP or dCK$^{low}$-sGluc-GFP in 100 µL RPMI. Thymidine (2 g/kg) was administered in saline and DI-39 in a mixture of 1.4% DMSO and 40% Captisol (Ligand Pharmaceuticals) mixture.

Tumors from CEM xenografts were harvested and fixed overnight in 10% buffered formalin solution. Samples were then paraffin-embedded and 5 µm sections were mounted on glass slides. TUNEL staining was performed according to the manufacturer's protocol (Roche Applied Science). Stained slides were subsequently scanned on an Aperio ScanScope AT (Aperio) and analysis was conducted using Definiens Tissue Studio 64 (Dual) 3.5 (Definiens AG).

dCK kinase and uptake assays were performed as previously described (Shu et al., 2010).

All mice were anesthetized and whole blood was obtained through cardiac puncture. For peripheral blood counts, samples were collected in tubes containing EDTA and submitted to UCLA Division of Lab Animal Medicine for analysis.

PET/CT studies were performed as previously described (Radu et al., 2008; Shu et al., 2010).

Pharmacokinetic studies of DI-39 in mice were performed as previously described (Murphy et al., 2013).

All statistics presented as averages of biological replicates with standard error of the mean (±SEM), unless indicated. P value significances were calculated from multiple replicates within a data set representative of multiple independent experiments, as indicated, using one sample t-test function in GraphPad Prism 5 (GraphPad Software).

References for Example 2

Austin, W. R., A. L. Armijo, D. O. Campbell, A. S. Singh, T. Hsieh, D. Nathanson, H. R. Herschman, M. E. Phelps, O. N. Witte, J. Czernin, and C. G. Radu. 2012. Nucleoside salvage pathway kinases regulate hematopoiesis by linking nucleotide metabolism with replication stress. J Exp Med. 209: 2215-28.

Bartek, J., M. Mistrik, and J. Bartkova. 2012. Thresholds of replication stress signaling in cancer development and treatment. Nature structural & molecular biology. 19:5-7.

Boulos, N., H. L. Mulder, C. R. Calabrese, J. B. Morrison, J. E. Rehg, M. V. Relling, C. J. Sherr, and R. T. Williams. 2011. Chemotherapeutic agents circumvent emergence of dasatinib-resistant BCR-ABL kinase mutations in a precise mouse model of Philadelphia chromosome-positive acute lymphoblastic leukemia. Blood. 117: 3585-95.

Chiuten, D. F., P. H. Wiernik, D. S. Zaharko, and L. Edwards. 1980. Clinical phase I-II and pharmacokinetic study of high-dose thymidine given by continuous intravenous infusion. Cancer Res. 40: 818-22.

Cohen, S., M. Megherbi, L. P. Jordheim, I. Lefebvre, C. Perigaud, C. Dumontet, and J. Guitton. 2009. Simultaneous analysis of eight nucleoside triphosphates in cell lines by liquid chromatography coupled with tandem mass spectrometry. J Chromatogr B Analyt Technol Biomed Life Sci. 877:3831-40.

Csapo, Z., G. Keszler, G. Safrany, T. Spasokoukotskaja, I. Talianidis, M. Staub, and M. Sasvari-Szekely. 2003. Activation of deoxycytidine kinase by gamma-irradiation and inactivation by hyperosmotic shock in human lymphocytes. Biochem Pharmacol. 65: 2031-9.

Datta, N. S., D. S. Shewach, B. S. Mitchell, and I. H. Fox. 1989. Kinetic properties and inhibition of human T lymphoblast deoxycytidine kinase. J Biol Chem. 264: 9359-64.

de Bono, J. S., and A. Ashworth. 2010. Translating cancer research into targeted therapeutics. Nature. 467: 543-9.

Fong, P. C., D. S. Boss, T. A. Yap, A. Tuft, P. Wu, M. Mergui-Roelvink, P. Mortimer, H. Swaisland, A. Lau, M. J. O'Connor, A. Ashworth, J. Carmichael, S. B. Kaye, J. H. Schellens, and J. S. de Bono. 2009. Inhibition of poly(ADP-ribose) polymerase in tumors from BRCA mutation carriers. The New England journal of medicine. 361: 123-34.

Hanahan, D., and R. A. Weinberg. 2011. Hallmarks of cancer: the next generation. Cell. 144: 646-74.

Hastak, K., R. K. Paul, M. K. Agarwal, V. S. Thakur, A. R. Amin, S. Agrawal, R. M. Sramkoski, J. W. Jacobberger, M. W. Jackson, G. R. Stark, and M. L. Agarwal. 2008. DNA synthesis from unbalanced nucleotide pools causes limited DNA damage that triggers ATR-CHK1-dependent p53 activation. Proc Natl Acad Sci USA. 105: 6314-9.

Jain, M., R. Nilsson, S. Sharma, N. Madhusudhan, T. Kitami, A. L. Souza, R. Kafri, M. W. Kirschner, C. B. Clish, and V. K. Mootha. 2012. Metabolite profiling identifies a key role for glycine in rapid cancer cell proliferation. Science. 336: 1040-4.

Jordheim, L. P., E. Cros, M. H. Gouy, C. M. Galmarini, S. Peyrottes, J. Mackey, C. Perigaud, and C. Dumontet. 2004. Characterization of a gemcitabine-resistant murine leukemic cell line: reversion of in vitro resistance by a mononucleotide prodrug. Clin Cancer Res. 10: 5614-21.

Kamphorst, J. J., J. Fan, W. Lu, E. White, and J. D. Rabinowitz. 2011. Liquid chromatography-high resolution mass spectrometry analysis of fatty acid metabolism. Anal Chem. 83: 9114-22.

Kufe, D. W., P. Beardsley, D. Karp, L. Parker, A. Rosowsky, G. Canellos, and E. Frei, 3rd. 1980. High-dose thymidine infusions in patients with leukemia and lymphoma. Blood. 55: 580-9.

Kufe, D. W., M. M. Wick, S. Moschella, and P. Major. 1981. Effect of high-dose thymidine infusions in patients with mycosis fungoides. Cancer. 48: 1513-6.

Luo, J., N. L. Solimini, and S. J. Elledge. 2009. Principles of cancer therapy: oncogene and non-oncogene addiction. Cell. 136: 823-37.

Maddocks, O. D., C. R. Berkers, S. M. Mason, L. Zheng, K. Blyth, E. Gottlieb, and K. H. Vousden. 2012. Serine starvation induces stress and p53-dependent metabolic remodelling in cancer cells. Nature. 493: 542-6.

Matsuoka, S., B. A. Ballif, A. Smogorzewska, E. R. McDonald, 3rd, K. E. Hurov, J. Luo, C. E. Bakalarski, Z. Zhao, N. Solimini, Y. Lerenthal, Y. Shiloh, S. P. Gygi, and S. J. Elledge. 2007. ATM and ATR substrate analysis reveals extensive protein networks responsive to DNA damage. Science. 316:1160-6.

Murphy, J. M., A. L. Armijo, J. Nomme, C. H. Lee, Q. A. Smith, Z. Li, D. O. Campbell, H. I. Liao, D. A. Nathanson, W. R. Austin, J. T. Lee, R. Darvish, L. Wei, J. Wang, Y. Su, R. Damoiseaux, S. Sadeghi, M. E. Phelps, H. R. Herschman, J. Czernin, A. N. Alexandrova, M. E. Jung, A. Lavie, and C. G. Radu. 2013. Development of new deoxycytidine kinase inhibitors and noninvasive in vivo evaluation using positron emission tomography. J Med Chem. 56: 6696-708.

Nomme, J., J. M. Murphy, Y. Su, N. D. Sansone, A. L. Armijo, S. T. Olson, C. Radu, and A. Lavie. 2014. Structural characterization of new deoxycytidine kinase inhibitors rationalizes the affinity-determining moieties of the molecules. Acta Crystallogr D Biol Crystallogr. 70: 68-78.

O'Dwyer, P. J., S. A. King, D. F. Hoth, and B. Leyland-Jones. 1987. Role of thymidine in biochemical modulation: a review. Cancer Res. 47: 3911-9.

Ooi, K., T. Ohkubo, M. Higashigawa, H. Kawasaki, and M. Sakurai. 1996. Increased deoxycytidine kinase activity by etoposide in L1210 murine leukemic cells. Biol Pharm Bull. 19: 1382-3.

Radu, C. G., C. J. Shu, E. Nair-Gill, S. M. Shelly, J. R. Barrio, N. Satyamurthy, M. E. Phelps, and O. N. Witte. 2008. Molecular imaging of lymphoid organs and immune activation by positron emission tomography with a new [18F]-labeled 2'-deoxycytidine analog. Nat Med. 14: 783-8.

Reichard, P. 1988. Interactions between deoxyribonucleotide and DNA synthesis. Annu. Rev. Biochem. 57: 349-374.

Schoppy, D. W., R. L. Ragland, O. Gilad, N. Shastri, A. A. Peters, M. Murga, O. Fernandez-Capetillo, J. A. Diehl, and E. J. Brown. 2012. Oncogenic stress sensitizes murine cancers to hypomorphic suppression of ATR. The Journal of clinical investigation. 122: 241-52.

Schwarzenberg, J., C. G. Radu, M. Benz, B. Fueger, A. Q. Tran, M. E. Phelps, O. N. Witte, N. Satyamurthy, J. Czernin, and C. Schiepers. 2011. Human biodistribution and radiation dosimetry of novel PET probes targeting the deoxyribonucleoside salvage pathway. European journal of nuclear medicine and molecular imaging. 38: 711-21.

Shields, A. F., J. R. Grierson, B. M. Dohmen, H. J. Machulla, J. C. Stayanoff, J. M. Lawhorn-Crews, J. E. Obradovich, O. Muzik, and T. J. Mangner. 1998. Imaging proliferation in vivo with [F-18]FLT and positron emission tomography. Nature medicine. 4: 1334-6.

Shu, C. J., D. O. Campbell, J. T. Lee, A. Q. Tran, J. C. Wengrod, O. N. Witte, M. E. Phelps, N. Satyamurthy, J. Czernin, and C. G. Radu. 2010. Novel PET probes specific for deoxycytidine kinase. J Nucl Med. 51: 1092-8.

Stella, V. J., and Q. He. 2008. Cyclodextrins. Toxicologic pathology. 36: 30-42.

Tannous, B. A. 2009. Gaussia luciferase reporter assay for monitoring biological processes in culture and in vivo. Nat Protoc. 4: 582-91.

Toy, G., W. R. Austin, H. I. Liao, D. Cheng, A. Singh, D. O. Campbell, T. O. Ishikawa, L. W. Lehmann, N. Satyamurthy, M. E. Phelps, H. R. Herschman, J. Czernin, O. N. Witte, and C. G. Radu. 2010. Requirement for deoxycytidine kinase in T and B lymphocyte development. Proc Natl Acad Sci USA. 107: 5551-6.

Vander Heiden, M. G. 2011. Targeting cancer metabolism: a therapeutic window opens. Nat Rev Drug Discov. 10: 671-84.

Warburg, O., F. Wind, and E. Negelein. 1927. The Metabolism of Tumors in the Body. The Journal of general physiology. 8: 519-30.

Williams, R. T., M. F. Roussel, and C. J. Sherr. 2006. Arf gene loss enhances oncogenicity and limits imatinib response in mouse models of Bcr-Abl-induced acute lymphoblastic leukemia. Proc Natl Acad Sci USA. 103: 6688-93.

Xu, Y. Z., P. Huang, and W. Plunkett. 1995. Functional compai mentation of dCTP pools. Preferential utilization of salvaged deoxycytidine for DNA repair in human lymphoblasts. J Biol Chem. 270: 631-7.

Yang, C., M. Lee, J. Hao, X. Cui, X. Guo, C. Smal, F. Bontemps, S. Ma, X. Liu, D. Engler, W. B. Parker, and B. Xu. 2012. Deoxycytidine kinase regulates the G2/M checkpoint through interaction with cyclin-dependent kinase 1 in response to DNA damage. Nucleic Acids Res. 40: 9621-32.

Yu, X.-C., M. Miranda, Z. Liu, S. Patel, N. Nguyen, K. Carson, Q. Liu, and J. C. Swaffield. 2010. Novel Potent Inhibitors of Deoxycytidine Kinase Identified and Compared by Multiple Assays. J. Biomol. Screening. 15: 72-79.

3. Example 3

Mammalian cells rely on two major pathways for the production and maintenance of deoxyribonucleotide triphosphates (dNTPs) for DNA replication and repair: the de novo pathway and the nucleoside salvage pathway.[1] The de novo pathway produces dNTPs from glucose and amino acids. The nucleoside salvage pathway produces dNTPs from preformed deoxyribonucleosides present in the extracellular environment.[1] The first enzymatic step in the cytosolic deoxyribonucleoside salvage pathway is catalyzed by deoxycytidine kinase (dCK) and by thymidine kinase 1 (TK1).[2] dCK catalyzes 5'-phosphorylation of deoxycytidine (dC), deoxyguanosine (dG) and deoxyadenosine (dA) to their monophosphate forms, exhibiting the highest affinity for dC.[3] The monophosphate deoxyribonucleotides are subsequently phosphorylated to their corresponding di- and triphosphate forms by other kinases.[4, 5] We have shown that dCK and TK1 play important roles in hematopoiesis by regulating dNTP biosynthesis in lymphoid and erythroid progenitors.[6, 7] In addition to its physiological role in nucleotide metabolism, dCK phosphorylates several clinically important antiviral and anticancer nucleoside analog prodrugs (e.g. gemcitabine, decitabine, fludarabine, cytarabine, clofarabine); phosphorylation by dCK is critically required for the activation of these prodrugs.[8] Recently, dCK was implicated in the regulation of the G2/M checkpoint in cancer cells in response to DNA damage.[9] The role of dCK in hematopoiesis and cancer has led to our interest in developing a small molecule inhibitor of this kinase. Such dCK inhibitors could represent new therapeutic agents for malignancies and immune disorders. To our knowledge, few dCK inhibitors have been reported,[10,11,12] and only one[13] has been demonstrated to inhibit dCK activity in vivo.

Positron emission tomography (PET) is a non-invasive in vivo imaging technique widely used for diagnosing, staging, restaging and therapy monitoring of various diseases.[14, 15] While PET using the radiotracer 2-$^{18}$F-fluoro-2-deoxy-D-glucose ($^{18}$F-FDG)[16, 17] has become an important diagnostic and treatment monitoring tool in cancer[18,19,20,21], another emerging application of PET concerns its use in drug discovery and development. Thus, by facilitating faster and more effective decision-making early in the drug discovery/development process, PET could accelerate the advancement of promising candidates and reduce failures.[22,23,24] For instance, PET can be used to demonstrate the need to modify lead candidates early in the drug discovery process by enabling non-invasive evaluations of drug pharmacodynamic (PD) and/or pharmacokinetic (PK) properties. In the specific context of our drug discovery and development program centered on dCK, PET could play a particularly important role given the availability of validated PET biomarkers to assess dCK activity in vivo. These PET PD biomarkers of dCK activity include a series of $^{18}$F-Fluoroarabinofuranosylcytosine analogs substrates of dCK developed by our group[25] which include $^{18}$F-1-(2'-deoxy-2'-FluoroArabinofuranosyl) Cytosine ($^{18}$F-FAC)[26] and $^{18}$F-L-1-(2'-deoxy-2'-FluoroArabinofuranosyl) Cytosine ($^{18}$F-L-FAC)[27]. Herein we describe the development of potent dCK inhibitors and demonstrate their in vivo efficacy using $^{18}$F-L-FAC PET as a non-invasive and clinically applicable PD biomarker.

Identification of Lead Compound 15c. To identify new small molecule inhibitors of dCK, we performed a high throughput screen (HTS) of a set of selected chemical libraries totaling ~90,000 small molecules. We screened the library for dCK inhibitory function using a Firefly luciferase-coupled assay with recombinant human dCK enzyme.[28] In this assay, inhibition of dCK prevents ATP depletion by dCK, thus resulting in higher luminescent signals in positive wells. The screen yielded two hit compounds, 1 and 2, which were validated to inhibit the uptake of tritiated deoxycytidine ($^3$H-dC) with micromolar potency in the L1210 murine leukemia cell line (FIG. 26).

Figure 26:
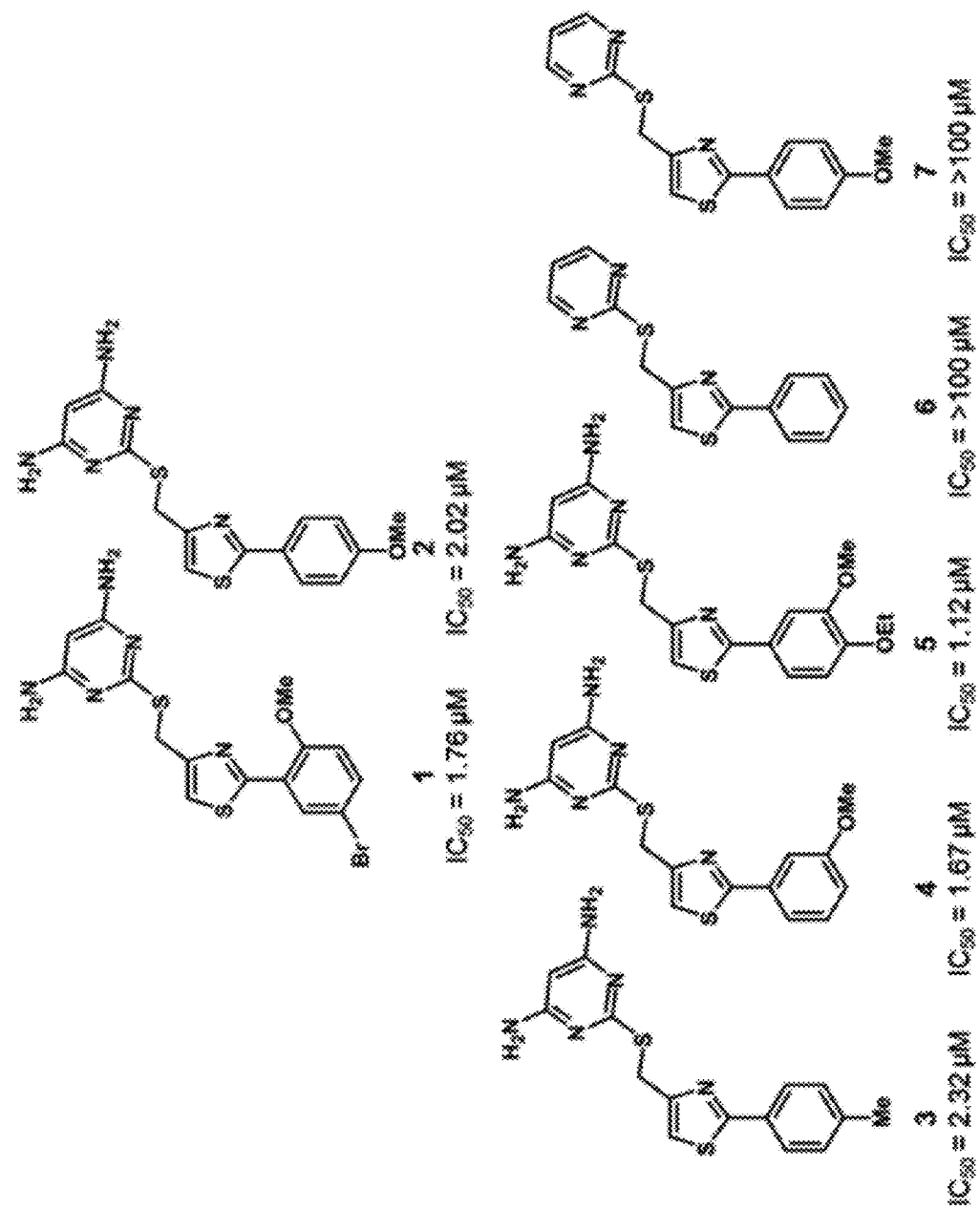
FIG. 26. Structures and $IC_{50}$ values determined using the $^3$H-dC uptake assay in L1210 cells for the initial HTS hits (1 and 2) and for commercially available compounds containing similar structural scaffolds (3-7).

Based on these results, five commercially available compounds containing similar structural scaffolds were tested; their IC$_{50}$ values against L1210 cells were determined by measuring inhibition of $^3$H-dC uptake (FIG. 26). Strikingly, compounds 6 and 7 were inactive, suggesting that the bis-amino functionality on the pyrimidine ring is crucial for dCK inhibition. Based on these results, we initiated a structure-activity relationship (SAR) study to develop a lead structure, which could be further optimized to compounds with potent in vivo activity.

We initially studied two main structural classes of compounds, pyrimidines and 1,3,5-triazines (Table 5). Two cell lines were used to determine the IC$_{50}$ values: the L1210 murine leukemia cells and the CCRF-CEM human acute T-lymophoblastic leukemia cells. In nearly all cases, substitution of the pyrimidine ring with the 1,3,5-triazine motif reduced dCK inhibitory activity; in some instances an approximate 2-fold reduction in potency was observed. Consequently, the pyrimidine motif was utilized as the preferred scaffold to advance. At this stage of the SAR, the presence of a fluoroethoxy side-chain on the phenyl ring was considered for eventual $^{18}$F-radiolabeling purposes. Substitutions around the phenyl ring with respect to the position of the fluoroethoxy side-chain were also examined. Moving the fluoroethoxy side-chain from the para position in 8a to the meta position in 9a increased the inhibitory activity approximately 2-fold. It was also apparent that alkoxy substituents in the para position were better than alkyl moieties, since compound 11a had substantially lower activity than either the methoxy 9a or ethoxy 10a analogs. Compound 12a, which contains a side-chain that was extended by one carbon to give a fluoropropoxy group at the meta position, gave slightly greater inhibitory activity, albeit not a significant increase from compounds 9a and 10a. Substitution at the ortho position of the phenyl ring, e.g. in compounds 13a and 14a, resulted in substantially lower dCK inhibitory activity, an approximate 10-fold decrease in potency was observed for compound 14a when compared to 9a. A general synthetic scheme for compounds in Table 5 can be found in the supporting information.

While the presence of fluorine in the small molecule may eventually enable the synthesis of an $^{18}$F-isotopolog of the dCK inhibitor, fluorine introduction also affects nearly all the physical and ADME (adsorption, distribution, metabolism, and excretion) properties of a compound.[29] The capacity of fluorine to enhance metabolic stability has become increasingly apparent in recent years.[30] Thus, a series of compounds were synthesized which contained fluorine attached directly on the aromatic ring of the inhibitors rather than linked by an ethoxy side-chain (compounds 16-18, Table 6). For each compound in this series, a set of three derivatives (a-c) were synthesized; in each case the group on the 5-position of the thiazole was either a methyl, ethyl or propyl substituent. For compounds 15a-c the fluoroethoxy side-chain was retained at the meta position of the phenyl ring, as was a methoxy group at the para position due to the favorable inhibitory results from the initial SAR in Table 5.

substituents against their respective methyl derivatives in CCRF-CEM cells also showed an increasing inhibitory trend in activity: 6-fold (compare 17c to 17a) or 3-fold (compare 18c to 18a). The most drastic effect from modi-

TABLE 5

In vitro biological data in L1210 and CEM cells for compounds 8-14

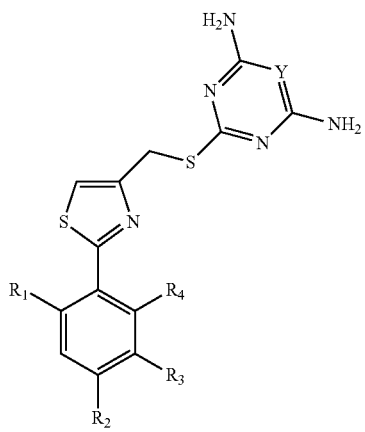

| Compound | $R_1$ | $R_2$ | $R_3$ | $R_4$ | IC$_{50}$ (μM) L1210 cells a Y = Cl | IC$_{50}$ (μM) L1210 cells b Y = N | IC$_{50}$ (μM) CEM cells a Y = CH | IC$_{50}$ (μM) CEM cells b Y = N |
|---|---|---|---|---|---|---|---|---|
| 8 | H | OCH$_2$CH$_2$F | OCH$_3$ | H | 0.808 (± 0.406) | 1.612 (± 0.543) | 0.421 (± 0.075) | 0.534 (± 0.012) |
| 9 | H | OCH$_3$ | OCH$_2$CH$_2$F | H | 0.538 (± 0.014) | 0.528 (± 0.015) | 0.230 (± 0.012) | 0.506 (± 0.138) |
| 10 | H | OCH$_2$CH$_3$ | OCH$_2$CH$_2$F | H | 0.513 (± 0.100) | 1.226 (± 0.450) | 0.251 (± 0.020) | 0.512 (± 0.409) |
| 11 | H | CH$_3$ | OCH$_2$CH$_2$F | H | 2.381 (± 0.042) | 3.201 (± 0.568) | 1.960 (± 1.001) | 1.922 (± 0.573) |
| 12 | H | OCH$_3$ | OCH$_2$CH$_2$CH$_2$F | H | 0.330 (± 0.160) | 0.603 (± 0.140) | 0.197 (± 0.109) | 0.297 (± 0.020) |
| 13 | OCH$_3$ | H | OCH$_2$CH$_2$F | H | 1.445 (± 0.060) | 2.649 (± 0.902) | 1.041 (± 0.084) | 0.849 (± 0.183) |
| 14 | H | OCH$_2$CH$_2$F | H | OCH$_3$ | 5.469 (± 1.336) | ND$^b$ | 2.367 (± 0.238) | ND$^b$ |

$^a$Inhibitory activity measured by $^3$H-deoxycytidine ($^3$H-dC) uptake in murine L1210 cells and in CCRF-CEM human cells. Values reported are the mean ± SD of at least n = 2 independent experiments.
$^b$ND = not determined (compounds was not synthesized).

Increasing non-polar functionality at the 5-position of the thiazole resulted in increasing inhibitory activity (Table 6). The IC$_{50}$ values in CCRF-CEM cells illustrate the same trend in potency as observed in L1210 cells with one exception; set 16 shows little difference between the methyl, ethyl or propyl substituents. However, for all compounds tested against L1210 cells, the propyl substituent yielded better inhibitory activity than the corresponding methyl derivatives. The best example in L1210 cells was the 12-fold increase in activity when comparing compound 15c to compound 15a. In addition, comparisons between the propyl fications at the 5-position of the thiazole ring was the change exhibited from 9a in Table 1 to 15c in Table 6, where the substitution of a hydrogen for a propyl moiety resulted in a 180-fold increase in potency in L1210 cells. In addition, removal of the fluoroethoxy side-chain (e.g. compound series 16-18) resulted in a significant decrease in potency in both cell lines. Compound 15c, the most potent compound in this series, contains both the fluoroethoxy side-chain at the meta position on the phenyl ring and also a propyl group at the 5-position of the thiazole ring.

TABLE 6 in vitro biological data in L1210 and CEM cells for compounds 15-18

[Structure: thiazole with Y substituent, linked via CH2-S to 2-position of 4,6-diaminopyrimidine; 2-position of thiazole bears phenyl ring with R1, R2, R3 substituents]

| Compound | R$_1$ | R$_2$ | R$_3$ | IC$_{50}$ (μM) L1210 cells | | | IC$_{50}$ (μM) CEM cells | | |
|---|---|---|---|---|---|---|---|---|---|
| | | | | a Y = Me | b Y = Et | c Y = Pr | a Y = Me | b Y = Et | c Y = Pr |
| 15 | H | OCH$_3$ | OCH$_2$CH$_2$F | 0.035 (± 0.015) | 0.030 (± 0.077) | 0.003 (± 0.000) | 0.018 (± 0.012) | 0.007 (± 0.002) | 0.003 (± 0.000) |
| 16 | F | H | F | 0.595 (± 0.163) | 0.620 (± 0.170) | 0.385 (± 0.262) | 0.150 (± 0.099) | 0.162 (± 0.019) | 0.173 (± 0.157) |
| 17 | H | F | H | 0.395 (± 0.134) | 0.265 (± 0.163) | 0.170 (± 0.099) | 0.230 (± 0.134) | 0.083 (± 0.043) | 0.037 (± 0.020) |
| 18 | H | H | F | 0.255 (± 0.021) | 0.510 (± 0.014) | 0.175 (± 0.007) | 0.092 (± 0.018) | 0.011 (± 0.0387) | 0.031 (± 0.024) |

$^a$Inhibitory activity measured by $^3$H-deoxycytidine ($^3$H-dC) uptake in murine L1210 and in CCRF-CEM human cells. Values reported are the mean ± SD of at least n = 2 independent experiments.

Compounds 15a-c were synthesized in six steps (Scheme 4). The commercially available 3-hydroxy-4-methoxybenzonitrile 19 was functionalized via alkylation with 1-bromo-2-fluoroethane in DMF with cesium carbonate as the base to obtain the nitrile 20 in 99% yield. Subjection of 20 to an aqueous ammonium sulfide solution under basic conditions afforded the thioamide 21 in excellent yield.[31] Cyclization to form the thiazole core of 15a-c was achieved via condensation of thioamide 21 with the respective ethyl 3-bromo-2-oxoalkanoate[32] in refluxing ethanol.[33] Reduction of the resulting compounds with diisobutylaluminum hydride afforded the respective alcohols 23a-c in 88-99% yield. The alcohols 23a-c were converted to the respective bromides 24a-c under mild conditions[34] in 74-80% yield. Finally, nucleophilic displacement of the bromide with 4,6-diamino-2-mercaptopyrimidine[35] generated the desired products 15a-c in 71-87% yield.

Scheme 4. Synthesis of compounds 15a-c$^a$

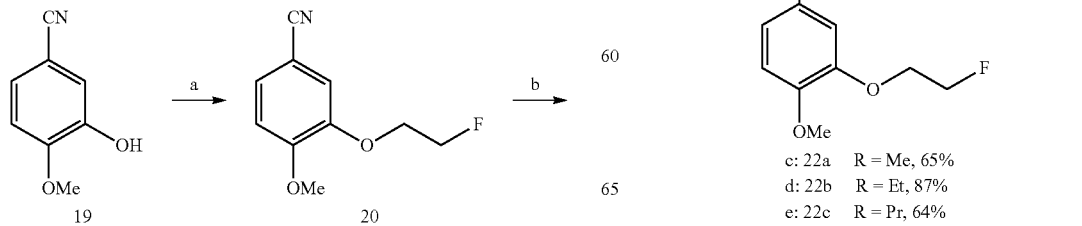

c: 22a R = Me, 65%
d: 22b R = Et, 87%
e: 22c R = Pr, 64%

-continued

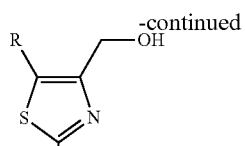

23a R = Me, 88%
23b R = Et, 82%
23c R = Pr, 99%

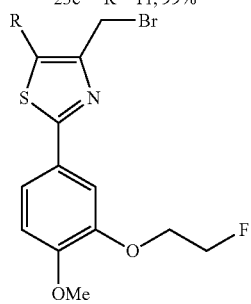

24a R = Me, 60%
24b R = Et, 92%
24c R = Pr, 74%

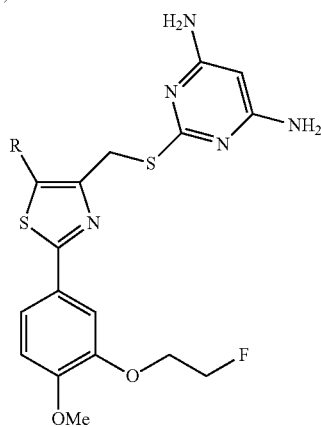

15a R = Me, 71%
15b R = Et, 92%
15c R = Pr, 87%

[a]Reagents and conditions: (a) 1-bromo-2-fluoroethane, Cs$_2$CO$_3$, DMF, 99%; (b) (NH$_4$)$_2$S (20% in H$_2$O), pyridine, Et$_3$N, quantitative; (c) ethyl 3-bromo-2-oxobutanoate, EtOH; (d) ethyl 3-bromo-2-oxopentanoate, EtOH; (e) ethyl 3-bromo-2-oxohexanoate, EtOH; (f) DIBAL—H, CH$_2$Cl$_2$; (g) 1,1,1,3,3,3-hexabromoacetone, PPh$_3$, CH$_3$CN; (h) 4,6-diamino-2-mercaptopyrimidine, NaOH, EtOH.

Figure 27C:
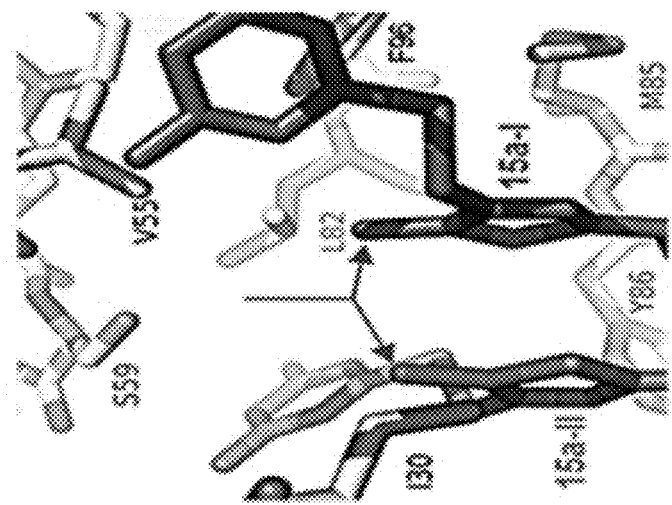
FIGS. 27A-27C. Binding of 15a to human dCK.
Figure 27B:
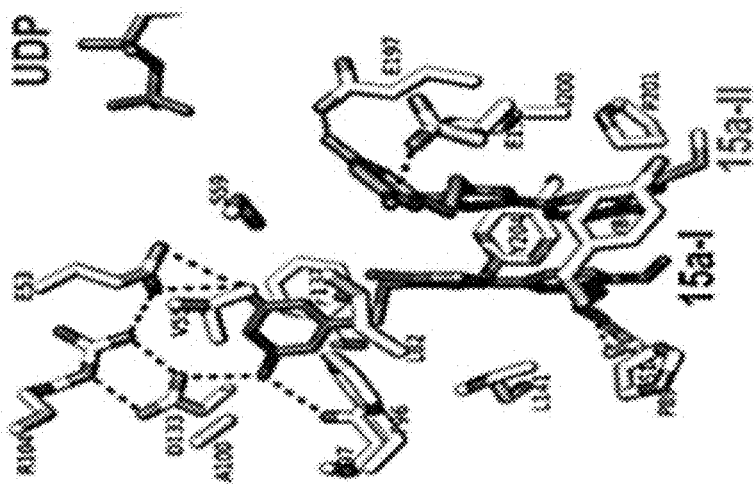
Figure 27A:
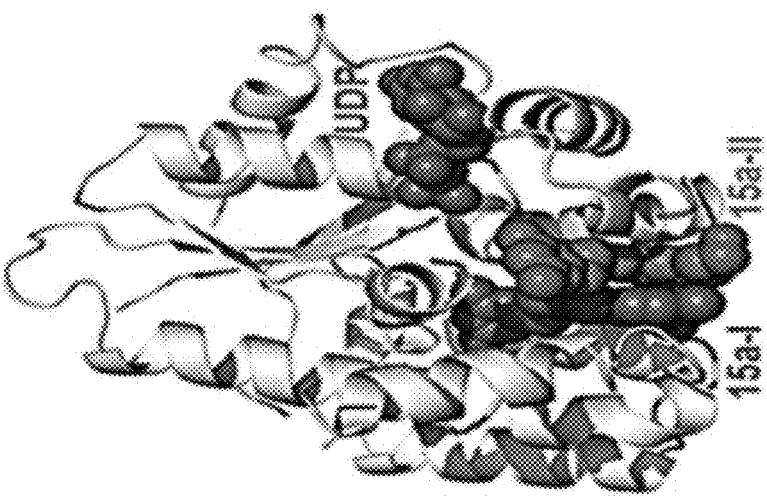

X-ray Crystal Structure of Compound 15a Bound to Human dCK. X-ray crystallographic studies of compound 15a were initiated to obtain information about its binding to dCK. Detailed analysis of the dCK-inhibitor interactions for this series of compounds was performed. In short, the crystal structure of the dCK:15a complex was solved at 1.9 Å resolution (FIGS. 27A-27C). Human dCK, a dimer of two identical subunits with a molecular weight of ~30 kDa per monomer, can bind either ATP or UTP as the phosphoryl donor for catalysis; in addition, dCK can adopt an open or closed conformation.[36,37,3] In complex with 15a, the enzyme adopts the open conformation. We observed two 15a molecules in each protomer of the dimeric enzyme ((15a-I) and (15a-II), FIG. 27A). Note that binding of 15a to dCK does not preclude nucleotide binding (FIG. 27A). The parallel orientation between 15a-I and 15a-II allows for optimal π-π stacking interactions between the phenyl and thiazole rings of each molecule.

While two molecules of 15a bind in the active site, it appears that 15a-I forms more key interactions and shorter hydrogen bond distances than 15a-II (FIG. 27B). The extensive hydrogen-bond network that exists between the pyrimidine moiety of 15a-I and residues E53, Q97 and D133 in the dCK nucleoside binding site are illustrated in FIG. 27B. FIG. 27C illustrates the hydrophobic pocket that exists, via V55, L82 and F96, around the methyl group of compound 15a. This figure demonstrates that the pocket will accept larger substituents, explaining the increased trend in potency obtained for compounds 15b and 15c.

A Monte Carlo[38] (MC)-based computational modeling approach using the free energy perturbation (FEP) method[39,40] was used to further investigate the inhibitory effects of alkyl chain lengthening at the 5-position of the thiazole. FEP allows calculation of the difference in binding energy of two molecules. The perturbation of molecule A into molecule B in a complex with a protein [$\Delta G_{protein}$ (A→B)] and in solution alone [$\Delta G_{water}$(A→B)] is part of a complete thermodynamic cycle (FIG. 3A). Because the sum of all components in such a cycle must equal zero, the binding energy difference may be calculated as the difference in free energies:

$$\Delta\Delta G_{binding} = \Delta G_{binding}(B) - \Delta G_{binding}(A) = \Delta G_{protein}(A \to B) - \Delta G_{water}(A \to B)$$

Models of structures 15b and 15c (FIG. 28B) each in a monomeric complex with dCK and in solution alone were equilibrated using MC. The equilibrated structure of 15c was subsequently perturbed into the structure of 15b ("shrinking" the propyl chain into an ethyl) and vice versa ("growing" the ethyl chain into a propyl) using FEP. These calculations were performed using the MCPRO 2.0[41] software package. The free energy changes for these perturbations are illustrated in FIG. 3C. Averaging the $\Delta\Delta G_{binding}$ obtained from the two simulations indicates that the propyl chain of 15c confers a 1.210 kcal/mol more favorable free energy of binding in comparison to the ethyl chain of 15b; this favorable effect is due to desolvation. The change in free energy upon extension of the alkyl chain is unfavorable both in the complex with the protein and in water alone (positive $\Delta G$ for chain lengthening, negative $\Delta G$ for chain shortening); however, the magnitude of the unfavorable $\Delta G$ is larger in solvent. The fact that this produces an overall favorable $\Delta\Delta G$ of binding suggests that the propyl chain is better able to exclude water from the interior cavity of the protein, allowing a greater association between the protein and the inhibitor.

Based on the potency trend in Table 6 and the existence of a hydrophobic pocket around the 5-position of the thiazole ring of 15a, further compounds in the SAR were made with the propyl chain installed at that position, to increase non-polar interactions between the dCK enzyme pocket and the inhibitors. The fluorine atom terminating the ethoxy side-chain was substituted for a hydroxyl or sulfonamide group, with the goal of improving the molecule's solubility properties as well as potential hydrogen bonding interactions that might exist in the active site. Moreover, since inhibitory activity in L1210 and CCRF-CEM cells demonstrated the same trend in potency, the SAR for all subsequently synthesized compounds were examined only in CCRF-CEM cells. The results are summarized in Table 7.

TABLE 7

In vitro biological data in CEM cells for compounds 25-37[a]

| Compound | $R_1$ | $R_2$ | $R_3$ | Y | $IC_{50}$ (nM) CEM cells |
|---|---|---|---|---|---|
| 25 | H | H | $OCH_2CH_2OH$ | $NH_2$ | 2.45 (±0.778) |
| 26 | H | F | $OCH_2CH_2OH$ | $NH_2$ | 1.07 (±0.230) |
| 27 | F | H | $OCH_2CH_2OH$ | $NH_2$ | 2.83 (±1.628) |
| 28 | H | H | $OCH_2CH_2NHSO_2CH_3$ | $NH_2$ | 11.58 (±3.353) |
| 29 | F | H | $OCH_2CH_2NHSO_2CH_3$ | $NH_2$ | 8.01 (±0.230) |
| 30 | H | $OCH_2CH_2OH$ | $OCH_2CH_2OH$ | $NH_2$ | 2.59 (±1.146) |
| 31 | H | $OCH_3$ | OH | $NH_2$ | 18.62[b] |
| 32 | H | $OCH_3$ | $OCH_2CH_2CH_2OH$ | $NH_2$ | 1.55 (±0.354) |
| 33 | H | $OCH_3$ | $OCH_2CH_2OH$ | $NH_2$ | 1.15 (±0.762) |
| 34 | H | $OCH_3$ | $OCH_2CH_2OH$ | H | 2.90 (±0.300) |
| 35 | H | $OCH_3$ | $OCH_2CH(CH_3)OH$ | $NH_2$ | 2.85 (±0.071) |
| 36 | H | $OCH_3$ | $OCH_2C(CH_3)_2OH$ | $NH_2$ | 1.44 (±0.538) |
| 37 | H | $OCH_3$ | $OCH_2CH_2NHSO_2CH_3$ | $NH_2$ | 4.89 (±2.014) |

[a]Inhibitory activity measured by $^3$H-deoxycytidine ($^3$H-dC) uptake in CCRF-CEM human cells. Values reported are the mean ± SD of at least n = 2 independent experiments.
[b]Value reported for n = 1.

Compounds 25-27 showed excellent (1-2 nM) potency against CCRF-CEM cells (Table 7). Substitution of the end-chain hydroxyl for a methyl sulfonamide resulted in a decrease in inhibitory activity of about 3-fold (compare 27 to 29) or 5-fold (compare 25 to 28). The initial SAR in Table 5 indicated that the presence of an alkoxy substituent at the para position led to increased inhibitory activity; therefore, the methoxy group was reinstalled at the para position. As expected, removal of the ethoxy side-chain (e.g. compound 31) resulted in a substantially lower inhibitory activity, reinforcing the data observed for compounds 16-18 (Table 6). The presence of the methoxy moiety at the para position, in addition to the hydroxylethoxy side chain at the meta position, generated compound 33, which has an inhibitory potency of 1 nM. To our surprise, removal of one of the amino groups from the pyrimidine ring led to a mere 2.5-fold decrease in inhibitory activity (compare 33 to 34). Initially, we observed that removal of both amino groups from the pyrimidine ring resulted in complete loss of inhibitory activity (compounds 6 and 7, FIG. 26); however, the presence of one amino group can provide suitable key hydrogen bonding interactions to inhibit the enzyme. Compound 32, which contains a side-chain that has been extended by one carbon to give a hydroxylpropoxy group, was also synthesized. However, this modification resulted in slightly decreased inhibitory activity in comparison with the hydroxylethoxy group. While compound 33 was a potent compound in cell culture, the presence of a primary hydroxyl group in the molecule raised concerns of a metabolic liability as a consequence of potential oxidation or glucuronidation.[42] Thus, compounds 35-37 were synthesized to decrease the possibility of metabolic degradation of 33. Eight of these compounds in Table 7, whose $IC_{50}$ values were lower than 15a and whose structural properties suggested that they would have the best in vivo efficacy, were selected for further investigation.

To confirm that the cell-based values reflect the potency of the compounds we also determined the $Ki^{app}$ values for select compounds using steady state kinetic assays. The cell-based assays indicated that compound 15a was 6-12 fold (depending on the cell line used for the assay) less potent than compound 15c (Table 6). Correspondingly, the steady state data showed a 6-fold higher $Ki^{app}$ value for compound 15a (Table 8). Likewise, the low nanomolar $IC_{50}$ observed in CEM cells for compounds 36 and 37 (Table 7) was recapitulated in the steady-state kinetics derived $Ki^{app}$ values for these compounds (Table 8). Hence, we conclude that our cell-based assays are providing us with relatively accurate data as to the strength of the interactions between the compounds and dCK.

TABLE 8

Steady state kinetics of selected dCK inhibitors

| Compound | $Ki^{app}$ (nM) | Error (nM) | $R^2$ |
|---|---|---|---|
| 15a* | 9.5 | 2.3 | 0.974 |
| 15c* | 1.5 | 0.3 | 0.998 |
| 36 | 0.8 | 0.7 | 0.982 |
| 37 | 0.5 | 0.5 | 0.988 |

*Data from Nomme et al.

Evaluation of In Vivo Inhibition of dCK Activity Via a New PET PD Assay. The nucleoside analog PET probe $^{18}$F-L-FAC is a high affinity substrate for dCK, which can be used to non-invasively estimate dCK enzymatic activity in vivo.[27] A schematic depicting the mechanism by which $^{18}$F-L-FAC accumulates in cells in a dCK-specific manner is shown in FIG. 4A. We reasoned that $^{18}$F-L-FAC PET could be used to rapidly identify the most potent dCK inhibitors based on their effectiveness at inhibiting the accumulation of the $^{18}$F-labeled dCK substrate PET tracer in various tissues. For the in vivo PET PD assay we selected dCK inhibitors that demonstrated 1-2 nM inhibitory activity in the cell culture $^3$H-dC uptake assay (Table 3). Mice were treated with a single dose (50 mg/Kg) of a given dCK inhibitor administered by intraperitoneal injection. Control mice received vehicle (40% Captisol in water) injections. Four hours later, treated mice were injected intravenously with $^{18}$F-L-FAC; one hour after probe injection, mice were imaged by mPET/CT. The readout for the PET PD assay was the reduction in the accumulation of $^{18}$F-L-FAC in dCK-positive tissues in dCK inhibitor versus vehicle treated mice. Previously, we showed that $^{18}$F-L-FAC accumulates in a dCK-dependent manner into various tissues such as the thymus, spleen, bone marrow and liver.[27] Accumulation in the bladder is a result of non-enzymatic renal clearance of the unmetabolized probe. Since the reproducibility in the dCK-dependent tissue retention of $^{18}$F-L-FAC was most consistent in the liver[27], we chose to quantify $^{18}$F-L-FAC liver retention in order to compare the in vivo efficacy of the various dCK inhibitors. Optimal conditions for the PET PD assay were determined by performing a dose escalation and time course study using compound 33.

Results from the $^{18}$F-L-FAC mPET/CT scans are summarized in FIGS. 29A-29D. Transverse PET images of the $^{18}$F-L-FAC liver scans for mice treated with either vehicle or compounds 15a, 36 or 37 are shown in FIG. 29B. FIG. 29C illustrates the uptake of $^{18}$F-L-FAC in the livers of mice treated dCK inhibitors. The efficacious compounds induced a greater reduction in the $^{18}$F-L-FAC uptake relative to vehicle treatment, as a result of their greater inhibition of dCK-mediated phosphorylation of its $^{18}$F-labeled substrate. Note the approximate 30% decrease in $^{18}$F-L-FAC signal compared to vehicle control induced by compounds 28, 29, 36 and 37, indicating their superior in vivo efficacy relative to the other dCK inhibitor candidates. In addition, compounds 30 and 32 show about a 20% decrease in probe uptake. Compound 33, a potent dCK inhibitors in the cell culture assay (Table 7) showed poor in vivo efficacy in the $^{18}$F-L-FAC liver PET assay, presumably due to its poor PK properties. As hypothesized, substitution of the hydroxyl group at the end of the ethoxy chain (e.g. compound 33) for the metabolically stable methylsulfonamide (compounds 28, 29 and 37) or hindering the hydroxyl group (compound 36) proved advantageous for in vivo efficacy. Compounds 36 and 37 have the lowest $IC_{50}$ values amongst all the efficacious compounds and were chosen for further study.

Figure 30:
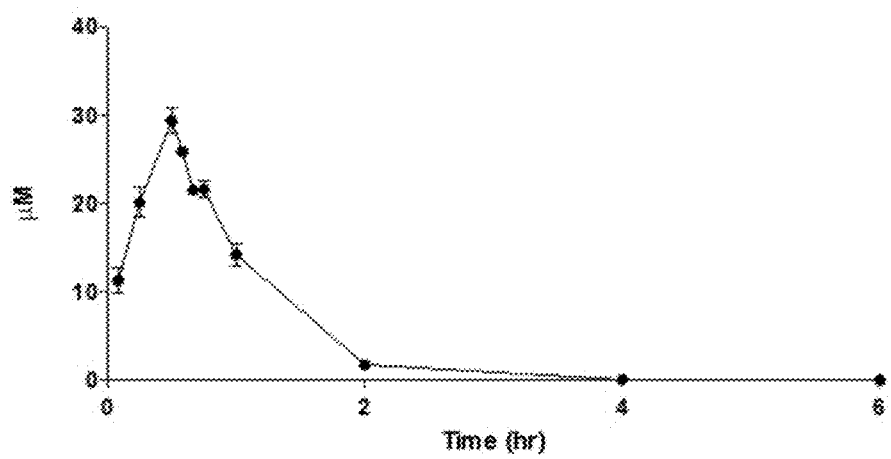
FIG. 30. Pharmacokinetic profile of compound 36. C57Bl/6 female mice were dosed with compound 37 via intraperitoneal injection. Dose formulation: 10% DMSO and 40% Captisol in water. Data are mean values±SEM for n=4 mice/time point.

Next we determined the efficacy of compound 36 at inhibiting dCK activity in tumor tissues in vivo. Mice bearing CCRF-CEM tumor xenografts were treated with compound 36 four hours prior to injection of $^{18}$F-L-FAC (FIG. 29D). One hour after the $^{18}$F-L-FAC injection, mice were imaged by mPET/CT. The retention of $^{18}$F-L-FAC in tumor xenografts from mice treated with compound 36 was reduced by about 30% compared to the retention of $^{18}$F-L-FAC in tumors from vehicle treated mice (FIG. 29D). To complement the PET assay, the pharmacokinetics of compound 36 was determined using standard analytical techniques and the approximated values are reported in FIG. 30.

Figure 31A:
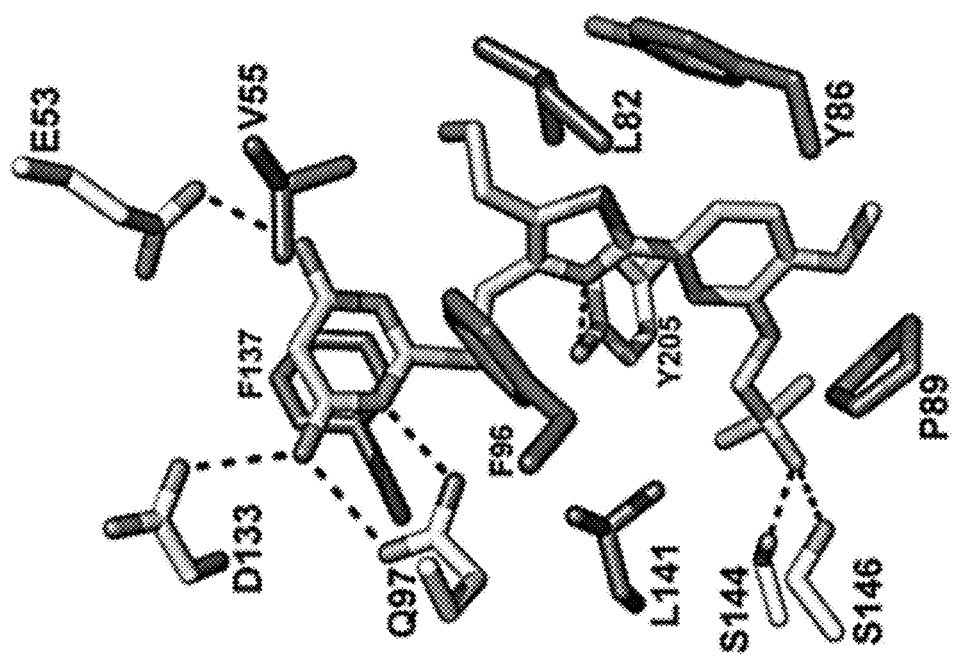
FIGS. 31A-31B. Crystal structure of dCK:36 complex.
Figure 31B:
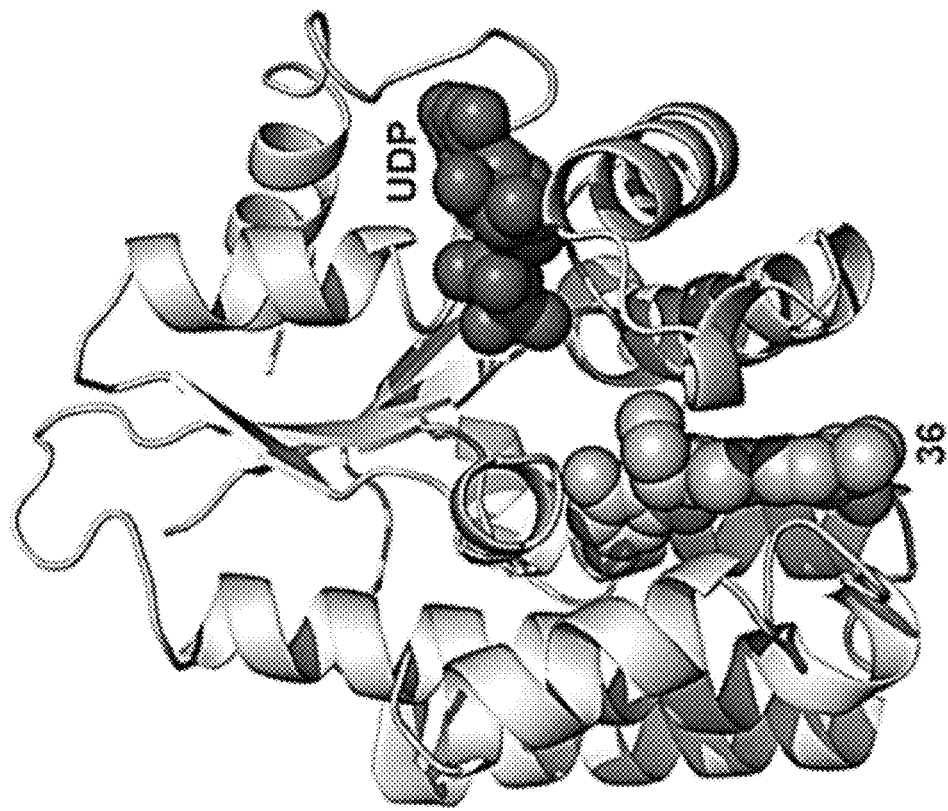

X-ray crystallographic studies of compound 36 were initiated to obtain information about its binding to dCK. The crystal structure of the dCK:36 complex was solved at 1.94 Å resolution (FIGS. 31A-31B and Table 9). Similar to our observations for compound 15a (FIGS. 27A-27C), in the case of 36, the enzyme also adopts the open conformation. We observed one 36 molecule in each protomer of the dimeric enzyme (FIG. 31A). This is contrast to the observation of two molecules bound per active site when the substituent at the 5-position is smaller than the propyl present in 36 (FIGS. 27A-27C). Note that binding of 36 to dCK does not preclude nucleotide binding (FIG. 31A). The specific dCK:36 interactions are shown in FIG. 31B. These include an extensive hydrogen-bond network between the pyrimidine moiety of 36 and residues E53, Q97 and D133 in the dCK nucleoside binding site, as well as several hydrophobic interactions.

The identification of potent small molecule human dCK inhibitors that demonstrate in vivo target inhibition is reported. Optimization of inhibitory activity was achieved by extending an alkyl chain from the 5-position of the thiazole ring. In vivo efficacy was improved by manipulation of the ethoxy side-chain present at the meta position of the phenyl ring. The utility of PET as a powerful tool for non-invasive measure of target inhibition and, consequently, as a measure of lack of target inhibition (most likely due to substrate metabolism in vivo), is also presented. Although the major clinical applications of PET are primarily for central nervous system (CNS) and oncology-based diagnostics/therapeutics, PET is playing an increasingly important role in drug development, given the capability of this molecular imaging platform to address key challenges that include evaluation of biodistribution, absorption, target affinity, plasma binding, metabolism, and dosing.[43] Here we used the radiotracer $^{18}$F-L-FAC as a PET PD biomarker to compare the in vivo efficacies of candidate dCK inhibitors, first identified and characterized by potency in cell culture assays. Moreover, we used PET to provide estimates of in vivo target inhibition in CCRF-CEM xenograft mouse models by one of our most promising compounds, 36. The ability of another promising compound, 37, to elicit a significant pharmacological response against CCRF-CEM tumors with minimal toxicity to normal tissues was evaluated by our group and is described in a separate publication. Further optimization offering improvements to the PK and solubility properties of our best dCK inhibitors will be addressed in subsequent studies. In addition, the presence of fluorine on the aromatic ring of one of our most promising dCK inhibitors, 29, makes it amenable to $^{18}$F radiolabeling. Synthesizing a small molecule dCK inhibitor with an $^{18}$F radioisotope could generate a positron-emitting version of the therapeutic candidate that can be detected and quantified non-invasively throughout the body of living individuals by PET imaging. This work will be the subject of a future communication.

TABLE 9

Data collection and refinement statistics

| PDB codes | Complex 36 + UDP 4L5B |
|---|---|
| Data collection statistics | |
| X-ray source and detector | LS-CAT ID-G MARCCD 300 |
| Wavelength (Å) | 0.97856 |
| Temperature (K) | 100 |
| Resolution$^a$ (Å) | 1.94 (1.94-2.05) |
| Number of Reflections | |
| Observed | 206005 |
| Unique | 40954 |
| Completeness (%) | 99.2 (98.1) |
| $R_{sym}$(%) | 4.5 (71.8) |
| Average I/σ(I) | 17.05 (2.05) |
| Space group | P 4$_1$ |
| Unit cell (Å) | |
| a = b | 68.67 |
| c | 120.02 |
| Refinement statistics | |
| Refinement program | REFMAC5 |
| Twinning fraction | 0.5 |
| Rcryst (%) | 18.8 |
| Rfree (%) | 23.3 |
| Resolution range (Å) | 30-1.94 |
| Protein molecules per a.u. | 2 |
| Number of atoms | |
| Protein (ProtA, ProtB) | 1932, 1925 |
| Inhibitor | 32 × 2 |
| UDP | 25 × 2 |
| Water | 75 |

TABLE 9-continued

Data collection and refinement statistics

| PDB codes | Complex 36 + UDP 4L5B |
|---|---|
| R.m.s. deviation from ideal | |
| Bond length (Å) | 0.011 |
| Bond angles (°) | 1.647 |
| Average B-factors (Å$^2$)/chain | |
| Protein (ProtA, ProtB) | 47.1, 47.3 |
| Inhibitor (ProtA, ProtB) | 45.1, 43.4 |
| UDP (ProtA, ProtB) | 47.8, 44.7 |
| Waters | 42.9 |
| Ramachandran plot (%) | |
| most favored regions | 89.1 |
| additionally allowed regions | 10.5 |
| generously allowed regions | 0.5 |
| disallowed regions | 0.0 |

[a]Last shell in parenthesis

High-throughput Screen. Recombinant human dCK at a concentration of 1 μM was incubated with 10 μM of drug, 10 μM of dC and 0.5 μM ATP with 50 mM Tris (pH 7.6), 5 mM MgCl$_2$, 2 mM DTT. The reaction was incubated at 37° C. for 4 hours before adding CellTiter-Glo (Promega): Briefly, 40 μL dCK enzyme were dispensed into 384 well plates (Greiner, Bahlingen, Germany) using a multidrop 384 (Thermo, Turku, Finnland) at concentration of 12.5 μg/ml; compounds were added using a Beckman-Coulter Biomek FX (Beckman Coulter, Brea, Calif.) equipped with a 500 nL custom pin tool (V&P Scientific, San Diego, Calif.). Columns 1, 2, 23 and 24 received only DMSO instead of any drugs. In addition, no dCK was added to column 23 and 24 as these columns served as additional controls (see below). After 30 min incubation at 37° C., dC and ATP were added to a final concentration of 10 μM and 0.5 μM, respectively for columns 1-22 using the multidrop in a volume of 10 μL. For column 23 and 24 the following controls were used: 10 μl of a 2.5 μM ATP solution containing the following additional controls was added: for wells A-D23, 1 μM dCTP, for wells E-H23 10 μM dCTP, for wells I-L23 10 μM L-FAC, for wells F-P23: 10 μM FAC, for wells A-D24: 0.5 μM ATP standard, for wells E-H24: 0.1 μM ATP standard, for wells I-L24 1 μM DCK only and for wells F-P24 10 μM UTP was added, respectively. These controls were included on each plate to exclude equipment failure. This was followed by a 4 hour incubation at 37° C. and addition of 25 μL Cell titer glo reagent (Promega, Fitchburg, Wis.) by multidrop followed by reading on an Acquest plate reader (Molecular Devices, Sunnyvale, Calif.). The libraries used were custom sets of compounds from the compound manufacturers Asinex (Winston-Salem, N.C.) and Enamine (Monmouth Jct., N.J.). These sets consisted of compounds selected extensively for drug-likeness using the Lipinski rule of five, rotatable bonds and maximal diversity using custom clustering algorithms.

Chemistry. General Procedures:

Unless otherwise noted, reactions were carried out in oven-dried glassware under an atmosphere of nitrogen using commercially available anhydrous solvents. Solvents used for extractions and chromatography were not anhydrous. 4,6-Diamino-2-mercapto-pyrimidine was obtained from drying the hydrate over dynamic vacuum at 110° C. for 20 hours. All other reagents obtained from commercial suppliers were reagent grade and used without further purification unless specified. Reactions and chromatography fractions were analyzed by thin-layer chromatography (TLC) using Merck precoated silica gel 60 F$_{254}$ glass plates (250 μm). Visualization was carried out with ultraviolet light, vanillin stain, permanganate stain, or p-anisaldehyde stain. Flash column chromatography was performed using E. Merck silica gel 60 (230-400 mesh) with compressed air. $^1$H and $^{13}$C NMR spectra were recorded on ARX500 (500 MHz) or Avance500 (500 MHz) spectrometers. Chemical shifts are reported in parts per million (ppm, δ) using the residual solvent peak as the reference. DMSO-d$_6$ (δ 2.50 ppm for $^1$H; δ 39.5 ppm for $^{13}$C) was used as the solvent and reference standards unless otherwise noted. The coupling constants, J, are reported in Hertz (Hz) and the resonance patterns are reported with notations as the following: br (broad), s (singlet), d (doublet), t (triplet), q (quartet), and m (multiplet). Electrospray mass spectrometry data were collected with a Waters LCT Premier XE time of flight instrument controlled by MassLynx 4.1 software. Samples were dissolved in methanol and infused using direct loop injection from a Waters Acquity UPLC into the Multi-Mode Ionization source. The purity of all final compounds was determined to be >95%. Analytical HPLC analysis was performed on a Knauer Smartline HPLC system with a Phenomenex reverse-phase Luna column (5 μm, 4.6×250 mm) with inline Knauer UV (254 nm) detector. Mobile phase: A: 0.1% TFA in H$_2$O, B: 0.1% TFA in MeCN. Eluent gradient is specified for each described compound in the supporting information. All chromatograms were collected by a GinaStar (raytest USA, Inc.; Wilmington, N.C., USA) analog to digital converter and GinaStar software (raytest USA, Inc.).

General Procedure for the Synthesis of Compounds 15a-c.

3-(2-fluoroethoxy)-4-methoxybenzonitrile (20)

To a solution of 3-hydroxy-4methoxybenzonitrile 19 (3.0 g, 20.1 mmol) in DMF (100 mL) was added Cs$_2$CO$_3$ (10.5 g, 32.2 mmol) and 1-bromo-2-fluoroethane (5.1 g, 40.2 mmol). The mixture was stirred for 18 h at 50° C. After concentration to remove residual solvent, the resulting residue was washed with brine and extracted with ethyl acetate. The organic layer was washed with water three times, dried over anhydrous MgSO$_4$ and concentrated in vacuo to yield crude 20 (3.91 g, 20.03 mmol, 99%) as an cream-colored solid. $^1$H NMR (500 MHz, CDCl$_3$) δ: 7.28 (dd, J=8.5, 2.0 Hz, 1H), 7.10 (d, J=2.0 Hz, 1H), 6.90 (d, J=8.5 Hz, 1H), 4.83-4.81 (m, 1H), 4.73-4.71 (m, 1H), 4.28-4.26 (m, 1H), 4.23-4.21 (m, 1H), 3.89 (s, 3H); $^{13}$C NMR (125 MHz, CDCl$_3$) δ: 153.6, 148.1, 127.3, 119.1, 116.5, 111.9, 103.8, 82.3 (d, J$_{CF}$=170.5 Hz), 68.7 (d, J$_{CF}$=20.3 Hz), 56.1.

3-(2-fluoroethoxy)-4-methoxybenzothioamide (21)

To a mixture of 20 (3.86 g, 19.8 mmol) in pyridine (41 mL) and triethylamine (3 mL) was added ammonium sulfide solution (20% wt. in H$_2$O, 13.52 mL, 39.6 mmol). The mixture was stirred for 18 h at 60° C. The reaction mixture was cooled and concentrated in vacuo to remove residual solvent. The resulting residue was washed with brine and extracted with ethyl acetate. The organic layer was dried over anhydrous MgSO$_4$ and concentrated in vacuo to yield 21 (4.5 g, 19.8 mmol, quantitative) as a yellow-orange solid. $^1$H NMR (500 MHz, acetone-d$_6$) δ: 8.81 (brs, 1H), 8.74 (brs, 1H), 7.73 (s, 1H), 7.72 (dd, J=8.5, 2.0 Hz, 1H), 7.00 (d, J=8.0 Hz, 1H), 4.79 (dt, J=48.0, 4.0 Hz, 2H), 4.32 (dt, J=29.5, 4.0 Hz, 2H), 3.89 (s, 3H); $^{13}$C NMR (125 MHz, acetone-$d_6$) δ: 200.4, 152.9, 147.2, 131.8, 121.5, 113.6, 110.8, 82.7 (d, $J_{cf}$=167.3 Hz), 68.5 (d, $J_{CF}$=19.6 Hz), 55.4.

Ethyl 2-(3-(2-fluoroethoxy)-4-methoxyphenyl)-5-methylthiazole-4-carboxylate (22a)

A mixture of thioamide 21 (1.50 g, 6.5 mmol) and ethyl 3-bromo-2-oxobutanoate (2.72 g, 13.0 mmol) in ethanol (32 mL) was stirred under refluxing conditions for 2.5 h. The resulting mixture was cooled and concentrated in vacuo to remove residual solvent. The crude residue was purified by flash column chromatography over silica gel (10:3 hexanes: ethyl acetate) to yield the desired thiazole intermediate 22a (1.45 g, 4.3 mmol, 65%) as a light brown solid. $^1$H NMR (500 MHz, DMSO-$d_6$) δ: 7.40 (dd, J=8.5, 2.0 Hz, 1H), 7.37 (d, J=2.0 Hz, 1H), 7.04 (d, J=8.5 Hz, 1H), 4.72 (dt, J=48.0, 4.0 Hz, 2H), 4.31-4.22 (m, 2H), 4.28 (q, J=7.0 Hz, 2H), 3.81 (s, 3H), 2.67 (s, 3H), 1.28 (t, J=7.0 Hz, 3H); NMR (125 MHz, DMSO-$d_6$) δ: 162.9, 162.1, 151.4, 148.2, 143.9, 141.9, 125.5, 120.5, 112.6, 110.8, 83.1 (d, $J_{CF}$=165.9 Hz), 68.3 (d, $J_{CF}$=19.0 Hz), 60.8, 56.0, 14.5, 13.3.

(2-(3-(2-fluoroethoxy)-4-methoxyphenyl)-5-methyl-thiazol-4-yl)methanol (23a)

To a stirred solution of intermediate 22a (860 mg, 2.5 mmol) in CH$_2$Cl$_2$ (30 mL) cooled to 0° C. was added slowly diisobutylaluminum hydride (1.0M in THF, 10 mmol, 10 mL). The reaction was allowed to warm to 23° C. and stirred for 1 h. The mixture was cooled to 0° C. and slowly quenched with a saturated aqueous solution of Rochelle's salt. The cloudy solution was stirred for 1 h at 23° C. until the solution became clear again. The resulting solution was extracted with ethyl acetate, washed with brine, dried over anhydrous magnesium sulfate and concentrated in vacuo to give the desired alcohol 23a (654 mg, 2.2 mmol, 88%) as a pale yellow solid. $^1$H NMR (500 MHz, DMSO-$d_6$) δ: 7.39 (d, J=2.0 Hz, 1H), 7.36 (dd, J=8.5, 2.0 Hz, 1H), 7.02 (d, J=8.5 Hz, 1H), 5.04 (t, J=5.5 Hz, 1H), 4.73 (dt, J=48.0, 3.5 Hz, 2H), 4.46 (d, J=5.5 Hz, 2H), 4.25 (dt, J=30.0, 3.5 Hz, 2H), 3.79 (s, 3H), 2.41 (s, 3H); $^{13}$C NMR (125 MHz, DMSO-$d_6$) δ: 162.7, 153.2, 150.8, 148.2, 129.5, 126.5, 119.8, 112.5, 110.4, 83.1 (d, $J_{CF}$=165.9 Hz), 68.4 (d, $J_{CF}$=18.5 Hz), 57.3, 55.9, 11.2.

4-(bromomethyl)-2-(3-(2-fluoroethoxy)-4-methoxy-phenyl)-5-methylthiazole (24a)

To a solution of 23a (1.90 g, 6.4 mmol) in acetonitrile (30 mL) was added PPh$_3$ (2.5 g, 9.6 mmol) followed by hexabromoacetone (1.70 g, 3.2 mmol) at 23° C. The mixture was stirred for 1 h at 40° C. when, by TLC analysis, all starting material had been consumed. The solvent was removed in vacuo and the crude residue was purified by flash column chromatography over silica gel (10:3 hexanes:ethyl acetate) to give the desired bromide 24a (1.84 g, 5.1 mmol, 80%) as a light brown solid. $^1$H NMR (500 MHz, CDCl$_3$) δ: 7.50 (d, J=2.0 Hz, 1H), 7.40 (dd, J=8.5, 2.0 Hz, 1H), 6.88 (d, J=8.0 Hz, 1H), 4.81 (dt, J=47.0, 4.0 Hz, 2H), 4.59 (s, 2H), 4.36 (dt, J=27.5, 4.0 Hz, 2H), 3.90 (s, 3H), 2.46 (s, 3H); $^{13}$C NMR (125 MHz, CDCl$_3$) δ: 164.1, 151.2, 148.1, 148.0, 131.7, 126.4, 120.4, 111.6, 111.5, 82.4 (d, $J_{CF}$=169.9 Hz), 68.4 (d, $J_{CF}$=20.5 Hz), 55.9, 25.8, 11.4.

2-(((2-(3-(2-fluoroethoxy)-4-methoxyphenyl)-5-methylthiazol-4-yl)methyl)thio)pyrimidine-4,6-di-amine (15a)

4,6-diamino-2-mercaptopyrimidine (336 mg, 2.36 mmol) and NaOH (94 mg, 2.36 mmol) were stirred in ethanol (20 mL) for 10 min at 23° C. To the reaction mixture was added a solution of bromide 24a (710 mg, 1.97 mmol) in hot ethanol (16 mL) and the resulting mixture was stirred for 3 h at 70° C. The solution was cooled, concentrated in vacuo and purified by flash column chromatography over silica gel (100:5 dichloromethane:methanol) to give the desired product 15a (590 mg, 1.40 mmol, 71%) as a pale yellow solid. $^1$H NMR (500 MHz, DMSO-$d_6$) δ: 7.36 (s, 1H), 7.34 (d, J=8.0 Hz, 1H), 7.02 (d, J=8.5 Hz, 1H), 6.09 (brs, 4H), 5.12 (s, 1H), 4.72 (dt, J=48.0, 3.5 Hz, 2H), 4.32 (s, 2H), 4.25 (dt, J=30.5, 3.5 Hz, 2H), 3.78 (s, 3H), 2.43 (s, 3H); $^{13}$C NMR (125 MHz, DMSO-$d_6$) δ: 168.3, 163.9 (2), 163.3, 150.9, 149.5, 148.3, 129.1, 126.4, 119.9, 112.7, 110.5, 83.2 (d, $J_{CF}$=165.9 Hz), 79.5, 68.5 (d, $J_{CF}$=18.7 Hz), 56.1, 27.9, 11.7; HRMS-ESI (m/z) [M+H]$^+$ calcd for C$_{18}$H$_{20}$FN$_5$O$_2$S$_2$H, 422.1121; found 422.1136.

2-(((5-ethyl-2-(3-(2-fluoroethoxy)-4-methoxyphenyl)thiazol-4-yl)methyl)thio)pyrimidine-4,6-diamine (15b)

$^1$H NMR (500 MHz, DMSO-$d_6$) δ: 7.37 (dd, J=8.0, 2.0 Hz, 1H), 7.36 (s, 1H), 7.02 (d, J=8.5 Hz, 1H), 6.13 (brs, 4H), 5.13 (s, 1H), 4.72 (dt, J=47.5, 4.0 Hz, 2H), 4.34 (s, 1H), 4.25 (dt, J=30.5, 4.0 Hz, 2H), 3.79 (s, 3H), 2.87 (q, J=7.5 Hz, 2H), 1.17 (t, J=7.5 Hz, 3H); $^{13}$C NMR (125 MHz, DMSO-$d_6$) δ: 168.2, 163.8 (2), 163.5, 151.0, 148.4, 148.3, 136.9, 126.5, 119.9, 112.7, 110.5, 83.3 (d, $J_{CF}$=165.9 Hz), 79.5, 68.5 (d, $J_{CF}$=18.8 Hz), 56.1, 28.0, 19.9, 17.1; HRMS-ESI (m/z) [M+H]$^+$ calcd for C$_{19}$H$_{22}$FN$_5$O$_2$S$_2$H, 436.1277; found 436.1263.

2-(((2-(3-(2-fluoroethoxy)-4-methoxyphenyl)-5-propylthiazol-4-yl)methyl)thio)pyrimidine-4,6-di-amine (15c)

$^1$H NMR (500 MHz, acetone-$d_6$) δ: 7.53 (d, J=2.0 Hz, 1H), 7.46 (dd, J=8.5, 2.0 Hz, 1H), 7.03 (d, J=8.5 Hz, 1H), 5.63 (brs, 4H), 5.38 (s, 1H), 4.80 (dt, J=48.0, 4.0 Hz, 2H), 4.45 (s, 2H), 4.34 (dt, J=29.5, 4.0 Hz, 2H), 3.87 (s, 3H), 2.91 (t, J=7.5 Hz, 1H), 1.66 (qt, J=7.5, 7.5 Hz, 2H), 0.97 (t, J=7.5 Hz, 3H); $^{13}$C NMR (125 MHz, acetone-$d_6$) δ: 169.2, 164.0 (2), 163.9, 163.6, 151.4, 149.0, 148.5, 134.6, 126.9, 119.8, 112.1, 111.1, 82.8 (d, $J_{CF}$=167.5 Hz), 79.5, 68.6 (d, $J_{CF}$=19.5 Hz), 55.3, 28.1, 25.2, 13.0; HRMS-ESI (m/z) [M+H]$^+$ calcd for C$_{20}$H$_{24}$FN$_5$O$_2$S$_2$H, 450.1434; found 450.1432.

1-(5-(4-(((4,6-diaminopyrimidin-2-yl)thio)methyl)-5-propylthiazol-2-yl)-2-methoxyphenoxy)-2-methyl-propan-2-ol (36)

$^1$H NMR (500 MHz, MeOD) δ: 7.51 (d, J=2.0 Hz, 1H), 7.39 (dd, J=8.5, 2.0 Hz, 1H), 7.00 (d, J=8.5 Hz, 1H), 5.48 (s, 1H), 5.32 (s, 1H), 4.48 (s, 2H), 3.89 (s, 3H), 3.86 (s, 2H), 2.88 (t, J=7.5 Hz, 2H), 1.67 (qt, J=7.5, 7.5 Hz, 2H), 1.33 (s, 6H), 0.98 (t, J=7.5 Hz, 3H); $^{13}$C NMR (125 MHz, MeOD) δ: 168.8, 165.2, 163.8 (2), 151.2, 148.9, 148.0, 135.4, 126.4, 119.7, 111.8, 110.7, 79.2, 77.0, 69.6, 55.2, 48.4, 27.9, 27.8, 25.0, 24.9, 12.6; HRMS-ESI (m/z) [M+H]$^+$ calcd for C$_{22}$H$_{29}$N$_5$O$_3$S$_2$H, 476.1790; found 476.1772.

N-(2-(5-(4-(((4,6-diaminopyrimidin-2-yl)thio) methyl)-5-propylthiazol-2-yl)-2-methoxyphenoxy) ethyl)methanesulfonamide (37)

$^1$H NMR (500 MHz, DMSO-$d_6$) δ: 7.41 (dd, J=7.5, 2.0 Hz, 1H), 7.39 (s, 1H), 7.25 (t, J=6.0 Hz, 1H), 7.05 (d, J=8.5 Hz, 1H), 6.13 (brs, 4H), 5.15 (s, 1H), 4.39 (s, 2H), 4.07 (t, J=5.5 Hz, 2H), 3.80 (s, 3H), 3.36 (dt, J=5.5, 5.5 Hz, 2H), 3.15 (d, J=5.5 Hz, 1H), 2.98 (s, 3H), 2.84 (t, J=7.5 Hz, 2H), 1.58 (qt, J=7.5, 7.5 Hz, 2H), 0.91 (t, J=7.5 Hz, 3H); $^{13}$C NMR (125 MHz, DMSO-$d_6$) δ: 168.3, 163.9 (2), 163.7, 151.1, 149.1, 148.3, 135.0, 126.5, 119.9, 112.7, 110.6, 79.5, 68.3, 60.2, 42.4, 31.2, 28.2, 28.0, 25.4, 13.9; HRMS-ESI (m/z) [M+H]$^+$ calcd for $C_2H_{28}N_6O_4S_3H$, 525.1412; found 525.1404.

dCK Uptake Assay Performed in Cell Culture. All L1210 and CCRF-CEM cell lines were cultured in RPMI medium 1640, supplemented with 5% FCS in a 5% $CO_2$ 37° C. incubator. For the uptake assays cells were seeded at a density of 50,000 cells/well in Millipore MultiScreen GV 96 well plates. 0.25 μCi of $^3$H-dC (Moravek Biochemicals) were added to the cells simultaneously with concentrations of dCK inhibitor at a final volume of 100 μL/well. After 1 h at 37° C., cells were washed four times with ice cold phosphate-buffered saline (PBS) using the Millipore Vacuum Manifold. The amount of incorporated probe was measured by scintillation counting with the PerkinElmer Microbeta.

Protein expression and purification. Details on C4S S74E dCK variant expression and purification are detailed in Nomme et al.

Crystallization, X-ray Data Collection, and Refinement. Crystallization, data collection and structure determination of dCK in complex with 15a and 36 were performed following the general procedure as detailed in Nomme et al. Specifically for compound 36, crystals of dCK in complex with UDP, $MgCl_2$ and a 2.5-fold excess of the 36 inhibitor were grown using the hanging drop vapor diffusion method at 12° C. The reservoir solution contained 0.9-1.5 M trisodium citrate dehydrate and 25 mM HEPES (pH 7.5). Diffraction data were collected at the Advanced Photon Source, Argonne National Laboratory on Life Sciences-Collaborative Access Team (LS-CAT) beamlines 21 ID-G.

Kinetic assay. Steady state kinetic assay and data fitting were performed as described in Nomme et al.

Computational Modeling. All simulations were performed using the MCPRO 2.0 package.[41] Initial coordinates were obtained from the X-ray structure of dCK in complex with compound 15c. The protein was solvated in a 30 Å water cap, represented by the TIP4P[44] classical water model. Solute atoms were represented by the OPLS-AA force field[45] was used. Equilibrations were performed using Metropolis Monte Carlo (MC) in the NPT ensemble at 25° C. and 1 atm. The backbone of the protein and all bond lengths within the protein were fixed; angles and torsions within 11 Å from the center of the bound molecule were sampled. All degrees of freedom of the inhibitor compound were sampled during equilibration simulations. Equilibration consisted of 5×10$^6$ configurations of sampling in which only solvent moves were allowed, and of 10×10$^6$ subsequent configurations for the protein-inhibitor complex and for the lone inhibitor in solution. The equilibrated systems were then subject to free energy perturbation (FEP)/MC simulations. These simulations consisted of 14 perturbing steps of double-wide sampling. During FEP, the system underwent 5×10$^6$ configurations of solvent equilibration, followed by 10×10$^6$ configurations of full equilibration, and 25×10$^6$ configurations of data collection. All degrees of freedom of the inhibitor were sampled except those bonds undergoing perturbation. The perturbed bond lengths were systematically varied from the original to the final length.

In Vivo MicroPET/CT Imaging Studies. Animal studies were approved by the UCLA Animal Research Committee and were carried out according to the guidelines of the Department of Laboratory Animal Medicine at UCLA. For the PET liver assay, C57BL/6 mice were intraperitoneally (i.p.) injected with the indicated amounts of dCK inhibitor (resuspended in 40% Captisol) 4 hours prior to intravenous injection of 70 μCi of $^{18}$F-L-FAC. For the tumor xenograft assay, NOD scid IL-2 receptor gamma chain knockout (NSG) bearing subcutaneous CCRF-CEM tumor xenografts were injected with 50 mg/kg of compound 36 or vehicle. Four hours post-treatment mice were injected intravenously with 70 μCi of $^{18}$F-L-FAC. For all mPET/CT studies, a 1 h interval was allowed between probe administration and mPET/CT scanning (Inveon, Siemens Medical Solutions USA Inc.; microCAT, Imtek Inc.). Static mPET images were acquired for 600 s. Images were analyzed using OsiriX Imaging Software Version 3.8.

Pharmacokinetic Studies. C57Bl/6 female mice, 8 weeks of age, were injected with a single dose of indicated compounds (50 mg/kg, i.p.). Blood samples (approximately 70 μL) were collected through retro-orbital bleeding into heparinized tubes at 5 min, 15 min, 30 min, 35 min, 40 min, 45 min, 1 h, 2 h, 4 h, and 6 h. The blood samples were centrifuged at 20,000×g for 5 min to isolate plasma. 1 mL of acetonitrile was added to 30 μL of plasma. The supernatant was transferred to new tubes and was evaporated using a SpeedVac. Samples were then resuspended in 50 μL of neat DMSO and supernatant was transferred to LC/MS sample vials. Samples were then run on an Agilent 6460 Triple Quad LC/MS.

Statistical analyses. All statistics presented as means of biological replicates with standard error of the mean (±SEM), standard deviation (±SD), or box plots with max and min whiskers. P-value significances were calculated using one sample Student's t test function in GraphPad Prism 5 (GraphPad Software).

PDB ID CODES: FIGS. 27A-27C and FIG. 28B: dCK+ 15a+UDP Code: 4JLK. FIGS. 31A-31B: dCK+36+UDP Code: 4L5B

References for Example 3

1. Reichard, P., Interactions between deoxyribonucleotide and DNA synthesis. Annu. Rev. Biochem. 1988, 57, 349-374.
2. Arner, E. S. J.; Eriksson, S., Mammalian Deoxyribonucleoside Kinases. Pharmac. Ther. 1995, 67, 155-186.
3. Sabini, E.; Hazra, S.; Ort, S.; Konrad, M.; Lavie, A., Structural Basis for Substrate Promiscuity of dCK. J. Mol. Biol. 2008, 378, 607-621.
4. Pasti, C.; Gallois-Montbrun, S.; Munier-Lehmann, H.; Vernon, M.; Gilles, A. M.; Deville-Bonne, D., Reaction of Human UMP-CMP Kinase with Natural and Analog Substrates. Eur. J. Biochem. 2003, 270, 1784-1790.
5. Krishnan, P.; Gullen, E. A.; Lam, W.; Dutschman, G. E.; Grill, S. P.; Cheng, Y. C., Novel Role of 3-Phosphoglycerate Kinase, a Glycolytic Enzyme, in the Activation of L-Nucleoside Analogs, a new class of Anticancer and Antiviral Agents. J. Biol. Chem. 2003, 278, 36726-36732.
6. Toy, G.; Austin, W. R.; Liao, H.-I.; Cheng, D.; Singh, A.; Campbell, D. O.; Ishikawa, T.-o.; Lehmann, L. W.; Satyamurthy, N.; Phelps, M. E.; Herschman, H. R.; Czernin, J.;

Witte, O. N.; Radu, C. G., Requirement for Deoxycytidine Kinase in T and B Lymphocyte Development. Proc. Natl. Acad. Sci. U.S.A. 2010, 107, 5551-5556.

7. Austin, W. R.; Armijo, A. L.; Campbell, D. O.; Singh, A. S.; Hsieh, T.; Nathanson, D.; Herschman, H. R.; Phelps, M. E.; Witte, O. N.; Czernin, J.; Radu, C. G., Nucleoside Salvage Pathway Kinases Regulate Hematopoiesis by Linking Nucleotide Metabolism with Replication Stress. J. Exp. Med. 2012, 209, 2215-2228.

8. Van Rompay, A. R.; Johansson, M.; Karlsson, A., Substrate Specificity and Phosphorylation of Antiviral and Anticancer Nucleoside Analogs by Human Deoxyribonucleoside Kinases and Ribonucleoside Kinases. Pharmacol. Ther. 2003, 100, 119-139.

9. Yang, C.; Lee, M.; Hao, J.; Cui, X.; Guo, X.; Smal, C.; Bontemps, F.; Ma, S.; Liu, X.; Engler, D.; Parker, W. B.; Xu, B., Deoxycytidine kinase regulates the G2/M checkpoint through interaction with cyclin-dependent kinase 1 in response to DNA damage. Nucleic Acids Res 2012, 40 (19), 9621-32.

10. Tarver, J. E.; Jessop, T. C.; Carlsen, M.; Augeri, D. J.; Fu, Q.; Healy, J. P.; Heim-Riether, A.; Xu, A.; Taylor, J. A.; Shen, M.; Keyes, P. E.; Kimball, S. D.; Yu, X.-C.; Miranda, M.; Liu, Q.; Swaffield, J. C.; Nouraldeen, A.; Wilson, A. G. E.; Rinch, R.; Jhaver, K.; Foushee, A. M. D.; Anderson, S.; Oravecz, T.; Carson, K. G., 5-Fluorocytosine Derivatives as Inhibitors of Deoxycytidine Kinase. Bioorg. Med. Chem. Lett. 2009, 19, 6780-6783.

11. Yu, X.-C.; Miranda, M.; Liu, Z.; Patel, S.; Nguyen, N.; Carson, K.; Liu, Q.; Swaffield, J. C., Novel Potent Inhibitors of Deoxycytidine Kinase Identified and Compared by Multiple Assays. J. Biomol. Screening 2010, 15, 72-79.

12. Ward, A. D.; Baker, B. R., Irreversible Enzyme Inhibitors: Active-Site-Directed Inhibitors of Deoxycytidine Kinase. J. Med. Chem. 1977, 20, 88-92.

13. Jessop, T. C.; Tarver, J. E.; Carlsen, M.; Xu, A.; Healy, J. P.; Heim-Riether, A.; Fu, Q.; Taylor, J. A.; Augeri, D. J.; Shen, M.; Stouch, T. R.; Swanson, R. V.; Tari, L. W.; Hunger, M.; Hoffman, I.; Keyes, P. E.; Yu, X.-C.; Miranda, M.; Liu, Q.; Swaffield, J. C.; Kimball, S. D.; Nouraldeen, A.; Wilson, A. G. E.; Foushee, A. M. D.; Jhaver, K.; Finch, R.; Anderson, S.; Oravecz, T.; Carson, K. G., Lead Optimization and Structure-based Design of Potent and Bioavailable Deoxycytidine Kinase Inhibitors. Bioorg. Med. Chem. Lett. 2009, 19, 6784-6787.

14. Weber, W. A.; Grosu, A. L.; Czernin, J., Technology Insight: Advances in Molecular Imaging and an Appraisal of PET/CT Scanning. Nat. Clin. Prac. Oncol. 2008, 5, 160-170.

15. Czernin, J.; Benz, M. R.; Allen-Auerbach, M. S., PET/CT Imaging: The Incremental Value of Assessing the Glucose Metabolic Phenotype and the Structure of Cancers in a Single Examination. Eur. J. Radiol. 2010, 73, 470-480.

16. Gambhir, S. S., Molecular Imaging of Cancer with Positron Emission Tomography. Nat. Rev. Cancer 2002, 2, 683-693.

17. Rigo, P.; Paulus, P.; Kaschten, B. J.; Hustinx, R.; Bury, T.; Jerusalem, G.; Benoit, T.; Foidart Willems, J., Oncological Application of Positron Emission Tomography with Fluorine-18. Eur. J. Nucl. Med. 1996, 23, 1641-1674.

18. Wood, K. A.; Hoskin, P. J.; Saunders, M. I., Positron Emission Tomography in Oncology: A Review. Clin. Oncol. 2007, 19, 237-255.

19. Weber, W. A., Positron Emission Tomography as an Imaging Biomarker. J. Clin. Oncol. 2006, 24, 3282-3292.

20. Oriuchi, N.; Higuchi, T.; Ishikita, T.; Miyakubo, M.; Hanaoka, H.; Iida, Y.; Endo, K., Present Role and Future Prospects of Positron Emission Tomography in Clinical Oncology. Cancer Sci. 2006, 97, 1291-1297.

21. Jadvar, H.; Alavi, A.; Gambhir, S. S., 18F-FDG Uptake in Lung, Breast, and Colon Cancers: Molecular Biology Correlates and Disease Characterization. J. Nucl. Med. 2009, 50, 1820-1827.

22. Hargreaves, R. J., The Role of Molecular Imaging in Drug Discovery and Development. Clin. Pharmacol. Ther. 2008, 83, 349-353.

23. Wang, J. L.; Maurer, L., Positron Emission Tomography: Applications in Drug Discovery and Drug Development. Curr. Top. Med. Chem. 2005, 5, 1053-1075.

24. Wagner, C. C.; Muller, M.; Lappin, G.; Langer, O., Positron Emission Tomography for Use in Microdosing Studies. Curr. Opin. Drug Discov. Devel. 2008, 11, 104-110.

25. Laing, R. E.; Walter, M. A.; Campbell, D. O.; Herschman, H. R.; Satyamurthy, N.; Phelps, M. E.; Czernin, J.; Witte, O. N.; Radu, C. R., Noninvasive Prediction of Tumor Responses to Gemcitabine using Positron Emission Tomography. Proc. Natl. Acad. Sci. U.S.A. 2009, 106, 2847-2852.

26. Radu, C. G.; Shu, C. J.; Nair-Gill, E.; Shelly, S. M.; Barrio, J. R.; Satyamurthy, N.; Phelps, M. E.; Witte, O. N., Molecular Imaging of Lymphoid Organs and Immune Activation by Positron Emission Tomography with a new [18F]-labeled 2'-deoxycytidine Analog. Nat. Med. 2008, 14, 783-788.

27. Shu, C. J.; Campbell, D. O.; Lee, J. T.; Tran, A. Q.; Wengrod, J. C.; Witte, O. N.; Phelps, M. E.; Satyamurthy, N.; Czernin, J.; Radu, C. R., Novel PET Probes Specific for Deoxycytidine Kinase. J. Nucl. Med. 2010, 51, 1092-1098.

28. Fan, F.; Wood, K. V., Bioluminescent assays for high-throughput screening. Assay Drug Dev Technol 2007, 5, 127-136.

29. Müller, K.; Faeh, C.; Diederich, F., Fluorine in Pharmaceuticals: Looking Beyond Intuition. Science 2007, 317, 1881-1886.

30. Park, B. K.; Kitteringham, N. R.; O'Neill, P. M., Metabolsim of Fluorine-containing Drugs. Annu. Rev. Pharmacol. Toxicol. 2001, 41, 443-470.

31. Crane, L. J.; Anastassiadou, M.; Stigliani, J.-L.; Baziard-Mouysset, G.; Payard, M., Reactions of Some Ortho and Para Halogenated Aromatic Nitriles with Ethylenediamine: Selective Synthesis of Imidazolines. Tetrahedron 2004, 60, 5325-5330.

32. Okonya, J. F.; Hoffman, R. V.; Johnson, M. C., Synthesis of 2-Oxazolone-4-Carboxylates from 3-Nosyloxy- and 3-Bromo-2-ketoesters. J. Org. Chem. 2002, 67, 1102-1108.

33. Trullinger, T. K.; Hunter, R.; Garizi, N.; Yap, M. C. H.; Buysse, A. M.; Pernich, D.; Johnson, T. C.; Bryan, K.; Deamicis, C.; Zhang, Y.; Niyaz, N. M.; McLeod, C. L.; Ross, R.; Zhu, Y.; Johnson, P. L.; Eckelbarger, J. D.; Parker, M. H., Pesticidal Compositions. Patent application US 2010/0292253 A1.

34. Joseph, K. M.; Larraza-Sanchez, I., Synthesis of Benzyl Bromides with Hexabromoacetone: an Alternative Path to Drug Intermediates. Tetrahedron Lett. 2011, 52, 13-16.

35. Laxer, A.; Major, D. T.; Gottlieb, H. E.; Fischer, B., (15N5)-Labeled Adenine Derivatives: Synthesis and Studies of Tautomerism by 15N NMR Spectroscopy and Theoretical Calculations. J. Org. Chem. 2001, 66, 5463-5481.

36. Chottiner, E. G.; Shewach, D. S.; Datta, N. S.; Ashcraft, E.; Gribbin, D.; Ginsburg, D.; Fox, I. H.; Mitchell, B. S., Cloning and Expression of Human Deoxycytidine Kinase cDNA. Proc. Natl. Acad. Sci. U.S.A. 1991, 88, 1531-1535.

37. Shewach, D. S.; Reynolds, K. K.; Hertel, L., Nucleotide Specificity of Human Deoxycytidine Kinase. Mol. Pharmacol. 1992, 42, 518-524.

38. Metropolis, N.; Ulam, S., The Monte Carlo Method. J. Am. Statistical Assn. 1949, 44, 335-341.

39. Zwanzig, R. W., High-Temperature Equation of State by a Perturbation Method. J. Chem. Phys. 1954, 22, 1420-1426.

40. Jorgensen, W. L.; Thomas, L. L., Perspective on Free-Energy Perturbation Calculations for Chemical Equilibria. J. Chem. Theory Comput 2008, 4, 869-876.

41. Jorgensen, W. L.; Tirado-Rives, J., Molecular Modeling of Organic and Biomolecular Systems Using BOSS and MCPRO. J. Comput. Chem. 2005, 26, 1689-1700.

42. Shu, Y. Z.; Johnson, B. M.; Yang, T. J., Role of biotransformation studies in minimizing metabolism-related liabilities in drug discovery. AAPS 2008, 10, 178-192.

43. Bhattacharyya, S., Application of Positron Emission Tomography in Drug Development. Biochem. Pharmacol. 2012, 1, 1000e128.

44. Jorgensen, W. L.; Chandrasekhar, J.; Madura, J. D.; Impey, R. W.; Klein, M. L., Comparison of Simple Potential Functions for Simulating Liquid Water. J. Chem. Phys. 1983, 79, 926-935.

45. Jorgensen, W. L.; Maxwell, D. S.; Tirado-Rives, J., Development and Testing of the OPLS All-Atom Force Field on Conformational Energetics and Properties of Organic Liquids. J. Am. Chem. Soc. 1996, 118, 11225-11236.

4. Example 4

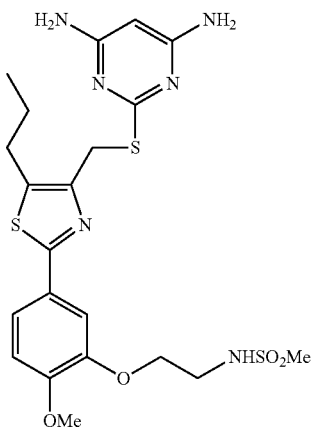

DI-39
$IC_{50}$ = 0.0043875± 0.001395 N = 34

-continued

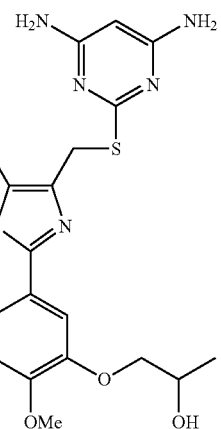

DI-40
MW: 461.60
ClogP: 3.55306
$IC_{50}$ = 0.0028 ± 0.00007; N = 2

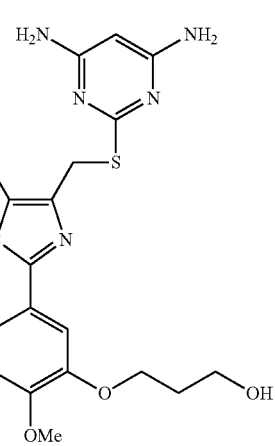

DI-41
MW: 461.60
CLogP: 3.63806
$IC_{50}$ = 0.0015 ± 0.00035; N = 2

DI-42
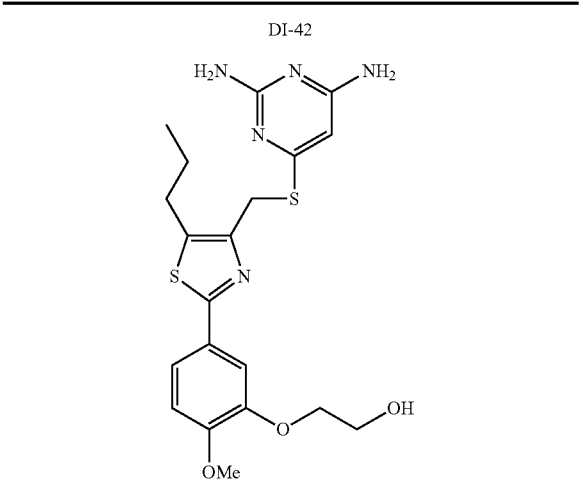
DI-42
MW: 447.57
CLogP: 3.24406
IC$_{50}$ = 0.33 ± 0.01; N = 2
DI-43
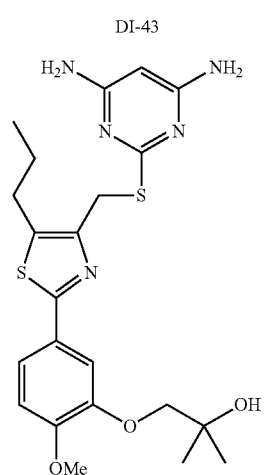
DI-43
MW: 475.63
CLogP: 3.95206
IC$_{50}$ = 0.0014 ± 0.00054; N = 4
DI-44
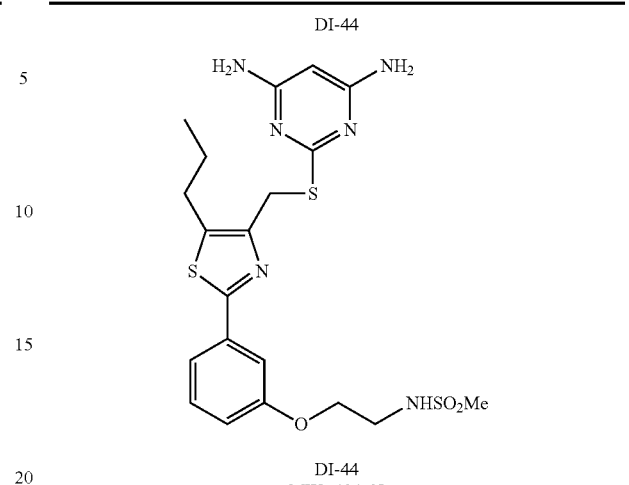
DI-44
MW: 494.65
CLogP: 3.64971
IC$_{50}$ = 0.011 ± 0.003; N = 2
DI-45
DI-45
MW: 512.64
CLogP: 3.86902
IC$_{50}$ = 0.008 ± 0.000928; N = 2
DI-46
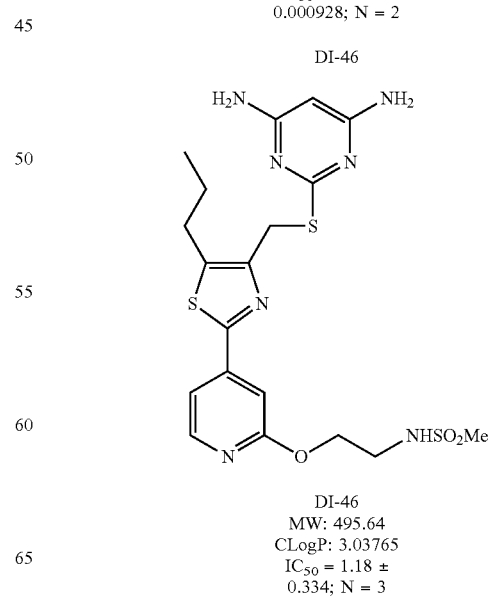
DI-46
MW: 495.64
CLogP: 3.03765
IC$_{50}$ = 1.18 ± 0.334; N = 3

DI-47
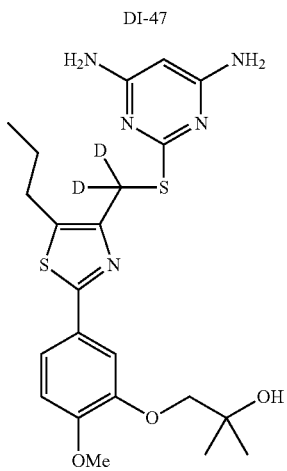
Molecular Weight:
477.65
IC$_{50}$ = 0.0047 ±
0.0022; N = 2
DI-48
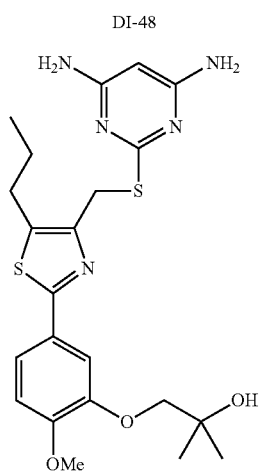
Molecular Weight:
477.64
IC$_{50}$ = 0.021 ±
0.0092; N = 2
DI-49
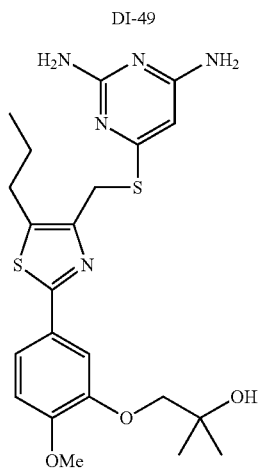
DI-49
MW: 475.63
IC$_{50}$ = 0.395 ±
0.0142; N = 2
DI-50
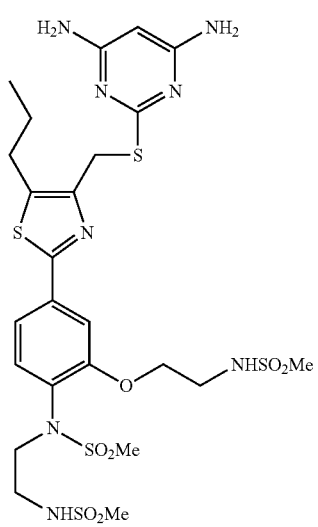
DI-50
MW: 708.92
CLogP: 2.31552
IC$_{50}$ = 1.20 ±
0.312; N = 2

141
-continued
DI-51
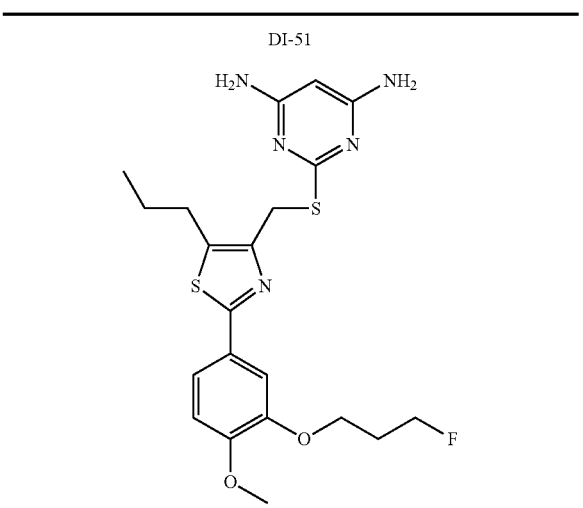
DI-51
MW: 463.59
$IC_{50}$ = 0.0025085 ± 0.00035; N = 2
DI-52
DI-52
$IC_{50}$ = 0.002856 ± 0.00162776; N = 2
142
-continued
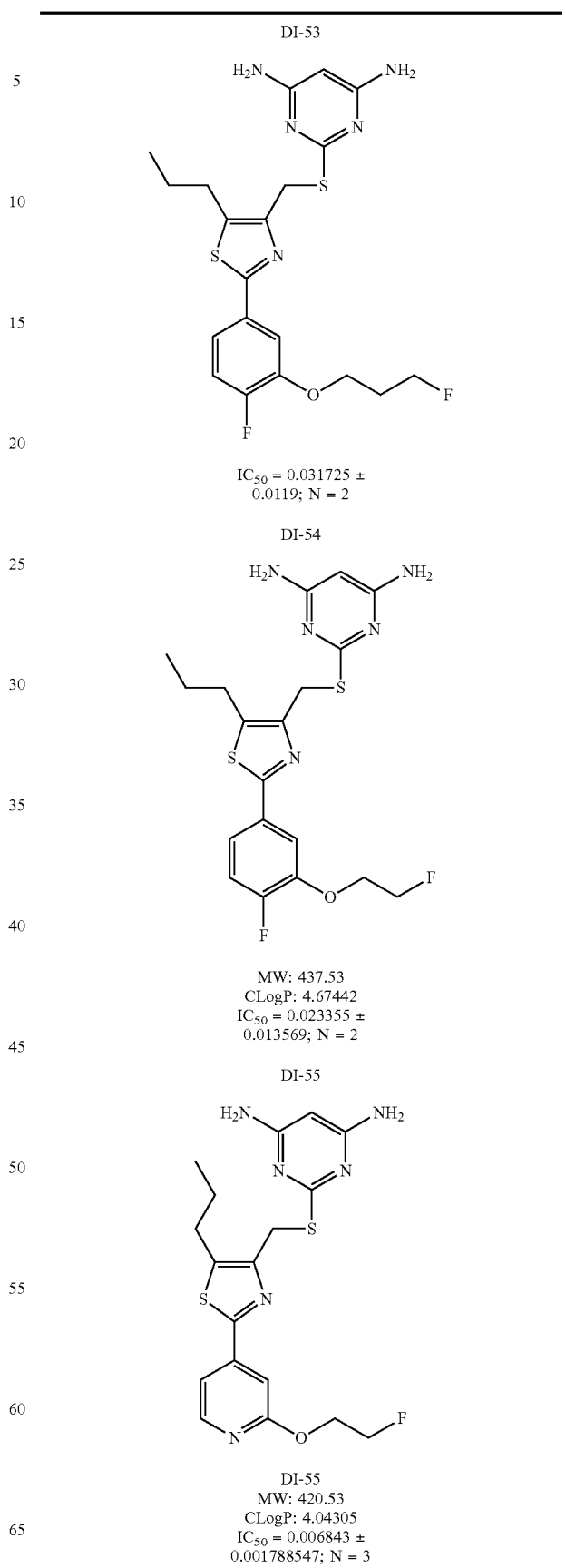
DI-53
$IC_{50}$ = 0.031725 ± 0.0119; N = 2
DI-54
MW: 437.53
CLogP: 4.67442
$IC_{50}$ = 0.023355 ± 0.013569; N = 2
DI-55
DI-55
MW: 420.53
CLogP: 4.04305
$IC_{50}$ = 0.006843 ± 0.001788547; N = 3

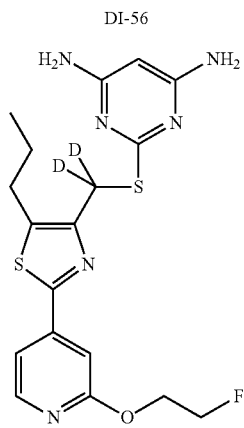
DI-56
MW: 422.54
CLogP: 1.99129
IC$_{50}$ = 0.029956 ±
0.004424; N = 3
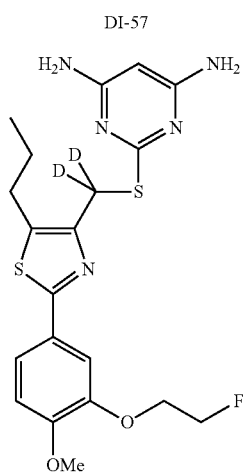
DI-57
IC$_{50}$ = 0.003143 ±
0.001053; N = 2
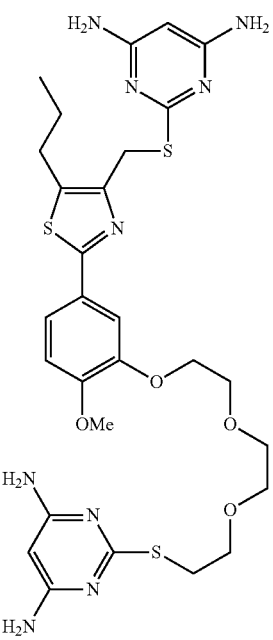 [SMILES: CCCc1sc(-c2ccc(OC)c(OCCOCCOCCSc3nc(N)cc(N)n3)c2)nc1CSc1nc(N)cc(N)n1]
DI-58
MW: 659.85
LogP: 5.13
tPSA: 202.8
CLogP: 4.36866
IC$_{50}$ = 0.004746 ±
0.001660; N = 2
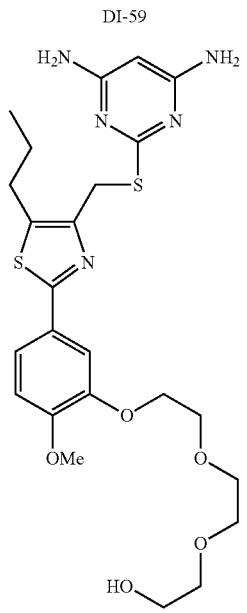
DI-59
Chemical Formula:
C$_{24}$H$_{33}$N$_5$O$_5$S$_2$
Molecular Weight:
659.85
IC$_{50}$ = 0.0010616 ±
0.0001448; N = 2

DI-60
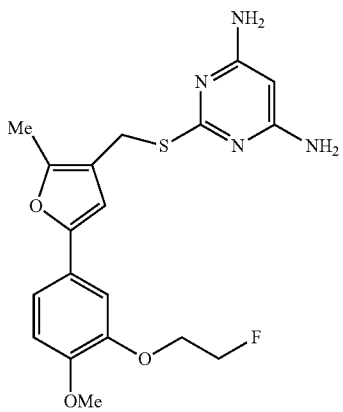 [SMILES: COc1ccc(-c2cc(CSc3nc(N)cc(N)n3)c(C)o2)cc1OCCF]
Chemical Formula:
C$_{19}$H$_{21}$FN$_4$O$_3$S
Exact Mass:
404.1318
Molecular Weight:
505.4604
IC$_{50}$ = 13.84 ±
0.28280; N = 2
DI-62
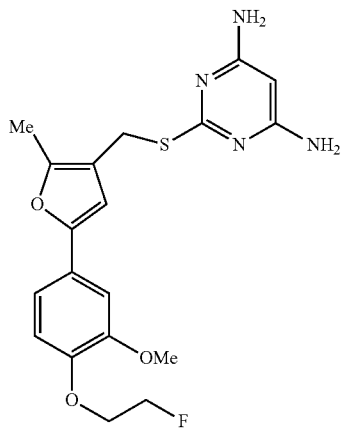
DI-62
Molecular Weight:
404.4604
LogP: 2.18
tPSA: 104.45
CLogP: 4.067
IC$_{50}$ = 0.2763 ±
0.179322; N = 2
DI-61
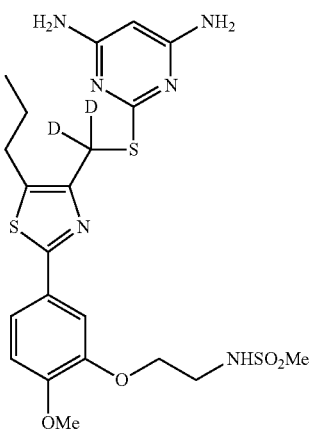
DI-61
Chemical Formula:
C$_{21}$H$_{26}$D$_2$N$_6$O$_4$S$_3$
Molecular Weight:
526.6852
IC$_{50}$ = 0.003038 ±
0.00070; N = 2
DI-63
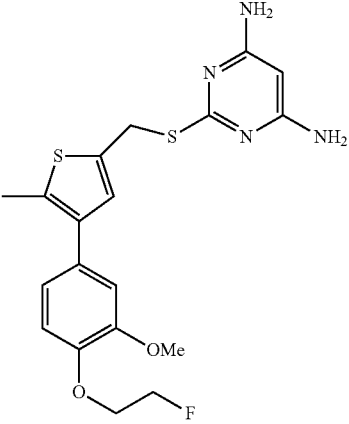 [SMILES: COc1cc(-c2cc(CSc3nc(N)cc(N)n3)sc2C)ccc1OCCF]
Molecular Weight:
420.5214
LogP: 2.23
tPSA: 95.22
CLogP: 4.09307
DI-63
IC$_{50}$ = 1.581 ±
0.0212; N = 2

DI-64
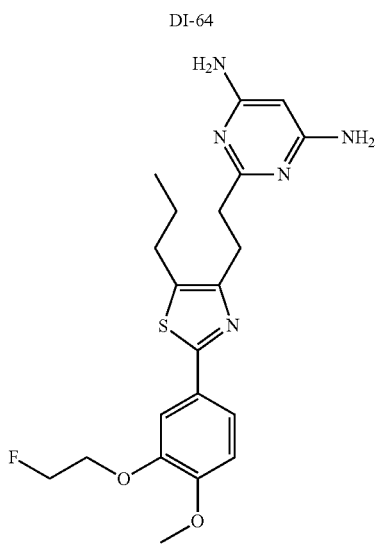
Chemical Formula:
$C_{21}H_{26}FN_5O_2S$
Molecular Weight:
431.5304
Log P: 3.59
tPSA: 107.58
CLogP: 4.04506
$IC_{50} = 0.6639 \pm 0.3655$; N = 3
DI-65
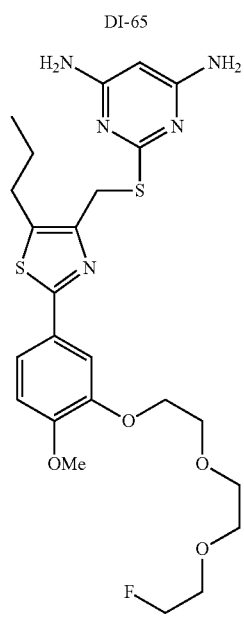
DI-65
MW: 537.67
Log P: 4.69
tPSA: 126.04
$IC_{50} = 0.00421 \pm 0.001983$; N = 2
DI-66
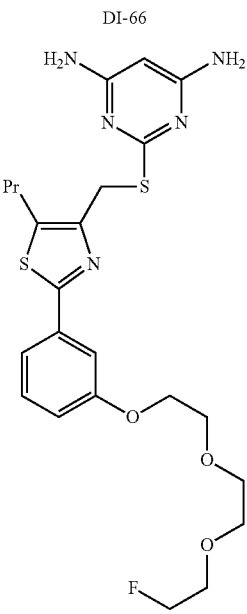
DI-66
Chemical Formula:
$C_{23}H_{30}FN_5O_3S_2$
Molecular Weight:
507.6434
Log P: 3.13
tPSA: 116.818
CLogP: 4.26931
$IC_{50} = 0.069085 \pm 0.046407$; N = 2
DI-67
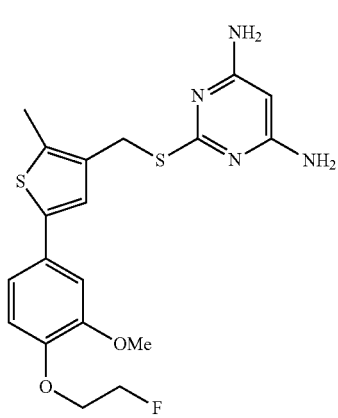 [SMILES: COc1cc(-c2cc(CSc3nc(N)cc(N)n3)c(C)s2)ccc1OCCF]
DI-67
Chemical Formula:
$C_{19}H_{21}FN_4O_2S_2$
Molecular Weight:
420.5214
Log P: 2.19
tPSA: 95.22
CLogP: 4.55307
$IC_{50} = 0.26295 \pm 0.15662$; N = 2

DI-69
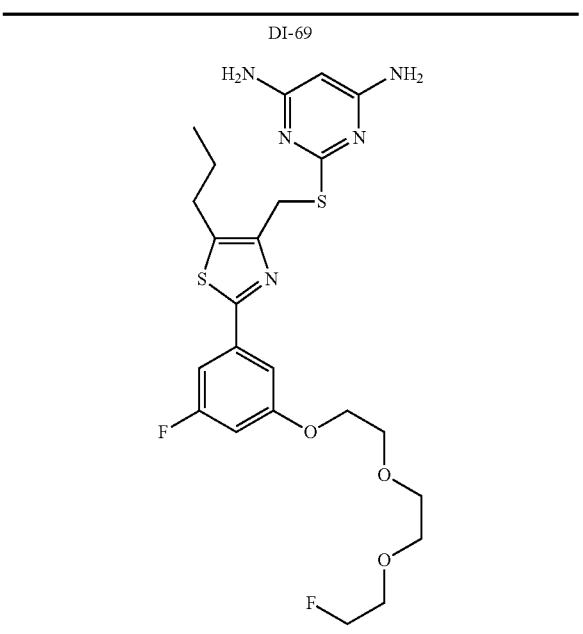
DI-69
MW: 525.6338
IC$_{50}$ = 0.033685 ±
0.00358; N = 2
DI-71
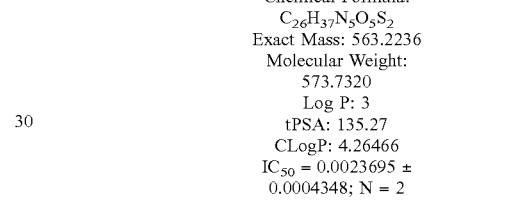
Chemical Formula:
C$_{26}$H$_{37}$N$_5$O$_5$S$_2$
Exact Mass: 563.2236
Molecular Weight:
573.7320
Log P: 3
tPSA: 135.27
CLogP: 4.26466
IC$_{50}$ = 0.0023695 ±
0.0004348; N = 2
DI-70
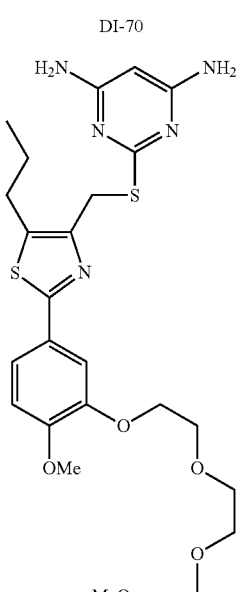
DI-70
MW: 549.7050
Log P: 4.34
tPSA: 135.27
IC$_{50}$ = 0.003307 ±
0.000442; N = 2
DI-77
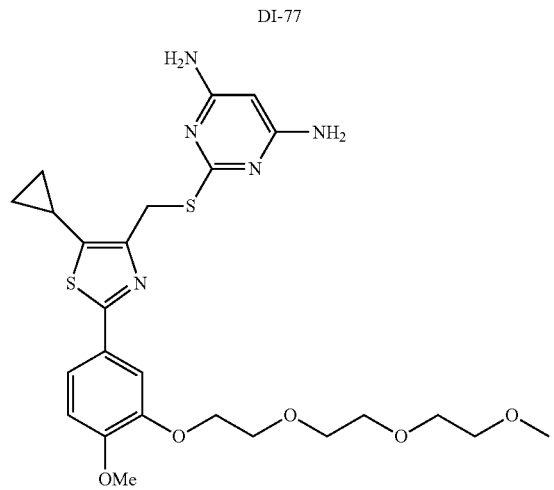
IC$_{50}$ = 0.0052835 ±
0.003533; N = 2

DI-78
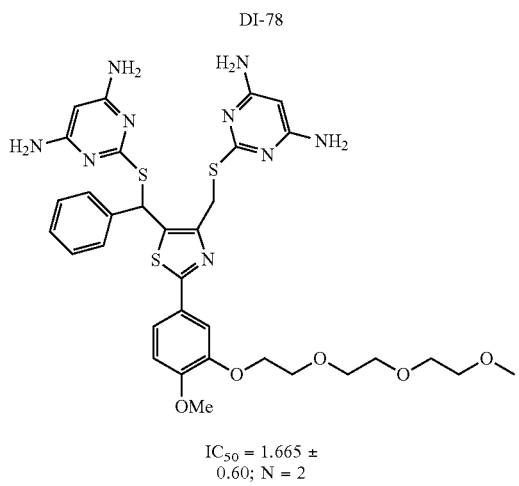
IC$_{50}$ = 1.665 ± 0.60; N = 2
DI-79
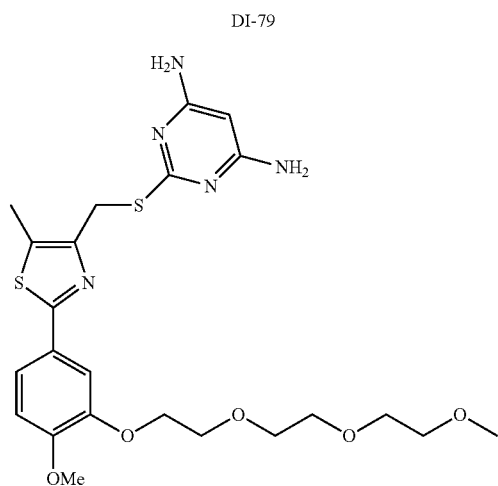
IC$_{50}$ = 0.009301 ± 0.0002418; N = 2
NC-1 JW
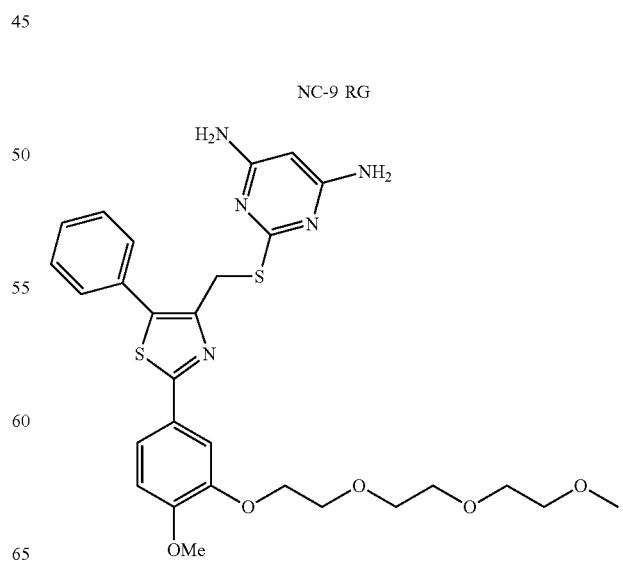
NC-2 JW
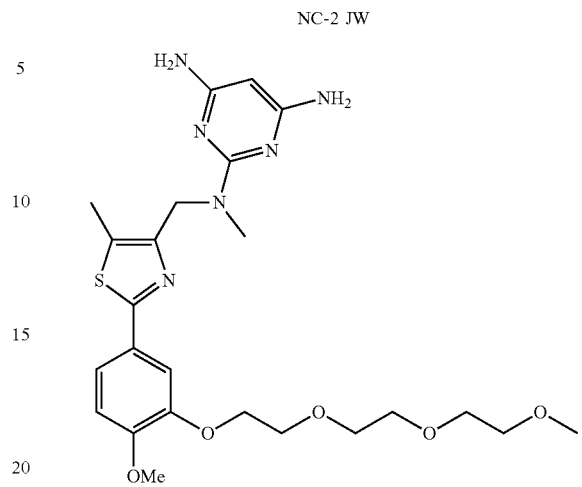
NC-4 RG
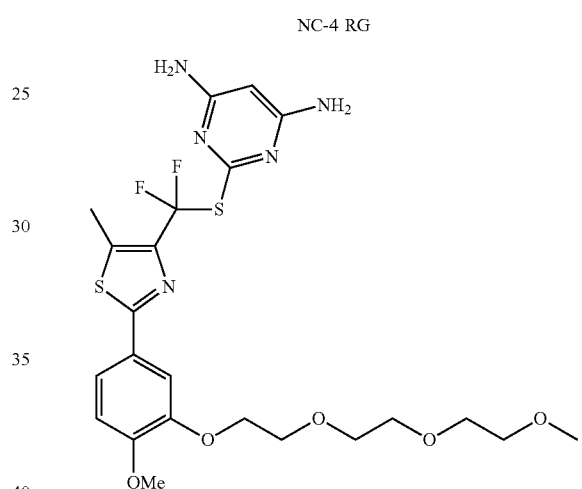
NC-9 RG 5. Example 5
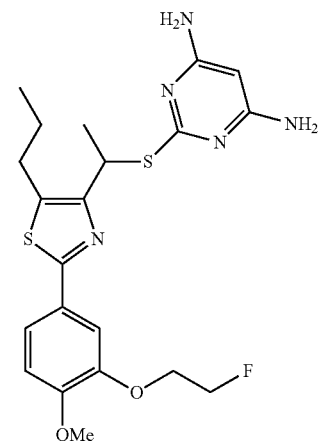 [SMILES: CCCc1sc(-c2ccc(OC)c(OCCF)c2)nc1C(C)Sc1nc(N)cc(N)n1]
IC$_{50}$ = 0.010 ± 0.0043; N = 3
-continued
DI-73
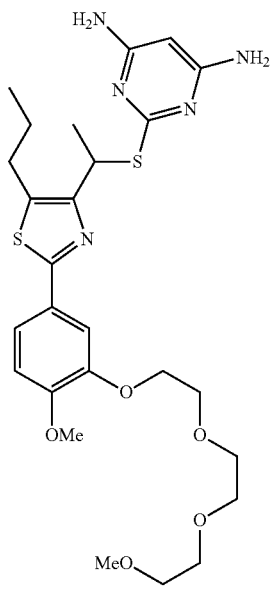 [SMILES: CCCc1sc(-c2ccc(OC)c(OCCOCCOCCOC)c2)nc1C(C)Sc1nc(N)cc(N)n1]
IC$_{50}$ = 0.006006 ± 0.002477; N = 2
DI-80
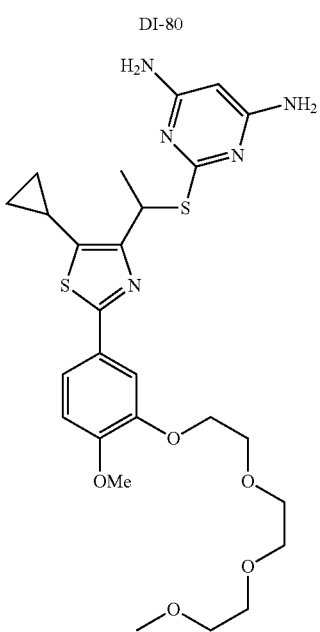
IC$_{50}$ = 0.002465 ± 0.003202; N = 2
DI-74
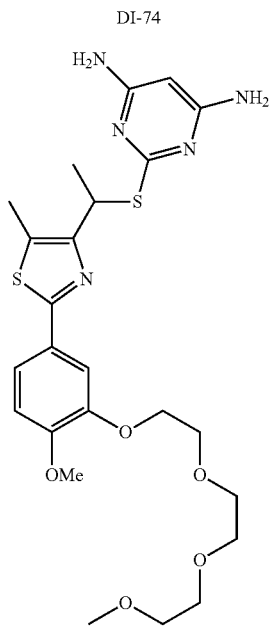
IC$_{50}$ = 0.0080306 ± 0.003160; N = 3

TABLE-continued
| 155 | 156 |
|---|---|
| DI-75 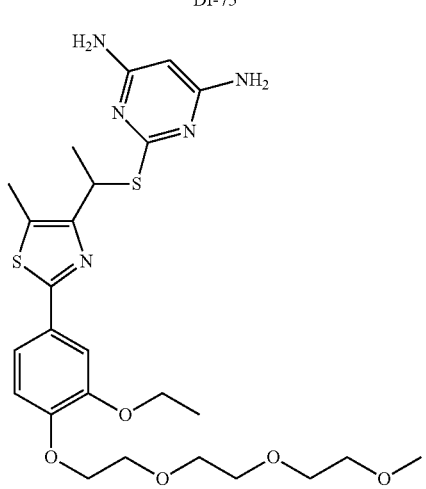 IC$_{50}$ = 0.0032 ± 0.003202; N = 2 | NC-5 ZL 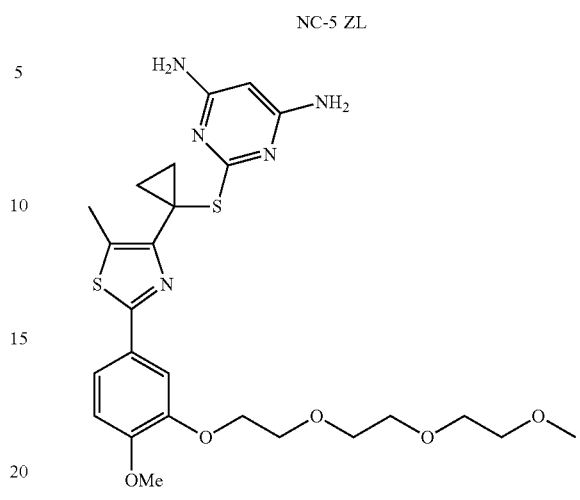 |
| DI-76 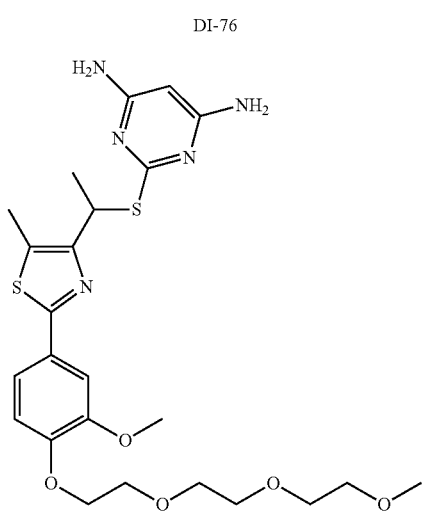 IC$_{50}$ = 0.006124 ± 0.003206; N = 2 | NC-6 All 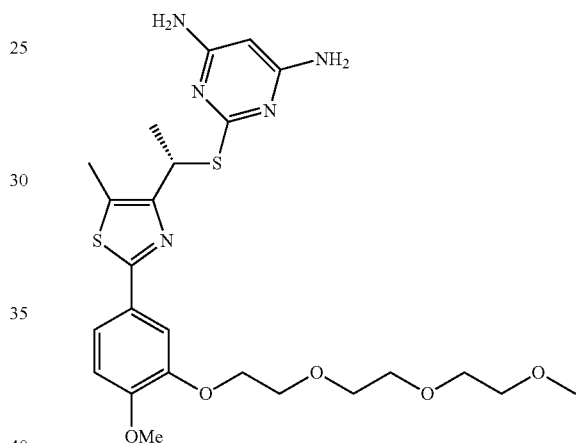 |
| NC-3 JW 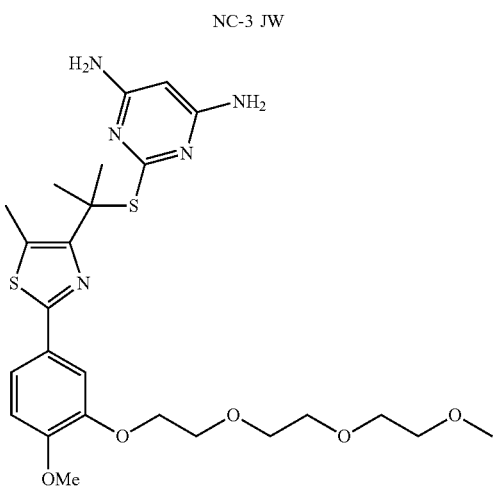 | NC-7 All 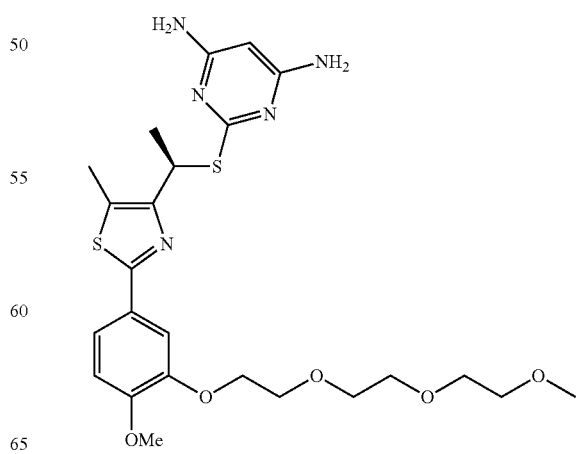 |

NC-8 RG

[Chemical structure: pyrimidine-2,4-diamine linked via S-CH(CH₃) to a phenyl-thiazole, with the thiazole connected to a phenyl bearing OMe and a triethylene glycol methyl ether chain]

VII. Embodiments

Embodiment P1 A compound of the formula (pI):

[Chemical structure (pI): triazine-2,4-diamine (with Y, Z = CR₈ or N) linked via CR₆R₇-X to a thiazole bearing R₅, connected to a phenyl ring with Y, R₁, R₂, R₃, R₄]

(pI)

or a salt thereof, wherein: each Y and Z is independently $CR_8$ or N; $R_8$ is H, F, Cl, Br, I, $CH_3$, $C_2H_5$, $C_3H_7$, $CF_3$, $^{18}F$ or $OR_9$; $R_9$ is independently $CH_3$, $C_2H_5$, $CD_3$, $CD_2CD_3$, $CH_2CH_2OH$, $CH_2CH_2CH_2OH$, $CH_2C(CH_3)_2OH$, $CH_2CH_2C(CH_3)_2OH$, $CH_2CH_2F$, $CH_2CH_2CH_2F$, $CH_2C(CH_3)_2F$, $CH_2CH_2C(CH_3)_2F$, $CH_2CH_2{}^{18}F$, $CH_2CH_2CH_2{}^{18}F$, $NHCH_2C_6H_4NO_2(p)$, $NHCH_2C_6H_4F(p)$, $NHCH_2C_6H_4{}^{18}F(p)$, $NHCH_2C_6H_4NO_2(o)$, $NHCH_2C_6H_4F(o)$, $NHCH_2C_6H_4{}^{18}F(o)$,

[Triazole structures with fluoroethyl/fluoropropyl and ¹⁸F-labeled variants]

L is H, OH, $NH_2$, $OCH_3$, F, Cl,

[Structure: glutamate-folate conjugate]

[Triazole structures with fluoroethyl/fluoropropyl and ¹⁸F-labeled variants]

$R_1$ and $R_4$ are independently H, F, Cl, Br, I, $CF_3$, $^{18}F$ or $OR_{10}$; $R_{10}$ is independently H, $CH_3$, $C_2H_5$, $C_3H_7$, $CD_3$, $CD_2CD_3$, $CH_2CH_2OH$, $CH_2CH_2CH_2OH$, $CH_2CH(OH)CH_3$, $CH_2CH_2CH(OH)CH_3$, $CH_2C(CH_3)_2OH$, $CH_2CH_2C(CH_3)_2OH$, $CH_2CH_2F$, $CH_2CH_2CH_2F$, $CH_2CH(F)CH_3$, $CH_2CH_2CH(F)CH_3$, $CH_2CH_2{}^{18}F$, $CH_2CH_2CH_2{}^{18}F$, $CH_2CH({}^{18}F)CH_3$, $CH_2CH_2CH({}^{18}F)CH_3$, $CH_2C(CH_3)_2F$, $CH_2CH_2C(CH_3)_2F$, $CH_2CH_2Cl$, $CH_2CH_2CH_2Cl$, $CH_2CH(Cl)CH_3$, $CH_2CH_2CH(Cl)CH_3$, $CH_2C(CH_3)_2Cl$, $CH_2CH_2C(CH_3)_2Cl$, $CH_2CH_2NHSO_2CH_3$, $CH_2CH_2CH_2NHSO_2CH_3$, $CH_2CH_2N$

[Structure: PEG-linked glutamate-folate conjugate with $CONH(CH_2CH_2O)_nNH$-]

$(CH_2CH_2O)_nCH_2CH_2G$ or $COCH_2CH_2COO(CH_2CH_2O)_nCH_2CH_2L$; n is 2-20; G is H, OH, $NH_2$, $OCH_3$, $OCF_3$, F, Cl, $N_3$, $^{18}F$, $NHCH_2C_6H_4NO_2(p)$, $NHCH_2C_6H_4F(p)$, $(CH_2CH_2OH)SO_2CH_3$, $CH_2CH_2CH_2N(CH_2CH_2OH)SO_2CH_3$, $CH_2CH_2N(CH_2CH_2F)SO_2CH_3$, $CH_2CH_2N(CH_2CH_2{}^{18}F)SO_2CH_3$, $CH_2CH_2N(CH_2CH_2Cl)SO_2CH_3$,

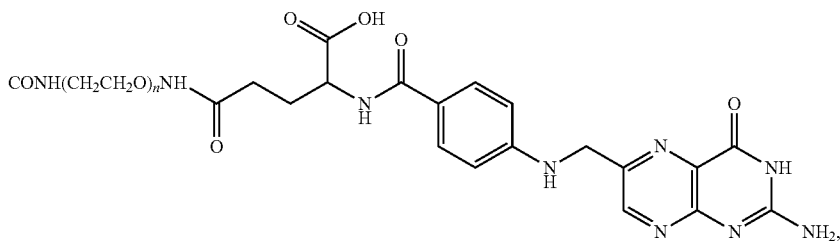

$(CH_2CH_2O)_nCH_2CH_2G$ or $COCH_2CH_2COO(CH_2CH_2O)_n$ $CH_2CH_2L$; n is 2-20; G is H, OH, $NH_2$, $OCH_3$, $OCF_3$, F, Cl, $N_3$, $^{18}F$, $NHCH_2C_6H_4NO_2(p)$, $NHCH_2C_6H_4F(p)$, $NHCH_2C_6H_4^{18}F(p)$, $NHCH_2C_6H_4NO_2(o)$, $NHCH_2C_6H_4F(o)$, $NHCH_2C_6H_4^{18}F(o)$,

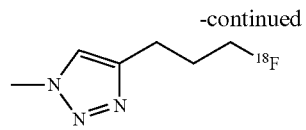

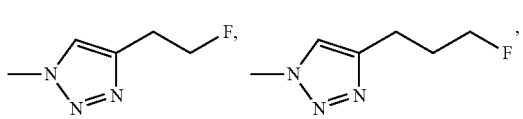

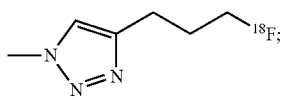

L is H, OH, $NH_2$, $OCH_3$, F, Cl

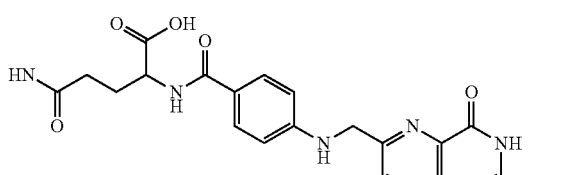

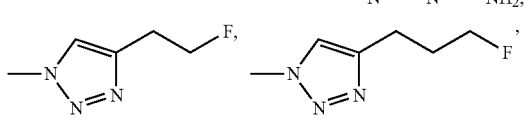

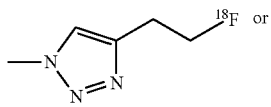

-continued

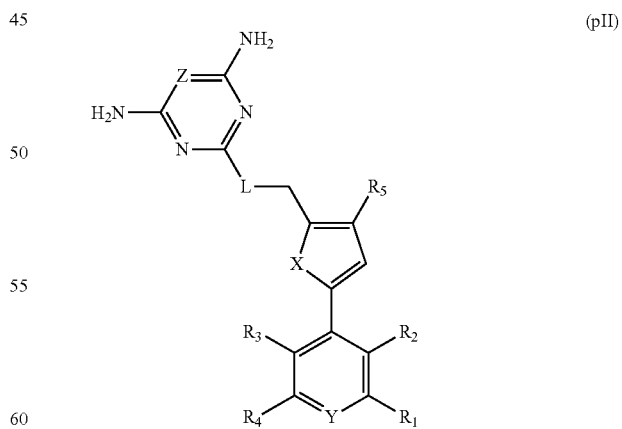

$R_2$ and $R_3$ are independently H, F, Cl, Br, I or $OR_{11}$; $R_{11}$ is independently H, $CH_3$, $C_2H_5$, $CD_3$, $CD_2CD_3$, $CH_2CH_2OH$, $CH_2CH_2F$, $CH_2CH_2^{18}F$, $CH_2CH_2NHSO_2CH_3$, $CH_2CH_2N(CH_2CH_2F)SO_2CH_3$, or $CH_2CH_2N(CH_2CH_2^{18}F)SO_2CH_3$; $R_5$ is independently H, $C_1$-$C_6$ n-alkyl chain, $C_1$-$C_6$ branched alkyl chain, $CH_2$—$C_3$-$C_6$ cycloalkyl, $(CH_2)_mOH$, $(CH_2)_mOCH_3$, $(CH_2)_mF$, $(CH_2)_m^{18}F$, $CH_2C_6H_5$, $CH_2C_6H_4^{18}F$, $CH_2CH_2C_6H_5$, $CH_2CH_2C_6H_4^{18}F$, $CH_2CH_2CH_2C_6H_5$, $C_6H_5$, $C_6H_4F$, $C_6H_4^{18}F$, $C_6H_4OCH_3$, $C_6H_4CH_2CH_2F$, $C_6H_4CH_2CH_2^{18}F$, 2-, 3- or 4-pyridyl, 3-fluoro-4-pyridyl, 3-[$^{18}F$]fluoro-4-pyridyl or $CH_2CH_2$-2-, 3- or 4-pyridyl; m is 1-6; X is $CH_2$, O, $NR_{12}$, S, SO or $SO_2$; $R_{12}$ is H, $CH_3$, $C_2H_5$, $C_3H_7$, $CH_2C_6H_5$; $R_6$ and $R_7$ are independently H, D, F, $CH_3$ or R and S $CH_3$ stereoisomers; and $R_6$ and $R_7$ together $C_3$-$C_6$ cycloalkyl.

Embodiment P2 A compound of the formula (pII):

or a salt thereof, wherein: each Y and Z is independently $CR_6$ or N; $R_6$ is H, F, Cl, Br, I, $CH_3$, $C_2H_5$, $C_3H_7$, $CF_3$, $^{18}F$ or $OR_7$; $R_7$ is independently $CH_3$, $CD_3$, $CH_2CH_2OH$, $CH_2C(CH_3)_2OH$, $CH_2CH_2F$, $CH_2C(CH_3)_2F$, $CH_2CH_2^{18}F$ or $CH_2CH_2CH_2^{18}F$,

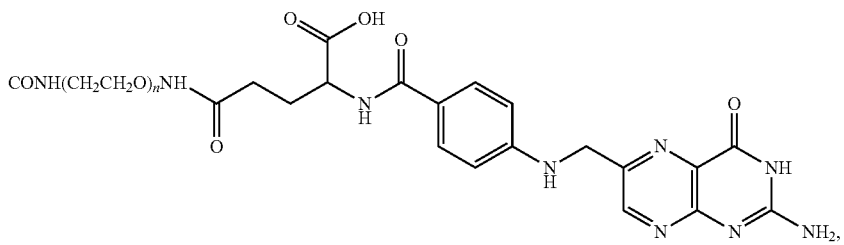

R$_1$ and R$_4$ are independently H, F, Cl, Br, I, $^{18}$F or OR$_8$; R$_8$ is independently H, CH$_3$, C$_2$H$_5$, CH$_2$CH$_2$OH, CH$_2$CH$_2$CH$_2$OH, CH$_2$C(CH$_3$)$_2$OH, CH$_2$CH$_2$F, CH$_2$CH$_2$CH$_2$F, CH$_2$CH$_2$$^{18}$F, CH$_2$CH$_2$CH$_2$$^{18}$F, CH$_2$C(CH$_3$)$_2$F, CH$_2$CH$_2$Cl, CH$_2$C(CH$_3$)$_2$Cl, CH$_2$CH$_2$NHSO$_2$CH$_3$, CH$_2$CH$_2$N(CH$_2$CH$_2$OH)SO$_2$CH$_3$, CH$_2$CH$_2$N(CH$_2$CH$_2$F)SO$_2$CH$_3$, CH$_2$CH$_2$N(CH$_2$CH$_2$$^{18}$F)SO$_2$CH$_3$, CH$_2$CH$_2$N(CH$_2$CH$_2$Cl)SO$_2$CH$_3$,

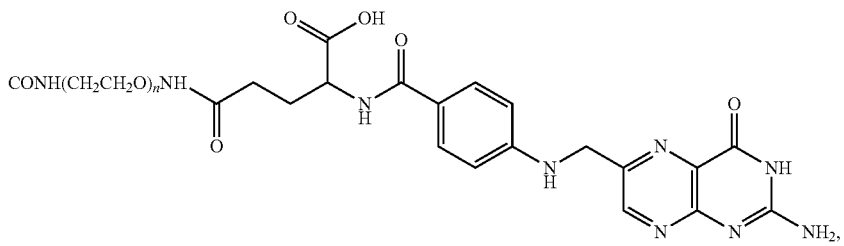

(CH$_2$CH$_2$O)$_n$CH$_2$CH$_2$G or COCH$_2$CH$_2$COO(CH$_2$CH$_2$O)$_n$CH$_2$CH$_2$K; n is 2-20; G is H, OH, NH$_2$, OCH$_3$, OCF$_3$, F, Cl, N$_3$, $^{18}$F, NHCH$_2$C$_6$H$_4$NO$_2$(p), NHCH$_2$C$_6$H$_4$F(p), NHCH$_2$C$_6$H$_4$$^{18}$F(p), NHCH$_2$C$_6$H$_4$NO$_2$(o), NHCH$_2$C$_6$H$_4$F(o), NHCH$_2$C$_6$H$_4$$^{18}$F(o),

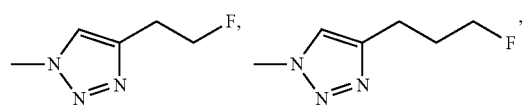

-continued

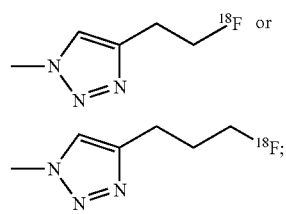

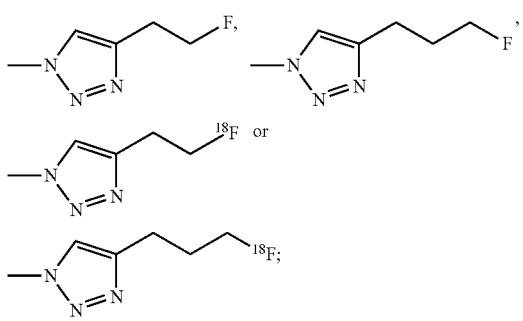

K is H, OH, NH$_2$, OCH$_3$, F, Cl,

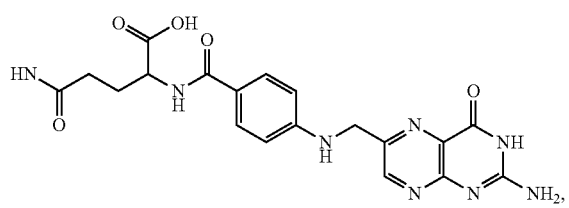

-continued

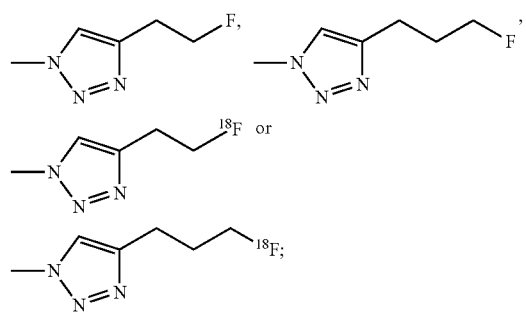

(CH$_2$CH$_2$O)$_n$CH$_2$CH$_2$G or COCH$_2$CH$_2$COO(CH$_2$CH$_2$O)$_n$CH$_2$CH$_2$K; n is 2-20; G is H, OH, NH$_2$, OCH$_3$, OCF$_3$, F, Cl, N$_3$, $^{18}$F, NHCH$_2$C$_6$H$_4$NO$_2$(p), NHCH$_2$C$_6$H$_4$F(p), NHCH$_2$C$_6$H$_4$$^{18}$F(p), NHCH$_2$C$_6$H$_4$NO$_2$(o), NHCH$_2$C$_6$H$_4$F(o), NHCH$_2$C$_6$H$_4$$^{18}$F(o),

K is H, OH, NH$_2$, OCH$_3$, F, Cl,

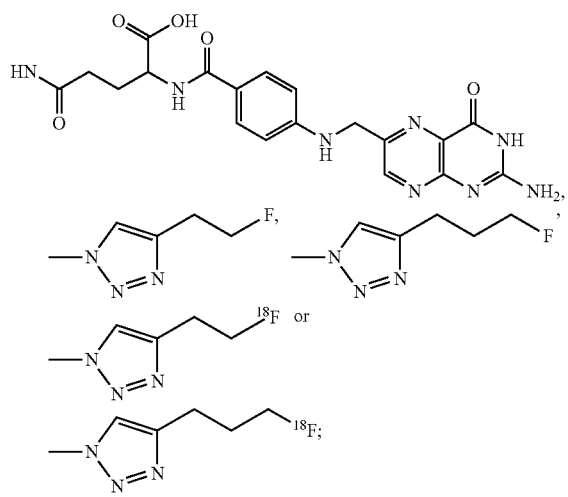

R$_2$ and R$_3$ are independently H, F, Cl, Br, I or OR$_9$; R$_9$ is independently H, CH$_3$, C$_2$H$_5$, CH$_2$CH$_2$OH, CH$_2$CH$_2$F, CH$_2$CH$_2$$^{18}$F, CH$_2$CH$_2$NHSO$_2$CH$_3$, CH$_2$CH$_2$N(CH$_2$CH$_2$F)SO$_2$CH$_3$, or CH$_2$CH$_2$N(CH$_2$CH$_2$$^{18}$F)SO$_2$CH$_3$; R$_5$ is independently H, C$_1$-C$_6$ n-alkyl chain, C$_1$-C$_6$ branched alkyl chain, CH$_2$—C$_3$-C$_6$ cycloalkyl, (CH$_2$)$_m$OH, (CH$_2$)$_m$OCH$_3$, (CH$_2$)$_m$$^{18}$F, (CH$_2$)$_m$$^{18}$F, CH$_2$C$_6$H$_5$, CH$_2$C$_6$H$_4$$^{18}$F, CH$_2$CH$_2$C$_6$H$_5$, CH$_2$CH$_2$C$_6$H$_4$$^{18}$F, CH$_2$CH$_2$CH$_2$C$_6$H$_5$, C$_6$H$_5$, C$_6$H$_4$F, C$_6$H$_4$$^{18}$F, C$_6$H$_4$OCH$_3$, C$_6$H$_4$CH$_2$CH$_2$F, C$_6$H$_4$CH$_2$CH$_2$$^{18}$F, 2-, 3- or 4-pyridyl, 3-fluoro-4-pyridyl, 3-[$^{18}$F]fluoro-4-pyridyl or CH$_2$CH$_2$-2-, 3- or 4-pyridyl; m is 1-6; X is O, NR$_{10}$, S, SO or SO$_2$; R$_{10}$ is H, CH$_3$, C$_2$H$_5$, C$_3$H$_7$, CH$_2$C$_6$H$_5$; and L is CH$_2$, O, NR$_{10}$, S, SO, SO$_2$.

Embodiment P3 A compound having a formula shown in Appendix A, Appendix B or Appendix C (Examples 1-5).

Embodiment P4 A compound of any one of embodiments P1 to P3, wherein the compound binds to a deoxycytidine kinase polypeptide.

Embodiment P5 A pharmaceutical composition comprising a compound of any one of embodiments P1 to P4, or a salt thereof, and a pharmaceutically acceptable carrier.

Embodiment P6 A method for inhibiting a deoxycytidine kinase (dCK) activity comprising contacting a compound of any one of embodiments P1 to P5 with the deoxycytidine kinase.

Embodiment P7 A method for treating cancer in an individual comprising administering to the individual an effective amount of a compound of any one of embodiments P1 to P5, or a pharmaceutically acceptable salt thereof, and thymidine, wherein the compound is administered in conjunction with thymidine.

Embodiment P8 The method of embodiment P7, wherein the cancer is leukemia, lymphoma, breast cancer, ovarian cancer, lung cancer, pancreatic cancer, hepatocellular carcinoma, melanoma, sarcoma, head and neck cancer, glioma, glioblastoma, or a cancer independent of tissue of origin that are characterized by genomic instability and/or activation of the DNA damage response.

Embodiment P9 A method for treating an immune disorder in an individual in need thereof comprising administering to the individual an effective amount of a compound of any one of embodiments P1 to P5, or a pharmaceutically acceptable salt thereof.

Embodiment P10 A PET probe comprising a compound of any one of embodiments P1 to P5.

Embodiment P11 A method of imaging, comprising: contacting a compound of embodiment P10 with a biological material; using PET imaging to determine a local concentration of the compound in the biological material; and correlating the local concentration of the compound with a local immune response or the presence of neoplastic tissue.

Embodiment P12 The method of embodiment P11, wherein contacting the compound with a biological material comprises administering a quantity of the compound to an animal or human; and correlating the local concentration of the compound in the animal or human with a local immune response or neoplastic tissue in the animal or human.

Embodiment P13 The method of embodiment P12, further comprising using the local concentration of the compound to diagnose cancer and/or monitor cancer treatment.

Embodiment P14 The method of embodiment P11, wherein the animal or human has a condition selected from the group consisting of cancer, an autoimmune disorder, a development disorder, viral infection, bacterial infection, parasitical infection, infection, a metabolic disease, and inflammation.

Embodiment P15 The method of embodiment P11, wherein the animal or human has a condition selected from the group consisting of lymphadenopathy, melanoma, leukemia, and glioma.

Embodiment P16 The method of embodiment P11, wherein the animal or human has a condition selected from the group consisting of rheumatoid arthritis, inflammatory bowel disease, Experimental Autoimmune Encephalomyelitis (EAE), multiple sclerosis, type 1 diabetes, and atherosclerosis.

Embodiment P17 The method of embodiment P11, wherein the animal or human is undergoing a therapy selected from the group consisting of cancer immunotherapy, immunotherapy, interferon therapy, vaccination, radiation therapy, chemotherapy, and antibiotic therapy.

Embodiment P18 A method of predicting resistance to an oncolytic agent, comprising: contacting a compound of any one of embodiments P1-P5 with a neoplasm; using PET imaging to determine a local concentration of the compound in the neoplasm; comparing the local concentration of the compound with a baseline level; correlating a local concentration of the compound substantially lower than the baseline level with low dCK expression of the neoplasm; correlating low dCK expression of the neoplasm with oncolytic nucleoside analog resistance, wherein the baseline level corresponds to a measured concentration of the compound in representative neoplastic cells that express dCK, concentration of the compound in representative neoplastic cells that do not express dCK, or a weighted average.

Embodiment P19 The method of embodiment P18, wherein the neoplasm is of the T lymphocyte lineage.

Embodiment P20 A method for examining the use of a compound in a PET process, the method comprising the steps: (a) incorporating a "cold" fluorine 19 atom at a defined position in the compound of any one of embodiments 1 to 5; (b) substituting the "cold" fluorine 19 atom with a "hot" fluorine 18 atom; (c) administering the compound of step (b) to a mammal; and (d) detecting and/or quantifying the compound of step (b) throughout the body of the mammal with PET imaging.

Embodiment P21 A compound of any one of embodiments P1 to P4, wherein R$_6$ is methyl.

Embodiment P22 A compound of any one of embodiments P1 to P4 and P21, wherein R$_6$ is attached to a carbon having (R) stereochemistry.

Embodiment P23 A compound of any one of embodiments P1 to P4 and P21 to P22, wherein $R_5$ is unsubstituted $C_1$-$C_6$ alkyl, preferably methyl.

Embodiment P24 A compound of any one of embodiments P1 to P4 and P21 to P23, wherein $R_7$ is hydrogen and is attached to a carbon having (R) stereochemistry Embodiment P25 A compound of any one of embodiments P1 to P4 and P21 to P24, wherein $R_9$ is —O(CH$_2$)$_2$NHS(O)$_2$CH$_3$.

Embodiment 1 A compound having the formula:

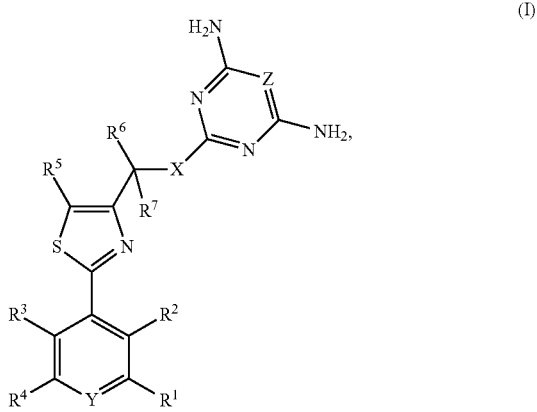

(I)

wherein: Y is C(R$^8$) or N; Z is C(R$^9$) or N; X is CH$_2$, O, N(R$^{10}$), S, S(O) or S(O)$_2$; R$^1$ is hydrogen, halogen, —N$_3$, —CF$_3$, —CCl$_3$, —CBr$_3$, —CI$_3$, —CN, —COR$^{1A}$, —OR$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ is hydrogen, halogen, —N$_3$, —CF$_3$, —CCl$_3$, —CBr$_3$, —CI$_3$, —CN, —COR$^{2A}$, —OR$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{1A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^3$ is hydrogen, halogen, —N$_3$, —CF$_3$, —CCl$_3$, —CBr$_3$, —CI$_3$, —CN, —COR$^{3A}$, —OR$^{3A}$, —NR$^{3A}$R$^{3B}$, —C(O)OR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^4$ is hydrogen, halogen, —N$_3$, —CF$_3$, —CCl$_3$, —CBr$_3$, —CI$_3$, —CN, —COR$^{4A}$, —OR$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^5$ is independently hydrogen, halogen, —N$_3$, —CF$_3$, —CCl$_3$, —CBr$_3$, —CI$_3$, —CN, —COR$^{5A}$, —OR$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^5$ and R$^6$ are optionally combined to form a substituted or unsubstituted cycloalkyl; R$^6$ is unsubstituted $C_1$-$C_6$ alkyl; R$^7$ is H, D, F or —CH$_3$; R$^8$ is hydrogen, halogen, —N$_3$, —CF$_3$, —CCl$_3$, —CBr$_3$, —CI$_3$, —CN, —COR$^{8A}$, —OR$^{8A}$, —NR$^{8A}$R$^{8B}$, —C(O)OR$^{8A}$, —C(O)NR$^{8A}$R$^{8B}$, —NO$_2$, —SR$^{8A}$, —S(O)$_{n8}$R$^{8A}$, —S(O)$_{n8}$OR$^{8A}$, —S(O)$_{n8}$NR$^{8A}$R$^{8B}$, —NHNR$^{8A}$R$^{8B}$, —ONR$^{8A}$R$^{8B}$, —NHC(O)NHNR$^{8A}$R$^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^9$ is hydrogen, halogen, —N$_3$, —CF$_3$, —CCl$_3$, —CBr$_3$, —CI$_3$, —CN, —COR$^{9A}$, —OR$^{9A}$, —NR$^{9A}$R$^{9B}$, —C(O)OR$^{9A}$, —C(O)NR$^{9A}$R$^{9B}$, —NO$_2$, —SR$^{9A}$, —S(O)$_{n9}$R$^{9A}$, —S(O)$_{n9}$OR$^{9A}$, —S(O)$_{n9}$NR$^{9A}$R$^{9B}$, —ONR$^{9A}$R$^{9B}$, —NHC(O)NHNR$^{9A}$R$^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ is H, —CH$_3$, —C$_2$H$_5$, —C$_3$H$_7$, —CH$_2$C$_6$H$_5$; R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{8A}$, R$^{8B}$, R$^{9A}$, and R$^{9B}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n8, and n9 are independently 1, 2, or 3.

Embodiment 2 The compound of embodiment 1, wherein R$^2$ and R$^3$ are hydrogen.

Embodiment 3 The compound of any one of embodiments 1 to 2, wherein R$^7$ is hydrogen.

Embodiment 4 The compound of embodiment 3, having the formula:

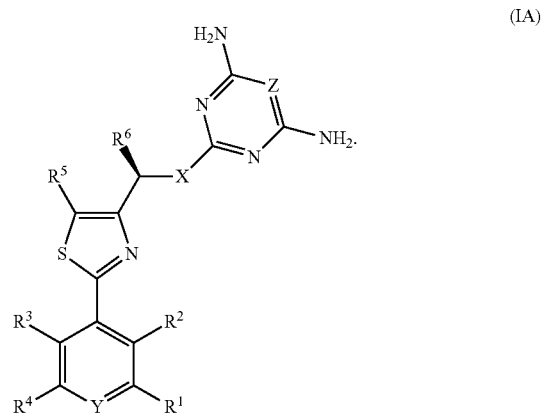

(IA)

Embodiment 5 The compound of any one of embodiments 1 to 4, wherein R$^5$ is substituted or unsubstituted alkyl.

Embodiment 6 The compound of any one of embodiments 1 to 4, wherein $R^5$ is unsubstituted alkyl.

Embodiment 7 The compound of any one of embodiments 1 to 4, wherein $R^5$ is unsubstituted $C_1$-$C_6$ alkyl.

Embodiment 8 The compound of any one of embodiments 1 to 4, wherein $R^5$ is methyl.

Embodiment 9 The compound of any one of embodiments 1 to 8, wherein $R^6$ is unsubstituted $C_1$-$C_4$ alkyl.

Embodiment 10 The compound of any one of embodiments 1 to 8, wherein $R^6$ is methyl, ethyl, or propyl.

Embodiment 11 The compound of any one of embodiments 1 to 20, wherein $R^6$ is methyl.

Embodiment 12 The compound of any one of embodiments 1 to 11, wherein $R^6$ is attached to a carbon having (R) absolute stereochemistry.

Embodiment 13 The compound of any one of embodiments 1 to 11, wherein $R^6$ is attached to a carbon having (S) absolute stereochemistry.

Embodiment 14 The compound of any one of embodiments 1 to 13, wherein $R^4$ is hydrogen or halogen.

Embodiment 15 The compound of any one of embodiments 1 to 14, wherein $R^1$ is hydrogen, halogen, —$OR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 16 The compound of any one of embodiments 1 to 15, wherein $R^1$ is —$OR^{1A}$, wherein $R^{1A}$ is hydrogen, substituted or unsubstituted alkyl, or substituted or unsubstituted heteroalkyl.

Embodiment 17 The compound of any one of embodiments 1 to 16, wherein $R^{1A}$ is substituted or unsubstituted alkyl, or substituted or unsubstituted heteroalkyl.

Embodiment 18 The compound of any one of embodiments 1 to 17, wherein $R^{1A}$ is —$CH_3$, —$C_2H_5$, —$C_3H_7$, —$CD_3$, —$CD_2CD_3$, —$(CH_2)_2OH$, —$(CH_2)_3OH$, —$CH_2CH(OH)CH_3$, —$(CH_2)_2CH(OH)CH_3$, —$CH_2C(CH_3)_2OH$, —$(CH_2)_2C(CH_3)_2OH$, —$(CH_2)_2F$, —$(CH_2)_3F$, —$CH_2CH(F)CH_3$, —$(CH_2)_2CH(F)CH_3$, —$(CH_2)_2C(CH_3)_2F$, —$(CH_2)_2Cl$, —$(CH_2)_3Cl$, —$CH_2CH(Cl)CH_3$, —$(CH_2)_2CH(Cl)CH_3$, —$CH_2C(CH_3)_2Cl$, —$(CH_2)_2C(CH_3)_2Cl$, —$(CH_2)_2NHSO_2CH_3$, —$(CH_2)_3NHSO_2CH_3$, —$(CH_2)_2N(CH_2CH_2OH)SO_2CH_3$, —$(CH_2)_3N(CH_2CH_2OH)SO_2CH_3$, —$(CH_2)_2N(CH_2CH_2F)SO_2CH_3$, —$(CH_2)_2N(CH_2CH_2Cl)SO_2CH_3$,

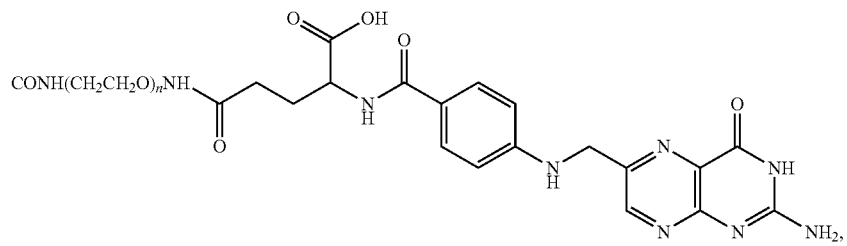

—$(CH_2CH_2O)_nCH_2CH_2$-$G^{1A}$ or —$COCH_2CH_2COO(CH_2CH_2O)_nCH_2CH_2$-$G^{1B}$, wherein; n is 2-20;

$G^{1A}$ is H, —OH, —$NH_2$, —$OCH_3$, —$OCF_3$, F, Cl, —$N_3$, —$NHCH_2C_6H_4NO_2$, —$NHCH_2C_6H_4F$, —$NHCH_2C_6H_4NO_2$, —$NHCH_2C_6H_4F$,

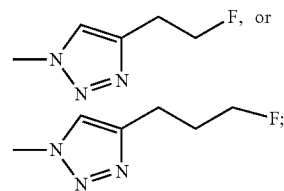

$G^{1B}$ is H, —OH, —$NH_2$, —$OCH_3$, F, Cl,

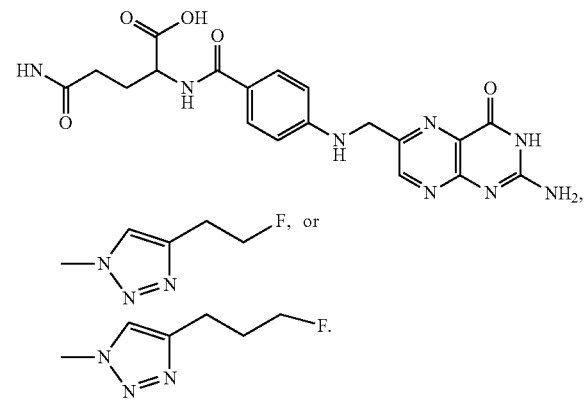

Embodiment 19 The compound of any one of embodiments 1 to 17, wherein $R^{1A}$ is —$OCH_3$, —$OCH_2CH_3$, —$O(CH_2)_2F$, —$(CH_2)_2NHSO_2CH_3$, —$(CH_2CH_2O)_nF$, —$(CH_2CH_2O)_nCH_3$, wherein n is 2 to 5.

Embodiment 20 The compound of any one of embodiments 1 to 19, wherein Y is $C(R^8)$.

Embodiment 21 The compound of any one of embodiments 1 to 19, wherein Y is N.

Embodiment 22 The compound of any one of embodiments 1 to 21, wherein $R^8$ is hydrogen, halogen, —$OR^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 23 The compound of any one of embodiments 1 to 22, wherein $R^8$ is —$OR^{8A}$, wherein $R^{1A}$ is hydrogen, substituted or unsubstituted alkyl, or substituted or unsubstituted heteroalkyl.

Embodiment 24 The compound of any one of embodiments 1 to 23, wherein $R^{8A}$ is substituted or unsubstituted alkyl, or substituted or unsubstituted heteroalkyl.-

Embodiment 25 The compound of any one of embodiments 1 to 24, wherein $R^{8A}$ is —CH$_3$, —C$_2$H$_5$, —CD$_3$, —CD$_2$CD$_3$, —(CH$_2$)$_2$OH, —(CH$_2$CH$_2$)$_3$OH, —CH$_2$C(CH$_3$)$_2$OH, —(CH$_2$)$_2$C(CH$_3$)$_2$OH, —(CH$_2$)$_2$F, —(CH$_2$)$_3$F, —CH$_2$C(CH$_3$)$_2$F, —(CH$_2$)$_2$C(CH$_3$)$_2$F,

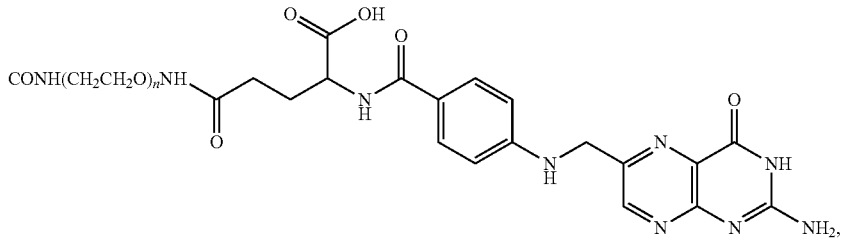

—(CH$_2$CH$_2$O)$_n$CH$_2$CH$_2$-G$^{8A}$, or —CO(CH$_2$)$_2$COO(CH$_2$CH$_2$O)$_n$CH$_2$CH$_2$-G$^{8B}$, wherein, n is 2-20; G$^{8A}$ is H, —OH, —NH$_2$, —OCH$_3$, —OCF$_3$, F, Cl, N$_3$, —NHCH$_2$C$_6$H$_4$NO$_2$, —NHCH$_2$C$_6$H$_4$F, NHCH$_2$C$_6$H$_4$NO$_2$, —NHCH$_2$C$_6$H$_4$F,

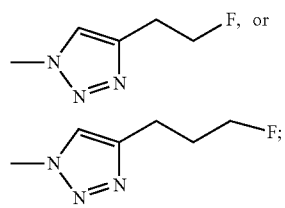

G$^{8B}$ is H, —OH, —NH$_2$, —OCH$_3$, F, Cl,

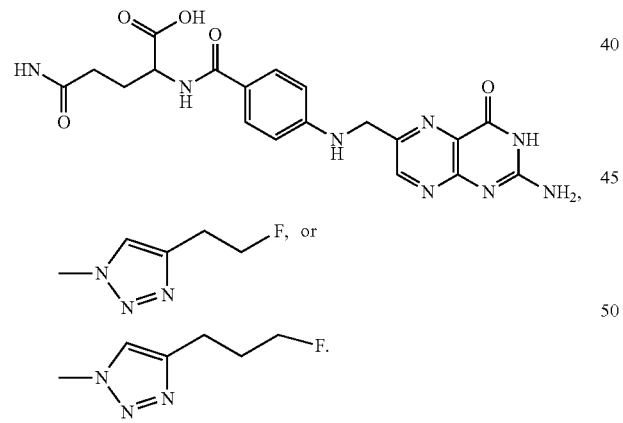

Embodiment 26 The compound of any one of embodiments 1 to 24, wherein $R^{8A}$ is —(CH$_2$)$_2$NHSO$_2$CH$_3$, —(CH$_2$)$_2$F, —(CH$_2$)$_3$F, —(CH$_2$CH$_2$O)$_n$F, or —(CH$_2$CH$_2$O)$_n$CH$_3$, wherein n is 2 to 5.

Embodiment 27 The compound of any one of embodiments 1 to 26, wherein Z is C(R$^9$).

Embodiment 28 The compound of any one of embodiments 1 to 27, wherein R$^9$ is independently hydrogen.

Embodiment 29 The compound of any one of embodiments 1 to 27, wherein Z is N.

Embodiment 30 The compound of any one of embodiments 1 to 29, wherein X is S.

Embodiment 31 The compound of any one of embodiments 1 to 30 having the formula:

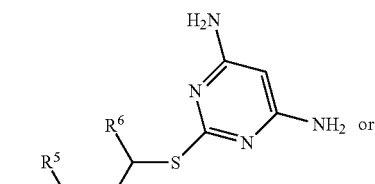

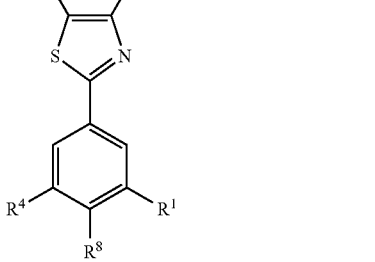

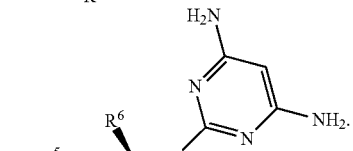

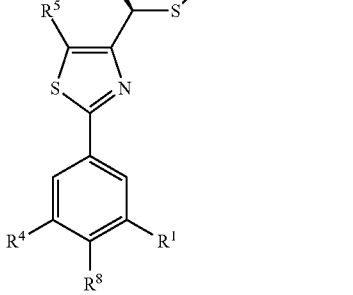

Embodiment 32 The compound of embodiment 31, wherein: R$^1$ is OR$^{14}$, wherein R$^{14}$ is —OCH$_3$, —OCH$_2$CH$_3$, —O(CH$_2$)$_2$F, —(CH$_2$)$_2$NHSO$_2$CH$_3$, —(CH$_2$CH$_2$O)$_n$F, —(CH$_2$CH$_2$O)$_n$CH$_3$, wherein n is 2 to 5; R$^4$ is hydrogen or halogen; R$^5$ is methyl or propyl; R$^6$ is methyl; and R$^8$ is —OR$^{8A}$, wherein R$^{8A}$ is —(CH$_2$)$_2$NHSO$_2$CH$_3$, —(CH$_2$)$_2$F, (CH$_2$)$_3$F, —(CH$_2$CH$_2$O)$_n$F, or —(CH$_2$CH$_2$O)$_n$CH$_3$, wherein n is 2 to 5.

Embodiment 33 A pharmaceutical formulation comprising the compound of one of embodiments 1 to 32 and a pharmaceutically acceptable excipient.

Embodiment 34 A method of treating cancer in a subject in need thereof, said method comprising administering to said subject an effective amount of the compound of one of embodiments 1 to 32.

Embodiment 35 The method of embodiment 34, wherein said cancer is leukemia, lymphoma, ovarian cancer, pancreatic cancer, lung cancer, glioblastoma, hepatocellular carcinoma, breast cancer, triple negative breast cancer, prostate cancer, or head and neck cancer.

Embodiment 36 The method of embodiment 34, wherein said cancer is leukemia or lymphoma.

Embodiment 37 The method of embodiment 34, wherein said cancer is ovarian cancer, pancreatic cancer, lung cancer, glioblastoma, hepatocellular carcinoma, breast cancer, triple negative breast cancer, prostate cancer, or head and neck cancer.

Embodiment 38 A method of inhibiting a deoxycytidine kinase, the method comprising contacting a deoxycytidine kinase with an effective amount of the compound of one of embodiments 1 to 34 thereby inhibiting said deoxycytidine kinase.

Embodiment 39 The method of embodiment 38, wherein said contacting is performed in vitro.

What is claimed is:

1. A compound having the formula:

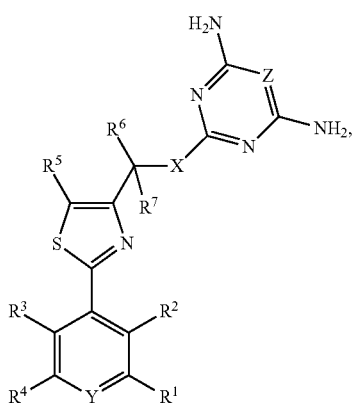

(I)

wherein:

Y is $C(R^8)$ or N;

Z is $C(R^9)$ or N;

X is $CH_2$, O, $N(R^{10})$, S, $S(O)$ or $S(O)_2$;

$R^1$ is hydrogen, halogen, $-N_3$, $-CF_3$, $-CCl_3$, $-CBr_3$, $-CI_3$, $-CN$, $-COR^{1A}$, $-OR^{1A}$, $-NR^{1A}R^{1B}$, $-C(O)OR^{1A}$, $-C(O)NR^{1A}R^{1B}$, $-NO_2$, $-SR^{1A}$, $-S(O)_{n1}R^{1A}$, $-S(O)_{n1}OR^{1A}$, $-S(O)_{n1}NR^{1A}R^{1B}$, $-NHNR^{1A}R^{1B}$, $-ONR^{1A}R^{1B}$, $-NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-N_3$, $-CF_3$, $-CCl_3$, $-CBr_3$, $-CI_3$, $-CN$, $-COR^{2A}$, $-OR^{2A}$, $-NR^{2A}R^{2B}$, $-C(O)OR^{2A}$, $-C(O)NR^{2A}R^{2B}$, $-NO_2$, $-SR^{2A}$, $-S(O)_{n2}R^{2A}$, $-S(O)_{n2}OR^{2A}$, $-S(O)_{n2}NR^{2A}R^{2B}$, $-NHNR^{2A}R^{2B}$, $-ONR^{2A}R^{2B}$, $O-NHR^{2A}R^{2B}$, $-NC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-COR^{3A}$, $-OR^{3A}$, $-NR^{3A}R^{3B}$, $-C(O)OR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$ $ONR^{3A}R^{3B}$, $-NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-N_3$, $-CF_3$, $-CCl_3$, $-CBr_3$, $-CI_3$, $-CN$, $-COR^{4A}$, $-OR^{4A}$, $-NR^{4A}R^{4B}$, $-C(O)OR^{4A}$, $-C(O)NR^{4A}R^{4B}$, $-NO_2$, $-SR^{4A}$, $-S(O)_{n4}R^{4A}$, $-S(O)_{n4}OR^{4A}$, $-S(O)_{n4}NR^{4A}R^{4B}$, $-NHNR^{4A}R^{4B}$, $-ONR^{4A}R^{4B}$, $-NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, $-N_3$, $-CF_3$, $-CCl_3$, $-CBr_3$, $-CI_3$, $-CN$, $-COR^{5A}$, $-OR^{5A}$, $-NR^{5A}R^{5B}$, $-C(O)OR^{5A}$, $-C(O)NR^{5A}R^{5B}$, $-NO_2$, $-SR^{5A}$, $-S(O)_{n5}R^{5A}$, $-S(O)_{n5}OR^{5A}$, $-S(O)_{n5}NR^{5A}R^{5B}$, $-NHNR^{5A}R^{5B}$, $-ONR^{5A}R^{5B}$, $-NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^5$ and $R^6$ are optionally combined to form a substituted or unsubstituted cycloalkyl;

$R^6$ is methyl;

$R^7$ is H;

$R^8$ is hydrogen, halogen, $-N_3$, $-CF_3$, $-CCl_3$, $-CBr_3$, $-CI_3$, $-CN$, $-COR^{8A}$, $-OR^{8A}$, $-NR^{8A}R^{8B}$, $-C(O)OR^{8A}$, $-C(O)NR^{8A}R^{8B}$, $-NO_2$, $-SR^{8A}$, $-S(O)_{n8}R^{8A}$, $-S(O)_{n8}OR^{8A}$, $-S(O)_{n8}NR^{8A}R^{8B}$, $-NHNR^{8A}R^{8B}$, $-ONR^{8A}R^{8B}$, $-NHC(O)NHNR^{8A}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-N_3$, $-CF_3$, $-CCl_3$, $-CBr_3$, $-CI_3$, $-CN$, $-COR^{9A}$, $-OR^{9A}$, $-NR^{9A}R^{9B}$, $-C(O)OR^{9A}$, $-C(O)NR^{9A}R^{9B}$, $-NO_2$, $-SR^{9A}$, $-S(O)_{n9}R^{9A}$, $-S(O)_{n9}OR^{9A}$, $-S(O)_{n9}NR^{9A}R^{9B}$, $-NHNR^{9A}R^{9B}$, $-ONR^{9A}R^{9B}$, $-NHC(O)NHNR^{9A}R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is H, $-CH_3$, $-C_2H_5$, $-C_3H_7$, $-CH_2C_6H_5$;

$R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{8A}$, $R^{8B}$, $R^{9A}$, and $R^{9B}$ are independently hydrogen, oxo, halogen, $-CF_3$, $-CN$, $-OH$, $-NH_2$, $-COOH$, $-CONH_2$, $-NO_2$, $-SH$, $-S(O)_2Cl$, $-S(O)_3H$, $-S(O)_4H$, $-S(O)_2NH_2$, $-NHNH_2$, $-ONH_2$, $-NHC(O)NHNH_2$, $-NHC(O)NH_2$, $-NHS(O)_2H$, $-NHC(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5, n8, and n9 are independently 1, 2, or 3.

2. The compound of claim 1, wherein $R^2$, $R^3$, $R^4$, and $R^7$ are hydrogen.

3. The compound of claim 2, having the formula:

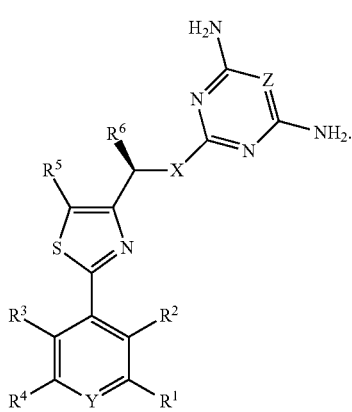

(IA)

4. The compound of claim 3, wherein $R^5$ is unsubstituted $C_1$-$C_6$ alkyl.

5. The compound of claim 4, wherein $R^1$ is hydrogen, halogen, —$OR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

6. The compound of claim 5, wherein $R^1$ is —$OR^{1A}$, and $R^{1A}$ is substituted or unsubstituted alkyl, or substituted or unsubstituted heteroalkyl.

7. The compound of claim 6, wherein $R^{1A}$ is —$CH_3$, —$C_2H_5$, —$C_3H_7$, —$CD_3$, —$CD_2CD_3$, —$(CH_2)_2OH$, —$(CH_2)_3OH$, —$CH_2CH(OH)CH_3$, —$(CH_2)_2CH(OH)CH_3$, —$CH_2C(CH_3)_2OH$, —$(CH_2)_2C(CH_3)_2OH$, —$(CH_2)_2F$, —$(CH_2)_3F$, —$CH_2CH(F)CH_3$, —$(CH_2)_2CH(F)CH_3$, —$(CH_2)_2C(CH_3)_2F$, —$(CH_2)_2Cl$, —$(CH_2)_3Cl$, —$CH_2CH(Cl)CH_3$, —$(CH_2)_2CH(Cl)CH_3$, —$CH_2C(CH_3)_2Cl$, —$(CH_2)_2C(CH_3)_2Cl$, —$(CH_2)_2NHSO_2CH_3$, —$(CH_2)_3NHSO_2CH_3$, —$(CH_2)_2N(CH_2CH_2OH)SO_2CH_3$, —$(CH_2)_3N(CH_2CH_2OH)SO_2CH_3$, —$(CH_2)_2N(CH_2CH_2F)SO_2CH_3$, or —$(CH_2)_2N(CH_2CH_2Cl)SO_2CH_3$.

8. The compound of claim 7, wherein Y is $C(R^8)$.

9. The compound of claim 8, wherein $R^8$ is hydrogen, halogen, —$OR^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

10. The compound of claim 9, wherein $R^8$ is —$OR^{8A}$, and $R^{8A}$ is hydrogen, substituted or unsubstituted alkyl, or substituted or unsubstituted heteroalkyl.

11. The compound of claim 10, wherein $R^{8A}$ is —$CH_3$, —$C_2H_5$, —$CD_3$, —$CD_2CD_3$, —$(CH_2)_2OH$, —$(CH_2CH_2)_3OH$, —$CH_2C(CH_3)_2OH$, —$(CH_2)_2C(CH_3)_2OH$, —$(CH_2)_2F$, —$(CH_2)_3F$, —$CH_2C(CH_3)_2F$, or —$(CH_2)_2C(CH_3)_2F$.

12. The compound of claim 11, wherein Z is CH.

13. The compound of claim 12, wherein X is S.

14. The compound of claim 1 having the formula

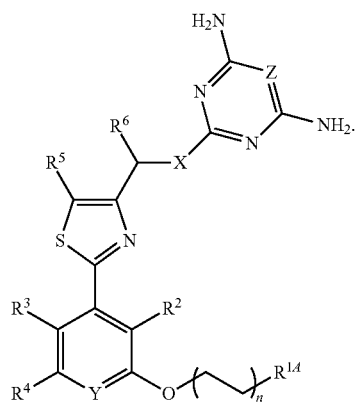

15. The compound of claim 14, wherein $R^{1A}$ is substituted or unsubstituted heterocycloalkyl.

16. The compound of claim 1 having the structure:

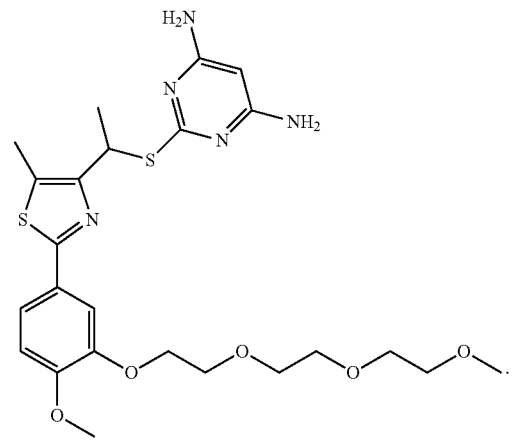

17. The compound of claim 1 having the structure:

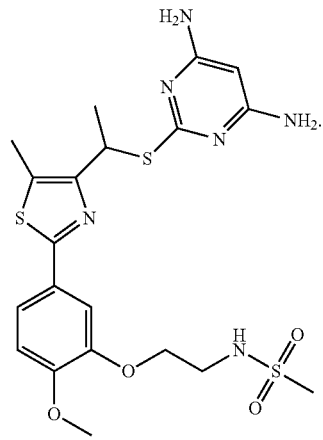

18. The compound of claim 1 having the structure:

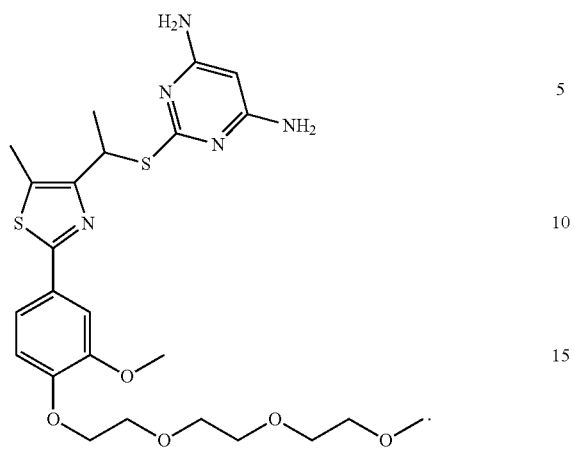

19. A pharmaceutical formulation, comprising the compound of claim 1 and a pharmaceutically acceptable excipient.

20. A method of treating hematological malignancy in a subject in need thereof, comprising administering to the subject an effective amount of the compound of claim 1.

21. The method of claim 20, wherein the hematological malignancy is leukemia.

22. The method of claim 21, wherein the leukemia is acute lymphoblastic leukemia (ALL).

23. The method of claim 1, wherein $R^5$ is methyl.

* * * * *